US012623094B2

(12) United States Patent
Agarwal et al.

(10) Patent No.: US 12,623,094 B2
(45) **Date of Patent: *May 12, 2026**

(54) INCOHERENT FIELD SONODYNAMIC THERAPY FOR TREATING CANCER

(71) Applicant: Alpheus Medical, Inc., Chanhassen, MN (US)

(72) Inventors: Vijay Agarwal, New York, NY (US); Braden Eliason, Minneapolis, MN (US); Jeremy Ling, Mendota Heights, MN (US); John Ballard, Waconia, MN (US); Gregg Miller, Boulder, CO (US)

(73) Assignee: Alpheus Medical, Inc., Chanhassen, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/813,602

(22) Filed: Aug. 23, 2024

(65) Prior Publication Data

US 2025/0121214 A1 Apr. 17, 2025

Related U.S. Application Data

(63) Continuation of application No. 18/215,497, filed on Jun. 28, 2023, now Pat. No. 12,097,392, which is a (Continued)

(51) Int. Cl.
*A61N 7/00* (2006.01)
*A61K 41/00* (2020.01)
(Continued)

(52) U.S. Cl.
CPC ............ *A61N 7/00* (2013.01); *A61K 41/0033* (2013.01); *A61M 37/0092* (2013.01); *A61N 7/02* (2013.01);
(Continued)

(58) Field of Classification Search
CPC .... A61N 7/00; A61N 7/02; A61N 2007/0021; A61N 2007/0043; A61N 2007/0073;
(Continued)

(56) References Cited

U.S. PATENT DOCUMENTS

| | | | |
|---|---|---|---|
| 4,576,177 | A | 3/1986 | Webster |
| 4,735,201 | A | 4/1988 | O'Reilly |

(Continued)

FOREIGN PATENT DOCUMENTS

| | | | |
|---|---|---|---|
| CN | 1775327 | A | 5/2006 |
| CN | 101022852 | A | 8/2007 |

(Continued)

OTHER PUBLICATIONS

Hendee et al., "Medical Imaging Physics, Fourth Edition", 2002, pp. 303-353 (Year: 2002).

(Continued)

*Primary Examiner* — Pascal M Bui Pho
*Assistant Examiner* — Michael Yiming Fang
(74) *Attorney, Agent, or Firm* — Knobbe, Martens, Olson & Bear, LLP

(57) ABSTRACT

Ultrasound transducer element arrays using acoustic ensonification drive patterns via a patient interface for sonosensitizer activation in sonodynamic therapy. Incoherent acoustic field generation varying phase, frequencies, and/or amplitude via controlled delivery of low intensity planar acoustic waves. Method includes generating a first and a second signal to generate respective acoustic ensonification drive patterns with phase, frequency, and amplitude and generating at least one relative phase, frequency or amplitude difference to generate a third incoherent acoustic ensonification pattern to activate a sonosensitizer. Calibration and complementary therapy procedures to improve cell susceptibility of cells to sonodynamic therapy are disclosed.

20 Claims, 55 Drawing Sheets

Related U.S. Application Data continuation of application No. 18/040,610, filed as application No. PCT/US2021/071101 on Aug. 4, 2021.

(60) Provisional application No. 63/062,879, filed on Aug. 7, 2020, provisional application No. 63/062,937, filed on Aug. 7, 2020, provisional application No. 63/062,915, filed on Aug. 7, 2020, provisional application No. 63/062,895, filed on Aug. 7, 2020, provisional application No. 63/062,926, filed on Aug. 7, 2020.

(51) Int. Cl.
*A61M 37/00* (2006.01)
*A61N 7/02* (2006.01)
*B06B 1/02* (2006.01)
*B06B 1/06* (2006.01)

(52) U.S. Cl.
CPC .......... *B06B 1/0215* (2013.01); *B06B 1/0625* (2013.01); *B06B 1/0629* (2013.01); *B06B 1/0633* (2013.01); *A61N 2007/0021* (2013.01); *A61N 2007/0043* (2013.01); *A61N 2007/0073* (2013.01); *A61N 2007/0078* (2013.01); *A61N 2007/0086* (2013.01); *B06B 2201/55* (2013.01); *B06B 2201/76* (2013.01)

(58) Field of Classification Search
CPC .... A61N 2007/0078; A61N 2007/0086; A61N 2007/0095; A61N 2007/0091; A61K 41/0033; A61M 37/0092; B06B 1/0215; B06B 1/0625; B06B 1/0629; B06B 1/0633; B06B 2201/55; B06B 2201/76; B06B 1/0637; A61B 2018/00011; A61B 2018/00023
See application file for complete search history.

(56) References Cited

U.S. PATENT DOCUMENTS 4,807,633 A 2/1989 Fry
4,875,487 A 10/1989 Seppi
5,344,974 A 9/1994 Descotes et al.
5,558,092 A 9/1996 Unger et al.
5,733,770 A 3/1998 Watanabe et al.
5,738,635 A 4/1998 Chapelon et al.
5,817,048 A 10/1998 Lawandy
6,176,842 B1 1/2001 Tachibana et al.
6,379,320 B1 4/2002 Lafon et al.
6,428,968 B1 8/2002 Molnar-Kimber et al.
6,498,945 B1 12/2002 Alheim et al.
6,514,258 B1 2/2003 Brown et al.
6,572,839 B2 6/2003 Sugita et al.
6,575,922 B1 6/2003 Fearnside et al.
6,576,257 B1 6/2003 Yarmut
6,599,246 B1 7/2003 Coffey et al.
6,613,005 B1 * 9/2003 Friedman ................ A61N 7/02
600/407
6,622,049 B2 9/2003 Penner et al.
6,723,750 B2 4/2004 Voet
6,733,450 B1 5/2004 Alexandrov et al.
6,739,872 B1 5/2004 Turri
7,018,395 B2 3/2006 Chen
7,125,387 B2 10/2006 Kawabata et al.
7,252,677 B2 8/2007 Burwell et al.
7,498,029 B2 3/2009 Hasan et al.
7,514,069 B2 4/2009 Achileu et al.
7,652,410 B2 1/2010 Prus
7,674,229 B2 3/2010 Hynynen et al.
7,699,783 B2 4/2010 Hanover et al.
7,713,203 B2 5/2010 Lacoste et al.
7,790,144 B2 9/2010 Achileu et al.
8,070,682 B2 12/2011 Zhu
8,123,789 B2 2/2012 Khanna
8,173,839 B2 5/2012 Tachiya et al.
8,206,326 B2 6/2012 Schafer et al.
8,318,133 B2 11/2012 Achileu et al.
8,318,794 B2 11/2012 Wang et al.
8,353,853 B1 1/2013 Kyle et al.
8,409,099 B2 4/2013 Vitek et al.
8,492,578 B2 7/2013 Glanzmann et al.
8,548,562 B2 10/2013 Trachtenberg et al.
8,574,174 B2 11/2013 Schafer et al.
8,603,014 B2 12/2013 Alleman et al.
8,613,714 B2 12/2013 Alleman et al.
8,617,073 B2 12/2013 Prus et al.
8,718,758 B2 5/2014 Wagner et al.
8,741,262 B2 6/2014 Ni et al.
8,747,811 B2 6/2014 Sharma et al.
8,758,725 B2 6/2014 Sharma et al.
8,770,203 B2 7/2014 Bourke, Jr. et al.
8,771,741 B2 7/2014 Adair et al.
8,932,237 B2 1/2015 Vitek et al.
8,977,354 B2 3/2015 Wagner et al.
8,979,775 B2 3/2015 Schafer et al.
8,992,958 B2 3/2015 Kanehira et al.
9,012,502 B2 4/2015 Chibazakura et al.
9,023,090 B2 5/2015 Palti
9,072,774 B2 7/2015 Zheng et al.
9,220,718 B2 12/2015 Park et al.
9,249,086 B2 2/2016 Braenden et al.
9,313,423 B2 4/2016 Wang et al.
9,326,964 B2 5/2016 Stensrud
9,371,555 B2 6/2016 Roberts
9,463,256 B2 10/2016 Lub et al.
9,475,028 B2 10/2016 Krishna et al.
9,492,121 B2 11/2016 Andrews et al.
9,492,681 B2 11/2016 Aydt et al.
9,493,810 B2 11/2016 Ezrin
9,498,650 B2 11/2016 Schafer et al.
9,510,909 B2 12/2016 Grant et al.
9,572,880 B2 2/2017 Harris et al.
9,764,029 B2 9/2017 Shibaguchi et al.
9,816,118 B2 11/2017 Lee et al.
9,833,634 B2 12/2017 Bourke et al.
9,963,724 B2 5/2018 Saito et al.
9,974,974 B2 5/2018 Groseth
9,999,760 B2 6/2018 Fang
10,035,027 B2 7/2018 Deisseroth et al.
10,098,539 B2 10/2018 Konofagou et al.
10,265,234 B1 4/2019 Zwierstra et al.
10,272,008 B2 4/2019 Zwierstra et al.
10,286,091 B2 5/2019 Desgranges et al.
10,456,603 B2 10/2019 Tlusty et al.
10,493,296 B2 12/2019 Vo-Dinh et al.
10,512,691 B2 12/2019 Kalifa et al.
10,555,861 B2 2/2020 Zwierstra et al.
10,589,129 B2 3/2020 Vortman et al.
10,653,653 B2 5/2020 Zhao et al.
10,675,482 B2 6/2020 Agarwal et al.
10,702,244 B2 7/2020 O'Reilly et al.
10,765,892 B1 9/2020 Vitek et al.
10,773,098 B2 9/2020 Liu et al.
10,835,756 B2 11/2020 Bourke, Jr. et al.
10,918,718 B2 2/2021 Mo et al.
10,974,077 B2 4/2021 Guha et al.
11,040,101 B2 6/2021 Nomikou
11,071,522 B2 7/2021 Hynynen et al.
11,305,133 B2 4/2022 Khuri-Yakub et al.
11,307,204 B2 4/2022 Ezrin
11,318,332 B2 5/2022 Agarwal et al.
11,344,498 B2 5/2022 Rwei et al.
11,382,987 B2 7/2022 Callan et al.
11,389,395 B2 7/2022 Wrenn et al.
11,491,353 B2 11/2022 Agarwal et al.
11,504,290 B2 11/2022 Hewes et al.
11,534,630 B2 12/2022 Ramamurthy
11,559,585 B2 1/2023 Li et al.
11,607,197 B2 3/2023 Muller et al.
11,617,904 B2 4/2023 Agarwal et al.

(56) References Cited

U.S. PATENT DOCUMENTS 11,639,360 B2 5/2023 Fan et al.
11,660,068 B2 5/2023 Kim et al.
11,660,342 B2 5/2023 Kim et al.
11,691,033 B2 7/2023 Sverdlik et al.
11,712,473 B2 8/2023 Callan et al.
11,724,132 B2 8/2023 Agarwal et al.
11,730,980 B2 8/2023 Agarwal et al.
11,771,370 B2 10/2023 Hynynen
11,793,490 B2 10/2023 Hynynen et al.
11,793,983 B2 10/2023 Chen et al.
11,794,040 B2 10/2023 Capelli
11,813,330 B2 11/2023 Mandel et al.
11,826,288 B2 11/2023 Hewes et al.
11,857,812 B2 1/2024 Ramamurthy
11,865,371 B2 1/2024 Capelli
11,865,372 B2 1/2024 Agarwal et al.
11,872,413 B2 1/2024 Carpentier et al.
11,878,059 B2 1/2024 Callan et al.
11,957,936 B2 4/2024 Yan et al.
11,975,156 B2 5/2024 Agarwal et al.
11,980,777 B2 5/2024 Agarwal et al.
11,998,395 B2 6/2024 Specht et al.
12,011,482 B2 6/2024 Zhao et al.
12,017,093 B2 6/2024 Ramamurthy et al.
12,097,392 B2 9/2024 Agarwal et al.
12,103,941 B2 10/2024 Zhu et al.
12,168,055 B2 12/2024 Marcus
12,201,643 B2 1/2025 Li et al.
12,290,403 B2 5/2025 Hynynen et al.
12,303,722 B2 5/2025 Zhang et al.
12,329,566 B2 6/2025 Kubanek
12,397,179 B2 8/2025 Noh et al.
12,403,333 B2 9/2025 Ramamurthy et al.
12,426,836 B2 9/2025 Hynynen
12,433,569 B2 10/2025 Ramamurthy et al.
2001/0041163 A1 11/2001 Sugita et al.
2002/0038086 A1 3/2002 Hynynen et al.
2003/0069526 A1 4/2003 Thopson et al.
2003/0092667 A1 5/2003 Tachibana et al.
2003/0114434 A1 6/2003 Chen et al.
2004/0002677 A1 1/2004 Gentsler
2004/0049134 A1 3/2004 Tosaya et al.
2004/0054282 A1 3/2004 Aubry et al.
2004/0171601 A1 9/2004 Fukumura et al.
2004/0210135 A1 10/2004 Hynynen et al.
2005/0060012 A1 3/2005 Voorhees et al.
2005/0085726 A1 4/2005 Lacoste et al.
2005/0118550 A1 6/2005 Turri
2005/0124897 A1 6/2005 Chopra
2005/0197577 A1 9/2005 Makin et al.
2005/0240124 A1 10/2005 Mast et al.
2005/0277824 A1 12/2005 Aubry et al.
2006/0241530 A1 10/2006 Ostrovsky et al.
2007/0005121 A1 1/2007 Khanna
2007/0038099 A1 2/2007 Sugita et al.
2007/0112344 A1 5/2007 Keilman et al.
2007/0260295 A1 11/2007 Chen et al.
2008/0194954 A1 8/2008 Unger et al.
2008/0319375 A1 12/2008 Hardy
2009/0049907 A1 2/2009 Wu et al.
2009/0062724 A1 3/2009 Chen
2009/0099483 A1 4/2009 Rybyanets
2010/0069746 A1 3/2010 St. John
2010/0106229 A1 4/2010 Gammons et al.
2010/0217160 A1 8/2010 Saguchi et al.
2010/0228523 A1 9/2010 Kajitani et al.
2010/0262115 A1 10/2010 Madiyalakan et al.
2011/0020429 A1 1/2011 Lauten et al.
2011/0263967 A1 10/2011 Bailey et al.
2012/0016429 A1 1/2012 Klorg
2012/0040312 A1 2/2012 Hinders
2012/0065494 A1 3/2012 Gertner et al.
2012/0089205 A1 4/2012 Boyden et al.
2012/0209150 A1* 8/2012 Zeng ........................ A61N 7/02 601/2
2012/0271167 A1 10/2012 Holland et al.
2012/0283605 A1 11/2012 Lewis, Jr.
2013/0101468 A1 4/2013 Boutin et al.
2013/0172739 A1* 7/2013 Paladini ............... A61B 6/5247 601/2
2013/0281890 A1 10/2013 Mishelevich
2014/0257262 A1 9/2014 Carpentier et al.
2014/0316269 A1 10/2014 Zhang et al.
2014/0316387 A1 10/2014 Harris et al.
2015/0126910 A1 5/2015 Koskela et al.
2015/0224345 A1* 8/2015 Warlick .................. A61N 7/00 601/2
2015/0320591 A1 11/2015 Smith et al.
2016/0151618 A1 6/2016 Powers et al.
2016/0157964 A1 6/2016 Suttin et al.
2016/0243381 A1 8/2016 Alford et al.
2016/0325110 A1 11/2016 Agarwal et al.
2017/0007699 A1* 1/2017 Park ..................... A61K 9/5192
2017/0095557 A1 4/2017 Fang
2017/0173351 A1 6/2017 Agarwal et al.
2018/0001114 A1 1/2018 Li et al.
2018/0049762 A1 2/2018 Seip et al.
2018/0177491 A1 6/2018 Hynynen et al.
2018/0207447 A1 7/2018 Liu
2018/0236270 A1 8/2018 Hananel et al.
2018/0296859 A1 10/2018 Guha et al.
2018/0344849 A1 12/2018 Trouard et al.
2018/0344872 A1 12/2018 Callan et al.
2019/0009111 A1 1/2019 Myhr et al.
2019/0021666 A1 1/2019 Hynynen
2019/0030375 A1 1/2019 Zachar
2019/0069949 A1 3/2019 Vrba et al.
2019/0070296 A1 3/2019 Wang et al.
2019/0105517 A1 4/2019 Tyler
2019/0175433 A1 6/2019 Zwierstra et al.
2019/0183457 A1 6/2019 Ramamurthy
2019/0184204 A1 6/2019 Ramamurthy
2019/0307472 A1 10/2019 Lu et al.
2019/0339387 A1 11/2019 Pang et al.
2019/0344099 A1 11/2019 Tlusty et al.
2020/0124607 A1 4/2020 Ezrin
2020/0139161 A1 5/2020 Gomori
2020/0146917 A1 5/2020 Zwierstra et al.
2020/0197659 A1 6/2020 Wilcox et al.
2020/0282196 A1 9/2020 Chen et al.
2021/0008385 A1 1/2021 Agarwal et al.
2021/0106849 A1 4/2021 Liu et al.
2021/0177759 A1 6/2021 Sosnik et al.
2021/0236862 A1 8/2021 Eliason
2021/0251599 A1 8/2021 Torp et al.
2021/0260411 A1 8/2021 Khuri-Yakub et al.
2021/0330294 A1 10/2021 Hynynen et al.
2021/0369843 A1 12/2021 Agarwal et al.
2021/0370102 A1 12/2021 Agarwal et al.
2021/0370103 A1 12/2021 Agarwal et al.
2022/0062417 A1 3/2022 Callan et al.
2022/0072128 A1 3/2022 Airan
2022/0126120 A1 4/2022 Zachar
2022/0175357 A1 6/2022 Ding et al.
2022/0175926 A1 6/2022 Karp et al.
2022/0184234 A1 6/2022 Marcus
2022/0226471 A1 7/2022 Marcus
2022/0233695 A1 7/2022 Yoo et al.
2022/0257214 A1 8/2022 Anquez et al.
2022/0257984 A1 8/2022 Agarwal et al.
2022/0266063 A1 8/2022 Emery et al.
2022/0347314 A1 11/2022 Callan et al.
2022/0370609 A1 11/2022 Park et al.
2022/0378692 A1 12/2022 Sontum et al.
2023/0037342 A1 2/2023 Agarwal et al.
2023/0041402 A1 2/2023 Tsuboi
2023/0201553 A1 6/2023 Levy et al.
2023/0218930 A1* 7/2023 Stopek .................. A61B 8/085 601/3
2023/0225748 A1 7/2023 Hassan et al.
2023/0226379 A1 7/2023 Agarwal et al.
2023/0277877 A1 9/2023 Agarwal et al.
2023/0293913 A1 9/2023 Achrol et al.
2023/0330441 A1 10/2023 Agarwal et al.

(56) References Cited

U.S. PATENT DOCUMENTS

| | | | |
|---|---|---|---|
| 2023/0330442 | A1 | 10/2023 | Agarwal et al. |
| 2023/0330443 | A1 | 10/2023 | Agarwal et al. |
| 2023/0338751 | A1 | 10/2023 | Agarwal et al. |
| 2023/0338752 | A1 | 10/2023 | Agarwal et al. |
| 2023/0338753 | A1 | 10/2023 | Agarwal et al. |
| 2023/0338754 | A1 | 10/2023 | Agarwal et al. |
| 2024/0024649 | A1 | 1/2024 | Agarwal et al. |
| 2024/0041429 | A1 | 2/2024 | Hynynen et al. |
| 2024/0042043 | A1 | 2/2024 | Kim et al. |
| 2024/0042242 | A1 | 2/2024 | Ramamurthy et al. |
| 2024/0050774 | A1 | 2/2024 | Capelli |
| 2024/0057967 | A1 | 2/2024 | Treeby et al. |
| 2024/0057971 | A1 | 2/2024 | Chiang et al. |
| 2024/0091363 | A1 | 3/2024 | Callan et al. |
| 2024/0091564 | A1 | 3/2024 | Capelli |
| 2024/0091758 | A1 | 3/2024 | Kwan et al. |
| 2024/0108917 | A1 | 4/2024 | Agarwal et al. |
| 2024/0131071 | A1 | 4/2024 | Heimberger |
| 2024/0156745 | A1 | 5/2024 | Alphandery |
| 2024/0189427 | A1 | 6/2024 | Marcus |
| 2024/0198139 | A1 | 6/2024 | Sverdlik et al. |
| 2024/0207652 | A1 | 6/2024 | Agarwal et al. |
| 2024/0216549 | A1 | 7/2024 | Sontum et al. |
| 2024/0269287 | A1 | 8/2024 | Khorsandi et al. |
| 2024/0269489 | A1 | 8/2024 | Kvale et al. |
| 2024/0278041 | A1 | 8/2024 | Agarwal et al. |
| 2024/0293683 | A1 | 9/2024 | Agarwal et al. |
| 2024/0335680 | A1 | 10/2024 | Achrol et al. |
| 2024/0342510 | A1 | 10/2024 | Hacker et al. |
| 2024/0423904 | A1 | 12/2024 | Robb et al. |
| 2025/0001219 | A1 | 1/2025 | Noh et al. |
| 2025/0032822 | A1 | 1/2025 | Sato et al. |
| 2025/0041577 | A1 | 2/2025 | Shapira et al. |
| 2025/0073504 | A1 | 3/2025 | Daft et al. |
| 2025/0099589 | A1 | 3/2025 | Wang et al. |
| 2025/0108237 | A1 | 4/2025 | Sato et al. |
| 2025/0114582 | A1 | 4/2025 | Canney et al. |
| 2025/0121216 | A1 | 4/2025 | Murphy et al. |
| 2025/0121219 | A1 | 4/2025 | Daft et al. |
| 2025/0177557 | A1 | 6/2025 | Keenan |
| 2025/0186343 | A1 | 6/2025 | Urbach et al. |
| 2025/0222281 | A1 | 7/2025 | Satir et al. |

FOREIGN PATENT DOCUMENTS

| | | | |
|---|---|---|---|
| CN | 101228460 | A | 7/2008 |
| CN | 201586334 | U | 9/2010 |
| CN | 102233159 | A | 11/2011 |
| CN | 102791332 | A | 11/2012 |
| CN | 102885648 | A | 1/2013 |
| CN | 104519960 | A | 4/2015 |
| CN | 107864633 | A | 8/2018 |
| CN | 211536251 | U | 9/2020 |
| EP | 1909908 | B1 | 3/2011 |
| EP | 2318086 | B1 | 4/2016 |
| EP | 3359134 | B1 | 10/2016 |
| EP | 2931290 | B1 | 8/2018 |
| EP | 3298066 | B1 | 8/2019 |
| EP | 3060255 | B1 | 12/2019 |
| EP | 3554378 | B1 | 7/2021 |
| EP | 3558457 | B1 | 11/2021 |
| EP | 3374024 | B1 | 7/2022 |
| EP | 2726152 | B1 | 8/2022 |
| EP | 3597111 | B1 | 5/2023 |
| EP | 4241763 | | 9/2023 |
| EP | 3229906 | B1 | 11/2023 |
| EP | 3924046 | B1 | 11/2023 |
| EP | 3419548 | B1 | 7/2024 |
| EP | 3487410 | B1 | 2/2025 |
| EP | 3890781 | B1 | 10/2025 |
| JP | S60-053131 | A | 3/1985 |
| JP | S62-087151 | | 4/1987 |
| JP | S62-202813 | U | 12/1987 |
| JP | H07-231894 | | 9/1995 |
| JP | H09-122164 | | 5/1997 |
| JP | 2001-104355 | | 4/2001 |
| JP | 2003503103 | A | 1/2003 |
| JP | 2005125075 | A | 5/2005 |
| JP | 2005152093 | A | 6/2005 |
| JP | 2005-537071 | | 12/2005 |
| JP | 2007-007279 | | 1/2007 |
| JP | 2008-188160 | | 8/2008 |
| JP | 4492818 | B | 6/2010 |
| JP | 2011509737 | A | 3/2011 |
| JP | 2013-512016 | A | 4/2013 |
| JP | 2015-517350 | | 6/2015 |
| KR | 100796450 | B1 | 1/2008 |
| KR | 20100027584 | | 3/2010 |
| WO | WO 92/10142 | A1 | 6/1992 |
| WO | WO 95/05214 | A1 | 2/1995 |
| WO | WO 96/28200 | A1 | 9/1996 |
| WO | WO 2009/026724 | A1 | 3/2009 |
| WO | WO 2009/095912 | A1 | 8/2009 |
| WO | WO 2010/078929 | A1 | 7/2010 |
| WO | WO 2011/057028 | | 5/2011 |
| WO | WO 2012/035747 | A1 | 3/2012 |
| WO | WO 2013/170223 | | 11/2013 |
| WO | WO 2014/083614 | | 6/2014 |
| WO | WO 2015/03484 | A1 | 7/2015 |
| WO | WO 2017/074509 | | 5/2017 |
| WO | WO 2018026738 | A1 | 2/2018 |
| WO | WO 2018035256 | A1 | 2/2018 |
| WO | WO 2018/112664 | A1 | 6/2018 |
| WO | WO 2019059027 | A1 | 3/2019 |
| WO | WO 2019/123411 | | 6/2019 |
| WO | WO 2019/205285 | | 10/2019 |
| WO | WO 2020/033764 | A1 | 2/2020 |
| WO | WO 2020/167922 | | 8/2020 |
| WO | WO 2020/167992 | A1 | 8/2020 |
| WO | WO 2020/217472 | A1 | 10/2020 |
| WO | WO 2020/243319 | A1 | 12/2020 |
| WO | WO 2021154730 | A1 | 8/2021 |
| WO | WO 2022/032283 | A1 | 2/2022 |
| WO | WO 2022/115695 | | 6/2022 |
| WO | WO 2023/105290 | | 6/2023 |
| WO | WO 2023/170231 | | 9/2023 |
| WO | WO 2023/178964 | | 9/2023 |
| WO | WO 2023/230246 | A1 | 11/2023 |
| WO | WO 2023/233475 | | 12/2023 |
| WO | WO 2023/240256 | | 12/2023 |
| WO | WO 2024/076537 | | 4/2024 |
| WO | WO 2024/211443 | A1 | 4/2024 |
| WO | WO 2024/148416 | | 7/2024 |
| WO | WO 2024/209347 | A1 | 10/2024 |
| WO | WO 2024/233948 | A1 | 11/2024 |
| WO | WO 2024/239160 | A1 | 11/2024 |
| WO | WO 2024/257021 | A1 | 12/2024 |
| WO | WO 2025/013486 | A1 | 1/2025 |
| WO | WO 2025/025574 | A1 | 2/2025 |
| WO | WO 2025/085439 | A1 | 4/2025 |
| WO | WO 2025/103733 | A1 | 5/2025 |
| WO | WO 2025/122626 | A1 | 6/2025 |
| WO | WO 2025/129148 | A1 | 6/2025 |
| WO | WO 2025/141545 | A1 | 7/2025 |
| WO | WO 2025/163636 | A1 | 8/2025 |

OTHER PUBLICATIONS

Olympus Corporation, "Ultrasonic Transducers", 2010 (Year: 2010).

Xu et al., "Protoporphyrin IX Induces a Necrotic Cell Death in Human TH P-1 Macrophages through Activation of Reactive Oxygen" Species/c-Jun N-Terminal Protein Kinase, 2014, Cellular Physiology and Biochemistry (Year: 2014).

Fisher et al., "ALA-Pp IX mediated photodynamic therapy of malignant gliomas augmented by hypothermia," PLoS One Jul. 31, 2017 ;12(7):e0181654. PMID: 28759636. (Year: 2017).

Galkin, "The Use of Transcranial Focused Ultrasound in CNS Diseases", Jan. 2016, Problems of Neurosurgery, pp. 1-108 (Year: 2016).

Hynynen et al. "Pre-clinical testing of a phased array ultrasound system for MRI-guided noninvasive surgery of the brain-A primate study", Apr. 7, 2006, European Journal of Radiology, pp. 149-156.

(56) References Cited

OTHER PUBLICATIONS

J. Chen, S. LeBlang, A. Hananel, R. Aginsky, J. Perez, M. Gofeld, Y. Shir & J. F. Aubry (2020) An incoherent HIFU transducer for treatment of the medial branch nerve: Numerical study and in vivo validation, International Journal of Hyperthermia, 37: 1, 1219-1228, DOI: 10.1080/02656736.2020.1828628 (Year: 2020).
Jain et al., "Ultrasound-based triggered drug delivery to tumors", Drug Delivery and Translational Search, Springer, Germany, vol. 8, No. 1, Dec. 4, 2017.
Kinoshita et al., Mechanism of Porphyrin-Induced Sonodynamic Effect: Possible Role of Hyperthermia, Radiation Research 165, pp. 229-306, 2006.
Li et al., "Cytotoxic Effect of Protoporphyrin IX to Human Leukemia U937 Cells under Ultrasonic Irradiation", Apr. 15, 2014, pp. 1186-1196 (Year: 2014).
McDannold et al., "Transcranial Magnetic Resonance Imaging-Guided Focused Ultrasound Surgery of Brain Tumors: Initial Findings in 3 Patients", Feb. 2010, Neurosurgery, vol. 66 No. 2, pp. 323-332.
Nonaka et al. "Sonodynamic therapy consisting of focused ultrasound and photosensitizer causes a selective antitumor effect in a rat intracranial glioma model", Anticancer Res 29: 943-950, 2009 (Year: 2009).
Ohmura et al., "Sonodynamic therapy with 5-aminolevulinic acid and focused ultrasound for deep-seated intracranial glioma in rat," Anticancer Res. Jul. 2011;31(7):2527-33. PMID: 21873170. (Year: 2011).
Serpe et al., "Sonodynamic antimicrobial chemotherapy: First steps towards a sound approach for microbe inactivation", Journal of Photochemistry and Photobiology B: Biology, vol. 150, Sep. 2015, pp. 44-49 (Year: 2015).
Song et al., "Overview of therapeutic hypothermia," Curr. Treat. Options. Neural. Dec. 2012; 14(6):541-8. PMID: 23007950. (Year: 2012).
Tetard et al., "Experimental use of photodynamic therapy in high grade gliomas: A revie focused on 5-aminolevulinic acid", Photodiagnosis and Photodynamic Therapy, vol. 11, No. 3, Sep. 1, 2014, pp. 319-330.
Umemura et al., "Recent advances in sonodynamic approach to cancer therapy" 1996, Ultrasonics Sonochemistry, pp. S187-S191.
Wang et al., "Rapid and selective cerebral hypothermia achieved using a cooling helmet," J. Neurosurg. 2004; 100(2):272-77. PMI D: 15086235. (Year: 2004).
Wang et al., "Study of cell killing effect on S180 by ultrasound activating protoporphyrin IX", Nov. 7, 2007 Ultrasonics, pp. 135-140.
Wood et al. "A Review of Low-Intensity Ultrasound for Cancer Therapy" Ultrasound in Med. & Biol., vol. 41, No. 4, pp. 905-928, 2015.
Yumita et al. "Sonodynamically induced antitumor effect of Photofrin II on colon 26 carcinoma." J Cancer Res Clin Oneal 126: 601-606, 2000 (Year: 2000).
International Search Report and Written Opinion for International PCT Application No. PCT/US2021/071101, dated Feb. 23, 2022 (7WO).
C. Adams et al., "Implementation of a Skull-Conformal Phased Array for Transcranial Focused Ultrasound Therapy," (in eng), IEEE Trans Biomed Eng, vol. 68, No. 11 , pp. 3457-3468, Nov. 2021, doi: 10.1109/tbme.2021 .3077802.
Chen et al., "Combination of sonodynamic with temozolomide inhibits C6 glioma migration and promotes mitrochondrial pathway apoptosis via suppressing NHE-1 expression", Ultrasonics Sonochemistry, Butterworth-Heinmann, GB, vol. 39, May 17, 2017 (May 17, 2017), pp. 654-661.
Hand et al., "A random phased array device for delivery of high intensity focused ultrasound", Physics in Medicine and Biology, 54(19), pp. 5675-5693, 2009.
Kast R, Salacz M. DIPG-30. A New Treatment Opportunity For DIPG: 5-ALA and Sonodynamic Augmented meV Irradiation, The Asai Protocol. Neuro Oncol. Jun. 2018;20(Suppl 2):i55. doi: 10.1093/neuonc/noy059.123. Epub Jun. 22, 2018. PMCID: PMC6012850.
Wu, SK., Santos, M.A., Marcus, S.L. et al. MR-guided Focused Ultrasound Facilitates Sonodynamic Therapy with 5-Aminolevulinic Acid in a Rat Glioma Model. Sci Rep 9, 10465 (2019). https://doi.org/10.1038/s41598-019-46832-2.

* cited by examiner

1240

1242

Generate a first signal to drive a first ultrasonic transducer element to generate a first acoustic ensonification drive pattern having a first phase, a first frequency, and a first amplitude

1244

Generate a second signal to drive a second ultrasonic transducer element to generate a second acoustic ensonification drive pattern having a second phase, a second frequency, and a second amplitude

1246

At least one of the relative phase difference, frequency, and amplitude of the first and second signals is selected to generate a third incoherent acoustic ensonification drive pattern to activate a sonosensitizer located in a patient tissue

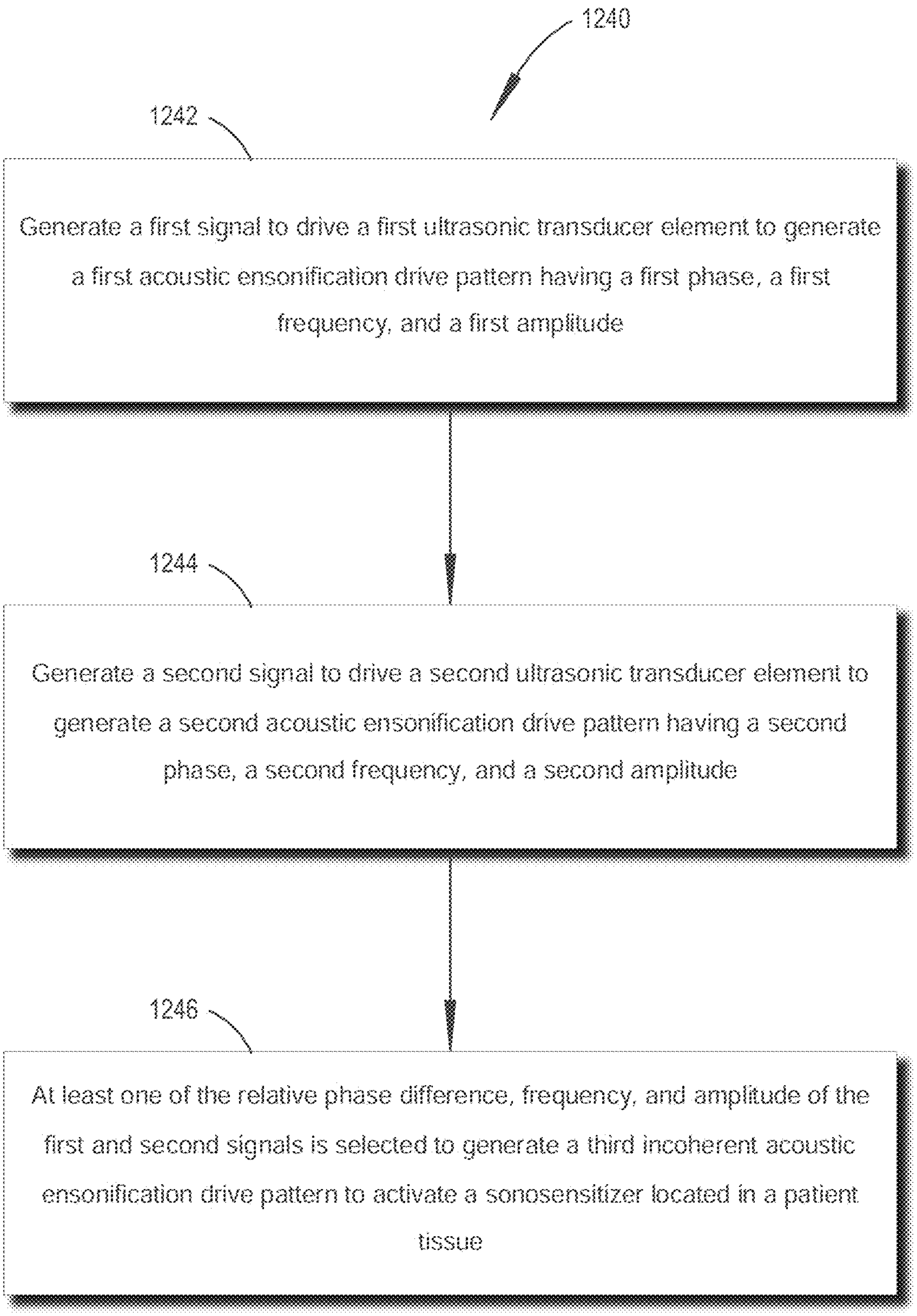

FIG. 28

End on View

End on View

1630

1632 — Initiate Sonodynamic Therapy

1634 — Introduce sonosensitizer to a targeted cell and/or tissue

1636 — Activate ROS in sonosensitizer to destroy targeted cell and/or tissue

1638 — Initiate immuotherapy to imbue cellular surfaces with resistance to recurrence

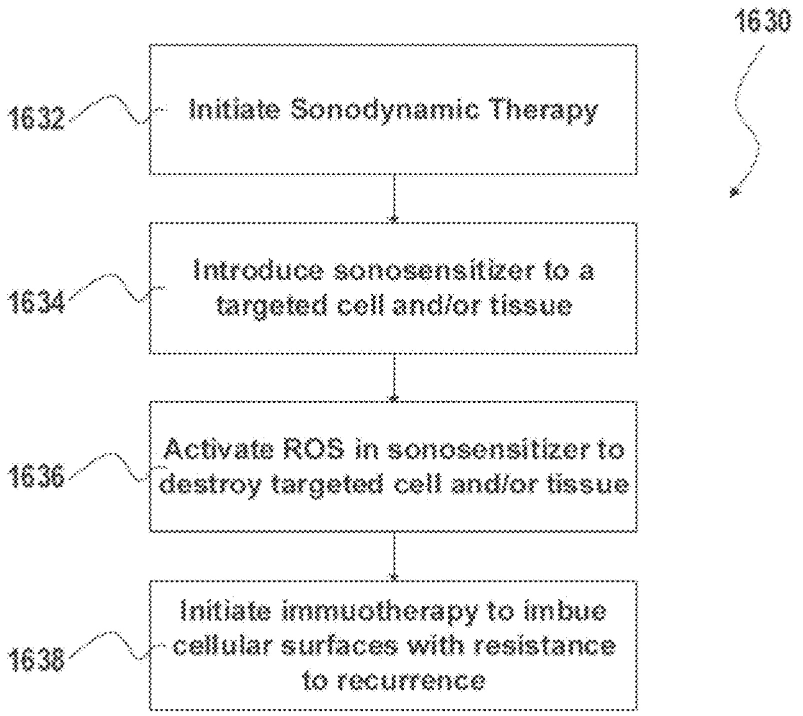

FIG. 54

Therapeutic Sonosensitizers to Enhance the Efficacy of a Sonodynamic Therapy

1640

1642 Overall Sensetizer

1644 Type-Specific

1646 Location-Specific

1648 Wavelength-Specific

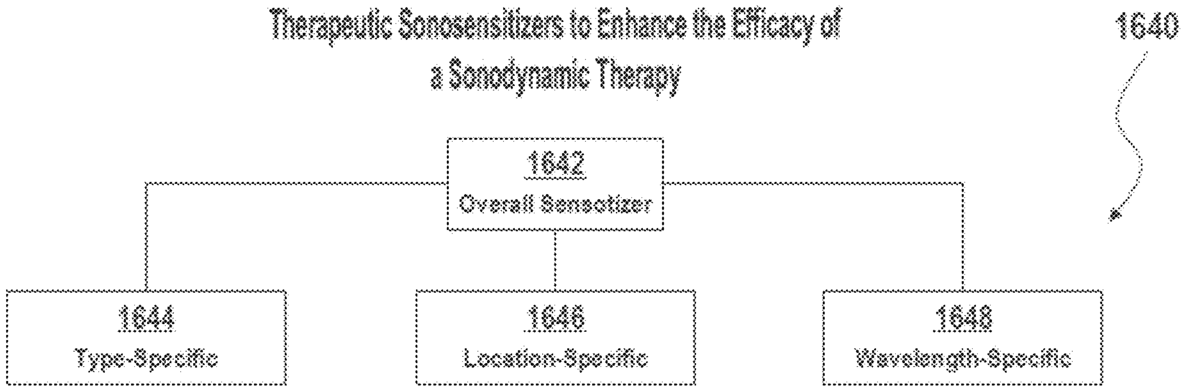

FIG. 55

INCOHERENT FIELD SONODYNAMIC THERAPY FOR TREATING CANCER

INCORPORATION BY REFERENCE TO ANY PRIORITY APPLICATIONS

This application is a continuation of U.S. patent application Ser. No. 18/215,497 filed Jun. 28, 2023 and entitled Incoherent Field Sonodynamic Therapy For Treating Cancer, which is a continuation of U.S. patent application Ser. No. 18/040,610 filed Feb. 3, 2023 and entitled Blood Brain Barrier Penetration To Treat Glioblastoma, which is a U.S. national phase application of International Application No. PCT/US2021/071101 filed Aug. 4, 2021 and entitled Ultrasound Arrays For Enhanced Sonodynamic Therapy For Treating Cancer, which claims priority from U.S. Provisional Patent Application 63/062,879 filed Aug. 7, 2020 and entitled Ensonification Drive Patterns For Sonodynamic Therapy; U.S. Provisional Patent Application 63/062,895 filed Aug. 7, 2020 and entitled Sonodynamic Therapy Methods and Systems For Treating Cancer; U.S. Provisional Patent Application 63/062,915 filed Aug. 7, 2020 and entitled Sonodynamic Therapy Methods and Systems For Treating Cancer; U.S. Provisional Patent Application filed 63/062,926 Aug. 7, 2020 and entitled Sonodynamic Therapy System for Treating Brain Cancer; and U.S. Provisional Patent Application filed 63/062,937 Aug. 7, 2020 and entitled Enhanced Sonodynamic Therapy, each of which is hereby incorporated by reference in its entirety, herein.

BACKGROUND

Field of the Invention

This document relates to methods and apparatuses for generating ensonification drive patterns using ultrasound transducer arrays for initiating and enhancing treatment of cancer with sonodynamic therapy.

Description of the Related Art

Sonodynamic therapy is a proposed form of cancer treatment that uses ultrasound energy to activate a drug, prodrug, and/or sonosensitizer that selectively accumulates in cancer cells. In one embodiment, a sonosensitizing agent (e.g., drug, prodrug, sonosensitizer) preferentially accumulates in the cells of the lesions. In one embodiment, the sonosensitizing agent increases a quantity, accumulation, or concentration of a sonosensitizer in the cancer cells. Sonosensitizers initiate a cytotoxic response in target tissues when exposed to ultrasonic energy. Upon activation by the ultrasonic energy, sonodynamic therapy drugs or "sonosensitizers" produce reactive oxygen species (ROS) that generate the cytotoxic effect. They can be used alone or in concert with other sonosensitizers, many of which are approved by the Food and Drug Administration (FDA) for use in neurosurgical diagnostic imaging or treatment of tumors throughout the body.

Many types of ultrasound devices (e.g., transducer arrays) and therapies have been developed over the years. However, none of these devices (e.g., arrays) and their respective ensonification patterns have been developed for the specific purpose of activating a sonosensitizer. For example, sonodynamic therapy research to date has largely repurposed ultrasound machines designed for high intensity focused ultrasound (HIFU). These machines coordinate the ensonification pattern to coherently focus energy in a particular region or regions. The fundamental principle is analogous to using a magnifying glass to focus beams of sunlight on a single point to burn a hole in a leaf. With focused ultrasound, an acoustic lens or electronic focusing is used to concentrate multiple intersecting beams of ultrasound on one target deep in the body with extreme precision and accuracy. Where each of the individual beams passes through the tissue, there is no effect. But, at the focal point, the convergence of the multiple beams of focused ultrasound energy results in indiscriminate tissue death in the region of interest through thermal ablation.

SUMMARY

The following summary is provided to facilitate an understanding of some of the innovative features unique to the aspects (e.g., embodiments) disclosed herein, and is not intended to be a full description. A full appreciation of the various aspects can be gained by taking the entire specification, claims, and abstract as a whole.

As described herein, in several embodiments, tumors are treated using sonosensitizers and ultrasound, wherein the ultrasound activates the sonosensitizer with cavitational, thermal energy to produce reactive oxygen species that interact with other molecules to intentionally damage cancer cells by via oxidation and associated thermal, chemical, and/or luminescent phenomena for enhancing a cytotoxic effect, stressing and/or inhibiting repair mechanisms of cancer cells, such as by affecting cancer cell production of Heme, removing iron ions, and/or inhibiting the action of ferrochelatase. Advantageously, in one embodiment, a sonodynamic therapy system delivers a signal that is attenuated and enhanced to reduce the amount of energy needed to destroy cancer cells, therapy limiting damage to surrounding healthy cells. In various embodiments, the sonodynamic therapy system generates electric drive signals to form modulated, incoherent acoustic wave parameters at relatively low energy intensity and frequency. In one embodiment, the ultrasound energy is not focused, thus simplifying the efficient treatment of larger areas of target tissue. In one embodiment, complementary treatment further augments the effectiveness of the sonodynamic cancer treatment. Low intensity, dispersed, non-focused sonodynamic therapy that is delivered through a comfortable, flexible patient interface that conforms to the patient's body allows for targeted treatment of undesired tissue while preserving healthy tissue.

In one embodiment, a target tissue for treatment is treated at a single site. In various embodiments, a target tissue is treated at one or more sites, such as at 1, 2, 3, 4, 5, 10, 15, 20, 25, 30, 50, 100, 200, 500, 1000 or more sites, in ranges of 1-1000, 1-500, 1-100, 1-50, 1-25, 1-10, and 1-5 sites (with any values and ranges therein). In one embodiment, sequential sonodynamic treatments affect a first portion of a target tissue, a second portions of the target tissue, and any subsequent portions of the target tissue. In one embodiment, a target tissue is partially treated or extracted, and then subsequent treatment(s) treat the remaining target tissue at one or more sites. In one embodiment, a target tissue is partially treated or extracted at a core or central portion, and then subsequent treatment(s) treat the remaining target tissue at one or more sites along the periphery of the target tissue. In one embodiment, a portion of a target tissue is treated, with the target tissue treated portion being 1%, 5%, 10%, 15%, 20%, 25%, 30%, 40%, 50%, 60%, 70%, 75%, 80%, 85%, 90%, 95%, 96%, 97%, 98%, 99%, 100%, and any values and ranges therein (e.g., 1-100%, 1-50%, 1-75%, 1-25%, 1-10%, 10-20%, 20-30%, 30-40%, 40-50%, 50-60%, 60-70%, 70-80%, 80-90%, 80-100%, 90-100%, 90-95%, 90-96%, 90-97%, 90-98%, 90-99%, 25-50%, 50-75%, 25-75%, 25-100%, 50-100%, 75-100%, etc.).

In one embodiment a targeting template is placed on the patient to facilitate alignment of the transducer to the various treatment sites. In various embodiments, the targeting template is a wearable elastic template with markers to facilitate treatment, such as by demarking a grid, positions based on anatomy, or marking of the skin with indicators. In one embodiment, the targeting template is a cap. In one embodiment, the targeting template is a band configured to wrap around a head, neck, chest, torso, back, waist, leg, buttock, genital area or other body part. In one embodiment, the targeting template is drawn on the body (e.g., ink, wax, make up, pencil, charcoal, tattoo (e.g., indelible and/or permanent), sticker, tab, or other marking). In one embodiment, the targeting template includes measurement gradients that allow the user to customize treatment locations to patient specific anatomical size. In some embodiments, the targeting template remains in place during ultrasound treatment. In some embodiments, the targeting template is made to be removable prior to ultrasound treatment.

In addition to treating brain cancer, cancerous tissue in the lung, breast, colorectal region, prostate, bladder, and pancreas may be treated using several embodiments described herein using for example, one or more sonosensitizers along with the ultrasound parameters described herein. Ovarian cancer is treated in some embodiments. Tumors that are difficult to access including those surrounded by bony structures are treated in various embodiments, including but not limited to brain or spinal tumors. Treatment of undesired tissue in joints and other orthopedic applications are also provided herein. In some embodiments, sonodynamic therapy is used to improve efficiency of chemotherapeutic molecules, sonoporation, and/or gene delivery.

In several embodiments, a system for sonodynamic therapy includes at least one ultrasound transducer array housed with a patient interface to acoustically couple the transducer to a patient. A controller coupled to the transducer is configured to generate an electrical drive signal from a set of modulated acoustic wave parameters, calibrate and/or modulate the drive signal for each element in an ultrasonic array, drive the transducer at a frequency to produce a modulated acoustic wave to produce an acoustic intensity sufficient to activate a sonosensitizer in a treatment region, and/or work with a complementary therapeutic system. Several embodiments of ensonification drive patterns using incoherent acoustic fields do not require beam focusing, and thus reduce the need for accuracy and expense with small area focused ultrasound technology and/or high resolution imaging or diagnostics. Thus, in some embodiments, one or more sonosensitizers is administered to a patient without imaging the location of the sonosensitizer(s) or its products, by-products, and/or metabolites (such as for tumor location purposes). Low intensity, dispersed, non-focused sonodynamic therapy that is delivered, according to one embodiment, through a comfortable interface such as a flexible patient interface that conforms to the patient's body allows for lower dosage over more time. A patient interface may include alignment features and anatomical landmarks to simplify cancer treatment in a hospital or office setting.

In various embodiments, sonodynamic therapy with an ultrasound array delivering a temporal-average intensity output below 8, 10, 15, 20 W/cm$^2$ (e.g., 0.1-8 W/cm$^2$, 0.1-4 W/cm$^2$, 0.5-5 W/cm$^2$ etc., and values and ranges therein) to cancer tissue can be used to induce and activate sonosensitizer at relative deep depths within a patient's body with or without cavitation and/or thermal effects and/or sonoluminescence to produce reactive oxygen species, intracellular singlet oxygen, and/or free radicals in a cascade of events that activate the sonosensitizer and in turn damage the cancer cells. In various embodiments, sonodynamic therapy can be used with or without other therapies, such as photodynamic therapy. In some embodiments, ultrasound is delivered at a temporal-average intensity output below 8, 10, 15, 20 W/cm$^2$ (e.g., 0.1-8 W/cm$^2$, 0.1-4 W/cm$^2$, 0.5-5 W/cm$^2$ etc. and values and ranges therein) to target tissue with cavitation and sonoluminescence to damage the target tissue (e.g., cancer cells).

Several embodiments described herein are used synergistically with other cancer therapies, including for example, radiation, chemotherapy and cell therapy. In one embodiment, the combination of ultrasound and a sonosensitizer as described herein reduces or eliminates the need for one or more additional complementary treatments. For example, lower doses or fewer additional treatments of chemotherapy, radiation, cell therapy etc. may be needed when cancerous tissue is treated by the combination of ultrasound and a sonosensitizer as described herein, thus enhancing patient care and reducing side effects.

Several embodiments described herein administer the ensonification patterns in a manner that appropriately optimizes sonosensitizer activation and establish and/or deliver array technologies that can provide the appropriate accompanying broad sonosensitizer activation into a therapy. Several embodiments treat types of cancers that are difficult to surgically remove, as well as types that suffer from high reoccurrence. For example, glioblastoma (GBM), a Grade IV (i.e., highly aggressive) diffuse astrocytic glioma, is the most frequent and lethal type of brain cancer. Despite aggressive multimodal treatment at the time of diagnosis, the median overall survival for glioblastoma is approximately 1 year, and 5-year survival rates are only 10%. The pattern of recurrence in glioblastoma highlights the limitations of current treatments in targeting and removing all cancer cells. Cancers such as glioblastoma have no clear margins and therefore surgical removal of the cancer cells is almost impossible, as finger-like tentacles undetectably extend into surrounding healthy tissue. In several embodiments, the compositions, devices and systems described herein are used to treat glioblastoma, as well as other tumors (both brain tumors and outside the brain). In various embodiments, cancers and tumors for sonodynamic treatment including, for example, hepatic cancer cells, murine sarcoma, leukemia, myeloid leukemia, cholangiocarcinoma, melanoma, squamous cells, osteosarcoma, gliosarcoma, astrocytoma, hepatocellular carcinoma, prostate, nephroblastoma, adenocarcinoma, and other cancers. Gliomas, glial cells and/or astrocytomas are treated (e.g., selectively or preferentially) in several embodiments.

In several embodiments, one or more of the following features is provided: ensonification patterns that optimize activation of the sonosensitizer; ensonification patterns that adequately saturate a large treatment volume to ensure extraneous cancer cells in surrounding tissue are also treated; ensonification patterns and transducer array approaches that reduce or avoid hazards of coordinating and steering coherently focused energy in a manner that requires MRI or other imaging guidance, diagnostics, and/or monitoring, as these systems are untenable for delivering office-based therapies such as sonodynamic therapy, according to one embodiment. In some embodiments, however, MRI or other imaging guidance, diagnostics, and/or monitoring are used in conjunction with the devices described herein. In several embodiments, sonodynamic therapy is performed as a non-invasive office-based treatment (e.g., oncology clinic) for cancer. In one embodiment, a sonodynamic therapy treatment plan includes multiple repeat treatments of sonodynamic therapy over a time span of weeks (very similar to chemotherapy). The sonodynamic therapy benefits over other cancer therapies would include one or more of the following: minimal to no side effects, the sonosensitizer class of drugs are affordable naturally occurring compounds, efficient outpatient treatment regimen, and complimentary to other treatment options. In one embodiment, one or more sonosensitizers (such as 5-aminolevulinic acid (5-ALA) is administered (e.g., orally) to a patient without imaging the location of the sonosensitizer(s) or its metabolites and/or products (such as protoporphyrin IX (PpIX)) for, e.g., tumor location purposes. In one embodiment, one or more sonosensitizers (such as 5-ALA) is administered (e.g., orally) to a patient without using the sonosensitizer(s) or its metabolites and/or products (such as PpIX) for diagnostic purposes (e.g., the administration of 5-ALA is therapeutic only).

In one embodiment, the present disclosure provides an ultrasound transducer for activating a sonosensitizer in conjunction with providing sonodynamic therapy. The ultrasound transducer comprises a plurality of ultrasonic transducer elements arranged in an array configured to generate an incoherent acoustic pressure field with an energy profile for activating a sonosensitizer located within tissue of a patient.

In one embodiment, the present disclosure provides at least one ultrasound transducer for activating a sonosensitizer in conjunction with providing sonodynamic therapy. In one embodiment, the ultrasound transducer(s) comprises a plurality of ultrasonic transducer elements (e.g., 64, 128, 256, 512 elements, etc.) arranged in an array configured to generate an incoherent acoustic pressure field (e.g., in various embodiments with an incoherent acoustic pressure filed greater than 5 $mm^3$, 10 $mm^3$, 20 $mm^3$, 50 $mm^3$, 100 $mm^3$, 200 $mm^3$, 500 $mm^3$, 1 $cm^3$, 5 $cm^3$, 10 $cm^3$, 25 $cm^3$, 50 $cm^3$, 75 $cm^3$, 100 $cm^3$, 200 $cm^3$, 500 $cm^3$ or larger) with an energy profile for activating a sonosensitizer located within tissue of a patient, wherein the incoherent acoustic pressure field comprises one or more of: a modulated phase across the plurality of ultrasonic transducer elements, a modulated frequency across the plurality of ultrasonic transducer elements, and a modulated amplitude across the plurality of ultrasonic transducer elements, wherein each piezoelectric transducer in the array of piezoelectric transducers comprises a planar emitting surface configured to emit a planar acoustic wave. In one embodiment, the modulated phase comprises a randomized phase difference. Optionally, a modulated frequency modulates the frequency in a single burst and/or between bursts. Optionally, a modulated amplitude modulates the amplitude in a single burst and/or between bursts. A cooling system as described herein may be optionally included. The sonosensitizer is optionally 5-aminolevulinic acid (5-ALA) and/or protoporphyrin IX (PpIX) or other related compounds. The energy profile, in one embodiment, is driven at ultrasonic frequencies in a range of 250 kHz to 3 MHZ (and values and ranges therein). In one embodiment, the incoherent acoustic pressure field comprises a temporal-average intensity output between 1 and 20 $W/cm^2$ (and values and ranges therein). Focused ultrasound characterized by High Intensity Focused Ultrasound (HIFU), acoustic wave focusing to a region of 50 $mm^3$, 20 $mm^3$, 10 $mm^3$, 5 $mm^3$, or 2 $mm^3$ or smaller, focusing to a point in tissue (such as focused to a point 50 $mm^3$, 20 $mm^3$, 10 $mm^3$, 5 $mm^3$, or 2 $mm^3$ or smaller in a tissue, tumor, bone, etc.) is not used in several embodiments.

In one embodiment, the ultrasound transducer includes a cooling system configured to remove excess heat from the patient, wherein the cooling system comprises a conduit or cavity (e.g., a flexible cavity for circulation of a cooling fluid).

In several embodiments, an ultrasound transducer for activating a sonosensitizer in conjunction with providing sonodynamic therapy includes a plurality of ultrasonic transducer elements arranged in an array configured to generate an incoherent acoustic pressure field with an energy profile for activating a sonosensitizer located within tissue of a patient.

In one embodiment, the present disclosure provides one or more ultrasound transducers for activating a sonosensitizer (such as 5-aminolevulinic acid (5-ALA) and/or protoporphyrin IX (PpIX) or metabolites of either, which can be administered orally or via other means) in conjunction with providing sonodynamic therapy In which the ultrasound transducer(s) comprises a plurality of ultrasonic transducer elements (e.g., 64, 128, 256, 512 elements, and values and ranges therein) arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements, wherein each piezoelectric transducer in the array of piezoelectric transducers comprises a planar emitting surface configured to emit a planar acoustic wave. Optionally, the ultrasound transducer includes a cooling system configured to remove excess heat from the patient, wherein the cooling system comprises a flexible cavity for circulation of a cooling fluid. The energy profile may be driven at ultrasonic frequencies in a range of 250 kHz to 3 MHz (and values and ranges therein). The incoherent acoustic pressure field optionally comprises a temporal-average intensity output between 1 and 20 $W/cm^2$. Each of the ultrasonic transducer elements may comprise an aperture sized and configured to contour with and/or are close fitting to a body of the patient, wherein optionally the size of the aperture is selected to be the same size or larger than a lesion being treated such that an embodiment ratio of the aperture to the lesion size enables initiation of a broad incoherent acoustic pressure field to treat the lesion and surrounding tissue. The ultrasonic transducer elements may be arranged in one of the group consisting of: a spiral configuration, a rectangular array, a concentric array, a randomly arranged and irregularly placed non-uniform distribution. The ultrasound transducer may define a concentric circular or rounded array geometry. The plurality of ultrasonic transducer elements may be arranged in an array disposed on a helmet configured to couple to the head of the patient. A diameter of the array may be in a range of 100 mm-200 mm (and values and ranges therein) and/or a diameter of the ultrasonic transducer element may be in a range of 2 mm to 10 mm (and values and ranges therein). The ultrasound may be optionally used for therapeutic purposes only (and not for imaging or diagnostic purposes). Focused ultrasound characterized by High Intensity Focused Ultrasound (HIFU), acoustic wave focusing to a region of 50 $mm^3$, 20 $mm^3$, 10 $mm^3$, 5 $mm^3$, or 2 $mm^3$ or smaller, focusing to a point in tissue (such as focused to a point 50 $mm^3$, 20 $mm^3$, 10 $mm^3$, 5 $mm^3$, or 2 $mm^3$ or smaller in a tissue, tumor, bone, etc.) is not used in several embodiments. The ultrasound may be used for such therapeutic purposes (and not for imaging or diagnostic purposes).

In one embodiment, each of the ultrasonic transducer elements comprises an aperture sized and configured to contour with and/or are close fitting to a body of the patient. In one embodiment, wherein the size of the aperture is selected to be the same size or larger than a lesion being treated such that an embodiment ratio of the aperture to the lesion size enables initiation of a broad incoherent acoustic pressure field to treat the lesion and surrounding tissue.

In one embodiment, the ultrasonic transducer elements are arranged in one of the group consisting of: a spiral configuration, a rectangular array, a concentric array, a randomly arranged and irregularly placed non-uniform distribution. In one embodiment, the ultrasonic transducer elements are arranged in a spiral configuration. In one embodiment, the ultrasonic transducer elements are arranged in an Archimedean spiral.

In one embodiment, the ultrasonic transducer elements are arranged in a sunflower spiral. In one embodiment, additional ultrasonic transducer elements are located on certain rings of the sunflower spiral. In one embodiment, the ultrasound transducer comprises pairs of ultrasonic transducer elements. In one embodiment, the ultrasound transducer comprises 128 active ultrasonic transducer elements disposed on a 128 element sunflower spiral grid. In one embodiment, the ultrasound transducer array comprises 256 elements. In one embodiment, the ultrasound transducer comprises a sparse spiral array of 128 active ultrasonic transducer elements disposed on a 256 element sunflower spiral grid skipping every 2 elements. In one embodiment, the ultrasound transducer comprises 128 active ultrasonic transducer elements disposed on a 384 element sunflower spiral grid skipping every 3 elements. In one embodiment, the ultrasound transducer comprises 128 active ultrasonic transducer elements disposed on a 512 element sunflower spiral grid skipping every 4 elements. In one embodiment, the ultrasound transducer comprises 128 active ultrasonic transducer elements disposed on 640 element sunflower spiral grid skipping every 5 elements to yield 128 actual ultrasonic transducer elements. In one embodiment, the ultrasound transducer comprises 128 active ultrasonic transducer elements disposed on a 768 element sunflower spiral grid skipping every 6 elements. In one embodiment, the ultrasound transducer comprises 128 active ultrasonic transducer elements disposed on a 896 element sunflower spiral grid skipping every 7 elements. In one embodiment, the ultrasonic transducer elements are arranged according to a predetermined element packing technique. In one embodiment, the ultrasonic transducer elements are randomly arranged and irregularly placed in a non-uniform distribution.

In one embodiment, the ultrasonic transducer elements define a circular geometry. In one embodiment, the ultrasound transducer defines a concentric circular array geometry. In one embodiment, the ultrasound transducer defines a linear array geometry. In one embodiment, the ultrasound transducer defines a rectangular array geometry. In one embodiment, the rectangle defines a square.

In one embodiment, the ultrasound transducer comprises a plurality of ultrasonic lens elements disposed over the plurality of ultrasonic transducer elements to geometrically focus each of the plurality of ultrasonic transducer elements. In one embodiment, the at least one of the plurality of ultrasonic lenses is repositionable. In one embodiment, at least one of the plurality of ultrasonic lenses provides a different degree of focusing. In one embodiment, at least one of the plurality of ultrasonic lenses changes at least one of a direction or a vergence of the ultrasound transducer, or a combination thereof. In one embodiment, at least one of the plurality of ultrasonic lenses is rotatable with three rotational degrees of freedom.

In one embodiment, the plurality of ultrasonic transducer elements is arranged in an array disposed on a helmet configured to couple to the head (e.g., at a scalp, forehead, base of skull, face, cheek, jaw, neck) of the patient. In one embodiment, the plurality of ultrasonic transducer elements is arranged in an array disposed on a dome helmet configured to couple to the head of the patient. In one embodiment, the plurality of ultrasonic transducer elements is arranged in an array disposed individually on the head of the patient. In one embodiment, the plurality of ultrasonic transducer elements is arranged in a flat array. In one embodiment, the plurality of ultrasonic transducer elements is arranged in a hemispherical array. In one embodiment, the plurality of ultrasonic transducer elements is arranged in a curved linear array.

In one embodiment, the plurality of ultrasonic transducer elements is arranged in a 2D matrix array. In one embodiment, a diameter of the array is in a range of 100 mm-200 mm, 100 to 150 mm, and/or 120 to 165 mm. In one embodiment, a diameter of the ultrasonic transducer element is in a range of 0.5 mm to 20 mm, and/or 2 mm to 10 mm. In one embodiment, the ultrasound transducer is configured to activate a sonosensitizer without focusing ultrasound. In one embodiment, the ultrasound transducer is configured for treating cancerous tissue in a brain, spine, mouth, in the lung, breast, colorectal region, prostate or pancreas. In one embodiment, the ultrasound transducer is configured for sonodynamic treatment with at least one of the group consisting of: radiation, chemotherapy and cell therapy. In one embodiment, the sonosensitizer is configured for oral administration to the patient. In one embodiment, the sonosensitizer is selected from the group consisting of: 5-aminolevulinic acid (5-ALA), protoporphyrin IX (PpIX), hematoporphyrin, Rose Bengal, curcumin, titanium nanoparticles, chlorine e6, pheobromide-a, ATX-S10 (4-formyloximethylidene-3-hydroxy-2-vinyl-deuterio-porphynyl(IX)-6,7-diaspartic acid), photofrin, DCPH-P-Na(I), NPe6 (mono-I-aspartyl chlorin e6), polyhydroxy fullerenes, hypocrellin-B, ZnPcS2P2, methylene blue, and sinoporphyrin sodium.

In one embodiment, the ultrasound transducer is minimally invasive. In one embodiment, the ultrasound transducer is configured for insertion into a natural orifice. In one embodiment, a plurality of ultrasonic transducer elements is acoustically coupled to the patient via a fluid filled cavity. In one embodiment, the ultrasound transducer includes a patient interface without a membrane.

In various embodiments, a system for applying sonodynamic therapy to an anatomical structure is disclosed. The system includes an ultrasonic transducer array, wherein each piezoelectric transducer in the array of piezoelectric transducers comprises a planar emitting surface configured to emit a planar acoustic wave, a patient interface to couple the ultrasonic transducer array to a patient, and a controller coupled to the ultrasonic transducer array. The patient interface is configured to acoustically couple to at least two alignment features configured to receive predetermined anatomical landmarks of the anatomical structure. The controller is configured to cause the ultrasonic transducer array to activate a sonosensitizer in a treatment region in the anatomical structure. In one embodiment, the anatomical structure is a patient's head, and wherein the at least two alignment features are configured to receive predetermined anatomical landmarks of the patient's head. In one embodiment, the predetermined anatomical landmarks comprise a zygomatic arch, a mastoid tip, middle arch of eyebrows, or combinations thereof. In one embodiment, the patient interface comprises a receptacle releasably couplable to the ultrasonic transducer array. In one embodiment, the receptacle is movable relative to the patient interface between a plurality of predefined treatment positions. In one embodiment, the patient interface comprises spaced apart receptacles, and wherein the ultrasonic transducer array is selectively releasably couplable to the receptacles to achieve an optimal treatment position for the ultrasonic transducer array.

In various embodiments, a system for applying sonodynamic therapy to an anatomical structure is disclosed. The system includes an ultrasonic transducer array, wherein each piezoelectric transducer in the array of piezoelectric transducers comprises a planar emitting surface configured to emit a planar acoustic wave, a patient interface to acoustically couple the ultrasonic transducer array to a patient, and a controller coupled to the ultrasonic transducer array. The patient interface includes an acoustic coupling membrane configured to conform to the anatomical structure. The controller is configured to cause the ultrasonic transducer array to activate a sonosensitizer in a treatment region in the anatomical structure.

In one embodiment, the acoustic coupling membrane is positioned over an exit plane of the ultrasonic transducer array. In one embodiment, the acoustic coupling membrane is an acoustically-neutral elastic membrane. In one embodiment, the acoustic coupling membrane defines a portion of a fluid filled cavity. In one embodiment, the ultrasonic transducer array projects from the patient interface toward the cavity. In one embodiment, the cavity is fillable with a fluid to a predetermined volume. In one embodiment, the fluid is degassed water. In one embodiment, the fluid is circulated through the cavity. In one embodiment, the fluid is chilled to remove residual heat during treatment.

In one embodiment, a system for applying sonodynamic therapy to an anatomical structure is disclosed comprising an ultrasonic transducer array wherein each piezoelectric transducer in the array of piezoelectric transducers comprises a planar emitting surface configured to emit a planar acoustic wave, a patient interface to acoustically couple the ultrasonic transducer array to a patient, and a controller coupled to the ultrasonic transducer array. The patient interface is configured, for example, to acoustically couple to at least two alignment features configured to receive predetermined anatomical landmarks of the anatomical structure. The controller may be configured to cause the ultrasonic transducer array to activate a sonosensitizer in a treatment region in the anatomical structure. The anatomical structure may be a patient's head (such as skull) or other body part, and wherein the at least two alignment features may be configured to receive predetermined anatomical landmarks of the patient's head. Optionally, the predetermined anatomical landmarks comprise a zygomatic arch, a mastoid tip, middle arch of eyebrows, or combinations thereof. The patient interface may comprise a receptacle releasably couplable to the ultrasonic transducer array, wherein the receptacle may movable relative to the patient interface between a plurality of predefined treatment positions. The patient interface may also comprise spaced apart receptacles, wherein the ultrasonic transducer array is selectively releasably couplable to the receptacles to achieve an optimal treatment position for the ultrasonic transducer array. The patient interface optionally includes one or more acoustic coupling membranes configured to conform to the anatomical structure. For example, the acoustic coupling membrane is positioned over an exit plane of the ultrasonic transducer array and may be an acoustically neutral elastic membrane. In one embodiment, each piezoelectric element has its own coupling membrane. The acoustic coupling membrane may define a conduit or cavity with the patient interface with the ultrasonic transducer array projecting from the patient interface toward the conduit or cavity. The acoustic coupling membrane may be open and seal against another patient interface or a patient's skin to form a conduit or cavity with the ultrasonic transducer array projecting from the patient interface toward the conduit or cavity. The cavity can be fillable with a fluid (e.g., to a predetermined volume). The fluid may include degassed water or other fluid, which is circulated through the conduit or cavity and is chilled to remove residual heat during treatment. Other types of heat sinks or heat shunts may also be provided. The ultrasound in several embodiments, when in use, activates a sonosensitizer (such as 5-aminolevulinic acid (5-ALA) and/or protoporphyrin IX (PpIX) or metabolites of either, which can be administered orally or via other means) that kills or otherwise impairs undesired tissue, including but not limiting to tumor cells which may be cancerous. The ultrasound may be used for such therapeutic purposes (and not for imaging or diagnostic purposes). Focused ultrasound characterized by High Intensity Focused Ultrasound (HIFU), acoustic wave focusing to a region of 2 $mm^3$ or smaller, focusing to a point in tissue (such as focused to a point 2 $mm^3$ or smaller in a tissue, tumor, bone, etc.) is not used in several embodiments.

In various embodiments, an ultrasound transducer system for applying sonodynamic therapy to an anatomical structure is disclosed. The system includes an ultrasonic transducer array, a patient interface to acoustically couple the ultrasonic transducer array to a patient, and a controller coupled to the ultrasonic transducer array. The patient interface includes an array holder couplable to the ultrasonic transducer array. The array holder is adjustable to move the ultrasonic transducer array relative to the patient interface between a plurality of treatment positions. The controller is configured to cause the ultrasonic transducer array to activate a sonosensitizer in a treatment region in the anatomical structure.

In one embodiment, the controller is configured to receive imaging data and select one of the plurality of treatment positions based on the imaging data. In one embodiment, the ultrasound transducer system comprises a user interface, and wherein the controller is configured to recommend a selected one of the plurality of treatment positions via the user interface. In one embodiment, the patient interface comprises an acoustic coupling membrane. In one embodiment, the acoustic coupling membrane is positioned over an exit plane of the ultrasonic transducer array. In one embodiment, the acoustic coupling membrane is an acoustically neutral elastic membrane. In one embodiment, the acoustic coupling membrane forms a seal with the patient. In one embodiment, the acoustic coupling membrane defines a cavity with the patient interface. In one embodiment, the ultrasonic transducer array projects from the patient interface toward the cavity. In one embodiment, the cavity is fillable with a fluid to a predetermined volume. In one embodiment, the fluid is degassed water. In one embodiment, a volume of the fluid in the cavity is selectively adjustable in concert with at least one motion of the array holder to control a location of the ultrasonic transducer array and a distance of the ultrasonic transducer array with respect to the anatomical structure.

In various embodiments, a system for applying sonodynamic therapy to an anatomical structure is disclosed. The system includes an ultrasonic transducer array, a patient interface to acoustically couple the ultrasonic transducer array to a patient, and a controller coupled to the ultrasonic transducer array. The controller is configured to cause the ultrasonic transducer array to activate a sonosensitizer in a treatment region in the anatomical structure per ultrasound ensonification parameters established by calibrating the ultrasonic transducer array to patient specific attributes. In one embodiment, a patient specific attribute is anatomical. In one embodiment, a patient specific attribute is non-anatomical, such as certain mechanical, acoustic, thermal and/or properties.

In various embodiments, the controller is configured to: receive image data of the anatomical structure; and perform the calibrating of the ultrasonic transducer array based on the image data. In various embodiments, the image data is indicative of thickness measurements of a skull of the patient, and wherein the controller is configured to determine whether the thickness measurements are within a predetermined thickness measurements range. In various embodiments, the system further comprising a user interface, and wherein the controller is configured to issue an alert through the user interface if a determined one or more of the thickness measurements is outside the predetermined thickness measurements range. In various embodiments, the controller is configured to adjust input signals of elements of the ultrasonic transducer array based on the image data. In various embodiments, the controller is configured to adjust input signals of elements of the ultrasonic transducer array based the thickness measurements of skull portions nearest to the elements.

In various embodiments, a system for applying sonodynamic therapy to a brain of a patient is disclosed. The system includes an ultrasonic transducer array including a plurality of elements, a patient interface to acoustically couple the ultrasonic transducer array to the patient, and a controller coupled to the ultrasonic transducer array. The controller is configured to select one of the plurality of elements of the ultrasonic transducer array for a calibration procedure, generate an ultrasound pulse with the one of the plurality of elements, detect reflections of the ultrasound pulse on the plurality of elements of the ultrasonic transducer array, set amplitude and frequency of the one of the plurality of elements based on the reflections to optimize, maximize, and/or modulate an ultrasound transmission rate through a skull of the patient, and select another one of the plurality of elements of the ultrasonic transducer array for the calibration procedure.

In one embodiment, the controller is configured to compute a minimum distance from the one of the plurality of elements to the skull of the patient based on the reflections of the ultrasound pulse. In one embodiment, the minimum distance is a distance from the one of the plurality of elements to a skull portion adjacent the one of the plurality of elements, and wherein the controller is further configured to compute a skull thickness at the skull portion based on the reflections of the ultrasound pulse. In one embodiment, the controller is configured to compare the skull thickness computed by the controller to a corresponding skull thickness ascertained from imaging data of the skull. In one embodiment, the setting of the amplitude and frequency by the controller is based on at least one of the minimum distance and the skull thickness. In one embodiment, a suitable maximum of the ultrasound transmission rate through the skull is ascertained based on a predetermined threshold. In one embodiment, the controller is configured to further set the amplitude and frequency of the one of the plurality of elements based on the reflections to minimize skull heating of the skull of the patient during the sonodynamic therapy. In one embodiment, a suitable minimum of the skull heating is ascertained based on a predetermined threshold. In one embodiment, ultrasound is configured to pass normal to a skull surface through the skull bone wall. In one embodiment, ultrasound is configured to focus in the skull bone wall.

In one embodiment, an ultrasound transducer system for applying sonodynamic therapy to a brain of a patient includes an ultrasonic transducer array comprising a plurality of elements, wherein each piezoelectric transducer in the array of piezoelectric transducers comprises a planar emitting surface configured to emit a planar acoustic wave; a patient interface to acoustically couple the ultrasonic transducer array to the patient; and a controller coupled to the ultrasonic transducer array, wherein the controller is configured to: select at least one of the plurality of elements of the ultrasonic transducer array for a calibration procedure; set at least one of an intensity, an amplitude, and a frequency of the at least one of the plurality of elements based on a digital imaging and communications image of a skull of the patient; and generate an ultrasound pulse with the at least one of the plurality of elements with the at least one of the intensity, the amplitude, and the frequency. The controller may be configured to compute the skull thickness or skull density based on the digital imaging and communications image, in which the setting of the intensity, amplitude and/or frequency by the controller is based on the skull thickness based on the digital imaging and communications image. The controller may be configured to compute a minimum distance from the one of the plurality of elements to the skull of the patient based on the digital imaging and communications image of the skull of the patient. For example, the minimum distance is a distance from the one of the plurality of elements to a skull portion adjacent the one of the plurality of elements, and wherein the controller is further configured to compute a skull thickness at the skull portion based on the digital imaging and communications image. The setting of the intensity by the controller may be based on at least one of the minimum distance and the skull thickness. For example, a suitable maximum of the ultrasound transmission rate through the skull may be ascertained based on a predetermined threshold. At least one of an intensity, an amplitude, and a frequency is optionally set to minimize a heating of the skull of the patient during sonodynamic therapy. In use, according to several such embodiments, the ultrasound transducer activates a sonosensitizer in conjunction with providing sonodynamic therapy includes a plurality of ultrasonic transducer elements arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements; wherein each piezoelectric transducer in the array of piezoelectric transducers comprises a planar emitting surface configured to emit a planar acoustic wave; a patient interface to acoustically couple the ultrasonic transducer array to the patient; and a controller coupled to the ultrasonic transducer array. Optionally, a patient interface with a conduit and/or cavity for housing or circulating fluid to remove residual heat during treatment. Other types of heat sinks or heat shunts may also be provided. For example, a heat radiator may be used to remove residual heat. In another example, a thermoelectric cooling device may be used to remove residual heat. Focused ultrasound characterized by High Intensity Focused Ultrasound (HIFU), acoustic wave focusing to a region of 50 $mm^3$, 20 $mm^3$, 10 $mm^3$, 5 $mm^3$, or 2 $mm^3$ or smaller, focusing to a point in tissue (such as focused to a point 50 $mm^3$, 20 $mm^3$, 10 $mm^3$, 5 $mm^3$, or 2 $mm^3$ or smaller in a tissue, tumor, bone, etc.) is not used in several embodiments. The ultrasound may be used for such therapeutic purposes (and not for imaging or diagnostic purposes). The ultrasound in several embodiments, when in use, activates a sonosensitizer (such as 5-aminolevulinic acid (5-ALA) and/or protoporphyrin IX (PpIX) or metabolites of either) that kills or otherwise impairs undesired tissue, including but not limiting to tumor cells which may be cancerous. The ultrasound may be used for such therapeutic purposes (and not for imaging 5-aminolevulinic acid (5-ALA) and/or protoporphyrin IX (PpIX) or metabolites of either, which can be administered orally or via other means).

The system includes an ultrasonic transducer array including a plurality of elements, a patient interface to acoustically couple the ultrasonic transducer array to the patient, and a controller coupled to the ultrasonic transducer array. The controller is configured to select one of the plurality of elements of the ultrasonic transducer array for a calibration procedure, generate a frequency sweep with the one of the plurality of elements, detect amplitude of energy reflected at each frequency of the frequency sweep, compute an optimal frequency for the one of the plurality of elements, wherein the optimal frequency is one that minimizes the energy reflected, set the one of the plurality of elements to the optimal frequency, and select another one of the plurality of elements of the ultrasonic transducer array for the calibration procedure.

In one embodiment, a suitable minimum of the energy reflected is one that is less than or equal to a predetermined threshold.

In one embodiment, the system includes an ultrasonic transducer array including a plurality of elements, a patient interface to acoustically couple the ultrasonic transducer array to the patient, and a controller coupled to the ultrasonic transducer array. The controller is configured to select one of the plurality of elements of the ultrasonic transducer array for a calibration procedure, generate an interrogation signal with the one of the plurality of elements, detect a reflected signal in response to the interrogation signal, wherein the reflected signal is reflected by a skull of the patient, compute an in-situ variable based on the reflected signal, adjust an ensonification pattern or an array placement of the ultrasonic transducer array with respect to the patient interface, or both, based on the in-situ variable, and select another one of the plurality of elements of the ultrasonic transducer array for the calibration procedure.

In one embodiment, the controller is further configured to compare the in-situ variable computed by the controller to external data. In one embodiment, the controller is configured to further adjust the ensonification pattern or the array placement of the ultrasonic transducer array with respect to the patient interface, or both, based on a result of the comparison.

In various embodiments, a method of enhancing the efficacy of a sonodynamic therapy is disclosed herein. The sonodynamic therapy is configured to treat a cell within an anatomical subject, wherein the cell includes a baseline susceptibility to the sonodynamic therapy, and the method includes: performing, via a complementary therapeutic system, a complementary therapy on the anatomical subject, inducing, via the complementary therapeutic system, a pre-sonodynamic condition within the cell, determining that the pre-sonodynamic condition exceeds a predetermined threshold, wherein the predetermined threshold is associated with an improved susceptibility of the cell to the sonodynamic therapy, administering a sonosensitizing agent to the cell within the anatomical subject, generating, via a sonodynamic therapy system, an acoustic wave using a transducer, and activating, via the acoustic wave, a sonosensitizer within the cell.

In one embodiment, assessing the pre-sonodynamic condition comprises determining that the pre-sonodynamic condition exceeds a predetermined threshold, wherein the predetermined threshold is associated with the improved susceptibility of the cell to the sonodynamic therapy. In one embodiment, the complementary therapy comprises an immunotherapy. In one embodiment, the complementary therapy comprises an anti-inflammatory therapy. In one embodiment, the method includes administering a microbubble, wherein the microbubble is configured to enhance cavitation. In one embodiment, the method includes administering a nanoparticle, wherein the nanoparticle is configured to enhance cavitation.

In one embodiment, assessing the pre-sonodynamic condition comprises determining that the pre-sonodynamic condition exceeds a predetermined threshold, wherein the predetermined threshold is associated with the improved susceptibility of the cell to the sonodynamic therapy. In one embodiment, the complementary therapy comprises an oxygenating therapy configured to provide the cell with supplemental oxygen. In one embodiment, the oxygen is provided to the cell via a respiratory system of a patient. In one embodiment, the oxygen is provided to the cell intravenously into a patient's bloodstream. In one embodiment, the oxygen therapy comprises a microparticle comprising supplemental oxygen, wherein the microparticle is configured to deliver the supplemental oxygen to the cell. In one embodiment, the microparticles are specifically configured to target a specific location of the cell within the anatomical structure. In one embodiment, the oxygenating therapy comprises extracorporeal membrane oxygenation. In one embodiment, the extracorporeal membrane oxygenation comprises: removing a portion of a patient's blood; oxygenating the removed portion of blood with the supplemental oxygen; and introducing the oxygenated portion of blood back into the patient. In one embodiment, the oxygenating therapy comprises injecting the supplemental oxygen directly into a targeted tissue. In one embodiment, the oxygenating therapy comprises hyperbaric oxygen therapy. In one embodiment, the hyperbaric oxygen therapy comprises delivering oxygen to the cell at pressures above atmospheric pressure. In one embodiment, the supplemental oxygenating therapy comprises delivering a drug to enhance the oxygen concentration in the cell. In one embodiment, the drug comprises an antihypoxic drug configured to increase a level of oxygen in the cell. In one embodiment, the supplemental oxygenating therapy comprises reducing a metabolism of the cell, thereby reducing the rate at which oxygen is used by the cell and increasing the oxygen level within the cell. In one embodiment, the pre-sonodynamic condition within the cell comprises an oxygen level within the cell. In one embodiment, the method includes monitoring the pre-sonodynamic condition within the cell using a cerebral oximeter. In one embodiment, the cerebral oximeter comprises near-infrared spectroscopy. In one embodiment, the method includes monitoring the pre-sonodynamic condition within the cell using a magnetic resonance imaging device. In one embodiment, the method includes altering sonodynamic therapy based, at least in part, on the determination that the pre-sonodynamic condition exceeds a predetermined threshold. In one embodiment, the method includes notifying a clinician that the pre-sonodynamic condition exceeds a predetermined threshold. In one embodiment, the acoustic wave is autonomously generated based, at least in part, on the determination that the pre-sonodynamic condition exceeds the predetermined threshold. In one embodiment, the method includes destroying, via the activation of the sonosensitizing agent, the cell. In one embodiment, the method includes destroying, via activation of a sonosensitizer, the cell.

The method includes administering a sonosensitizing agent to the cell within the anatomical subject, generating, via a sonodynamic therapy system, an acoustic wave using a transducer, activating, via the acoustic wave, a sonosensitizer within the cell, destroying, via the activation of the sonosensitizer, the cell within the anatomical structure; and inducing, via the activation of the sonosensitizer, an immunotherapeutic effect within the anatomical structure.

In one embodiment, the immunotherapeutic effect comprises a resistivity to a recurrence of the cell within the anatomical structure. The method includes administering a sonosensitizing agent to the cell within the anatomical subject, generating, via a sonodynamic therapy system, an acoustic wave using a transducer, activating, via the acoustic wave, the sonosensitizer within the cell, and destroying, via the activation of the sonosensitizer, the cell within the anatomical structure. In one embodiment, the destroying the cell initiates a biological signal. In one embodiment, the biological signal is a damage-associated molecular pattern. In one embodiment, destroying the cell activates an immune response.

In one embodiment, the sonosensitizing agent comprises at least one of a type-specific sonosensitizer, a location-specific sonosensitizer, or a wavelength-specific sonosensitizer, or any combination thereof. In one embodiment, the sonosensitizing agent is specifically configured to target a specific type of cell in a specific location of the anatomical subject. In one embodiment, the specific type of cell is at least one of a wound, an ulcer, an abscess, or a tumor, or any combination thereof. In one embodiment, the acoustic wave comprises a specific wavelength, and wherein a sonosensitizer is specifically configured to react to the specific wavelength. In one embodiment, the sonosensitizing agent comprises a nanoparticle sonosensitizer configured to produce a desired cytotoxic effect. In one embodiment, the desired cytotoxic effect comprises at least one of a reduce toxicity, an increased biodegradability, or an improved ability to target the cell, or any combination thereof. In one embodiment, the sonosensitizing agent comprises 5-aminolevulinic acid, which, for example, results in the accumulation in tumor cells as protoporphyrin IX (PpIX), and wherein ultrasound treatment is applied post accumulation.

In various embodiments, an enhanced sonodynamic system configured to treat a cell within an anatomical subject, wherein the cell includes a baseline susceptibility to the sonodynamic therapy, is disclosed herein. The system includes a complementary therapeutic system configured to induce a pre-sonodynamic condition within the cell, a sonosensitizing agent configured to target the cell within the anatomical subject, a sonodynamic therapy system configured to generate an acoustic wave using a transducer, wherein the acoustic wave is configured to activate a sonosensitizer within the cell, a memory configured to store a predetermined threshold, wherein the predetermined threshold is associated with an improved susceptibility of the cell to the sonodynamic therapy, and a control circuit coupled to the complementary therapy system and sonodynamic therapy system, wherein the control circuit is configured to: receive a signal from the complementary therapy system, determine, based on the signal, whether the pre-sonodynamic condition exceeds the predetermined threshold; and control the sonodynamic therapy system to generate the acoustic wave based, at least in part, on a determination that the pre-sonodynamic condition exceeds the predetermined threshold.

In another embodiment, the present disclosure provides an acoustic ensonification drive pattern for activating a sonosensitizer in conjunction with providing sonodynamic therapy. The acoustic ensonification drive pattern creates an incoherent acoustic field for distributing low intensity energy. The acoustic ensonification drive pattern comprises a first acoustic ensonification drive pattern having a first phase, a first frequency, and first amplitude; and a second acoustic ensonification drive pattern having a second phase, a second frequency, and second amplitude. The at least one of the relative phase difference, frequency, and amplitude of the first and second acoustic ensonification drive patterns is selected to generate a third incoherent acoustic ensonification pattern to activate a sonosensitizer located in a patient tissue.

In one embodiment, the acoustic ensonification drive pattern further includes a fourth acoustic ensonification drive pattern having a fourth phase, and a fifth acoustic ensonification drive pattern having a fifth phase; wherein the relative phase difference, of the fourth and fifth acoustic ensonification drive patterns is selected to generate a sixth incoherent acoustic ensonification pattern to activate the sonosensitizer located in the patient tissue, wherein the sixth incoherent acoustic ensonification pattern is different than the third incoherent acoustic ensonification pattern.

In one embodiment, the acoustic ensonification drive pattern further includes a fourth acoustic ensonification drive pattern having a fourth frequency, and a fifth acoustic ensonification drive pattern having a fifth frequency; wherein the relative frequency difference, of the fourth and fifth acoustic ensonification drive patterns is selected to generate a sixth incoherent acoustic ensonification pattern to activate the sonosensitizer located in the patient tissue, wherein the sixth incoherent acoustic ensonification pattern is different than the third incoherent acoustic ensonification pattern.

In one embodiment, the acoustic ensonification drive pattern further includes a fourth acoustic ensonification drive pattern having a fourth amplitude, and a fifth acoustic ensonification drive pattern having a fifth amplitude; wherein the relative amplitude difference, of the fourth and fifth acoustic ensonification drive patterns is selected to generate a sixth incoherent acoustic ensonification pattern to activate the sonosensitizer located in the patient tissue, wherein the sixth incoherent acoustic ensonification pattern is different than the third incoherent acoustic ensonification pattern.

In one embodiment, the first and second phases are different. In one embodiment, the first and second frequencies are different. In one embodiment, the first and second amplitudes are different. In one embodiment, the first or second acoustic ensonification drive patterns are pulsed. In one embodiment, each of the pulsed first or second acoustic ensonification drive patterns is pulsed at a period and comprises a pulse defined by a magnitude and a predetermined number of cycles having a pulse width that is less than the period. In one embodiment, the pulse includes ten to one-thousand cycles. In one embodiment, a time between pulses is defined as the time to enable restoration of local oxygen supplies and to regulate the temperature of the patient tissue. In one embodiment, the acoustic ensonification drive pattern comprises modulating the pulse. In one embodiment, modulating the pulse comprises modulating the phase, frequency, or amplitude, or any combination thereof of the first pulse.

In one embodiment, the phase difference between of the first and second acoustic ensonification drive patterns is randomized.

In one embodiment, the first and second acoustic ensonification drive patterns are frequency modulated. In one embodiment, the first and second acoustic ensonification drive patterns are amplitude modulated. In one embodiment, the first and second acoustic ensonification drive patterns are phase modulated. In one embodiment, the amplitude of the first acoustic ensonification drive pattern is greater than the amplitude of the second acoustic ensonification drive pattern.

In one embodiment, the present disclosure provides a method of generating an acoustic ensonification drive pattern for activating a sonosensitizer in conjunction with providing sonodynamic therapy. The acoustic ensonification drive pattern creates an incoherent acoustic field for distributing low intensity energy. The method comprises generating a first signal to drive a first ultrasonic transducer element to generate a first acoustic ensonification drive pattern having a first phase, a first frequency, and a first amplitude; and generating a second signal to drive a second ultrasonic transducer element to generate a second acoustic ensonification drive pattern having a second phase, a second frequency, and a second amplitude. At least one of the relative phase difference, frequency, and amplitude of the first and second signals is selected to generate a third incoherent acoustic ensonification pattern to activate a sonosensitizer located in a patient tissue.

In one embodiment, the first and second phases of the first and second signals are different. In one embodiment, the first and second frequencies of the first and second signals are different. In one embodiment, the first and second amplitudes of the first and second signals are different.

In one embodiment, the method comprises pulsing the first signal, the second signal, or both the first and second signals to generate pulsed first or second acoustic ensonification drive patterns. In one embodiment, each of the pulsed first or second signals is pulsed at a period and comprises a pulse defined by a magnitude and a predetermined number of cycles having a pulse width that is less than the period. In one embodiment, the pulse includes ten to one-thousand cycles. In one embodiment, a time between pulses is defined as the time to enable restoration of local oxygen supplies and to regulate the temperature of the patient tissue. In one embodiment, the method comprises modulating the pulse. In one embodiment, modulating the pulse comprises modulating the phase, frequency, or amplitude, or any combination thereof of the first pulse.

In one embodiment, the method comprises randomly selecting the phases of the first and second signals; driving the first and second ultrasonic transducer elements with the respective first and second signals; and generating first and second acoustic ensonification patterns having a randomized phase difference.

In one embodiment, the method comprises selecting the phase of each element across the array in a randomized manner between 0-220 degrees (e.g., 0-45, 0-90, 1-135, 0-180, 0-200, 45-90, 45-135, 45-180, 45-220, 90-135, 90-180, 90-220, 120-220, 120-180, 120-150, 180-220, and/or 200-220 degrees of the phase and values and ranges therein, followed by dispersion adjustments to select groups of elements for the remaining 140-360 degrees of the phase (e.g., 140-300, 140-270, 140-225, 140-180, 140-150 degrees and values and ranges therein).

In one embodiment, the method comprises modulating a frequency of the first and second signals; driving the first and second ultrasonic transducer elements with the respective frequency modulated first and second signals; and generating first and second frequency modulated acoustic ensonification patterns.

In one embodiment, the method comprises modulating an amplitude of the first and second signals; driving the first and second ultrasonic transducer elements with the respective amplitude modulated first and second signals; and generating first and second amplitude modulated acoustic ensonification patterns.

In one embodiment, the method comprises modulating a phase of the first and second signals; driving the first and second ultrasonic transducer elements with the respective phase modulated first and second signals; and generating first and second phase modulated acoustic ensonification patterns.

In one embodiment, the method comprises varying an amplitude of the and second signals; and driving the first and second ultrasonic transducer elements with the respective amplitude of the first and second signals. In one embodiment, the first amplitude is greater than the second amplitude.

In another embodiment, the present disclosure provides a method of enhancing the efficacy of a sonodynamic therapy configured to treat a cell within an anatomical subject, the method including administering a sonosensitizing agent to the cell within the anatomical subject; generating, via a sonodynamic therapy system, a plurality of planar acoustic waves using a transducer array; activating, via the plurality of planar acoustic waves, a sonosensitizer within the cell; destroying, via the activation of the sonosensitizer, the cell within the anatomical structure; and inducing, via the activation of the sonosensitizing agent, an immunotherapeutic effect within the anatomical structure.

In one embodiment, the immunotherapeutic effect comprises a resistivity to a recurrence of the cell within the anatomical structure.

In another embodiment, the present disclosure provides method of enhancing the efficacy of a sonodynamic therapy configured to treat a cell within an anatomical subject, the method including administering a sonosensitizing agent to the cell within the anatomical subject; generating, via a sonodynamic therapy system, a plurality of planar acoustic waves using a transducer array; activating, via the plurality of planar acoustic waves, a sonosensitizer within the cell; and destroying, via the activation of the sonosensitizer, the cell within the anatomical structure.

In one embodiment, the sonosensitizing agent comprises at least one of a type-specific sonosensitizer, a location-specific sonosensitizer, or a wavelength-specific sonosensitizer, or any combination thereof. In one embodiment, the sonosensitizing agent is specifically configured to target a specific type of cell in a specific location of the anatomical subject. In one embodiment, the specific type of cell is at least one of a wound, an ulcer, an abscess, or a tumor, or any combination thereof. In one embodiment, the acoustic wave comprises a specific wavelength, and wherein a sonosensitizer is specifically configured to react to the specific wavelength. In one embodiment, the sonosensitizing agent comprises a nanoparticle sonosensitizer configured to produce a desired cytotoxic effect. In one embodiment, the desired cytotoxic effect comprises at least one of a reduce toxicity, an increased biodegradability, or an improved ability to target the cell, or any combination thereof. In one embodiment, the sonosensitizing agent comprises 5-ALA and the sonosensitizer comprises protoporphyrin IX (PpIX).

In another embodiment, the present disclosure provides an ultrasound transducer for activating a sonosensitizer in conjunction with providing sonodynamic therapy, the ultrasound transducer including a plurality of ultrasonic transducer elements arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements; wherein each piezoelectric transducer in the array of piezoelectric transducers comprises a planar emitting surface configured to emit a planar acoustic wave; a patient interface to acoustically couple the ultrasonic transducer array to a patient, wherein the patient interface comprises at least one of: (i) at least two alignment features configured to receive predetermined anatomical landmarks of the anatomical structure, (ii) an acoustic coupling membrane configured to conform to the anatomical structure, and (iii) an array holder couplable to the ultrasonic transducer array, wherein the array holder is adjustable to move the ultrasonic transducer array relative to the patient interface between a plurality of treatment positions; and a controller coupled to the ultrasonic transducer array, wherein the controller is configured to cause the ultrasonic transducer array to activate a sonosensitizer in a treatment region in the anatomical structure.

In another embodiment, the present disclosure provides an ultrasound transducer for activating a sonosensitizer in conjunction with providing sonodynamic therapy, the ultrasound transducer including a plurality of ultrasonic transducer elements arranged in an array configured to generate an incoherent acoustic pressure field with an energy profile for activating a sonosensitizer located within tissue of a patient; a patient interface to acoustically couple the ultrasonic transducer array to a patient, wherein the patient interface comprises at least one of: (i) an alignment feature configured to receive predetermined anatomical landmarks of the anatomical structure, (ii) an acoustic coupling membrane configured to conform to the anatomical structure, and (iii) an array holder couplable to the ultrasonic transducer array, wherein the array holder is adjustable to move the ultrasonic transducer array relative to the patient interface between a plurality of treatment positions; and a controller coupled to the ultrasonic transducer array, wherein the controller is configured to cause the ultrasonic transducer array to activate a sonosensitizer in a treatment region in the anatomical structure.

In another embodiment, the present disclosure provides an ultrasound transducer for activating a sonosensitizer in conjunction with providing sonodynamic therapy, the ultrasound transducer including a plurality of ultrasonic transducer elements arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements; wherein each piezoelectric transducer in the array of piezoelectric transducers comprises a planar emitting surface configured to emit a planar acoustic wave; a patient interface to acoustically couple the ultrasonic transducer array to the patient; and a controller coupled to the ultrasonic transducer array, wherein the controller is configured to: select one of the plurality of elements of the ultrasonic transducer array for a calibration procedure; generate an ultrasound pulse with the one of the plurality of elements; detect reflections of the ultrasound pulse on the plurality of elements of the ultrasonic transducer array; set amplitude and frequency of the one of the plurality of elements based on the reflections to maximize an ultrasound transmission rate through a skull of the patient; and select another one of the plurality of elements of the ultrasonic transducer array for the calibration procedure.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient; a patient interface to acoustically couple the ultrasonic transducer array to the patient; and a controller coupled to the ultrasonic transducer array, wherein the controller is configured to: select one of the plurality of elements of the ultrasonic transducer array for a calibration procedure; generate an ultrasound pulse with the one of the plurality of elements; detect reflections of the ultrasound pulse on the plurality of elements of the ultrasonic transducer array; set amplitude and frequency of the one of the plurality of elements based on the reflections to maximize an ultrasound transmission rate through a skull of the patient; and select another one of the plurality of elements of the ultrasonic transducer array for the calibration procedure.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements; wherein each piezoelectric transducer in the array of piezoelectric transducers comprises a planar emitting surface configured to emit a planar acoustic wave; and an acoustic ensonification drive pattern for activating a sonosensitizer in conjunction with providing sonodynamic therapy, wherein the acoustic ensonification drive pattern creates an incoherent acoustic field for distributing low intensity energy, the acoustic ensonification drive pattern including: a first acoustic ensonification drive pattern having a first phase, a first frequency, and first amplitude; and a second acoustic ensonification drive pattern having a second phase, a second frequency, and second amplitude; wherein at least one of the relative phase difference, frequency, and amplitude of the first and second acoustic ensonification drive patterns is selected to generate a third incoherent acoustic ensonification pattern to activate a sonosensitizer located in a patient tissue.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient; and an acoustic ensonification drive pattern for activating a sonosensitizer in conjunction with providing sonodynamic therapy, wherein the acoustic ensonification drive pattern creates an incoherent acoustic field for distributing low intensity energy, the acoustic ensonification drive pattern including: a first acoustic ensonification drive pattern having a first phase, a first frequency, and first amplitude; and a second acoustic ensonification drive pattern having a second phase, a second frequency, and second amplitude; wherein at least one of the relative phase difference, frequency, and amplitude of the first and second acoustic ensonification drive patterns is selected to generate a third incoherent acoustic ensonification pattern to activate a sonosensitizer located in a patient tissue.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements; wherein each piezoelectric transducer in the array of piezoelectric transducers comprises a planar emitting surface configured to emit a planar acoustic wave; and a complementary therapeutic system configured to perform a complementary therapy on the anatomical subject by inducing, via the complementary therapeutic system, a pre-sonodynamic condition within the cell; by assessing whether the pre-sonodynamic condition corresponds to an improved susceptibility of the cell to the sonodynamic therapy; by administering a sonosensitizing agent to the cell within the anatomical subject; by generating, via a sonodynamic therapy system, an acoustic wave using a transducer; and by activating, via the acoustic wave, a sonosensitizer within the cell.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient; and a complementary therapeutic system configured to perform a complementary therapy on the anatomical subject by inducing, via the complementary therapeutic system, a pre-sonodynamic condition within the cell; by assessing whether the pre-sonodynamic condition corresponds to an improved susceptibility of the cell to the sonodynamic therapy; by administering a sonosensitizing agent to the cell within the anatomical subject; by generating, via a sonodynamic therapy system, an acoustic wave using a transducer; and by activating, via the acoustic wave, a sonosensitizer within the cell.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient, wherein the incoherent acoustic pressure field comprises one or more of: a randomized phase difference across the plurality of ultrasonic transducer elements, a modulated frequency across the plurality of ultrasonic transducer elements, and a modulated amplitude across the plurality of ultrasonic transducer elements; wherein each piezoelectric transducer in the array of piezoelectric transducers comprises a planar emitting surface configured to emit a planar acoustic wave; a complementary therapeutic system configured to induce a pre-sonodynamic condition within the cell; a sonosensitizing agent configured to target the cell within the anatomical subject; a sonodynamic therapy system configured to generate an acoustic wave using a transducer, wherein the acoustic wave is configured to activate a sonosensitizer within the cell; a memory configured to store a predetermined threshold, wherein the predetermined threshold is associated with an improved susceptibility of the cell to the sonodynamic therapy; and a control circuit coupled to the complementary therapy system and sonodynamic therapy system. In one embodiment, the control circuit is configured to: determine whether the pre-sonodynamic condition exceeds the predetermined threshold. In one embodiment, the control circuit is configured to: receive a signal from the complementary therapy system; determine, based on the signal, whether the pre-sonodynamic condition exceeds the predetermined threshold. In one embodiment, the control circuit is configured to control the sonodynamic therapy system to generate the acoustic wave based, at least in part, on a determination that the pre-sonodynamic condition exceeds the predetermined threshold.

In another embodiment, the present disclosure provides an ultrasound transducer for activating a sonosensitizer in conjunction with providing sonodynamic therapy, the ultrasound transducer including: a plurality of ultrasonic transducer elements arranged in an array configured to generate an incoherent acoustic pressure field with an energy profile for activating a sonosensitizer located within tissue of a patient; a complementary therapeutic system configured to induce a pre-sonodynamic condition within the cell; a sonosensitizing agent configured to target the cell within the anatomical subject; a sonodynamic therapy system configured to generate an acoustic wave using a transducer, wherein the acoustic wave is configured to activate a sonosensitizer within the cell; a memory configured to store a predetermined threshold, wherein the predetermined threshold is associated with an improved susceptibility of the cell to the sonodynamic therapy; and a control circuit coupled to the complementary therapy system and sonodynamic therapy system, wherein the control circuit is configured to: receive a signal from the complementary therapy system; determine, based on the signal, whether the pre-sonodynamic condition exceeds the predetermined threshold; and control the sonodynamic therapy system to generate the acoustic wave based, at least in part, on a determination that the pre-sonodynamic condition exceeds the predetermined threshold.

In another embodiment, the present disclosure provides a use of a compound of Formula (I):

(I)

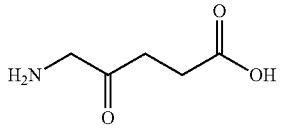

for an increased production of protoporphyrin IX, wherein said protoporphyrin IX is preferentially accumulated in a cancer, activating said protoporphyrin IX to produce a reactive oxygen species (ROS) thereby causing apoptosis of a plurality of cancer cells; and further including cooling a patient by circulating a cooling fluid to a membrane configured for conforming to a skin surface of the patient.

In another embodiment, the present disclosure provides a use of a compound of Formula (I):

(I)

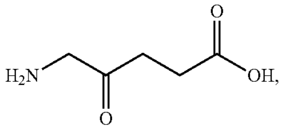

including instructing oral administration of a prodrug comprising the compound of Formula (I) to a patient with cancer, wherein said prodrug results in increased production of a compound of Formula (II):

(II)

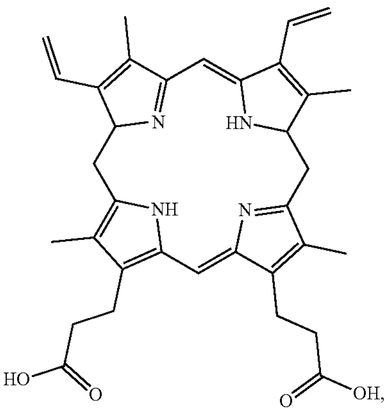

wherein said compound of formula (ii) is preferentially accumulated in said cancer, activating said compound of formula (ii) to produce a reactive oxygen species (ROS) thereby causing apoptosis of a plurality of cancer cells; and cooling the patient by circulating a cooling fluid to a membrane configured for conforming to a skin surface of the patient.

In another embodiment, the present disclosure provides a method of treating cancer with a compound of Formula (I):

(I)

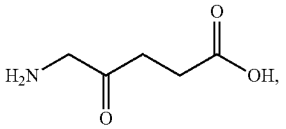

including instructing oral administration of a pro drug including the compound of Formula (I) to a patient with cancer, wherein the prodrug comprises 5-aminolevulinic acid (5-ALA), wherein said 5-ALA results in increased production of protoporphyrin IX, wherein said protoporphyrin IX is preferentially accumulated in said cancer, activating said protoporphyrin IX to produce a reactive oxygen species (ROS) thereby causing apoptosis of a plurality of cancer cells; and cooling the patient by circulating a cooling fluid to a membrane configured for conforming to a skin surface of the patient.

In one embodiment, the skin surface to be cooled is on a head, wherein the activating of said protoporphyrin IX maintains a temperature of the plurality of cancer cells below 45° C. to cause necrotic cell death of the plurality of cancer cells while preserving healthy tissue. In one embodiment, the 5-ALA administration escalates a heme biosynthesis pathway. In one embodiment, said protoporphyrin IX accumulates in the plurality of cancer cells and converts dissolved molecular oxygen into the reactive oxygen species. In one embodiment, the protoporphyrin IX becomes cytotoxic in producing said reactive oxygen species. In one embodiment, the activating said protoporphyrin IX comprises sonoluminescence. In one embodiment, the activating said protoporphyrin IX comprises pyrolysis. In one embodiment, the method further including oxygenating the plurality of cancer cells. In one embodiment, the method further including treating an area around the plurality of cancer cells to reduce a recurrence of a malignant tumor. In one embodiment, said protoporphyrin IX accumulates in a glioblastoma multiforme (GBM) in the brain. In one embodiment, said protoporphyrin IX accumulates in the plurality of cancer cells in a cancer selected from the group consisting of: a brain, a lung, a breast, a stomach, a liver, a pancreas, an intestine, a rectum, a vagina, testes, a prostate or a cervix. In one embodiment, the activating said protoporphyrin IX maintains a temperature of the plurality of cancer cells below 43° C. and causes thermal damage to the plurality of the plurality of cancer cells. In one embodiment, the activating said protoporphyrin IX produces a non-thermally ablative treatment with a temporal average intensity without increasing a temperature of a healthy tissue in a treatment region above 43° C. In one embodiment, the method includes measuring the temperature of the cooling fluid. In one embodiment, the method includes measuring the temperature of a skin surface. In one embodiment, the method includes measuring the temperature of the plurality of cancer cells. In one embodiment, the method includes cooling the patient before activating said protoporphyrin IX. In one embodiment, the method includes cooling the patient before treating said cancer. In one embodiment, the cooling the patient keeps a temperature of the cooling fluid from rising. In some embodiments, one or more sensors are used to measure temperature and/or other parameters. Automatic shut offs and/or notifications are provided in one embodiment based upon sensor information (e.g., if a temperature exceeds a certain point).

BRIEF DESCRIPTION OF THE DRAWINGS

The following drawings are illustrative of particular aspects (e.g., embodiments) of the present disclosure and therefore do not limit the scope of the appended claims. The drawings are intended for use in conjunction with the explanations in the following description. The disclosed aspects will hereinafter be described in conjunction with the appended drawings, wherein like numerals denote like elements.

FIG. 28 is a logic flow diagram for generating ensonification drive patterns for sonodynamic therapy in accordance with at least one aspect of the present disclosure.

FIG. 54 is a flow diagram of a method of using immunotherapy to enhance the efficacy of a sonodynamic therapy, according to at least one aspect of the present disclosure.

FIG. 55 is a block diagram of a block diagram depicting various therapeutic sonosensitizers configured to enhance the efficacy of a sonodynamic therapy, according to at least one aspect of the present disclosure.

Like reference numbers represent corresponding parts throughout.

DETAILED DESCRIPTION

Figure 1:
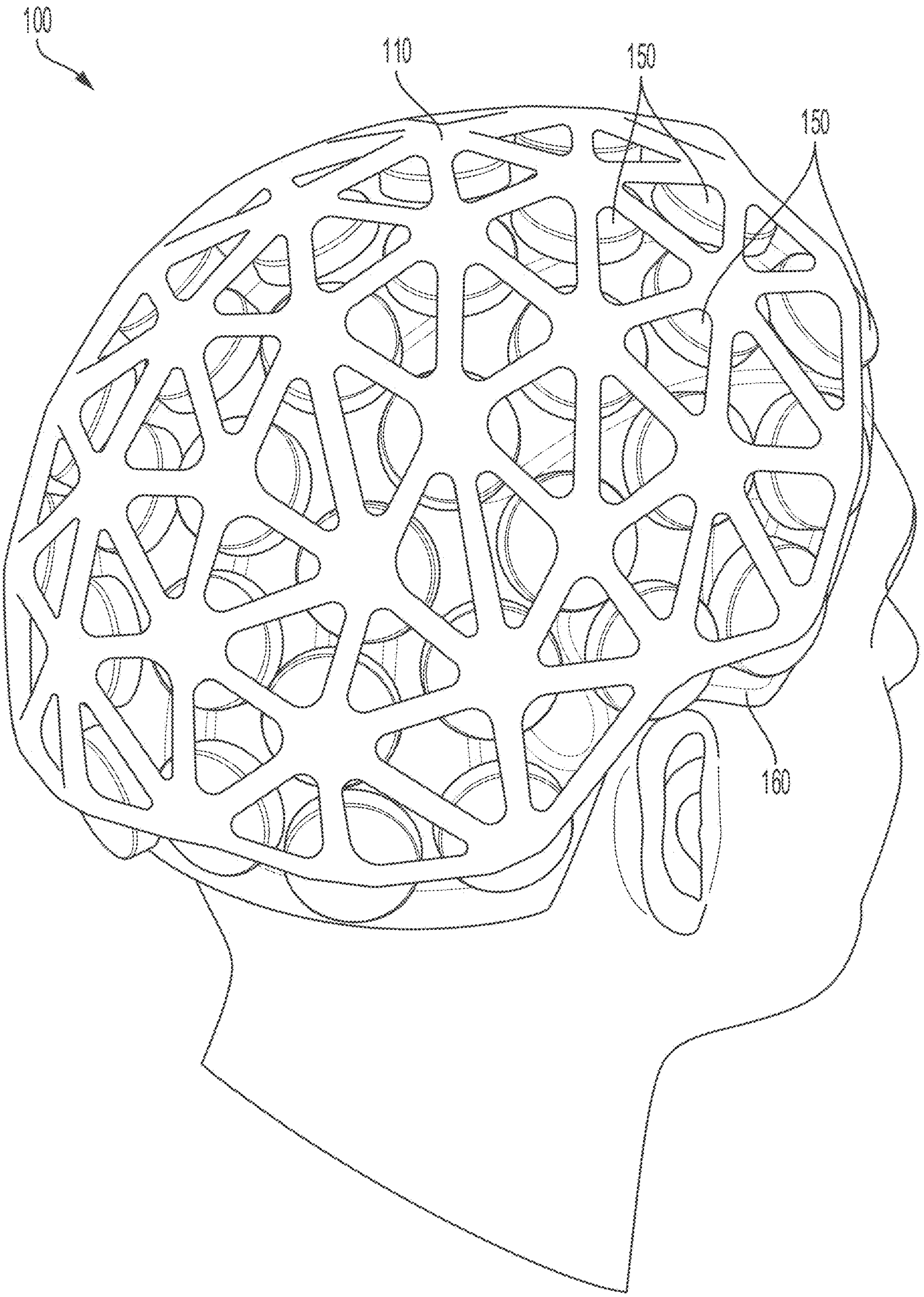
FIG. 1 is a perspective view of a transcranial sonodynamic therapy device with a shell having multiple transducers and a cooling system placed over the head of a patient, according to at least one aspect of the present disclosure.

Prior to launching into a description of the figures, the present disclosure first turns to a general description of various aspects of non-invasive sonodynamic therapy systems. In several embodiments, the present disclosure is directed to a system for sonodynamic therapy that comprises, or consists essentially of, a transducer, a patient interface to acoustically couple the transducer to a patient, and a controller coupled to the transducer. The controller is configured to generate an electrical drive signal from a set of modulated acoustic wave parameters, modulate the drive signal, and drive the transducer with the modulated drive signal at a frequency to produce a modulated acoustic wave to produce an acoustic intensity sufficient to activate a sonosensitizer in a treatment region. In several embodiments, non-invasive therapy systems are not implanted in a patient. Minimally invasive systems are provided in other embodiments.

In another aspect, the present disclosure is directed to another system for sonodynamic therapy. The system comprises a first transducer, a second transducer, and a controller coupled to the first and second transducers. The controller is configured to generate a first electrical drive signal from a set of modulated acoustic wave parameters, generate a second electrical drive signal from the set of modulated acoustic wave parameters, drive the first transducer at the first electrical drive signal to produce a first acoustic wave, and drive the second transducer at the second electrical drive signal to produce a second acoustic wave. The first and second acoustic waves are combinable to produce an acoustic intensity sufficient to activate a sonosensitizer in a treatment region.

In yet another aspect, the present disclosure is directed to yet another system for sonodynamic therapy. The system comprises, or consisting essentially of, a plurality of transducers and a controller coupled to the plurality of transducers. The controller is configured to generate a plurality of electrical drive signals from a set of modulated acoustic wave parameters and drive the plurality of transducers at the plurality of electrical drive signals to produce a plurality of modulated acoustic waves. The plurality of modulated acoustic waves is combinable to produce an acoustic intensity sufficient to activate a sonosensitizer in a treatment region.

The following description provides illustrative examples of applications of non-invasive sonodynamic therapy techniques to treat tissues, such as tumors within the body, such as in the brain, spine, lung, breast, mouth, tongue, stomach, liver, pancreas, intestines, rectum, colon, vagina, ovary, testes, leukemia, lymphoma, among others, whether the tumors are malignant or nonmalignant. It will be appreciated, however, that such techniques can be applied to treat tumors or undesired tissue/cells within other body parts. For example, cancerous tissue in the lung, breast, colorectal region, prostate and pancreas may be treated using several embodiments described herein using for example, one or more sonosensitizers along with the ultrasound parameters described herein. Tumors that are difficult to access including those surrounded by bony structures are treated in various embodiments, including but not limited to spinal tumors. Treatment of undesired tissue in joints and other orthopedic applications are also provided herein.

In some embodiments, sonodynamic therapy is used herein to improve efficiency of chemotherapeutic molecules, sonoporation, and/or gene delivery. In various embodiments, sonodynamic therapy with an ultrasound array delivering a temporal-average intensity output below 8, 10, 15, 20 $W/cm^2$ (e.g., 0.1-8 $W/cm^2$, 0.1-4 $W/cm^2$, 0.5-5 $W/cm^2$ etc.) to cancer tissue can be used to induce and activate sonosensitizer at relative deep depths within a patient's body with or without cavitation and/or thermal effects and/or sonoluminescence to produce reactive oxygen species, intracellular singlet oxygen, and/or free radicals in a cascade of events that activate the sonosensitizer and in turn damage the cancer cells. In various embodiments, sonodynamic therapy can be used with or without photodynamic therapy.

Several embodiments described herein are used synergistically with other cancer therapies, including for example, radiation, chemotherapy and cell therapies. In one embodiment, the combination of ultrasound and a sonosensitizer as described herein reduces or eliminates the need for one or more additional complementary treatments. For example, lower doses or fewer additional treatments of chemotherapy, radiation, cell therapy etc. may be needed when cancerous tissue is treated by the combination of ultrasound and a sonosensitizer as described herein, thus enhancing patient care and reducing side effects.

Applicant of the present application owns the following PCT International Patent Applications, the disclosure of each of which is herein incorporated by reference in its respective entirety: (1) PCT International Application No. PCT/US2015/010053 entitled Device and Method For Use Of Photodynamic Therapy filed Jan. 2, 2015, national phase now U.S. Pat. No. 10,675,482; (2) PCT International Application No. PCT/US2019/045802 entitled Tissue Treatment with Sensitizer and Light and/or Sound filed Aug. 8, 2019; and (3) PCT International Application No. PCT/US2020/017983 entitled Non-Invasive Sonodynamic Therapy filed Feb. 12, 2020.

Turning now to FIG. 1, human skulls can vary by gender and anatomical location. One aspect of the present disclosure provides a non-invasive sonodynamic therapy device 100 as shown in FIG. 1. The non-invasive sonodynamic therapy device 100 may comprise a shell 110 with transducers 150 that can provide predictable and consistent insonication and/or ensonification despite these variations. The shell 110 may comprise a rigid material. Known relative positions of the transducers 150 can allow for imaging of the head, even in low resolution with large transducers 150. In one embodiment, the illustrated aspect may include a mobile stand to hold in position on the patient while he/she waits in a seated or supine position. In one embodiment, the rigid shell 110 may be a lightweight helmet that can be worn by the patient during treatment, allowing for predictable placement of the transducers 150 with little infrastructure requirements. In one embodiment, the rigid shell 110 may be part of a positionable system attached to an arm and/or mobile stand.

The non-invasive sonodynamic therapy device 100 may comprise a flexible shell 110 (e.g., a helmet) with transducers 150 placed over a liquid-cooled skull cap 160 as described further elsewhere herein, requiring little infrastructure to support the array of transducers 150. It may be possible for the patient to don the skull cap 160 and shell 110 in any chair while he/she waits for treatment to complete. The lightweight design may minimize neck pain from the patient holding up his/her head for extended periods with the weight of the transducers 150 and cooling cap. The flexible shell 110 can conform to the shape of each skull. Such a device may account for subtle variations between treatments depending on the shape of each patient's head curving some transducers 150 more inward or outward.

The non-invasive sonodynamic therapy device 100 may comprise rigid or flexible patches with several transducers 150 that can be removably applied to the head. Such an aspect may involve clinicians applying each patch individually. Having separate patches can allow for some treatment flexibility without requiring each transducer 150 to be planned and placed individually. An illustrative non-invasive sonodynamic therapy device 100 may minimize sores caused by adhering patches to the head repeatedly, which may be a particular concern for older and sicker patients.

The non-invasive sonodynamic therapy device 100 may comprise patches with single transducers 150 that can be removable applied to the head. Individual transducers 150 can provide the most treatment flexibility. Such a device may involve a detailed process for planning to apply and applying the transducers 150. Given the additional flexibility, the illustrative non-invasive sonodynamic therapy device 100 may accommodate for greater usability risk.

Figure 2:
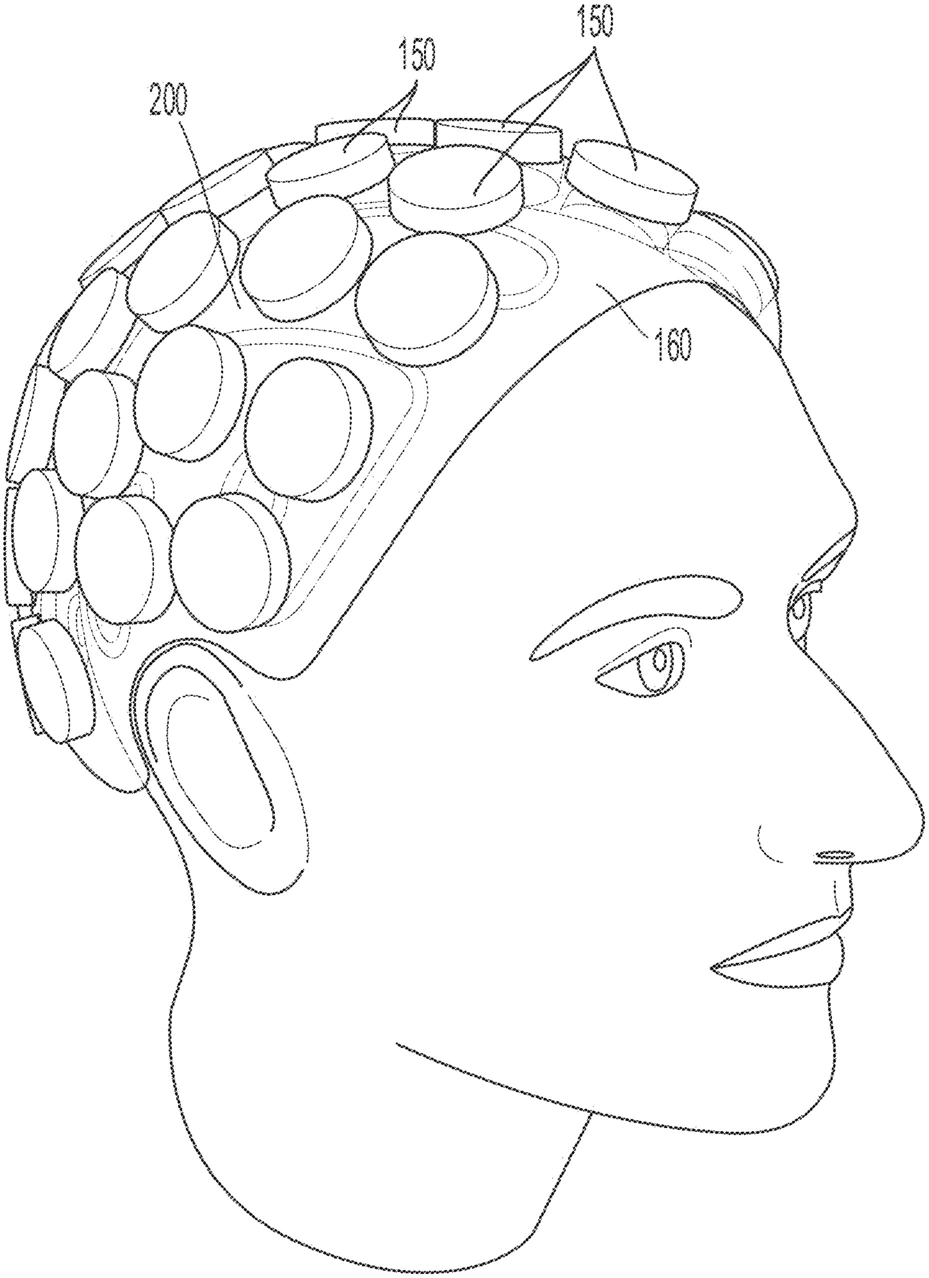
FIG. 2 is a perspective view of a transcranial sonodynamic therapy device with multiple transducers and a cooling system placed over the head of a patient, according to at least one aspect of the present disclosure.

The size and shape of the transducers 150, as can be seen in FIG. 2, may vary across various disclosed aspects. For a cost-effective and simple system, larger transducers 150, which produce directional acoustic waves, may be used. Large transducers 150 can be made less directional by applying to each transducer 150 an acoustic lens that bends the acoustic waves as described further elsewhere herein. For a system that can conform to the head, smaller transducers 150, which can radiate more broadly than larger transducers 150, can be used. Such small transducers 150 can have a greater ability to image or beam steer as an array.

Figure 3:
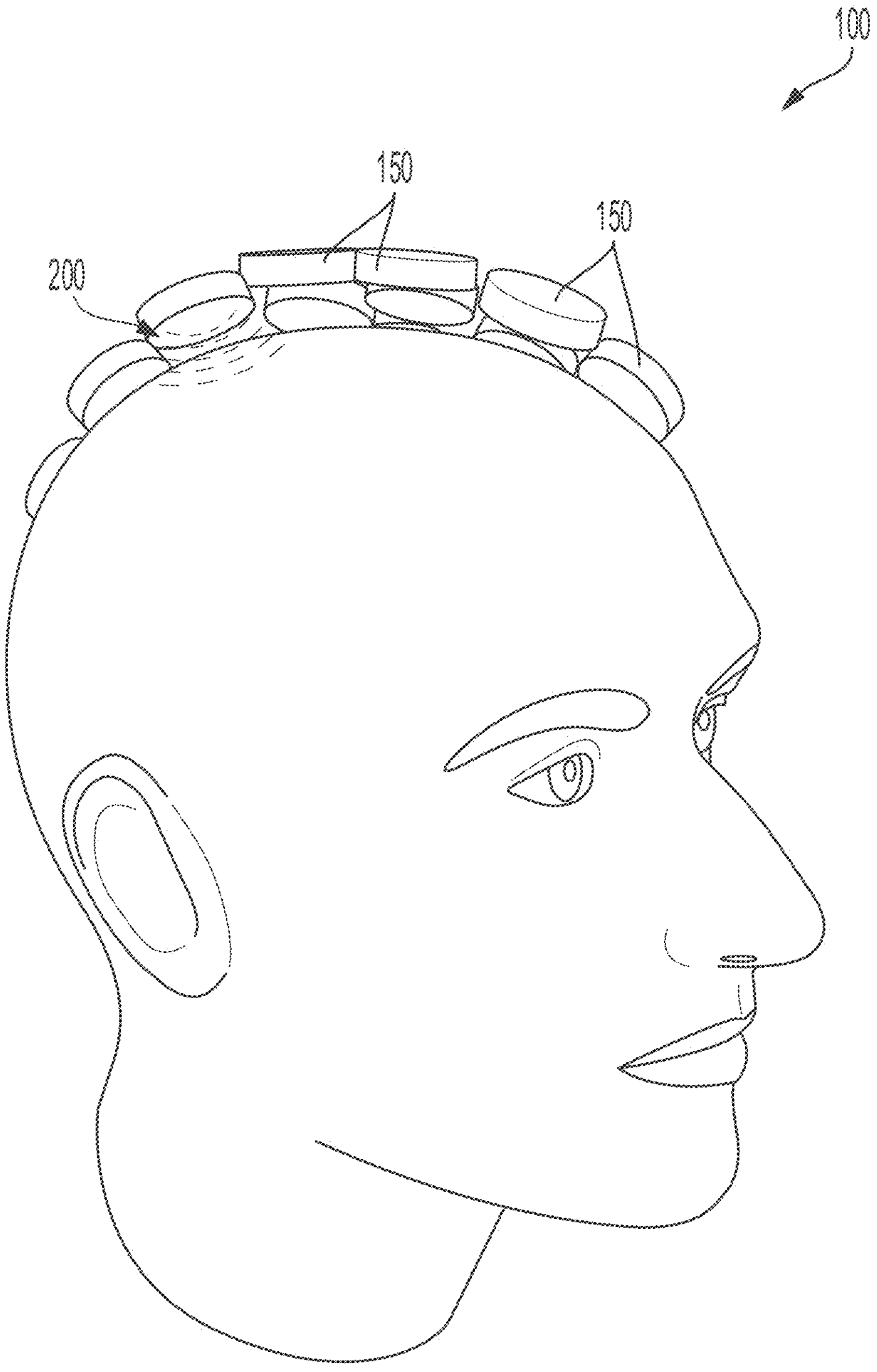
FIG. 3 is a partial cutaway view of a transcranial sonodynamic therapy device placed over the head of a patient showing a partial view of the multiple transducers, according to at least one aspect of the present disclosure.

FIG. 3 is a partial cutaway view of a transcranial sonodynamic therapy device 100 placed over the head of a patient showing a partial view of the multiple transducers 150, according to at least one aspect of the present disclosure. Instead of focusing an acoustic wave 200 to a small point, the acoustic wave 200 can be defocused to minimize the spatial variation of the acoustic wave intensity in the brain.

In various embodiments, the size and/or shape of the transducers 150 and/or one or more lenses may defocus or focus each transducer 150. In various embodiments, the size and shape of the transducer elements may defocus or focus each transducer element. As used herein (unless described otherwise), the term focused refers to an acoustic wavefront that is more convergent than a wavefront produced by a transducer 150 with a planar emitting surface and the term defocused refers to an acoustic wavefront that is more divergent than a wavefront produced by a transducer 150 with a planar emitting surface. Whether a lens needs to be concave or convex to make a wave more divergent depends on whether the acoustic wave is transitioning from a region of low acoustic impedance to a region of high acoustic impedance or the acoustic wave is transitioning from a region of high acoustic impedance to a region of low acoustic impedance. In this regard, if a lens is made of a material with higher acoustic impedance than the target medium (water/tissue), the acoustic wave originates in the high-impedance material and transitions to the low-acoustic impedance target medium. If the lens is concave, the lens will "focus" the acoustic wave to make it more convergent. If the lens is convex, the lens will "defocus" the acoustic wave to make it more divergent.

Figure 4:
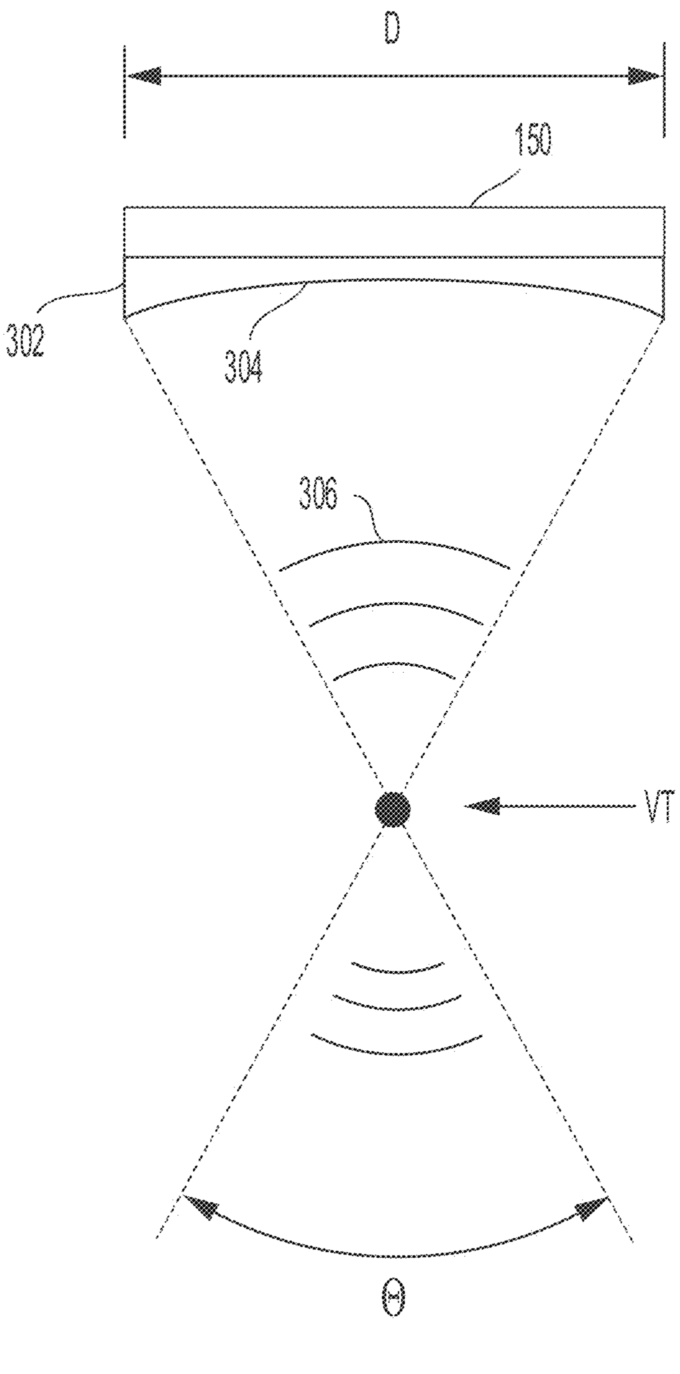
FIG. 4 is a schematic view of a transducer with a lens defining a concave surface, according to at least one aspect of the present disclosure.

FIG. 4 is a schematic view of a transducer 150 with a lens 302 defining a concave surface 304, according to at least one aspect of the present disclosure. The lens 302 may be acoustically coupled to the transducer 150 or may be formed integrally therewith. In the illustrated example, the lens 302 is made of a material with higher acoustic impedance than the target medium (water/tissue) such that the acoustic wave 306 originates in the high-impedance material and transitions to the low-acoustic impedance target medium causing the acoustic wave 306 "focus" or converge to the target tissue. In one embodiment of the illustrated example, the lens 302 is made of a material with higher acoustic impedance than the target medium (water/tissue) such that the acoustic wave 306 originates in the high-impedance material and transitions to the low-acoustic impedance target medium causing the acoustic wave 306 "focus" or converge to the target tissue.

Figure 5:
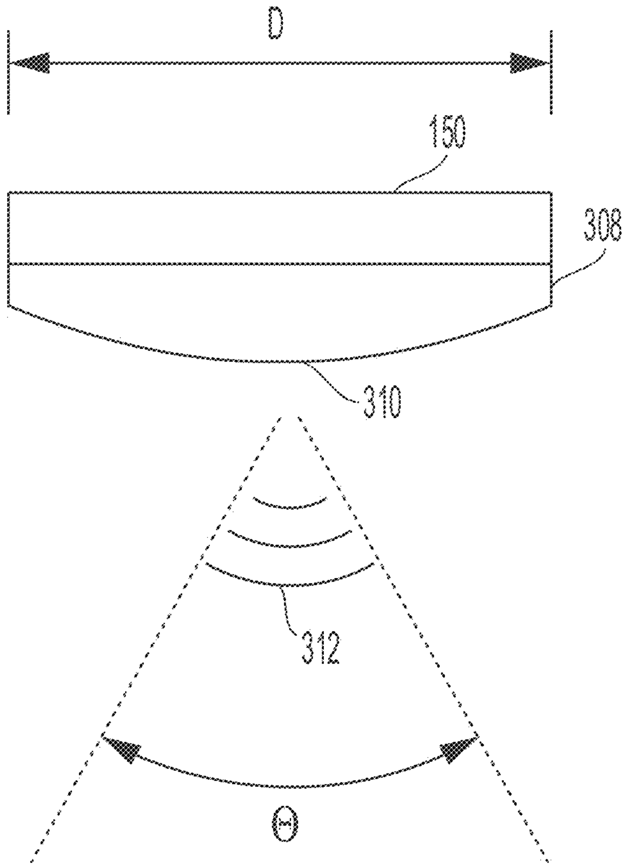
FIG. 5 is a schematic view of a transducer with a lens defining a convex surface, according to at least one aspect of the present disclosure.

FIG. 5 is a schematic view of a transducer 150 with a lens 308 defining a convex surface 310, according to at least one aspect of the present disclosure. The lens 308 may be acoustically coupled to the transducer 150 or may be formed integrally therewith. In the illustrated example, the lens 308 is made of a material with higher acoustic impedance than the target medium (water/tissue). Accordingly, an acoustic wave 312 originates in the high-impedance material and transitions to the low-acoustic impedance target medium causing the acoustic wave 312 to "defocus" or diverge to the target tissue. In one embodiment of the illustrated example, the lens 308 is made of a material with higher acoustic impedance than the target medium (water/tissue). Accordingly, an acoustic wave 312 originates in the high-impedance material and transitions to the low-acoustic impedance target medium causing the acoustic wave 312 to "defocus" or diverge to the target tissue.

The focus of the transducers 150 also depends on the material and shape of the lens (not shown). The defocus of the transducers 150 also depends on the material and shape of the lens (not shown). Using a lens 302, 308 allows the transducers 150 to be flat, which may minimize manufacturing costs. Both the lens 302 with the concave surface 304 and the lens 310 with the convex surface 310 may be configured to produce a fixed focus. In one embodiment, both the lens 302 with the concave surface 304 and the lens 310 with the convex surface 310 may be configured to produce a fixed or beam broadening focus. In one embodiment, the lens 302 with the concave surface 304 and the lens 310 with the convex surface 310 may be configured to produce a defocused beam.

It may be possible to produce a lens that can adjust its shape to create different focuses. It may be possible to create an elastic, fluid-filled pocket that functions as a lens. In one embodiment, a fluid-filled pocket is configured to converge an acoustic wave. In one embodiment, a fluid-filled pocket is configured to diverge an acoustic wave. In one embodiment, a fluid-filled pocket does not affect the convergence or divergence of an acoustic wave. In one embodiment, a fluid-filled pocket does not affect a planar acoustic wave. The fluid can be pumped in or out of the lens to adjust shape of the pocket and thus the focus of the transducers.

Figure 6:
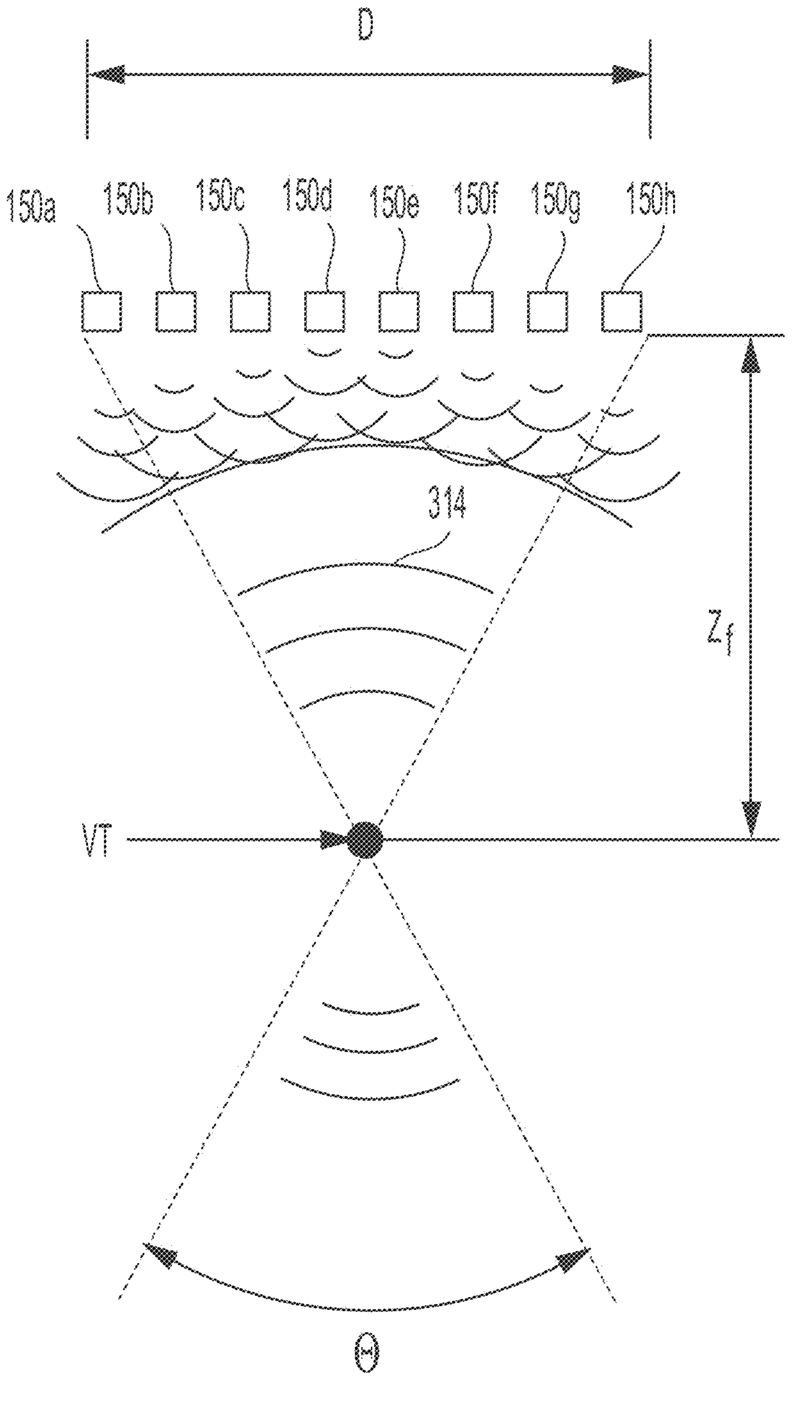
FIG. 6 is a schematic view of a transducer with multiple elements that can be individually energized to produce a variety of acoustic waves, including for example converging, diverging, and/or planar acoustic waves, according to at least one aspect of the present disclosure.

FIG. 6 is a schematic view of a transducer 150 with multiple elements **150*a*-150*h* that can be individually energized to produce a variety of acoustic waves, according to at least one aspect of the present disclosure. As shown in FIG. 6, multiple transducer elements 150*a*-150*h* can be arranged in an array to produce converging, diverging, or planar, acoustic waves. In one embodiment, one or more of the individual elements 150*a*-150*h* includes a flat, planar emitting surface that produces a planar acoustic wave. In various embodiments, one or more (e.g., 1, 5, 10, 20, 50, 100, 200, 250, 256, 300, 500, 1000, or more, and in some embodiments, all) elements of an array include flat planar emitting surfaces. In some embodiments, the array consists essentially of flat planar emitting surfaces ranging, for example, from 150-350 elements, 100-300 elements, 200-300 elements, 800-1200 elements, and values and ranges therein. In one embodiment, the array of flat, plan emitting surfaces is arranged on a flat array. In one embodiment, the array of flat, plan emitting surfaces is arranged with a curvature configured to direct each flat element in the array to emit the planar acoustic wave normal to a body surface, such as a skull, other bony structure. In some embodiments, the abdomen, back, waist, shoulder, or other body structure is treated. In various embodiments, for example, the transducer elements 150*a*-150*h* can be activated in a predetermined sequence to selectively generate convergent/divergent/planar acoustic waves, such as, for example, the convergent acoustic wave 314, shown in FIG. 4, or a divergent acoustic wave 312 shown in FIG. 5. To generate a converging acoustic wave 314, for example, the outer transducer elements 150*a*, 150*h* are initially energized and after a time delay the adjacent inner transducer elements 150*b*, 150*g* are energized. In various embodiments, a time delay is in a range of 0.1 μs to 10 s, including 0.1 μs, 0.2 μs, 0.3 μs, 0.4 μs, 0.5 μs, 1 μs, 5 μs, 10 μs, 15 μs, 20 μs, 25 μs, 30 μs, 35 μs, 40 μs, 50 μs, 60 μs, 70 μs, 80 μs, 90 μs, 0.1 ms, 0.2 ms, 0.3 ms, 0.4 ms, 0.5 ms, 1 ms, 5 ms, 10 ms, 50 ms, 100 ms, 500 ms, 1 s, 2 s, 5 s, and 10 s and any values and ranges therein. The next adjacent inner transducer elements 150*c*, 150*f* are energized after a second time delay. Finally, the inner transducer elements 150*d*, 150*e* are energized after a third time delay. This pattern can be repeated to generate the converging acoustic wave 314. The first, second, and third time delays may be equal or may vary in order to generate more complex acoustic waves. Alternatively, the transducer elements 150*a*-**

150*h* may be energized in reverse order to produce a diverging acoustic wave using equal or different time delays. The transducer elements 150*a*-150*h* can be interchangeably configured to transmit or receive acoustic waves.

Figure 7:
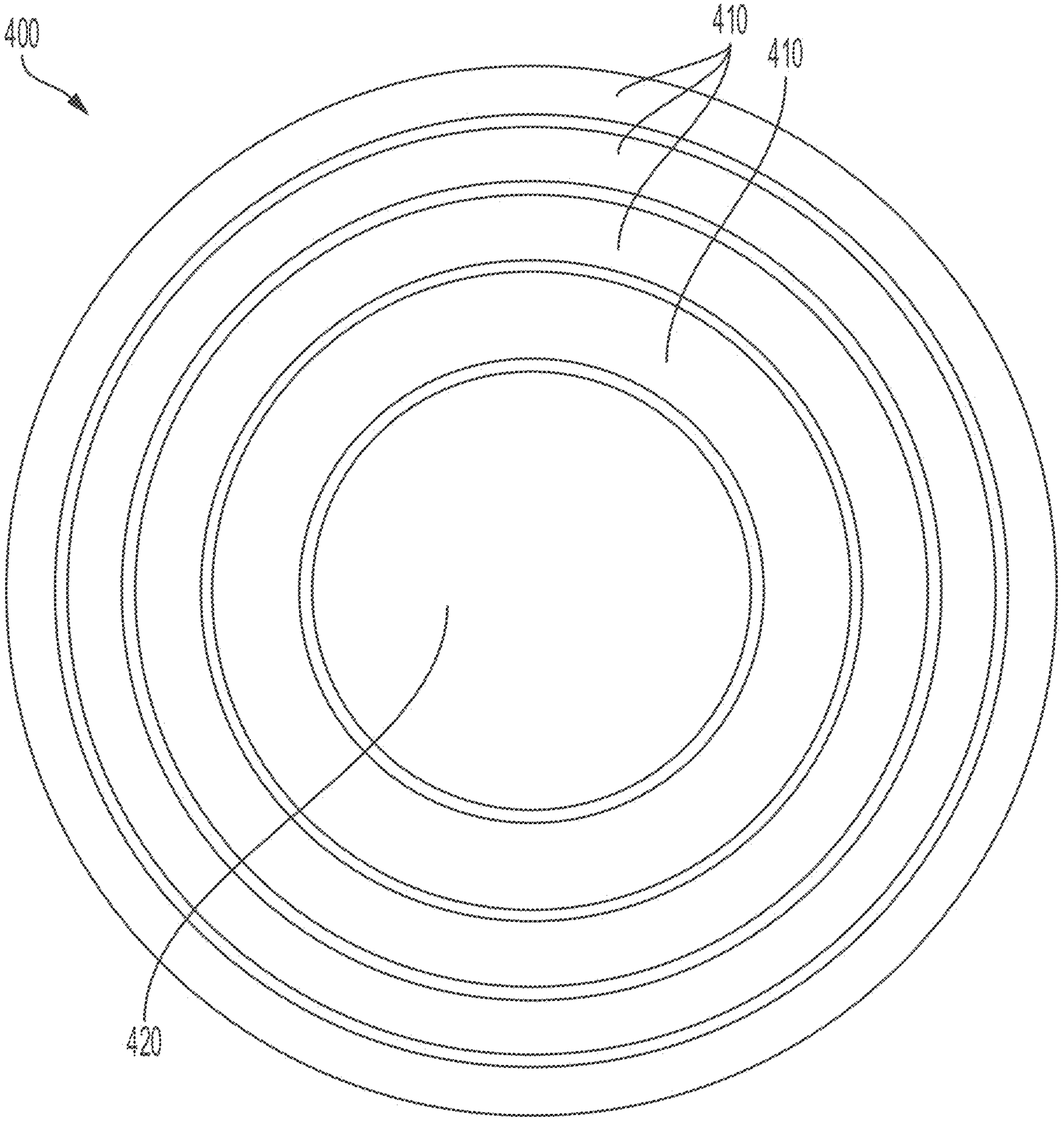
FIG. 7 is a bottom view of a transducer having an internal element surrounded by concentric rings, according to at least one aspect of the present disclosure.

FIG. 7 is a bottom view of a transducer 400 having an internal element 420 surrounded by concentric rings 410, according to at least one aspect of the present disclosure. In one embodiment, an internal element 420 is surrounded by concentric elements 410. Each transducer 150 can be adapted and configured to produce an acoustic wave with variable focus. One way to accomplish this can be with each transducer 400 having concentric rings 410 (e.g., an annular array) as shown in FIG. 7. Each concentric ring 410 can be driven with a different signal. In one embodiment to focus the acoustic wave, the signal going to the inner element 420 may be progressively more delayed than the outer of the concentric ring 410. The acoustic waves from each concentric ring 410 may converge at a point. In one embodiment to defocus the acoustic wave coming from an annular array, the acoustic wave at the outer of the concentric rings 410 may be progressively more delayed relative to the inner element 420. One way to make an embodiment of an annular array can be with concentric rings 410 of equal area. In another aspect, the annular array may comprise concentric rings 410 of unequal area.

Figure 8:
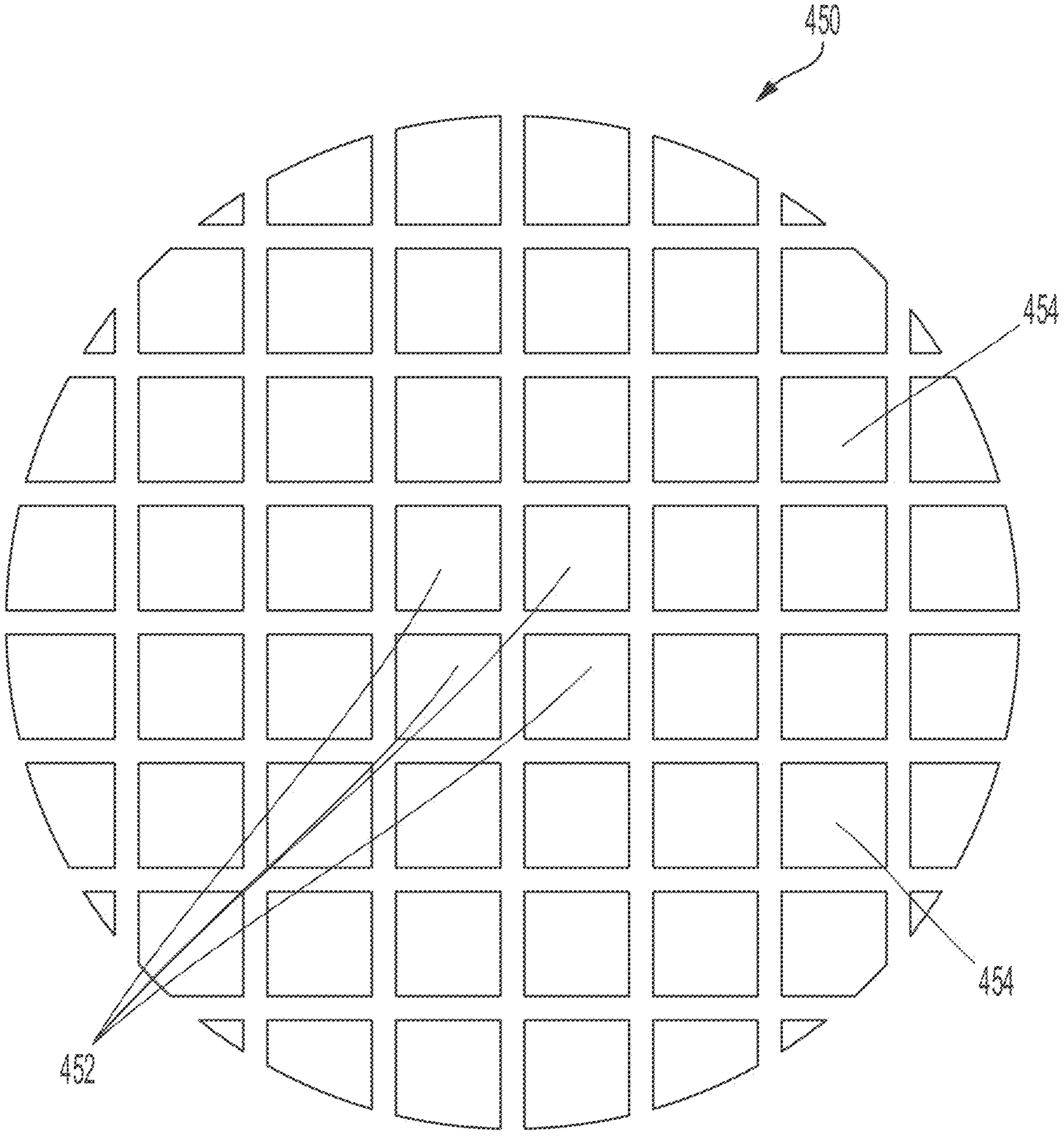
FIG. 8 is a bottom view of a transducer having internal elements arranged in 2-dimensional (2D) grid array, according to at least one aspect of the present disclosure.

FIG. 8 is a bottom view of a transducer comprising internal elements 452 arranged in 2-dimensional (2D) grid array 450, according to at least one aspect of the present disclosure. In one embodiment, one or more elements 452, 454 in the 2-dimensional (2D) grid array 450 is a flat, planar emitting surface that produce a planar acoustic wave. Each internal element 452 of the 2D grid transducer array 450 can be driven with a different signal. In one embodiment, to produce a converging acoustic wave (e.g., "focus") from the dimensional (2D) grid array 450, the signal applied to the inner element 454 may be progressively more delayed than the signal applied to the outer elements of the 2D grid transducer array 450. In one embodiment to produce a diverging acoustic wave (e.g., "defocus") from the dimensional (2D) grid array 450, the acoustic wave produced by the outer elements 452 may be progressively more delayed relative to the inner element 454. In one embodiment to produce a steered beam, elements are delayed in a standard delay pattern such that the acoustic beams converge at the desired location. In one aspect, each of the internal elements 452 of the 2D grid transducer array 450 may define an equal area. In another aspect, each of the internal elements 452 of the 2D grid transducer 450 array may define an unequal area.

In one aspect, the transducer 150, 400, 450 may be implemented as a single transducer comprising multiple piezoelectric elements with acoustically/electrically-independent sections arranged in an array. In other aspects, the transducer 150, 400, 450 may be implemented as different transducers working in a coordinated manner. In one embodiment, there is little or no distinction from a physics perspective between a single transducer with multiple elements and different transducers working in coordination. In one embodiment, there are several and/or significant distinctions from a physics perspective between a single transducer with multiple elements and different transducers working in coordination. The elements of an array can be sized on the order of a wavelength. In various embodiments, the wavelength is 0.1 mm-5 mm, 0.1 mm-4 mm, 0.1 mm-3 mm, 0.1 mm-2 mm, 0.1-1.5 mm, 0.1 mm-1 mm, 0.5 mm-3 mm, 0.5 mm-2 mm, 0.5 mm-1.5 mm, 0.5 mm-1 mm, 1 mm-5 mm, 1 mm-4 mm, 1 mm-3 mm, 1 mm-2 mm, 1 mm-1.5 mm, 1.5 mm-4 mm, 1.5 mm-3 mm, 1.5 mm-2 mm, 2 mm-5 mm, 2 mm-4 mm, 2 mm-3 mm, 3 mm-5 mm, 3 mm-4 mm, 0.1 mm-10 mm, and values therein.

In one aspect, the transducer 150, 400, 450 may be implemented as a single transducer comprising a plurality of elements implemented as an annular array as shown in FIG. 7 or as a grid array as shown in FIG. 8. In another aspect, the transducer 150, 400, 450 may be implemented as a plurality of individual transducers.

In one aspect, each of the transducers 150, 400, 450 shown in FIGS. 4-8, or elements thereof, are non-invasive and may be implemented in a suitable size and shape to fit on the body part of the patient. Also, the individual number and arrangement of transducer elements may be selected to fit on the body part of the patient. In one embodiment, an array of flat, plan emitting surfaces is arranged with a curvature configured to direct each flat element in the array to emit the planar acoustic wave normal to a body surface, such as a skull. In one embodiment, an array of flat elements may be arranged along a surface configured specifically to position one or more of the individual flat elements normal or perpendicular to a body surface in order to emit each individual planar acoustic wave normal or perpendicular to that body surface. For example, this arrangement to align the flat, planar acoustic waves emitted from the flat elements may be arranged to surround a body structure, such as a skull, with a radius of curvature in a range of 50 mm to 200 mm, including 50 mm to 175 mm, 50 mm to 150 mm, 50 mm to 125 mm, 50 mm to 100 mm, 60 mm to 150 mm, 60 mm to 140 mm, 70 mm to 130 mm, 70 mm to 110 mm, 75 mm to 150 mm, 75 mm to 125 mm, 75 mm to 100 mm, 80 mm to 120 mm, 80 mm to 100 mm, 90 mm to 130 mm, 90 mm to 110 mm, 100 mm to 125 mm, 100 mm to 150 mm, 100 mm to 175 mm, 125 mm to 150 mm, 125 mm to 175 mm, 125 mm to 200 mm, 150 to 175 mm, 150 mm to 200 mm, 125 mm, 150 mm, 165 mm, 175 mm, 200 mm, and values therein. In various embodiments, the arrangement may have a single radius of curvature, as in a portion of a sphere. In various embodiments, this arrangement may have 2 or more radii of curvature, such as a primary curvature across an anterior/posterior axis of a skull, and a secondary curvature across a lateral axis of the skull. In one aspect, the transducer 150, 400, 450, or elements thereof, may be made of piezoelectric or single crystal material which converts electrical energy to ultrasonic energy. The transducer 150, 400, 450 also can receive back ultrasonic energy and converts it to electrical energy. Each of the transducers 150, 400, 450, or elements thereof, may be adaptively focused to produce acoustic waves by collaborative transducer performance. For example, each of the transducers 150, 400, 450, or elements thereof, may be selectively controlled to operate either as a transmitter or as a receiver by a controller as described hereinbelow. Further, each of the transducers 150 400, 450, or elements thereof, may be selectively energized and actuated to produce convergent, divergent, or planar acoustic waves as discussed in more detail in the present description.

With reference now to FIGS. 4-8, in one aspect, the acoustic wave produced by the transducer 150, 400, 450 may be defined by vergence—a measure of the curvature of the acoustic wavefront. A negative vergence is when the acoustic wavefront propagates away from a point (e.g., divergence). A positive vergence is when the acoustic wavefront propagates towards a point (e.g., convergence). A zero vergence is a planar acoustic wavefront that does not converge or diverge. Vergence is a property of a single acoustic wavefront. In one embodiment, a single converging/diverging acoustic wavefront may be produced by multiple elements of a transducer 150, 400, 450 (e.g., a transducer comprising an annular array 400 or a grid array 450). In one embodiment, a converging/diverging acoustic wavefront may be produced by each individual element of a transducer 150, 400, 450 (e.g., a transducer comprising an annular array 400 or a grid array 450).

In one aspect, the acoustic wave produced by the transducer 150, 400, 450 may be characterized by phase and/or delay. The phase and/or delay may be employed to measure a relative shift in time between two acoustic waves. The phase is the amount of time shifted between two acoustic waves relative to the period of the two acoustic waves (e.g., measured in degrees or radians). The delay is a measure of the amount of time shifted between two acoustic waves (e.g., measured in milliseconds). In various embodiments, a time delay is in a range of 0.1 μs to 10 s, including 0.1 μs, 0.2 μs, 0.3 μs, 0.4 μs, 0.5 μs, 1 μs, 5 μs, 10 μs, 15 μs, 20 μs, 25 μs, 30 μs, 35 μs, 45 μs, 50 μs, 60 μs, 70 μs, 80 μs, 90 μs, 0.1 ms to 10 s, including 0.1 ms, 0.2 ms, 0.3 ms, 0.4 ms, 0.5 ms, 1 ms, 5 ms, 10 ms, 50 ms, 100 ms, 500 ms, 1 s, 2 s, 5 s, and 10 s and any values and ranges therein. Delay and phase are often used interchangeably. For example, although "delay" may be described in units of degrees or radians, it is well understood that in certain embodiments, "delay" is an abbreviation for "phase delay." In various embodiments, the phase delay is 0.2, 0.4, 0.5, 0.6, 0.8, 1.0, 1.2, 1.4, 1.5, 1.6, 1.8, 2.0, 2.2, 2.4, 2.5, 2.6, 2.8, 3.0, 3.5, 4.0, 4.5, 5.0, 5.5, 6.0, 6.28 radians and values and ranges therein. In various embodiments, the phase delay is 10, 20, 40, 50, 60, 80, 100, 120, 130, 140, 150, 160, 170, 180, 190, 200, 220, 240, 250, 260, 280, 300, 310, 320, 340, 350, 360 degrees and values and ranges therein. For a single acoustic wave pulse, it is clearer to discuss delay between the peaks of two acoustic wave pulses in terms of time because a phase shift requires a periodic signal. For repeating acoustic waves, the relative delay is often measured terms of phase. For continuous, periodic acoustic waves, delaying an integer number of periods should have no effect because, by definition, a periodic signal exhibits symmetry over full period shifts. For pulses of a repeating acoustic wave (e.g., 1000 cycles of a sine wave), the acoustic wave can be delayed by an integer number of cycles. The beginning and end of the wave packet will have some edge effect when one signal begins/ends before the other. In the middle of the two wave packets, there will be no effect (provided the signals still overlap).

In one aspect, the transducers 150, 400, 450 may be adapted and configured to produce a "focused" acoustic wave by producing a convergent acoustic wave that converges to a point. In another aspect, the transducers 150, 400, 450 may be adapted and configured to produce a "defocused" acoustic wave, e.g., a divergent acoustic wave. In other aspects, the transducers 150, 400, 450 may be adapted and configured to produce a planar acoustic wave (e.g., zero vergence) where the acoustic wave is neither "focused" nor "defocused."

In various aspects, the transducers 150, 400, 450 may be driven at ultrasonic frequencies in a range of about 20.00 kHz to about 12.00 MHz, including, for example, 20 kHz, 50 kHz, 100 kHz, 250 KHz, 400 kHz, 500 kHz, 550 kHz, 600 kHz, 650 kHz, 700 kHz, 750 kHz, 800 kHz, 850 kHz, 900 KHz, 950 kHz, 1 MHZ, 1.1 MHz, 1.2 MHZ, 1.3 MHz, 1.4 MHZ, 1.5 MHZ, 2 MHZ, 3 MHZ, 4 MHZ, 5 MHZ, 10 MHZ, 12 MHz, 20 MHZ, 25 MHZ, 50 MHz, 75 MHZ, 100 MHZ, and any values and ranges therein, such 0.5 to 1.5 MHz, 0.6 to 1.4 MHz, 0.7 to 1.1 MHz, 0.8 to 1.2 MHZ, 1 to 5 MHZ, etc. More particularly, the transducers 150, 400, 450 may be driven at ultrasonic frequencies in a range of about 650.00 KHz to about 2.00 MHz. In one preferred range, the transducers 150, 400, 450 may be driven at ultrasonic frequencies in a range of about 900.00 kHz to about 1.20 MHZ, 975 kHz-1.1 MHz, and as examples, in one embodiment, at about 1 MHZ, 1.03 MHZ, 1.06 MHZ, 1.10 MHZ, 1.20 MHZ, etc.)

Figure 9:
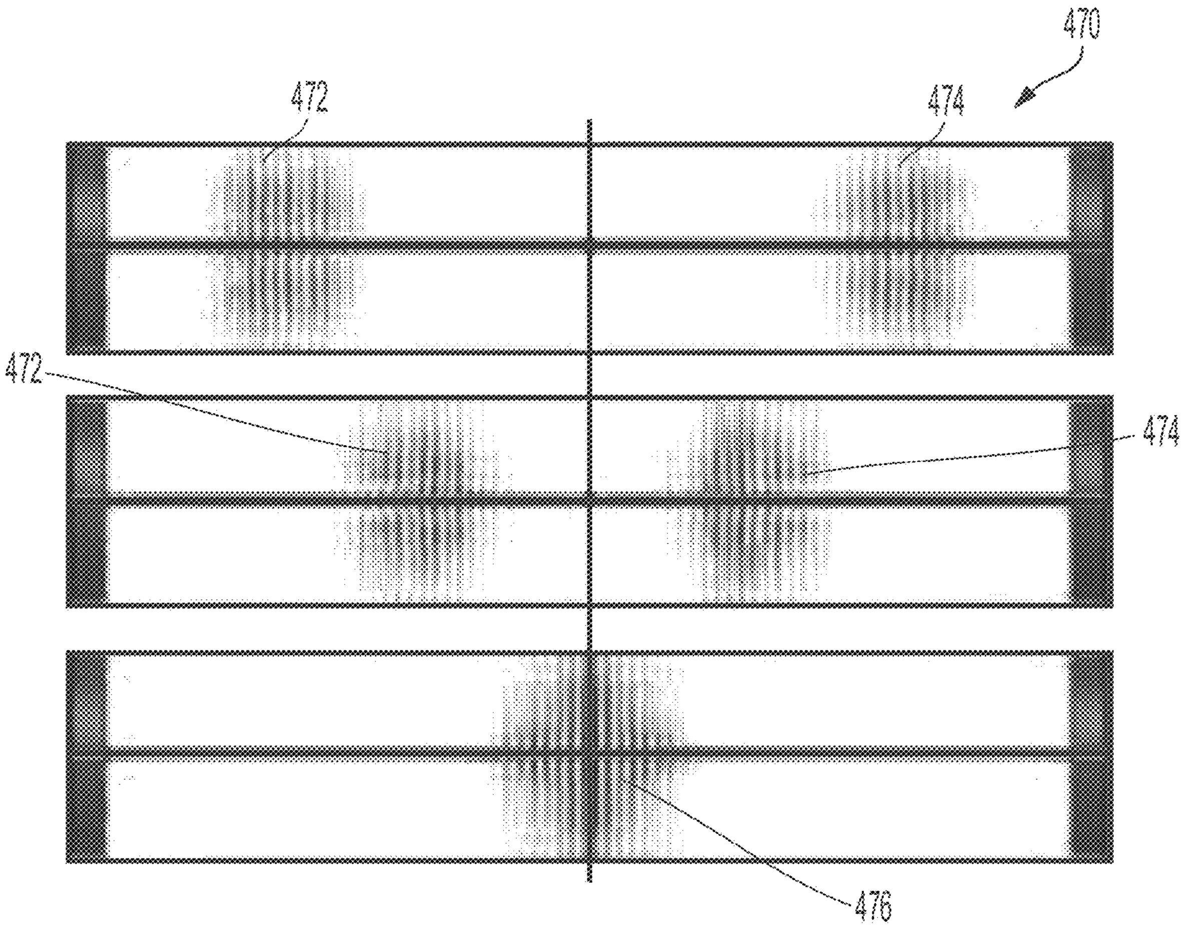
FIG. 9 is a diagram of two acoustic ultrasonic pulses without delay that constructively interfere, according to at least one aspect of the present disclosure.

FIG. 9 is a diagram 470 of two acoustic ultrasonic pulses 472, 474 without delay that constructively interfere, according to at least one aspect of the present disclosure. As previously described, the transducers 150, 400, 450 may be adapted and configured to produce a "focused", "defocused", or planar acoustic wave by coordinating time between multiple acoustic wavefronts and producing wavefronts that constructively interfere. The coordination of acoustic wavefronts is independent of the vergence of the acoustic wavefronts. The point at which the wavefronts focus can be adjusted by delaying one signal relative to another. The diagram 470 shown in FIG. 9 shows two pulses 472, 474 produced without any relative delay. The two pulses 472, 474 constructively interfere when they reach the center and may be said to be focused or defocused in the center to produce a combined pulse 474. If the acoustic pulse 472 on the left is delayed relative to the acoustic pulse 474 on the right, the two pulses 472, 474 would meet at a point left of center, thus shifting the point of constructive interference to the left of center. Likewise, if the acoustic pulse 474 on the right is delayed relative to the acoustic pulse 474 on the right, the two pulses 472, 474 would meet at a point to the right of center, thus shifting the point of constructive interference to the right of center.

In another aspect, a mixture of convergent/divergent/planar acoustic waves may be timed to meet and constructively interfere at one location. A divergent acoustic wave may be timed to meet and destructively interfere at one location. In other embodiments, a mixture of convergent/divergent/planar acoustic waves may be timed to meet and constructively interfere at one, two, three, five, ten, or more locations.

Control of the converging and diverging wavefronts produced by the transducers 150, 400, 450 can be taken into account as part of pretreatment planning. Based on inputs from the pretreatment planning processes the controller can adaptively modulate the transducers 150, 400, 450 such that the acoustic wavefronts coordinate to preferentially target a desired treatment region. In one aspect a digital imaging and communications (DICOM) image from a computerized tomography (CT) or other imaging source could be an input to the device controller to generate customized modulation pattern that optimizes the treatment region for a particular patient. In one embodiment, a DICOM image is used to determine a skull thickness, and/or use image processing to interpret an average skull thickness of a patient and any one or more of intensity, amplitude, and frequency of the treatment is calibrated based on the skull thickness and/or average skull thickness. In one embodiment, average skull thickness of a patient is used to calibrate a treatment intensity. In one embodiment, average skull thickness of a patient is used to calibrate a treatment amplitude. In one embodiment, average skull thickness of a patient is used to calibrate a treatment frequency. In one embodiment, a DICOM image is used to determine a skull density, and/or use image processing to interpret an average skull density of a patient and any one or more of intensity, amplitude, and frequency of the treatment is calibrated based on the skull density and/or average skull density. In one embodiment, average skull density of a patient is used to calibrate a treatment intensity. In one embodiment, average skull density of a patient is used to calibrate a treatment amplitude. In one embodiment, average skull density of a patient is used to calibrate a treatment frequency. In another aspect the pretreatment planning could include selection of a preferred transducer type or arrangement of transducer types that will produce an optimized treatment region for a particular disease state. In another aspect, the patient interface may come in various arrangements that can be selected during pretreatment planning to coordinate the transducer(s) in preferred arrangement for treatment. In one embodiment, volumetric imaging data is acquired to plan the targeting of a sonodynamic treatment.

In one embodiment, "defocused" acoustic waves may be measured based on the volume of tissue treated according to the number of nodes and antinodes. A histogram of intensities or pressures over some volume may be employed to measure "defocused" acoustic waves. In one aspect, a dose-volume histogram may be employed in planning sonodynamic therapy. Alternatively, a cumulative histogram may be employed.

Figure 10:
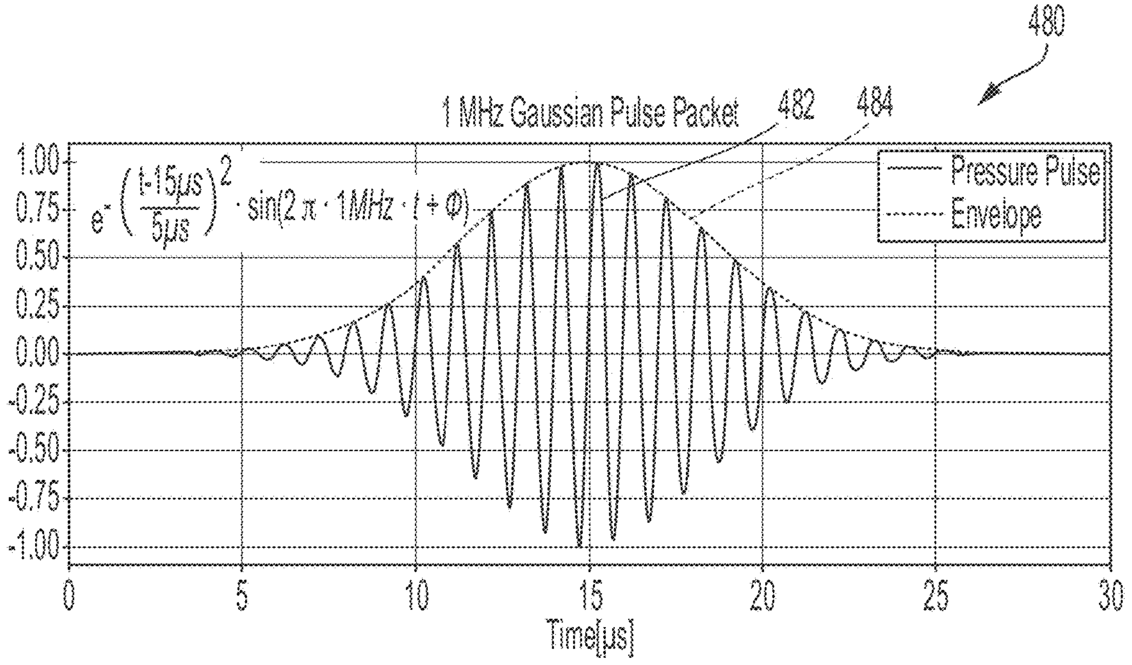
FIG. 10 is a diagram of a pulse packet made of a sine wave signal modulated by a Gaussian pulse signal, according to at least one aspect of the present disclosure.

FIG. 10 is a diagram of an acoustic pulse packet 480 made of a repeating signal modulated by a Gaussian pulse signal, according to at least one aspect of the present disclosure. In one aspect, the acoustic wave generated by the transducer 150, 400, 450 may be amplitude modulated. The acoustic pulse packet 480 may be produced by modulating a repeating signal, such as a sine wave, with a Gaussian pulse where the repeating signal is independent from the Gaussian pulse. When the transducer 150, 400, 450 is driven by the modulated signal, it produces an acoustic pressure pulse 482 where the amplitude varies according to the envelope 484, which is in the form of the Gaussian pulse. Although, in the illustrated example, the repeating signal is a sine wave, the repeating signal may take many forms. The repeating signal may be modulated by rectangular pulses, triangular pulses, or pulses of a predefined mathematical shape. In addition to amplitude modulation, a repeating signal may be pulse-width modulated, duty-cycle modulated, phase modulated, frequency modulated, randomized phase modulated, or may be modulated using any suitable modulation technique to produce a desired acoustic pulse packet. The repeating signal may include inter or intra pulse variations. In various embodiments, a wave comprises a square, rectangular, sinusoidal, triangular, or other wave form with phases that are randomized across all elements in the array, with inner valances having a slight delay during the last 45, 60, 90, 100, 110, 120, 130, 140, 150, 160, 170, 180, 190, 200, 210, 220, 230, 240 or more degrees of the phase randomization. In various embodiments, a duty cycle is randomized from pulse to pulse within a range of 10-50% (e.g., 10-40%, 10-20%, 10-30%, 10-20%, 12-36%, 12-24%, 12-18%, 15-30%, 15-60%, duty cycle. In various embodiments, and average duty cycle across the randomized pulses is between 5-60%, e.g., 5%, 10%, 15%, 20%, 25%, 30%, 35%, 40%, 45%, 50%, 55%, 60% and values and ranges therein.

Figure 11:
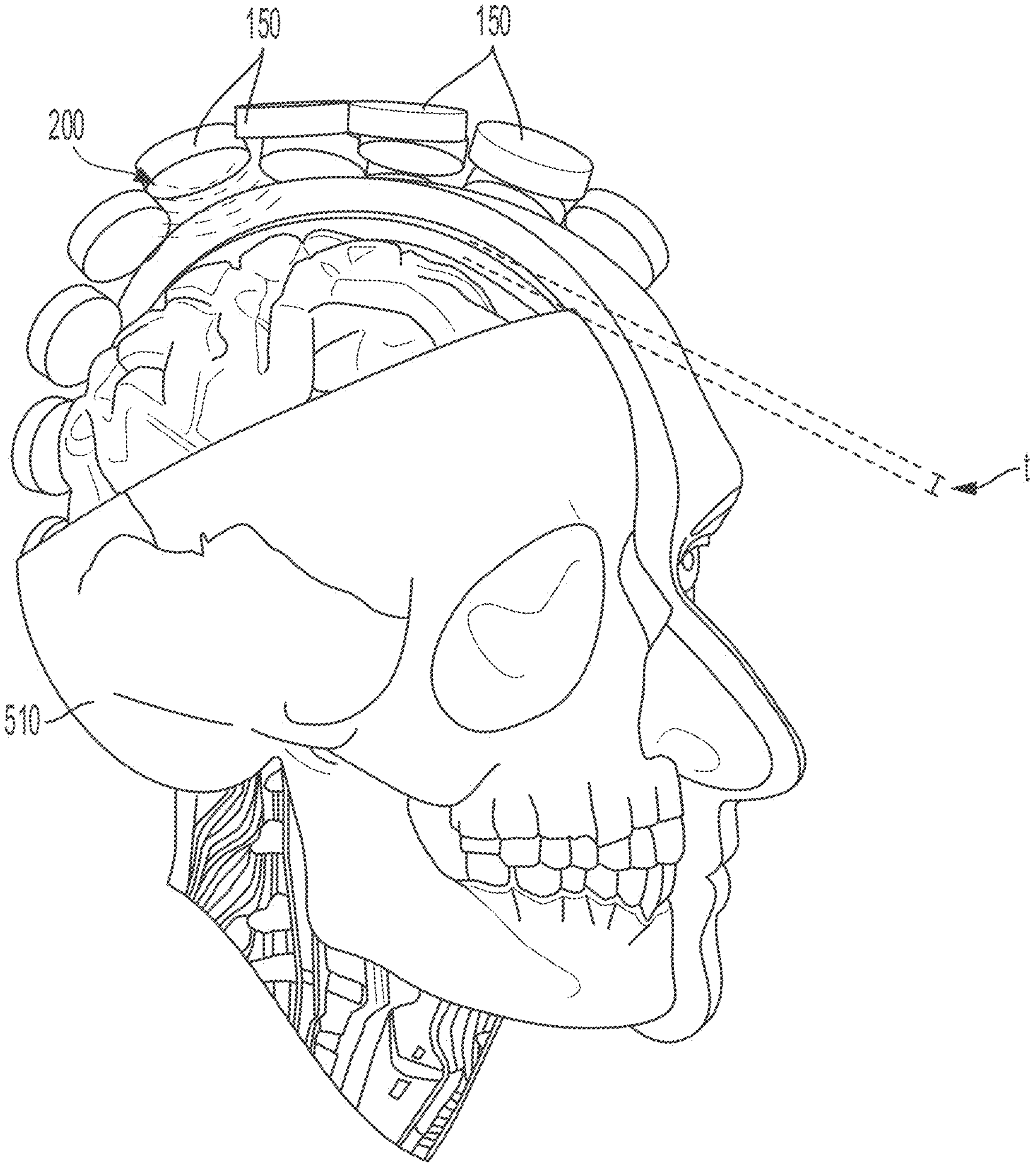
FIG. 11 is a partial cutaway view of a transcranial sonodynamic therapy device placed over the head of a patient showing a partial view of the skull and brain of the patient and multiple transducers with one transducer emitting energy into the brain of the patient, according to at least one aspect of the present disclosure.

FIG. 11 is a partial cutaway view of a transcranial sonodynamic therapy device placed over the head of a patient showing a partial view of the skull 510 and brain of the patient and multiple transducers 150 with one transducer emitting energy 200 into the brain of the patient, according to at least one aspect of the present disclosure. It can be possible to take measurements or get a rough image of the skull 510 as shown in FIG. 11. This can be facilitated if the transducers 150 are fixed to a rigid shell and their relative positions and orientations are known. Rough measurements can be used to adjust the treatment algorithm by measured parameters such as skull thickness, "t" or skull density, "p." Each transducer 150 may send out an acoustic pulse and listen for an echo. The echoes can be used for a quick estimate of the skull thickness, "t," or skull density, "p," under each transducer 150. For treatment of tumors in other body parts of the patient, the sonodynamic therapy device may be adapted and configured to the couple to the body of the patient.

For designs with transducers 150 that have an adjustable focus, the focus of each transducer 150 can be set beforehand with treatment planning. Alternatively, the transducers 150 can adjust their focus automatically based on temperature readings of the head or based on skull thickness, "t," measurements. In one embodiment, temperature readings are used as feedback for increasing or decreasing intensity to stay within a safe thermal dose ranges for tissue, such as a temperature below 45° C., such as 44° C., 43° C., 42° C., 41° C., 40° C., 39° C., 38° C., 37° C., 36° C., or 35° C., and any range or value therein.

The amplitude of the electrical drive signal driving the transducers 150 can be controlled or modulated. In some cases, it can be beneficial to modulate the electrical drive signal driving the transducers 150 based on the temperature of the head or other body part being treated. For example, if the temperature sensors are detecting a sharp rise in temperature, the amplitude of the transducers 150 can be decreased, shut off for a period, or the duty cycle can be decreased. By modulating the intensity of the acoustic pulses, the temporal average acoustic intensity may be regulated to activate the sensitizer while maintaining the temperature of the tumor cells below a temperature (e.g., below 45° C., 44° C., 43° C., or 42° C., such as 41° C., 40° C., 39° C., 38° C., 37° C., 36° C., or 35° C., and any range or value therein) capable of causing thermal damage to the cell and in some circumstances necrotic cell death in some embodiments. In another aspect, sonodynamic therapy can function at a variety of different frequencies. Each frequency can transmit through a skull 510 efficiently with certain thicknesses of skulls. Using a variety of frequencies can allow a non-invasive sonodynamic therapy device 100 to operate on a broad range of skull thicknesses, "t."

In aspects where the transducers 150 can operate at multiple frequencies, the frequency of each transducer 150 can be selected manually by an operator or automatically. As stated in the foregoing description, the transducers 150 may be driven at ultrasonic frequencies in a range of about 20.00 kHz to about 12.00 MHZ, including, for example, 20 kHz, 50 kHz, 100 kHz, 250 kHz, 500 KHz, 1 MHZ, 1.1 MHZ, 1.2 MHz, 1.3 MHz, 1.4 MHZ, 1.5 MHZ, 2 MHz, 3 MHZ, 4 MHZ, 5 MHZ, 10 MHZ, 12 MHZ, and any values and ranges therein. More particularly, the transducers 150 may be driven at ultrasonic frequencies in a range of about 650.00 kHz to about 2.00 MHz. In one preferred range, the transducers 150 may be driven at ultrasonic frequencies in a range of about 900.00 KHz to about 1.20 MHz and more preferably (in some embodiments) at about 1 MHZ, 1.03 MHZ, 1.06 MHZ, 1.10 MHZ, 1.20 MHZ, etc. The frequencies can be preselected by a physician. The frequencies can be selected based on a measurement of head anatomy (e.g., skull thickness, "t" or skull density, "p"). For example, each transducer 150 can send out a sequence of pulses to measure the thickness of the skull 510 closest to it. Based on the result of the skull thickness, "t," or skull density, "p," measurement, an algorithm can be used to select frequencies from a set of frequencies or from a range of frequencies that may be best suited for the skull thickness, "t," or skull density, "p," and energize the transducers 150 accordingly.

The size and shape of the transducers 150, as can be seen in FIG. 2, may vary across various disclosed aspects. For a cost-effective and simple system, larger transducers 150, which may have directional acoustic waves, and which may have more directional acoustic waves, may be used. Large transducers 150 can be made less directional by applying to each transducer 150 an acoustic lens that bends the acoustic waves as described further elsewhere herein. For a system that can conform to the skull, smaller transducers 150, which can radiate more broadly than larger transducers 150, can be used. Such small transducers 150 can have a greater ability to image or beam steer as an array.

In some embodiments, the acoustic wave 200 is focused to a small region (e.g., as shown in FIG. 4), such as a point, sphere, oval, circular etc. region (e.g., 0.1-1 $mm^3$, 0.5-2 $mm^3$, 0.75-2.5 $mm^3$, 3-5 $mm^3$, 2-6 $mm^3$, 1 $mm^3$, 2 $mm^3$, 3 $mm^3$, 4 $mm^3$, 5 $mm^3$, 6 $mm^3$, 7 $mm^3$, 8 $mm^3$ and values and ranges therein), Instead of focusing an acoustic wave 200 to a small point, in some embodiments, the acoustic wave 200 can be defocused to minimize the spatial variation of the acoustic wave intensity in a body part, such as the brain (e.g., over the volume of the entire brain, a portion of the brain, 100 $mm^3$-10,000 $mm^3$, 2000 $mm^3$-6000 $mm^3$, 4000 $mm^3$-8000 $mm^3$, 10,000 $mm^3$, 9000 $mm^3$, 8000 $mm^3$, 7000 $mm^3$, 6000 $mm^3$, 5000 $mm^3$, 6000 $mm^3$, 3000 $mm^3$, 2000 $mm^3$, 1000 $mm^3$, 500 $mm^3$, 250 $mm^3$, 100 $mm^3$, or more) as shown in FIGS. 5 and/or 6. The size and shape of the transducers 150 may defocus or focus each transducer 150. Defocused transducers can be formed using a transducer 150 with a convex emitting surface 310 as seen in FIG. 5. As seen in FIG. 4, design of the transducers can focus the sound from each transducer 150 using a concave emitting surface 304 with a center of curvature where the sound can focus. As shown in FIG. 6, an array of transducers 150*a*-150*h* can be used to generate acoustic waves that are convergent, divergent, or more complex. In various embodiments, the array has a dimension (length, width, diameter, etc.) In various embodiments, the transducers 150*a*-150*h* and/or elements 452, 1302, 1308, 1326, 1327, have a dimension (e.g., length, radius, diameter) in the range of 0.5 mm to 20 mm, including 0.5 mm, 1 mm, 3 mm, 5 mm, 7 mm, 10 mm, 12 mm, 15 mm, 18 mm, and 20 mm including any values and ranges therein. In various embodiments, the transducers 150*a*-150*h* and/or elements 452, 1302, 1308, 1326, 1327, have a dimension (e.g., length, radius, diameter) in the range of 5 mm to 150 mm, including 5 mm, 10 mm, 30 mm, 50 mm, 70 mm, 100 mm, 120 mm, 130 mm, 140 mm, 150 mm, 160 mm, 170 mm, 180 mm, 190 mm, and 200 mm including any values and ranges therein. In some embodiments, the diameter at the exit plane of the transducer is at least 10-50% (e.g., 10, 20, 30, 40, 50% and values and ranges therein) larger than the radius of curvature.

Each transducer 150 can cycle through several frequencies so that at least one of the frequencies can transmit nearly optimally for the given skull thickness, "t" or skull density, "p." Each transducer 150 may also sweep continuously from one frequency to another. A frequency can be pre-selected for each transducer 150 based on the thickness of skull 510 nearest to it (e.g., during treatment planning by the physician). Prior to treatment, each transducer 150 can transmit test signals and monitor the reflected sound to automatically determine which frequency or frequencies can work best for that one of the transducers 150. The test signals can be used to measure the skull thickness, "t," or skull density, "p," directly by measuring delays in pulse echoes, or they can be used to detect the relative amount of reflected acoustic energy.

Each transducer 150 can be made up of a broad-spectrum ultrasonic transducer or can be made up of several smaller transducers (e.g., piezo-electric elements as shown in FIGS. 6-8) designed to work at particular frequencies. Each transducer 150 can have an element specifically designed to monitor the waves reflected from the head. In the case where the transducers 150 are made of several smaller transducers 150, while one transducer 150 is transmitting sound, the other transducers 150 may be used to transmit and/or monitor the incoming acoustic pulses.

Of all the frequencies that work with sonodynamic therapy, a subset of frequencies can be selected to best cover a range of common skull thicknesses, "t." Frequencies that share many common factors (e.g., harmonics such a 1 MHz and 2 MHZ) may not make good choices to cover the greatest number of skull thicknesses because many of the transmission peaks between the two frequencies can be shared. Frequencies without many or any common factors (e.g., coprime numbers) may make for good choices for frequencies because the transmission peaks can occur at different skull thicknesses. In one embodiment, a sensor detects ultrasound signals and the system reviews a signal spectrum to identify harmonics, subharmonics, and/or ultraharmonics to alter the ultrasound signal frequency, intensity, or other parameter.

Figure 12:
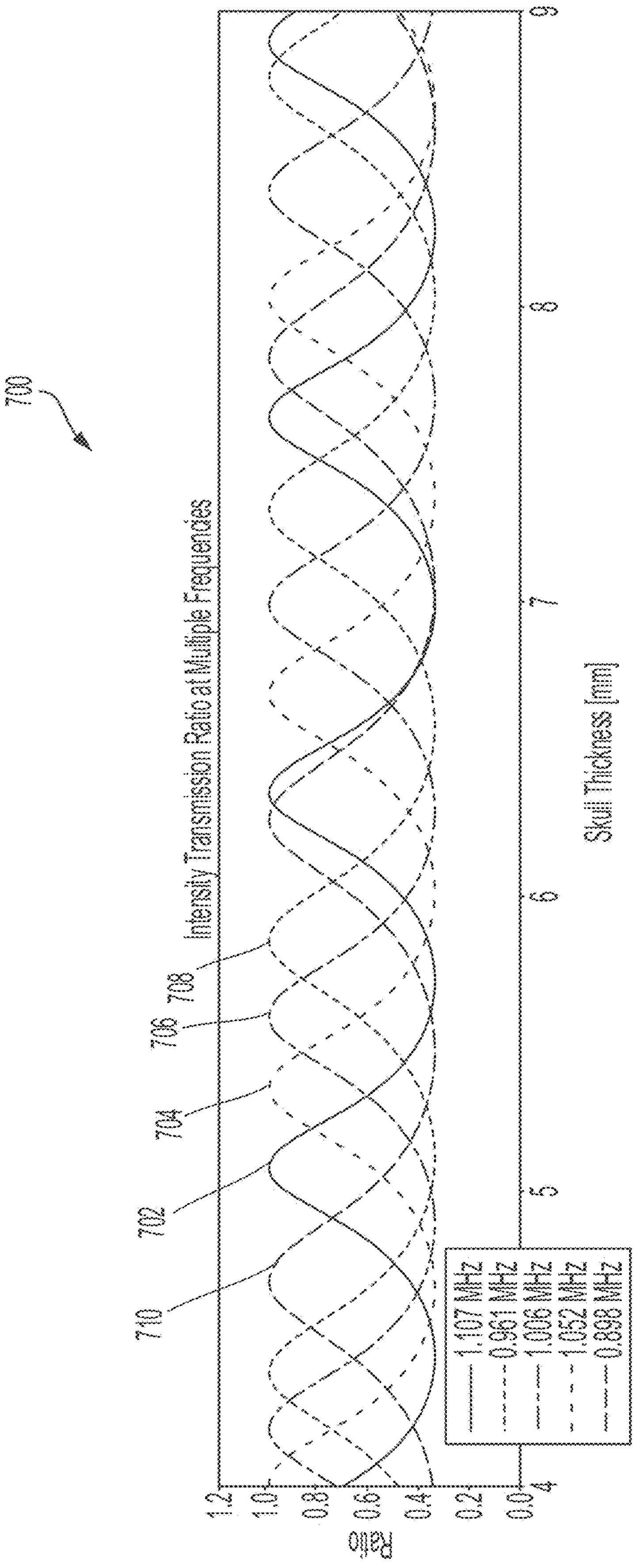
FIG. 12 is a chart showing an intensity transmission ratio across multiple frequencies, according to at least one aspect of the present disclosure.

FIG. 12 is a chart 700 showing an intensity transmission ratio across multiple frequencies, according to at least one aspect of the present disclosure. As shown in FIG. 12, the transmission of 5 different frequencies across different skull thicknesses between 4 mm and 9 mm. A first frequency 702 at 1.107 MHZ, a second frequency 704 at 1.052 MHZ, a third frequency 706 at 1.000 MHZ, a fourth frequency 708 at 0.961 MHZ, and a fifth frequency at 0.898 MHZ. There can be good coverage of different skull thicknesses. In this example, each skull thickness can have at least one frequency that can transmit 75% or more of its energy. This can be accomplished with frequencies between about 900 kHz to 1.1 MHZ (e.g., 898 kHz and 1.107 MHZ), a range of only 0.2 MHz.

Transmission of sound through an absorbing layer of tissue may not monotonically decrease as function of thickness. Instead, transmission can be enhanced when the thickness of the skull is a multiple of half the wavelength of the sound in that layer. Similarly, when the thickness of the skull is an odd multiple of quarter wavelengths (halfway between $\lambda/2$ multiples), the transmission can be reduced.

Figure 13A:
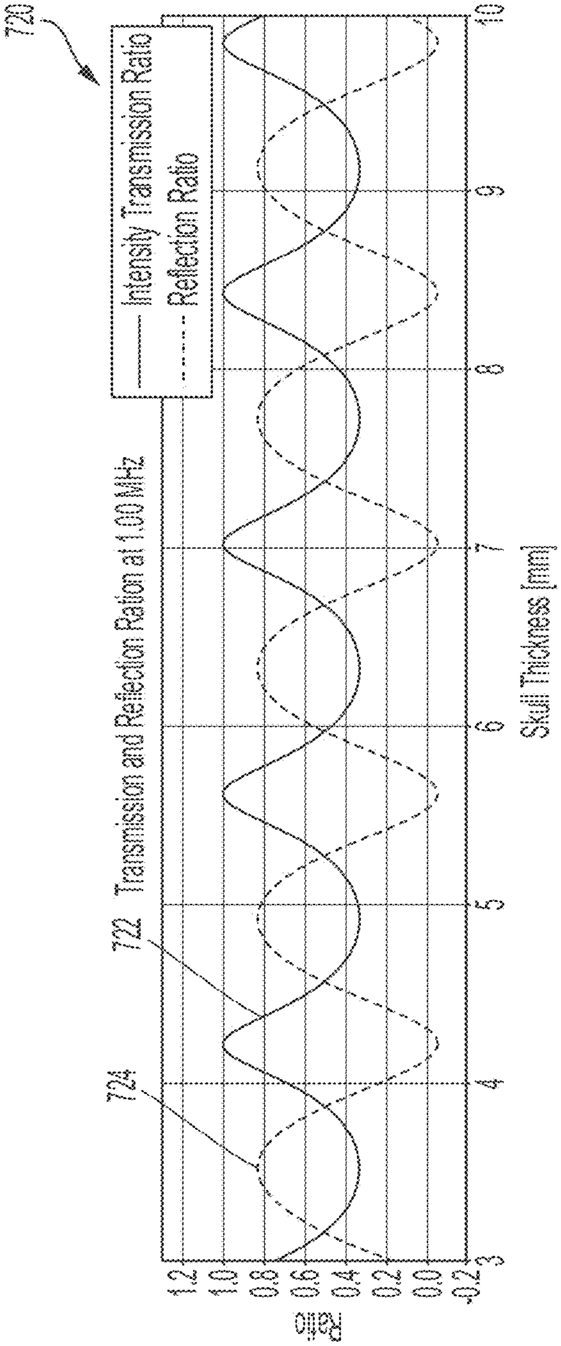
FIG. 13A is a chart showing a transmission and reflection ratio at 1 MHz versus skull thickness in millimeters, according to at least one aspect of the present disclosure.
Figure 13B:
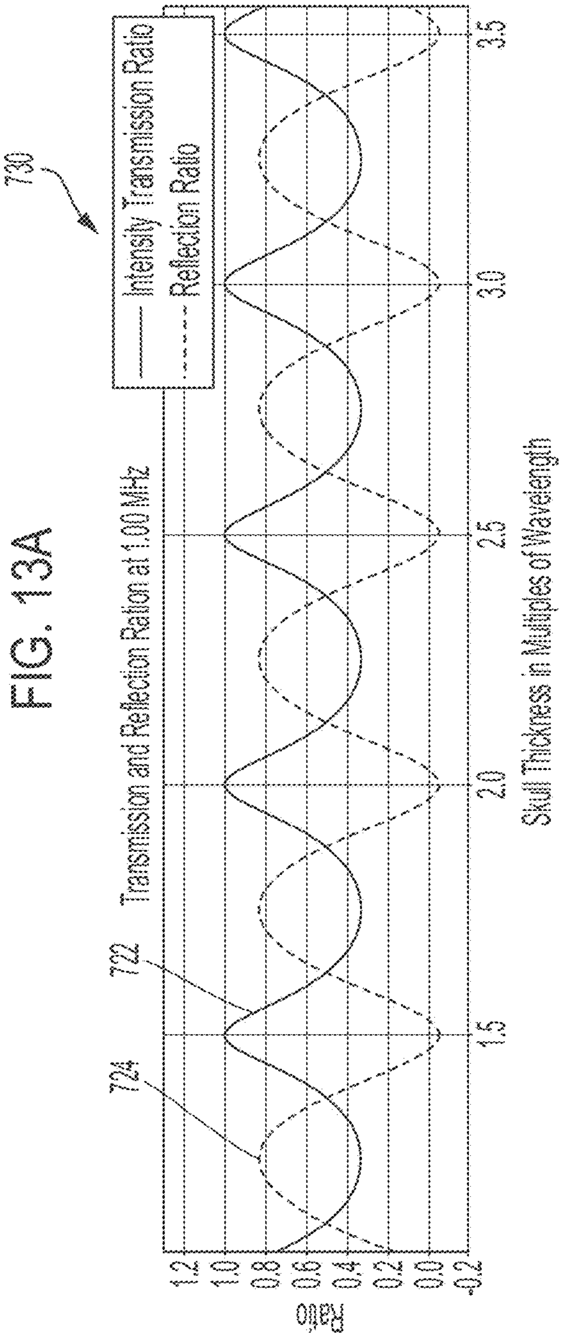
FIG. 13B is a chart showing a transmission and reflection ratio at 1 MHz versus skull thickness in wavelengths, according to at least one aspect of the present disclosure.

FIG. 13A is a chart 720 showing an intensity transmission and pressure reflection ratio at 1 MHz versus skull thickness in millimeters and FIG. 13B is a chart 730 showing a transmission and reflection ratio at 1 MHz versus skull thickness in wavelengths, according to at least one aspect of the present disclosure. As shown in FIGS. 13A and 13B, the transmission of a 1 MHz soundwave through various skull thicknesses. FIG. 7A shows the skull thickness in millimeters and FIG. 13B shows the skull thickness in multiples of wavelength of the intensity transmission ratio 722 and the reflection ratio 724. The intensity transmission ratio 722 can reach a peak whenever the skull is a multiple of a half wavelength. Likewise, the ratio of sound reflected shown as the reflection ration 724 can be at a minimum whenever the skull is a multiple of a half wavelength.

Figure 14B:
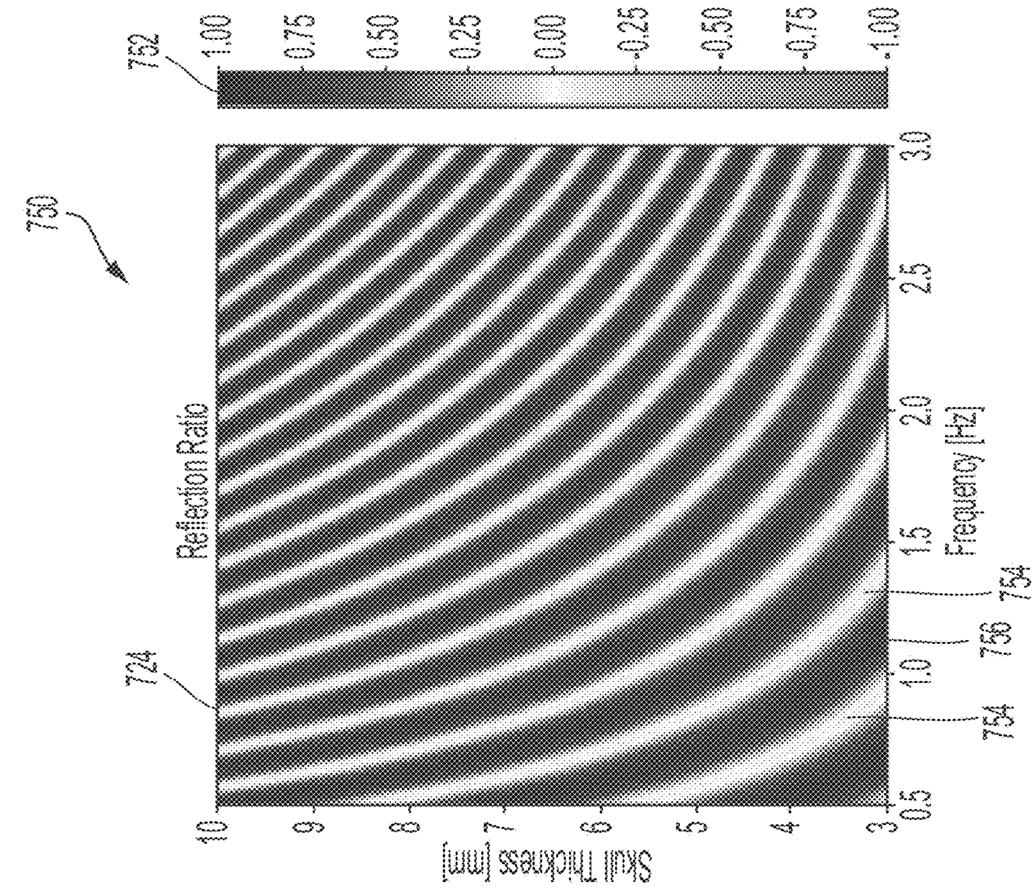
FIG. 14B is a chart showing a reflection ratio as a function of frequency, according to at least one aspect of the present disclosure.
Figure 14A:
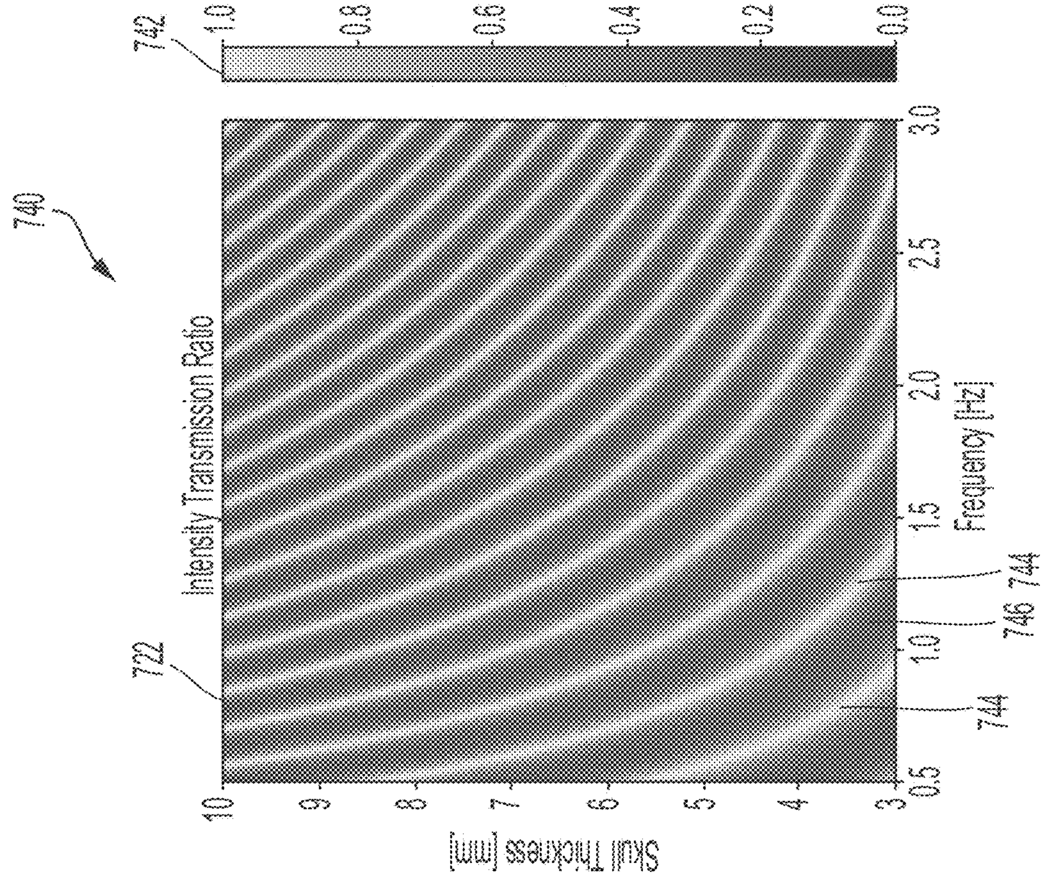
FIG. 14A is a chart showing an intensity transmission ratio as a function of frequency, according to at least one aspect of the present disclosure.

The intensity transmission ratio 722 and the pressure reflection ratio 724 can be functions of both the skull thickness and the frequency. FIG. 14A is a chart 740 showing an intensity transmission ratio 722 as a function of frequency and FIG. 14B is a chart 750 showing a reflection ratio 724 as a function of frequency, according to at least one aspect of the present disclosure. To the right of the chart 740 in FIG. 14A is a scale 742 of the intensity transmission ratio 722 ranging from 0.0 to 1.0 and the right of the chart 750 in FIG. 14B is a scale of the reflection ratio 724 ranging from −1.0 to +1.0. FIGS. 14A and 14B show how the intensity transmission ratio 722 and the reflection ratio 724 change with skull thickness and frequency. Negative reflection ratios can be achieved wherever peak transmission may be occurring. Negative reflection ratios can indicate that the reflected wave can be phase shifted 180° relative to the incident wave. As shown in the chart 740 of FIG. 14A, the intensity transmission ratio 722 has a maximum ratio 744 of about 1.0 and a minimum ratio 746 of about 0.4, which is consistent with the maximum/minimum ratios shown in charts 720, 730 in FIGS. 13A and 13B. The chart 750 shown in FIG. 14B shows that the reflection ratio 724 has a minimum ratio 754 of about 0.0 and a maximum ratio 756 of about 0.8, which is consistent with maximum/minimum ratios shown in the charts 720, 730 in FIGS. 13A and 13B.

Frequencies that are different by an irrational number may make good choices because they can have peak transmissions at different thicknesses. The golden ratio (e.g., the "most irrational number") may be useful in selecting frequencies. It may not be sufficient for selected frequencies' transmission to avoid peaking at the same skull thickness, "t."

It can also be allowable for two frequencies to share a peak transmission at a certain thickness, provided that the shared peak occurs at a skull thickness, "t," outside of the thicknesses expected to occur naturally. If the device can select the best frequency (e.g., the greatest transmission ratio) at each skull thickness, "t," then to get optimal coverage across many skull thicknesses, "t," with a limited number of frequencies can mean to maximize the average transmission ratio of the best frequency across the selected skull thicknesses, "t," or to maximize the minimum transmission ratio of the best frequency within the selected skull thicknesses, "t."

Hair on the patient's head may need to be shaved or shortened to allow for efficient transmission of sound into the brain. Some aspects may allow the hair to remain untouched. A comb-like structure can be able to pass through hair to contact the skull in many locations to transmit sound. The hair may also be wet and matted down to allow for the sound to transmit relatively unimpeded.

Figure 15:
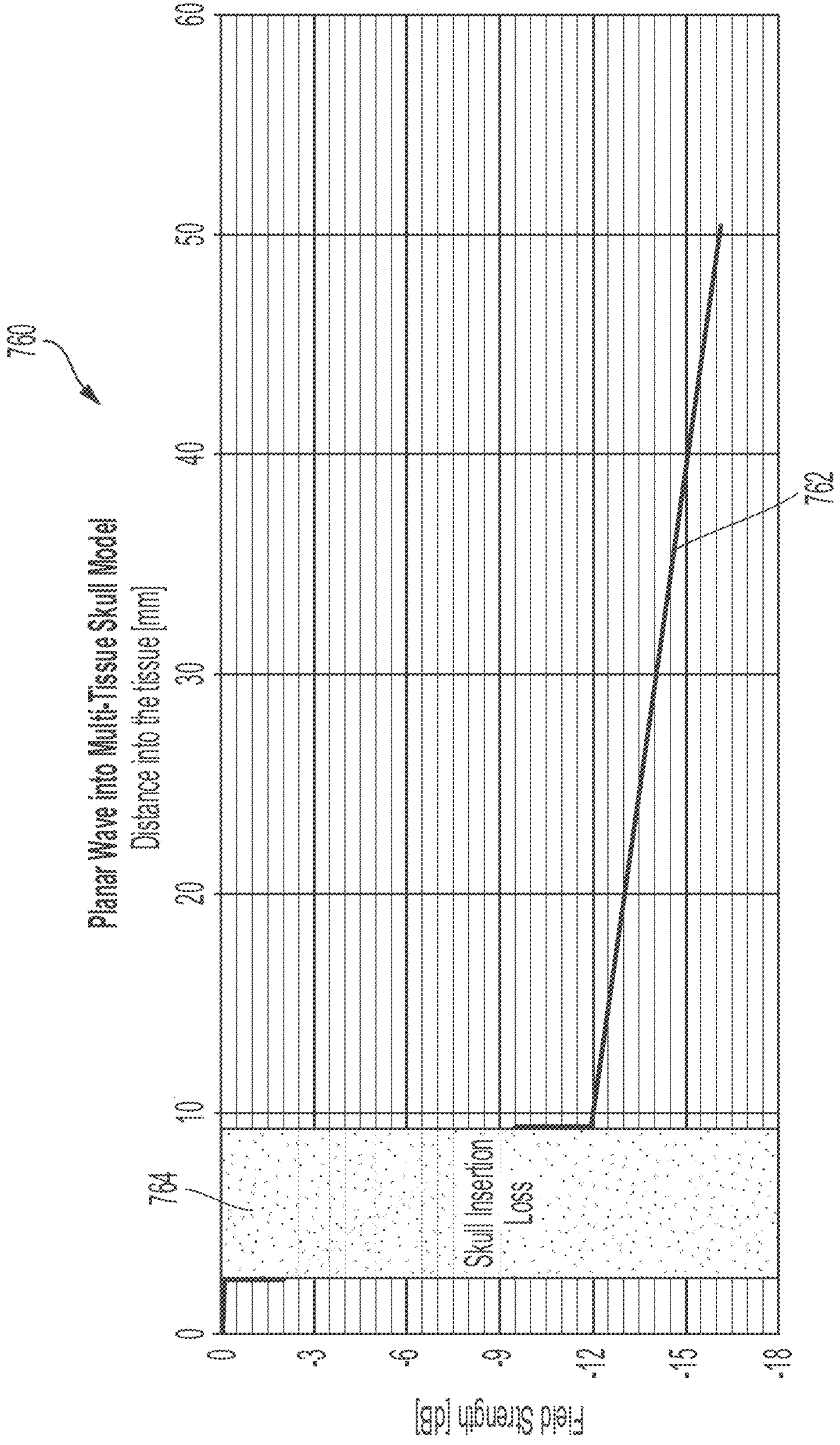
FIG. 15 is a chart showing the field strength of a planar wave into a multi-tissue skull model, according to at least one aspect of the present disclosure.

FIG. 15 is a chart 760 showing the field strength of a planar wave 762 into a multi-tissue skull model, according to at least one aspect of the present disclosure. With reference to FIG. 15, the skull may absorb a large proportion of the ultrasonic energy in a short distance. The insertion loss 764 (the amount of energy that can be lost by adding the skull into the acoustic wave 200) can be centered around 12 dB. Every additional 3 dB worth of loss can correspond to approximately half of the energy being reduced. A 12 dB loss can be equivalent to a sixteenth of the energy introduced at the surface of the skin being left at the surface of the skull. Because of this, the skull may heat up during transcranial sonodynamic therapy.

Table 1 is a summary of the parameters that can be used in the model of the skull. In addition to the intrinsic acoustic properties of the skull, the skin can be assumed to be 2.5 mm thick, and the skull can be assumed to be around 6.8 mm thick. FIG. 15 shows the acoustic intensity in terms of field strength (dB) as a function of distance within the head model. The insertion loss 764 highlighted region emphasizes the jumps of energy lost at the interfaces and steep attenuation within the skull.

TABLE 1

Parameters Used In the Model of the Skull Interface Transmission Loss

| Interface | Ratio | dB |
|---|---|---|
| Skin-Bone | T = 0.650 | −1.87 |
| Bone-Skin | T = 0.567 | −2.46 |

| Frequency | | 1 MHz |
|---|---|---|
| Attenuation | Skin | −0.50 dB/(cm-MHz) |
| | Bone | −11.10 dB/(cm-MHz) |
| | Brain | −1.00 dB/(cm-MHz) |
| Acoustic Impedance | Skin | 1.99 kg/(sec-$m^2$) × $10^6$ |
| | Bone | 7.75 kg/(sec-$m^2$) × $10^6$ |
| | Brain | 1.60 kg/(sec-$m^2$) × $10^6$ |

The model uses an average of various human skull thicknesses. The thickness of the "frontal, parietal and occipital bones were (in mm) 6.58, 5.37 and 7.56, respectively, for the male; and 7.48, 5.58 and 8.17, respectively, for the female." As mentioned elsewhere herein, human skulls vary considerably by gender and anatomical location. The model can represent an average amount of attenuation, but thicker sections of skull can have a greater amount of attenuation. In general, every additional 2.7 mm worth of skull can increase the attenuation by 3 dB (a factor of 2).

This model can be based on a simple plane wave model impinging on planar layers of tissue. Each layer of tissue can be assumed to be homogenous and uniform thickness. The effect of the acoustic wavelength (A) matching with various thicknesses of skull are ignored in this model. It can also be assumed that all reflected waves are lost and do not reenter the brain.

Pichardo et al. investigated the transmission of ultrasound through freshly excised human skulls at various frequencies. They report the ratio of absorbed energy for seven skulls at several locations at the frequencies of 0.270, 0.836, and 1.402 MHZ. While they did not measure the energy lost at 1 MHz specifically, their study allows interpolation and estimation that the insertion loss can be centered around 12 dB. Their study also can confirm that the insertion loss can be expected to vary by skull and anatomical location.

Figure 16:
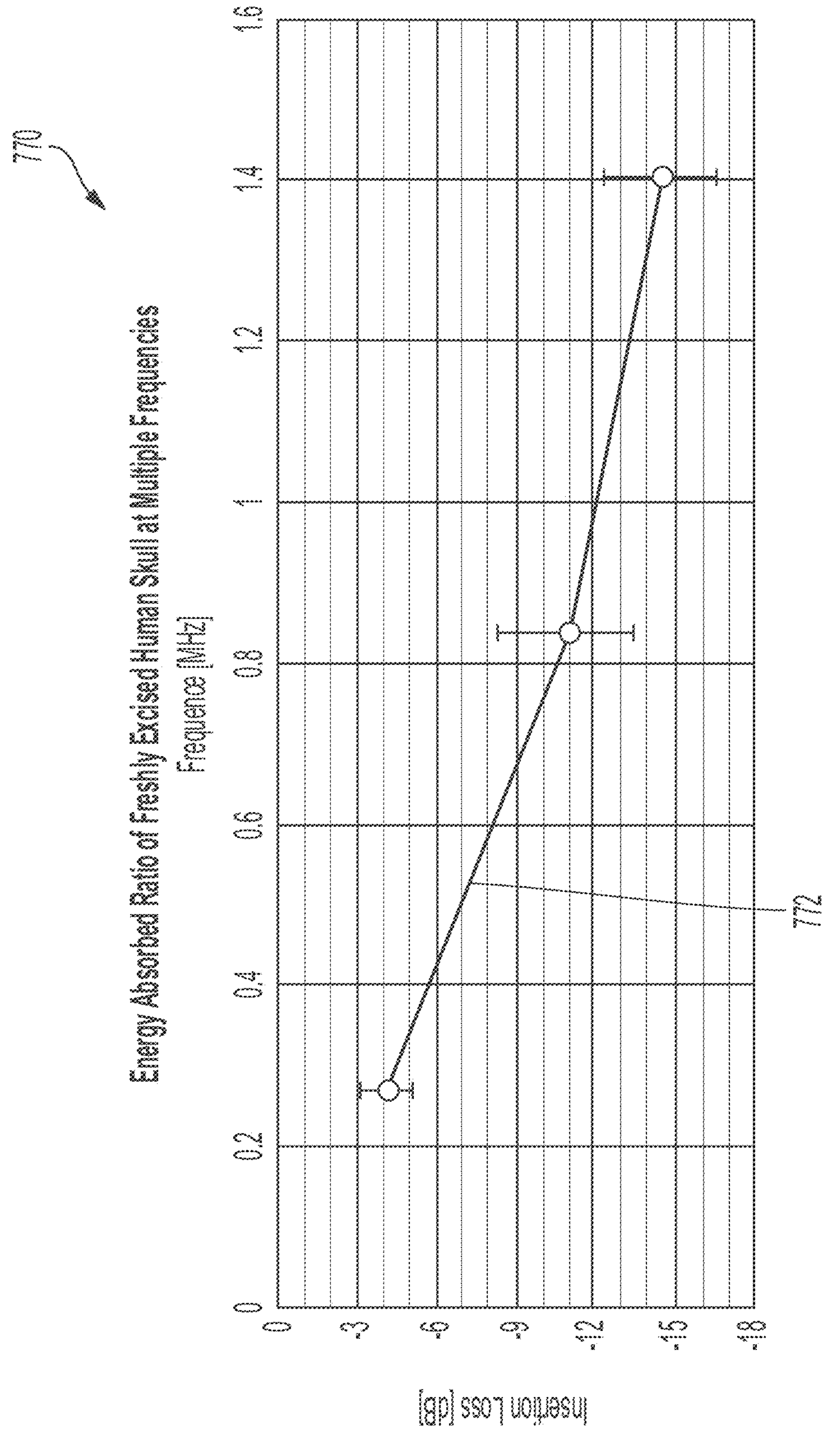
FIG. 16 is a chart showing the energy absorbed ratio of a freshly excised human skull at multiple frequencies, according to at least one aspect of the present disclosure.

FIG. 16 is a chart 770 showing the energy absorbed ratio 772 of a freshly excised human skull at multiple frequencies, according to at least one aspect of the present disclosure. As shown in FIG. 16, Pinton et al. also measured the attenuation at 1 MHz of nine points along an 8 mm thick section of skull bone and found an insertion loss of 12.6±1.33 dB (higher loss due to a thick skull section). Both the simplified head model and measurements taken from different laboratories agree that the insertion loss (the amount of energy lost by adding the skull into the model) can be centered around 12 dB (a factor of 16) with considerable variation.

The energy lost as the sound passes through the skull may be converted into heat primarily in the skull. The temperature of the skull can begin to heat up and, over time, heat can disperse to nearby tissue. Most of the heating can originate at the outer surface of the skull and disperse into the skin and other layers of bone. Above certain intensities, the blood can be unable to transport enough heat away, and the temperature in the bone and skin can rise to unsafe levels. Adding more transducers into the system can decrease the intensity at which this threshold can be reached because the blood can be warmed by each successive transducer it passes and lose its ability to absorb additional heat from the tissue.

There can be several ways to combat the effects of heating. In particular, cooling, intermittent treatment, monitoring, and transducer modulation can be used to reduce the consequences of heating.

Figure 17:
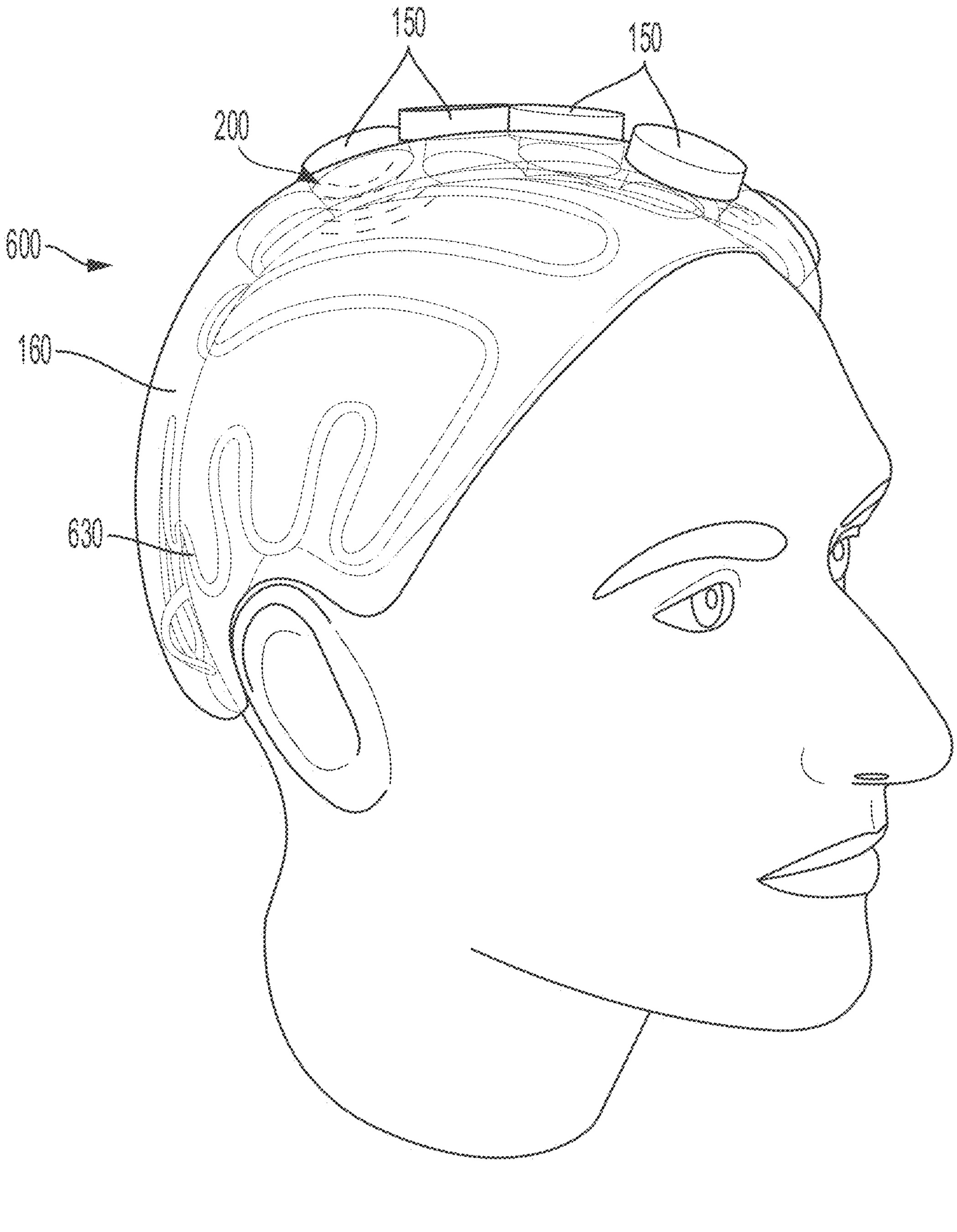
FIG. 17 is a partial cutaway view of a transcranial sonodynamic therapy device placed over the head of a patient showing a partial view of the multiple transducers and a full view of a cooling system, according to at least one aspect of the present disclosure.

FIG. 17 is a partial cutaway view of a transcranial sonodynamic therapy device placed over the head of a patient showing a partial view of the multiple transducers 150 and a full view of a cooling system 600, according to at least one aspect of the present disclosure. The cooling system 600 shown in FIG. 17 may be implemented to keep the temperature of the skull and surrounding tissue within safe levels. A cooling layer (e.g., of water) may be provided between the transducers 150 and the patient's head. The cooling layer can be made of a flexible membrane or balloon that can conform to each patient's head. A large cooling layer may be reusable and, thus, may involve cleaning between each use.

The cooling system 600 can be made of a flexible cavity (not shown in FIG. 17) with an inlet and an outlet for a coolant such as water to circulate. The head of the patient can be inserted into a concave shape (e.g., a "bowl") with an elastic opening. The elastic opening can seal against the head of the patient. Water can fill up the space between the patient's head and the bowl.

Similar to the single cavity design, water can be circulated to keep the temperature of the water from rising. One advantage of such a system can be that water in the cooling system 600 can be in direct contact with the patient's head. The air around the patient's hair can be removed by the water, which may help couple the ultrasound transducers 150 to the patient's head.

Figure 18A:
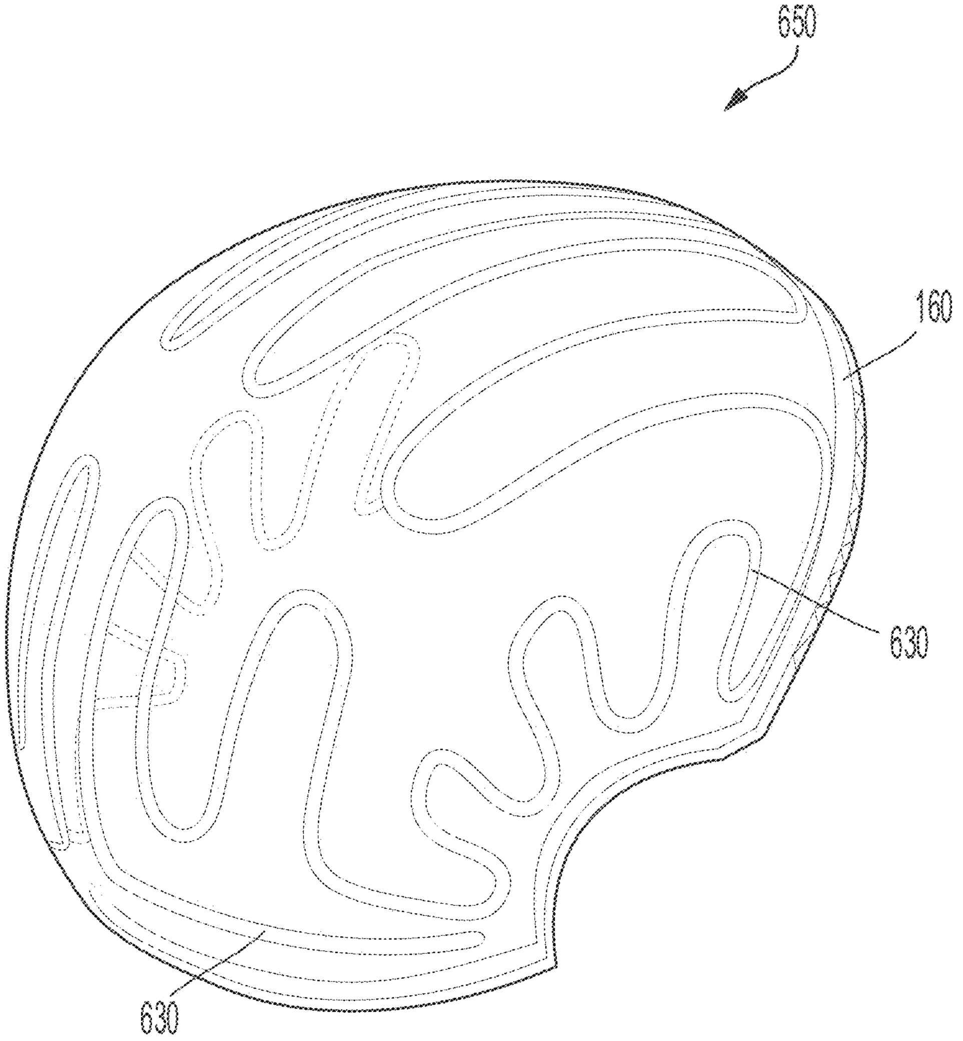
FIG. 18A is a perspective view of a patient interface, according to at least one aspect of the present disclosure.

FIG. 18A is a perspective view of a patient interface 650, according to at least one aspect of the present disclosure. The cooling system 600 can be a cap 160 with cooling channels 630 distributed throughout. The cap 160 can have one long loop of cooling channels 630, or it can have several independent loops. A system with several cooling loops can be connected to a single inlet and outlet tube via a manifold, or they can be controlled independently. Water or other heat transfer fluid can be circulated through the cooling channels 630 to exchange heat generated either by the transducers 150, the patient's body, or a combination thereof.

Figure 18B:
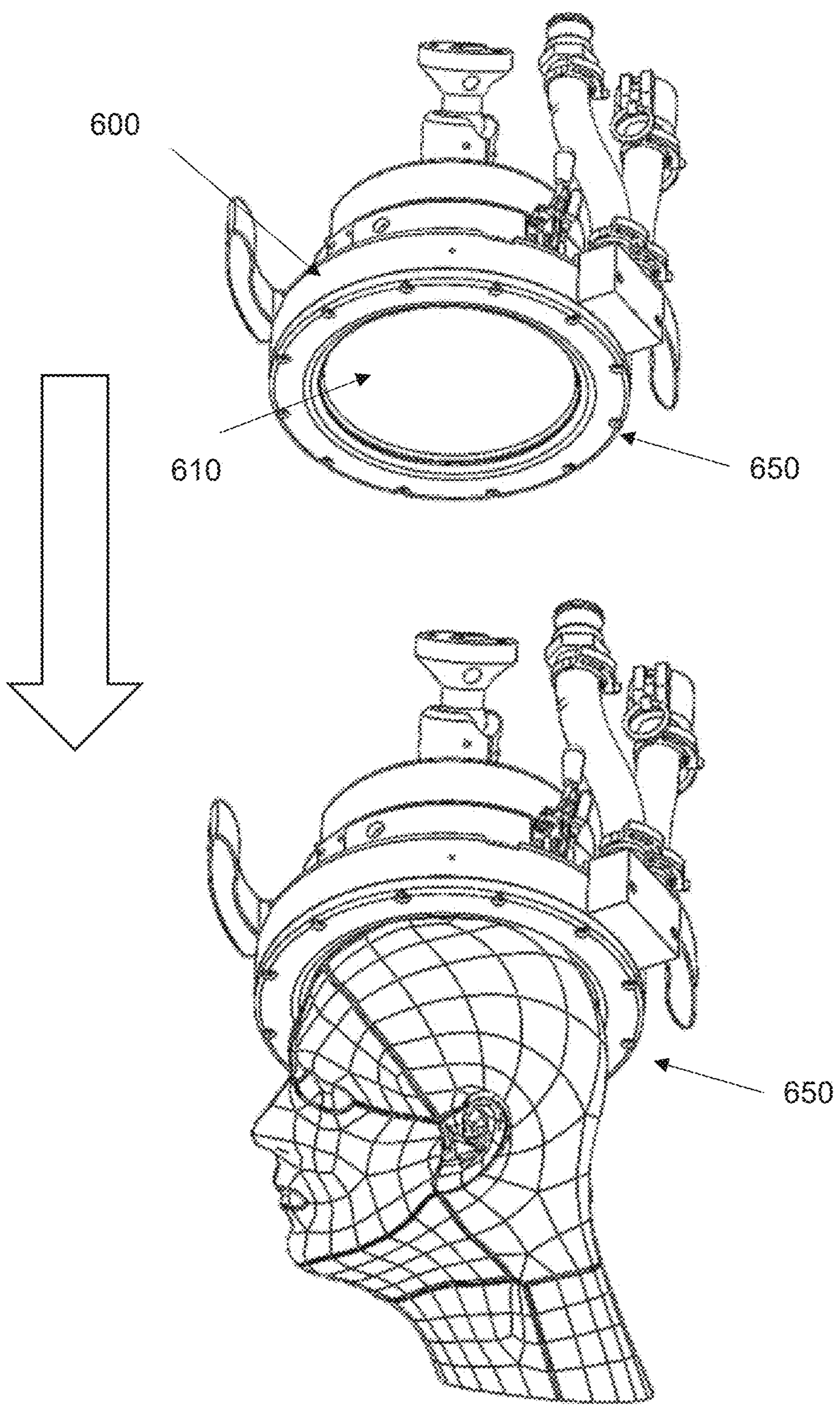
FIG. 18B is a schematic view of a patient interface with a fluid filled coupling membrane, according to at least one aspect of the present disclosure.

FIG. 18B illustrates an embodiment of the patient interface 650 with an integrated cooling system 600. In one embodiment, a thin film compliable membrane 610 that is installed across the face of the transducer that is flexible, elastic, and configured to conform to a shape of the body of the patient for treatment. In one embodiment, a thin film compliable membrane 610 forms a fluid-filled pocket configured for thermal and/or acoustic coupling to the portion of the body of the patient. In one embodiment, the cooling system 600 comprises the membrane 610 to provide active cooling to the portion of the body of the patient for treatment.

In one embodiment, the coupling membrane 610 is configured to trap a degassed circulating fluid (e.g., water, saline, cooling fluid, acoustic coupling material, gel) between the ultrasound array and the patient. The degassed circulating fluid provides an acoustical coupling pathway from the individual ultrasound elements to the membrane 610 face. The circulating fluid also provides active cooling that mitigates the potential for residual heat buildup at the patient entry plane and/or the ultrasonic elements. A manifold with a plurality of nozzles may be incorporated into the membrane assembly to further direct circulating fluid towards the wet face of the coupling membrane to increase cooling capacity directly at the patient interface.

In one embodiment, the coupling membrane 610 with fluid backing provides a conformable interface that adapts and molds to the shape of the local anatomy at the treatment site. In one embodiment, ultrasonic coupling gel is additionally placed at the treatment site as part of the interface between the patient and coupling membrane. The conformable fluid filled membrane 610, along with ultrasonic coupling gel ensures good acoustical coupling between the transducers and patient. The conformable fluid filled membrane 610, along with ultrasonic coupling gel ensures good thermal coupling between the transducers and patient.

In one embodiment, the coupling membrane 610 is the only portion of the sonodynamic treatment device that has direct patient contact. The membrane 610 is made from a well characterized elastomer with a known biocompatibility profile for patient contact.

In one embodiment, the coupling membrane 610 can be removed and replaced as needed between patient uses. In one embodiment, the coupling membrane 610 is attached to a de-couplable bezel or housing that can be removably attached (e.g., with one or more interfaces, locking features, latches, threads, etc.) from the ultrasound array.

In various embodiments, the fluid (e.g., water) can flow past all regions of the body (e.g., head, torso, etc.) that can absorb heat. The fluid can be pumped to keep the fluid temperature from rising which would decrease the cooling efficacy of the fluid. Like patches with multiple transducers 150, each patch may have its own cooling channels 630. The cooling channels 630 can be fluid-filled tubes that may be larger and heavier than the wires going to the transducers 150. The number of unique cooling channels 630 can be optimized to avoid excessive weight in the cooling layer.

The effect of heating can be readily monitored with temperature sensors and reduced with the fluid cooling system 600. A layer of cool, degassed water between the ultrasonic transducers 150 and the head can serve a dual function of coupling the head to the transducers 150 and controlling the temperature of the skull. Prior to any insonication, the head can be cooled for several minutes by a constant flow of cool water. Once the treatment begins, the temperature of the skull can be monitored continuously, which can modulate the treatment over the entire skull, or it can individually modulate each transducer 150. Even without continuous monitoring of the skull temperature, a safe treatment algorithm can be devised with intermittent treatment and continuous cooling with a margin of safety for all patients. Intermittent treatment can also be more effective than the same effective treatment time done continuously due to the rate limiting step of oxygen diffusion around the sonosensitizer.

It can be likely that just surface temperature monitoring can be necessary. In any case, it can be possible to monitor the temperature throughout the skull using a variety of thermometry of deep-seated tissues. Any surface measurements of temperature may need to be insulated from the cooling layer of water to prevent the probe from being dominated by the cooling layer's effect.

In one embodiment, the temperature of the patient's head is monitored. Temperature sensors (not shown) are placed between the cooling layer and the head, so the temperature sensor can read the head temperature and/or the cooling layer temperature.

There can be several ways that the temperature sensor can be isolated from the temperature of the cooling layer. A layer of insulation can be placed between the cooling layer and each temperature sensor. In such instances, the area around each temperature sensor can receive less or no cooling.

Figure 19:
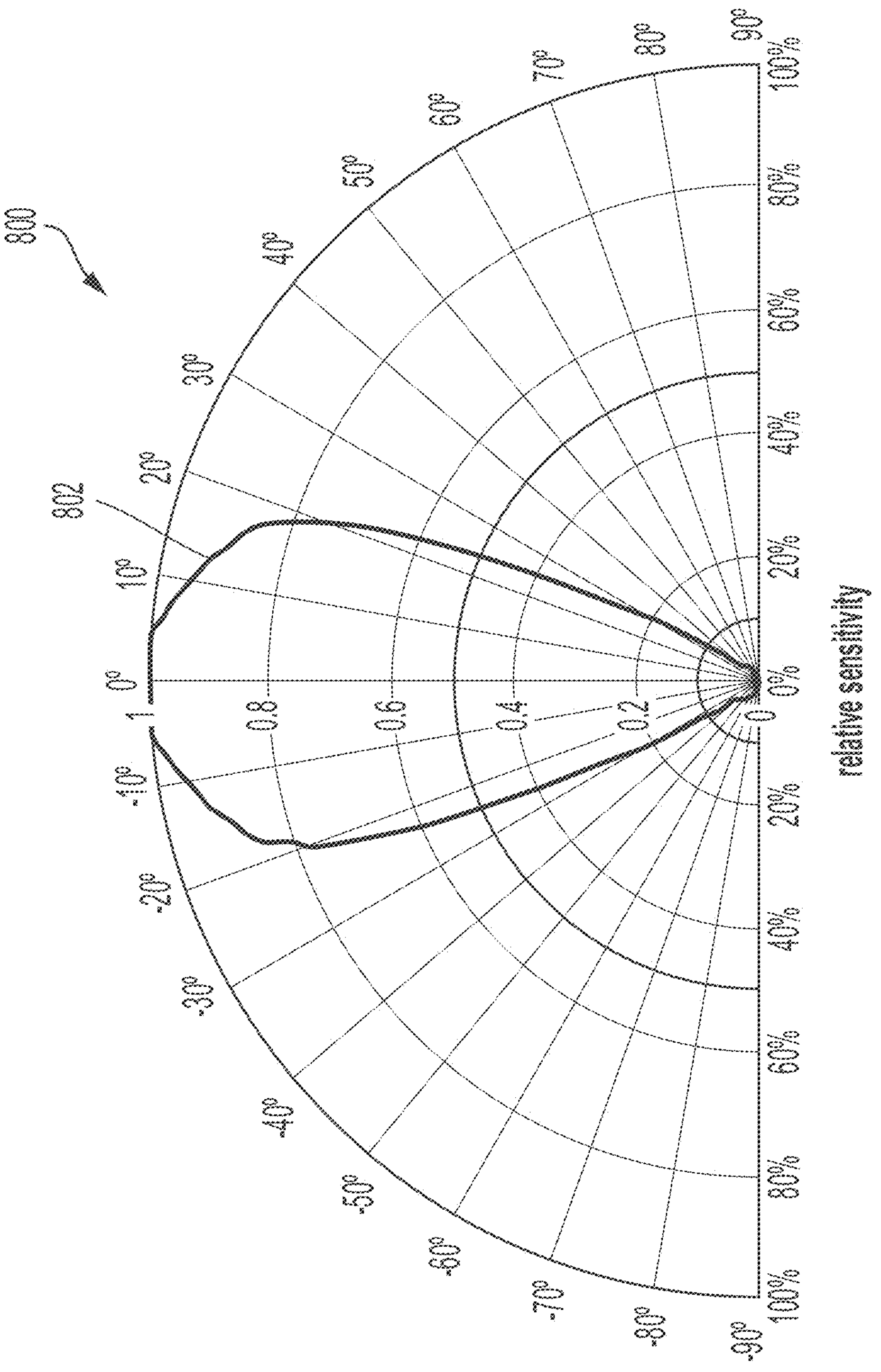
FIG. 19 is a chart showing the relative sensitivity plot of an infrared (IR) temperature sensor, according to at least one aspect of the present disclosure.

FIG. 19 is a chart 800 showing the relative sensitivity plot 802 of an infrared (IR) temperature sensor, according to at least one aspect of the present disclosure. As shown in FIG. 19, a temperature probe (not shown) that measures only in one direction (e.g., unidirectional) can be utilized. An example of a unidirectional temperature sensor can be an IR temperature sensor. IR temperature sensors measure the infrared light being emitted by an object via black body radiation. IR temperature sensors accept radiation coming in from a small range of angles (e.g., an acceptance cone). In this application, one or more IR sensors can be oriented so that the cone of acceptance of each sensor can be facing the patient's head. One or more methods above can be combined to accurately monitor the temperature of the patient's head.

Figure 20:
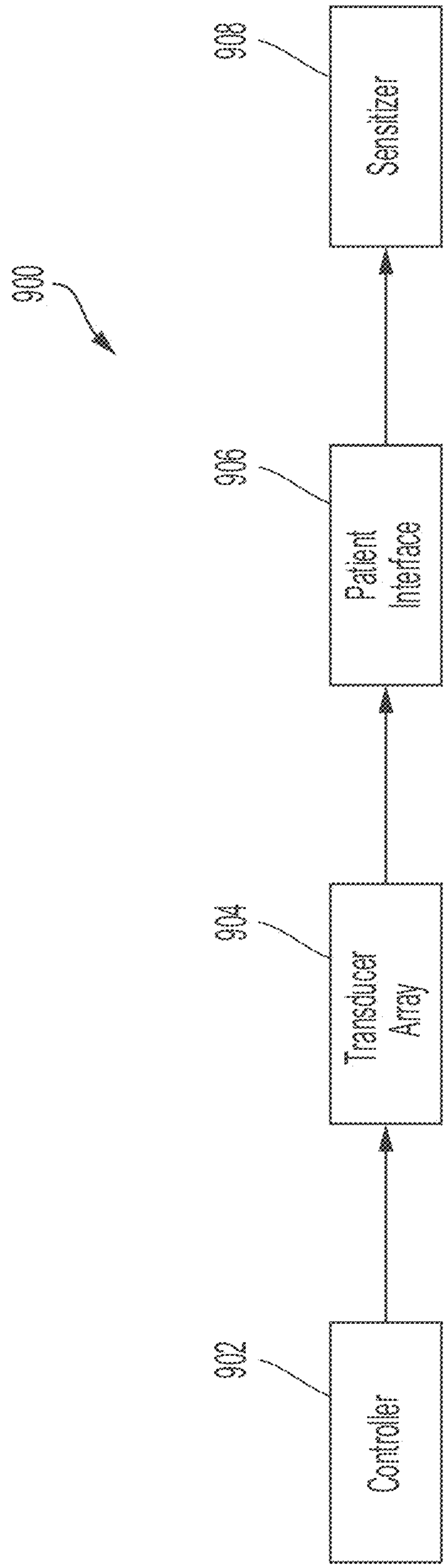
FIG. 20 is a block diagram of a general non-invasive sonodynamic therapy system, according to at least one aspect of the present disclosure.

FIG. 20 is a block diagram of a general non-invasive sonodynamic therapy system 900, according to at least one aspect of the present disclosure. The non-invasive sonodynamic therapy system 900 comprises a controller 902 coupled to an ultrasonic transducer array 904 to control the operation of the ultrasonic transducer array 904 to generate a suitable ultrasonic acoustic wave. The ultrasonic transducer array 904 is coupled to a patient interface 906 to couple the ultrasonic acoustic wave produced by the ultrasonic transducer array 904 to a sensitizer 908 that accumulates in tumor cells within the patient's body. In one embodiment, through a process called sonoluminescence, the ultrasonic acoustic wave produces light that activates the sensitizer 908 and causes necrosis of the tumor cells. In one embodiment, an ultrasound acoustic wave produces light through a process called sonoluminescence. Sonoluminescence occurs when the ultrasound acoustic wave collapses fluid bubbles causing cavitation and produces light in the process. The production of light happens far away from the ultrasonic transducer. The light produced through sonoluminescence activates protoporphyrin IX (PpIX) to produce ROS. Sonoluminescence can occur anywhere the intensity of the ultrasound acoustic wave is sufficient, which allows sonodynamic therapy to treat much deeper than photodynamic therapy. The ROS species cause oxidative stress which results in the cancer cell undergoing programmed cell death (apoptosis). In one embodiment, ultrasound acoustic sonication causes cavitation and microbubble generation, the collapse of which generate photons within the tissue. In one embodiments, the photons activate sensitizers such as 5-aminolevulinic acid (5-ALA) and/or protoporphyrin-IX, thereby treating tumorous or other undesired tissue. Photons may have wavelengths between about 250-750 nm, 300 nm-700 nm, 400-800 nm and values and ranges therein.

Sonodynamic therapy treatment employs a sensitizer 908 drug that only become cytotoxic upon exposure to ultrasound. Upon activation, sonodynamic therapy drugs generally referred to as "sonosensitizers" produce ROS that generate the cytotoxic effect to kill the tumor cell. Sonodynamic therapy provides much greater tissue depth that can be reached non-invasively by ultrasound as compared to photodynamic therapy (using light alone). In one aspect, the sensitizer 908 may comprise 5-aminolevulinic acid (5-ALA), protoporphyrin IX (PpIX), hematoporphyrin, Rose Bengal, curcumin, titanium nanoparticles, chlorin e6, pheobromide-a, ATX-S10 (4-formyloximethylidene-3-hydroxy-2-vinyl-deuterio-porphynyl (IX)-6,7-diaspartic acid), photofrin, photofrin II, DCPH-P-Na(I), NPe6 (mono-1-aspartyl chlorin e6), polyhydroxy fullerenes, hypocrellin-B, ZnPcS2P2, methylene blue, sinoporphyrin sodium, and any combinations and derivatives thereof.

In one embodiment, the chemical compound for 5-aminolevulinic acid (5-ALA) is represented by the structure:

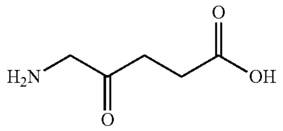

In one embodiment, the chemical compound for protoporphyrin IX (PpIX) is represented by the structure:

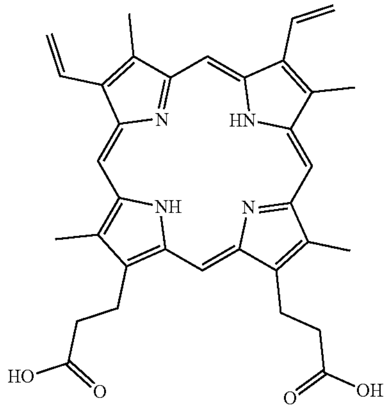 [SMILES: C=CC1=C(C)c2cc3[nH]c(cc4nc(cc5[nH]c(cc1n2)c(C)c5CCC(=O)O)C(CCC(=O)O)=C4C)c(C)c3C=C]

In one embodiment, the chemical compound for Heme b is represented by the structure:

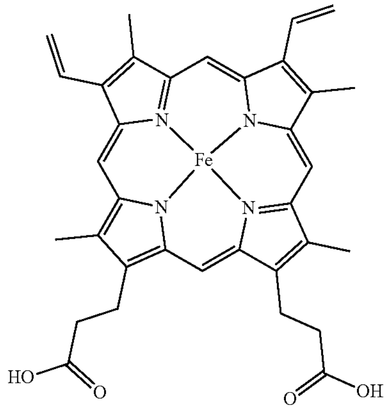

heme b

In one embodiment, the chemical compound for hematoporphyrin is represented by the structure:

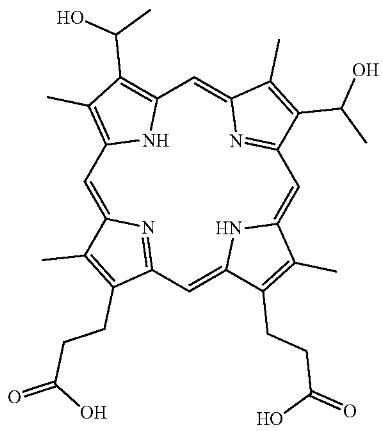 [SMILES: CC1=C(CCC(=O)O)c2cc3[nH]c(cc4nc(cc5[nH]c(cc1n2)c(C)c5C(C)O)C(C)=C4C(C)O)c(C)c3CCC(=O)O]

In one embodiment, the chemical compound for Rose Bengal is represented by the structure:

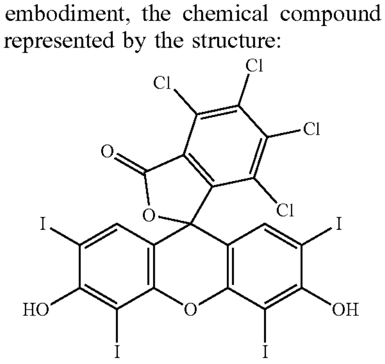

In one embodiment, the chemical compound for curcumin is represented by the structure:

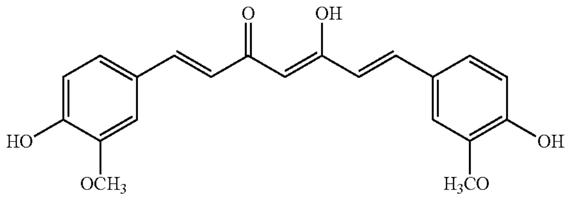 [SMILES: COc1cc(/C=C/C(=O)/C=C(O)/C=C/c2ccc(O)c(OC)c2)ccc1O]

In one embodiment, the chemical compound for chlorin e6 is represented by the structure:

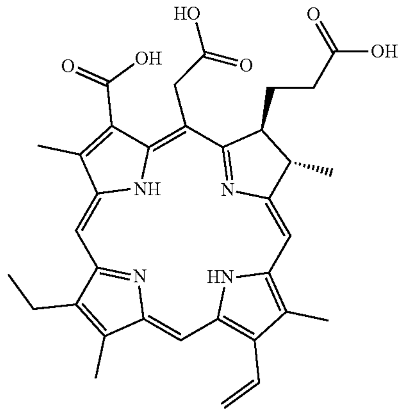 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C]

In one embodiment, the sensitizer is administered to the patient orally. In one embodiment, the sensitizer is administered to the patient through routes other than intravenously and/or other than topically. In one embodiment, the sensitizer is administered to the patient via injection. In several embodiments, one, two or more sensitizers (such as 5-ALA alone or combined with another compound) are administered to a subject orally, intratumorally, topically, intravenously, and/or intrathecally. Ear or nasal drops and/or inhalation of one or more sonosensitizers is provided in some embodiments. Oral doses may include sublingual doses. In some embodiments, one, two or more agents (such as 5-ALA) that enhance or potentiate a sensitizer is administered with the sensitizer (before, after or simultaneously with the sensitizer). Examples of such agents include but are not limited to vitamins (such as vitamin D3), tetracycline antibiotics (such as doxycycline, minocycline, etc.), deferoxamine, calcitriol, gefitinib, metformin and imiquimod and methotrexate. 5-ALA and iron chelator(s) are used in one embodiment. In some embodiments, one or more sonosensitizers (such as 5-ALA) are administered (e.g., orally) to a patient without imaging the location of the sonosensitizer(s) or its products and/or metabolites (such as protoporphyrin IX (PpIX)) for, e.g., tumor location purposes. In one embodiment, one or more sonosensitizers (such as 5-ALA) is administered (e.g., orally) to a patient without using the sonosensitizer(s) or its products and/or metabolites (such as protoporphyrin IX (PpIX)) for diagnostic purposes (e.g., the administration of 5-ALA is therapeutic only).

In several embodiments, one or more sonosensitizers (such as 5-ALA) are administered orally to a patient and its products and/or metabolites (such as protoporphyrin IX (PpIX) accumulates in tumor cells preferentially as compared to non-tumor cells. Ultrasound is then used after this accumulation. The oral dose may be in the form of capsules, tablets, caplets, pills, oral strips, sublingual forms, gels, liquids and powders (such as lyophilized powders that can be mixed with liquids such as water, saline, juice etc. for consumption by a patient) Liquicaps, liquitabs, and/or gel caps are used in some embodiments. In various embodiments, doses may be 1, 5, 10, 15, 20, 25, 30, 40, 50, 60, 70, 80, 90, 100, 200, 300, 400, 500, 600, 700, 800, 900, or 1000 mg per kg of patient body weight and any values and ranges therein, and may be divided into 2, 3 or more doses. Extended release and/or enteric coating compositions and formulations are provided in embodiment. 5-ALA, taken orally, penetrates the blood-brain barrier in several embodiments. In various embodiments, a dosage of sonosensitizer is administered, or instructed for administration, 5, 10, 20, 30, 45, 60, 90, 120 minutes, 1, 2, 3, 4, 5, 6, 7, 8, 12, 24, 36, or 48 hours before a sonodynamic treatment.

In some embodiments, the sonodynamic process described herein may comprise injecting or otherwise administering microbubbles into the tumor tissue to "seed" cavitation, enabling bubble to accumulate in the tumor tissue, or injecting a drug to oxygenate tumor tissue. The sonodynamic therapy process described herein may be combined with one or more other adjuvant therapies such as chemotherapy, immunotherapy, radiotherapy, and/or HIFU. In some embodiments, ultrasound is used therapeutically to both act on PpIX (or another compound) and perform one or more therapeutic functions (such as additional effects on blood brain barrier, angiogenesis, vascularization, resistance to chemotherapy, metabolic pathways, etc.). HIFU, light, lasers, fluorescence, and other photo/illumination and/or other forms of energy delivery, cryotherapy, or mechanical/surgical procedures may be used in connection with the ultrasound sonodynamic therapies disclosed herein. In some embodiments, only incoherent ultrasound is used herein to effect sonoluminescence. Non-invasive ultrasound is used in several embodiments that is extremal to a patient. In some embodiments, an ultrasound system or device that is at least partially implantable is used. In some embodiments, a device that is not implantable is used.

In one embodiment, 5-aminolevulinic acid (5-ALA), can be provided in any pharmaceutically acceptable formulation, and may be provided as the free acid, a pharmaceutically acceptable salt, or a pharmaceutically acceptable ester. In some embodiments, the 5-ALA is sterilized by for example irradiation or another sterilization process (such as gamma irradiation). In some embodiments, ultrasound is delivered to a subject several hours after a sensitizer (such as 5-ALA) is delivered to enhance efficacy (e.g., 1-24 hours, 1-5 hours, 2-4 hours, and values and ranges therein). In various embodiments, a dosage of sonosensitizer is administered, or instructed for administration, 5, 10, 20, 30, 45, 60, 90, 120 minutes, 1, 2, 3, 4, 5, 6, 7, 8, 12, 24, 36, or 48 hours before a sonodynamic treatment. In one embodiment, multiple doses of a sensitizer (such as 5-ALA) are delivered periodically (with spacing between doses ranging from 1 minute to 1 hour, 1-6 hours, etc. as an example).

In some embodiments, to enhance stability and/or penetration, a sensitizer, including but not limited to 5-ALA, straight chain, unsubstituted alkyl 5-ALA esters, or PpIX, which demonstrate additional selectivity for tumor tissue are used. 5-ALA or its methyl or hexyl ester and/or branched alkyl 5-ALA esters and substituted benzyl 5-ALA esters may be used herein. Compounds having hydrolysable groups at carbon 4 of 5-aminolevulinic acid may be used in one embodiment. Hydrophobic sensitizers are used in some embodiments. For example, a sonosensitizer is provided within or on a surface of a microbubble in one embodiment. In one embodiment, a microbubble complex that includes a microbubble coupled to a sensitizer and another agent (such as an activating agent, a potentiator, a chemotherapeutic agent, etc.) is provided, which may be coupled directly or indirectly via a linker. In one embodiment, 5-ALA results in the accumulation of PPIX in cancer through one or more mechanisms. First, cancer cells preferentially transport 5-ALA through the cell membrane because of an overexpression of peptide transporter 2 (PEPT2). Secondly, PpIX accumulates because cancer cells have reduced expression of ferrochelatase (FECH), which completes the synthesis of the heme group. These two mechanisms result in PpIX growing in concentration in tumor cells while remaining low in health cells. In one embodiment, during sonodynamic therapy, PpIX behaves as a catalyst that converts molecular oxygen from a low-energy state into a higher energy state. These high-energy oxygen molecules are violently reactive and will damage cellular components. In particular, this reactive oxygen species (ROS) damages the mitochondria of cancer cells where the highest concentrations of PpIX occurs.

The non-invasive sonodynamic therapy system 900 may be employed to treat a variety of tumors and to treat the area around the tumor cavity, whether malignant or nonmalignant. The area around the tumor cavity includes cells that cause the recurrence and eventual mortality in malignant tumors. In one aspect, the non-invasive sonodynamic therapy system 900 may be configured to treat prostate cancer via trans-rectal ultrasound sonodynamic therapy and cervical cancer via trans-vaginal ultrasound sonodynamic therapy, for example. In one embodiment, the treatment is direct to neuromodulation applications, such as spasticity, pain, or disorders associated with coordination or movement of the body.

In one aspect, the controller 902 may be configured to drive the ultrasonic transducer array 904. The controller 902 may be configured to execute one or more than one control algorithm setup/reflection assessment and tune the drive frequency to skull thickness. This can be done automatically. In one aspect, the control algorithm may be configured to pulse or control the "duty cycle" of the ultrasonic transducer array 904 drive waveform to generate high temporal peak acoustic intensity of ultrasonic acoustic waves with low temporal average acoustic intensity sufficient to activate the sensitizer 908 while preventing thermal necrotic death of the tumor cells in the treatment region. In another aspect, the control algorithm may be configured to generate packets of waves that are delayed to overlap the tumor. In another aspect, the control algorithm may be configured to control the intensity of the ultrasonic acoustic wave.

In another aspect, the control algorithm may be configured to control the phase of the ultrasonic acoustic wave. In another aspect, the control algorithm may be configured to randomize the phase of the ultrasonic acoustic wave. Modulating acoustic waves with phase randomization promotes broad consistent coverage across a treatment region where acoustic wavefronts constructively combine at varying pseudo random locations within the treatment region, rather than the exact same location with each cycle. This control scheme provides a more homogeneous treatment region to aid broad consistent treatment coverage and avoid sub therapeutic dead spots in the treatment region. Phase randomization provides additional benefit in adapting to the treatment environment. Repeating the exact same excitation pattern in some types of acoustical environments could lead to the potential for standing waves to form. Standing waves are inherently dangerous as they can deliver unintended treatment energy to the patient. A controller scheme that provides phase randomization of the acoustic waveform can mitigate the risks of repetitive excitation that can lead to standing waves.

A feedback loop may be provided back to the controller 902 to adjust the drive signal to the ultrasonic transducer array 904 based on in situ variables such as tissue depth, tissue thickness, tissue volume, skull thickness, temperature, among other variables. In one aspect, the controller 902 may be located in an ultrasonic generator or may be located elsewhere. In various aspects, in situ variables may include a disease state or an inner body location. The disease state may include alternative treatment ultrasonic transducer probe that is driven differently for each disease state. Examples of feedback loops are described hereinbelow in connection with FIGS. 22-24.

In one aspect, the ultrasonic transducer array 904 may be configured according to the transducers 150, 400, 450 described hereinabove. In various aspects, however, the form factor of the ultrasonic transducer array 904 may be configured to couple ultrasonic acoustic waves in various locations on the patient's body other than the head. For example, the ultrasonic transducer array 904 may be configured to generate ultrasound that activates a sensitizer 908 to treat tumors in the brain, such as glioblastoma, spine, lung, breast, mouth, tongue, stomach, liver, pancreas, intestines, rectum, colon, vagina, ovary, testes, leukemia, lymphoma, among others, whether the tumors are malignant or nonmalignant.

In various configurations, the ultrasonic transducer array 904 is non-invasive and produces ultrasonic acoustic waves capable of reaching the target tumor cells non-invasively. As described hereinabove, the ultrasonic transducer array 904 may be configured as annular array, 2D grid array, a linear array, and the like, to generate an adaptively focused ultrasonic acoustic wave optimized based on in situ variables such as tissue depth, tissue thickness, tissue volume, skull thickness, among other variables. In other aspects, the ultrasonic transducer array 904 may adaptively focus or adjust the ultrasonic acoustic wave based on pretreatment planning or safety. In one aspect, the controller 902 executes a control algorithm to generate selectively convergent/divergent ultrasonic acoustic waves including adaptive focus for collaborative transducer performance. The ultrasonic acoustic array 904 may be configured to perform transmitter and receiver functions that may be controlled by the controller 902.

The ultrasonic transducer array 904 is coupled to the patient interface 906 to facilitate acoustic coupling of the ultrasonic vibrations generated by the ultrasonic transducer array 904 into the patient's body. The patient interface 906, like the ultrasonic transducer array 904, is non-invasive. In one aspect, the patient interface 906 may be configured to remove air between the ultrasonic transducer array 904 and the patient's body to facilitate acoustic coupling. In one aspect, the patient interface 906 may be configured to remove excess heat from the patient's body. In some configurations, the patient interface 906 may comprise a variety of sensors, such as a temperature sensor, for example. Signals from such sensors may be provided as feedback to the controller 902 (see FIG. 22 for example). Such feedback may be employed to control the ultrasonic transducer array 904 to generate a desired ultrasonic acoustic wave. The patient interface 906 also may include gel or hydrogel layers to improve the acoustical coupling between the ultrasonic transducer array 904 and the patient's body. In one aspect, the patient interface 1022 may be configured to locally apply cooling. In one aspect, the patient interface 1022 may be configured for sensor feedback to the processing unit 902.

Finally, the non-invasive sonodynamic therapy system 900 comprises a sensitizer 908 that may be absorbed by the tumor cells. In one embodiment, sonodynamic therapy may include the combination of the sensitizer 908, such as a sensitizing drug, ultrasound generated by the ultrasonic transducer array 904 coupled into the patient's body by the patient interface 906, and molecular oxygen. Although these components are non-toxic individually, when combined together, a cytotoxic ROS is generated to kill the tumor cells. Sonodynamic therapy may be configured to provide penetration of ultrasound through the patient's body and can be used to treat a wide array of deep and hard to access tumors.

Figure 21:
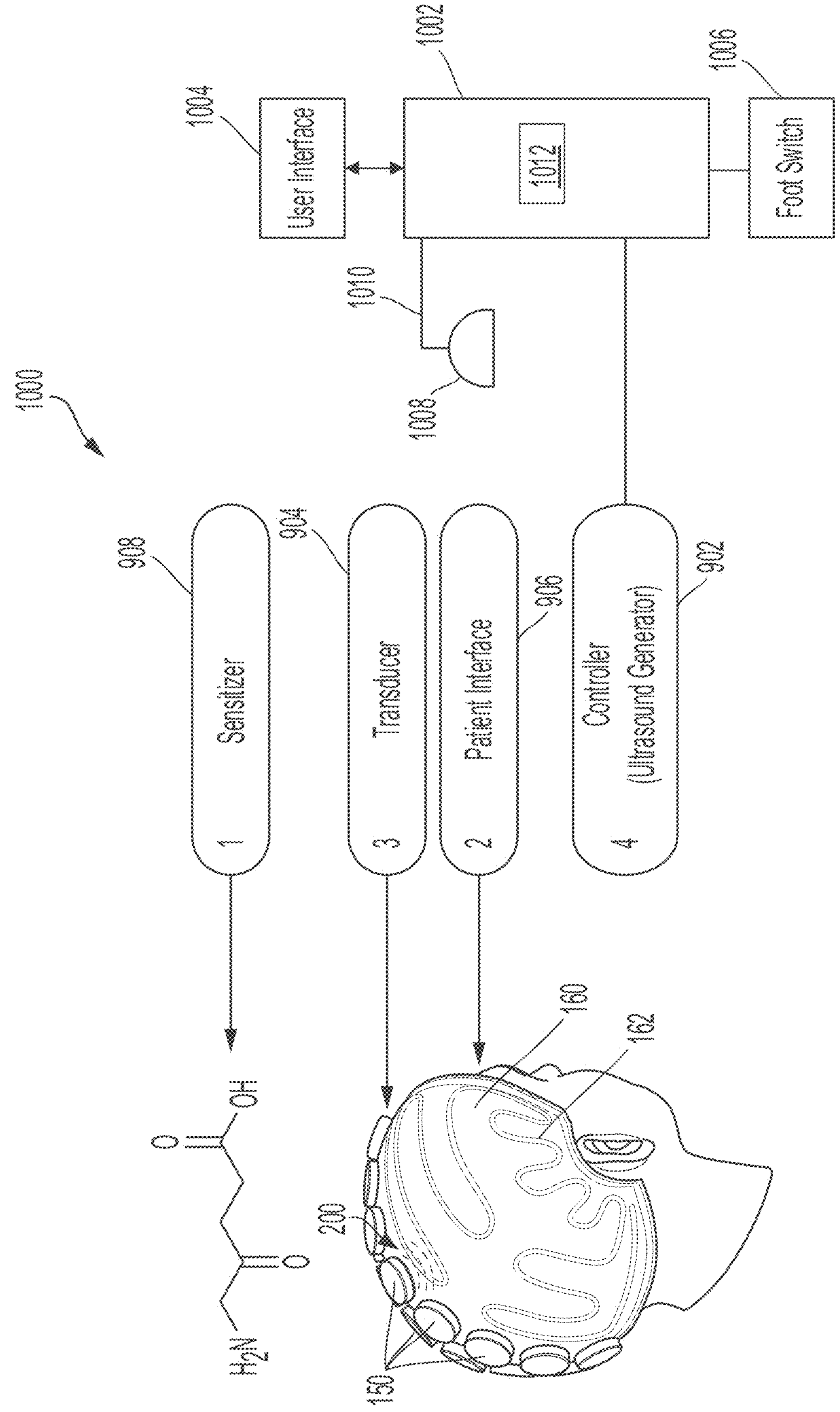
FIG. 21 is an illustrative diagram of the sonodynamic therapy system shown in FIG. 18, according to at least one aspect of the present disclosure.

FIG. 21 is an illustrative diagram 1000 of the sonodynamic therapy system 900 shown in FIG. 20, according to at least one aspect of the present disclosure. In one aspect, the sonodynamic therapy system 900 comprises a controller 902 that may be located in an ultrasonic generator 1002. The ultrasonic generator 1002 comprises a controller 1012, a user interface 1004, a foot switch 1006 for activating the controller 1012, and a cap or helmet 1008 that is placed over the head of the patient. A cable 1010 that carries electrical signals to and from the ultrasonic transducer array 904 couples the transducer array 904 and the ultrasonic generator 1002. The ultrasonic transducer array 904 comprises an array of ultrasonic transducers 150, 400, 450 placed over a patient interface 906 such as the skull cap 160. The ultrasonic generator 1002 drives the ultrasonic transducers 150, 400, 450 to generate an ultrasonic acoustic wave 200 that is coupled into the body of the patient to excite the sensitizer 908 ingested by the patient and absorbed by the tumor cells. The controller 1012 shapes the acoustic wave to achieve a convergent, divergent, or planar acoustic wave, or more complex acoustic waves. As previously described, in one aspect the sensitizer 908 may comprise and ALA sensitizing drug that is activated in a sonoluminescence process, for example.

Figure 22:
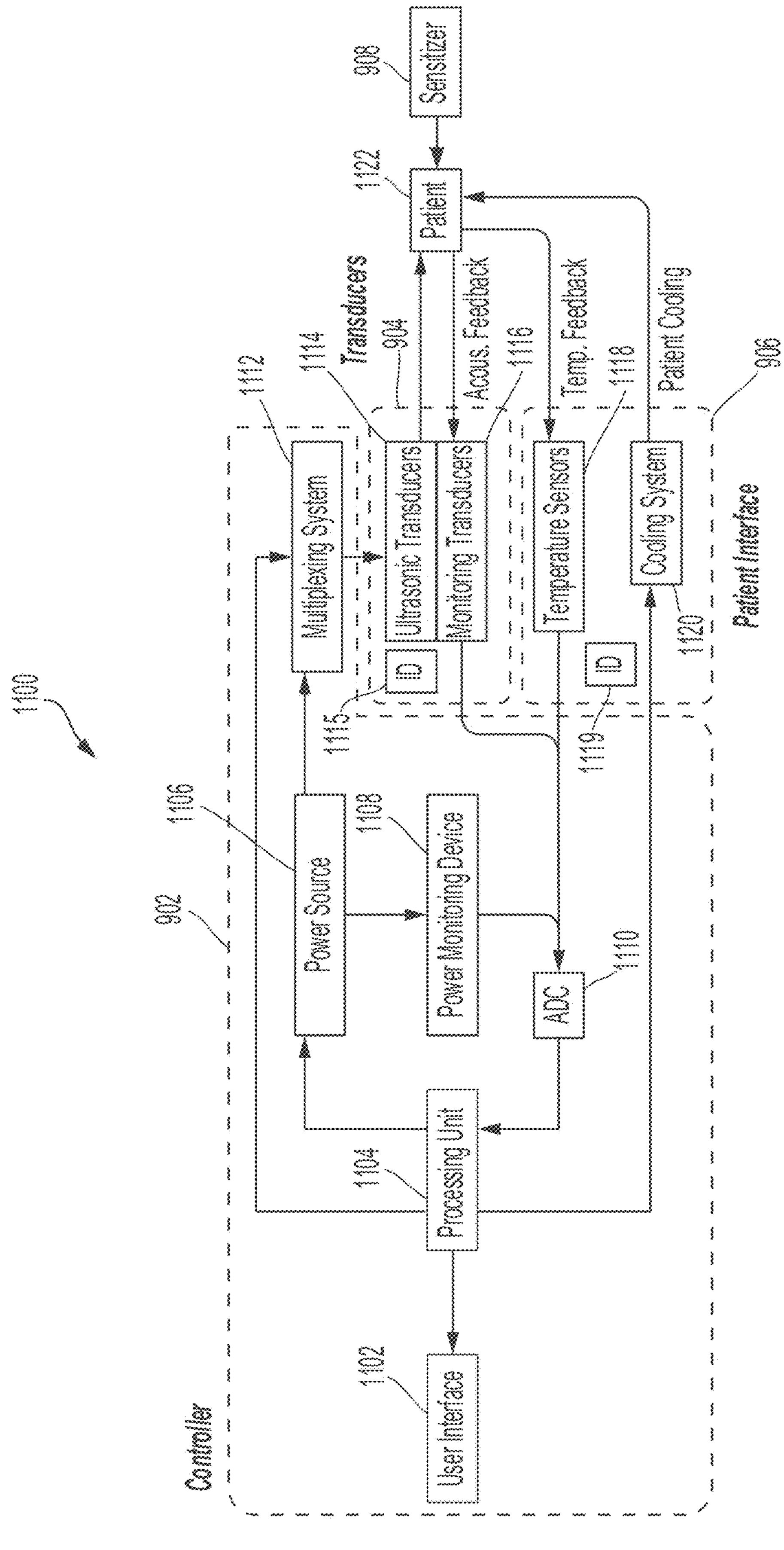
FIG. 22 is a schematic diagram of the sonodynamic therapy system shown in FIGS. 18 and 19, according to at least one aspect of the present disclosure.

FIG. 22 is a schematic diagram 1100 of the sonodynamic therapy system 900 shown in FIGS. 20 and 21, according to at least one aspect of the present disclosure. The controller 902 of the sonodynamic therapy system 900 comprises a user interface 1102 coupled to a processing unit 1104 and configured to receive input from a user and providing output to the user. The processing unit 1104 may be a processor or microcontroller coupled to a memory (e.g., memory circuit), a control circuit, or a combination thereof. The ultrasonic transducer array 904 comprises one or more than one ultrasonic transducer 1114 and one or more than one monitoring ultrasonic transducer 1116. It will be appreciated that the same ultrasonic transducer element may be configured to implement an ultrasonic transmitter function as well as a receiver function (see FIG. 24 for example). The patient interface 906 comprises one or more than one temperature sensors 1118 to monitor the temperature of the patient 1122. The patient interface 906 also comprises a cooling system 1120 to reduce the temperature of the patient 1122. In one aspect, the patient interface 906 may be configured to eliminate air gaps between the transducer 1114 and the patient 1122 to enable acoustical coupling.

The processing unit 1104 is configured to execute machine executable instructions to implement various control algorithms as previously described. The processing unit 1104 may comprise a memory to store such machine executable instructions and processing engines to execute the control algorithms. The processing unit 1104 also may be implemented in hardware with digital and analog electronic components. The processing unit 1104 is coupled to a multiplexing system 1112 and a power source 1106 suitable for driving the ultrasonic transducers 1114.

The ultrasonic transducers 1114 are coupled to the body of the patient 1122 to activate the sensitizer 908 administered to the patient 1122. In one aspect, at least one sonosensitizer 908 agent may be configured for preferential accumulation in selective tissue of the patient 1122. Monitoring ultrasonic transducers 1116 monitor acoustic feedback from the patient 1122 and generate signals that are provided as feedback to the processing unit 1104 via an analog-to-digital converter 1110 (ADC). In addition to the acoustic feedback, a power monitoring device 1108 monitors the power source 1106 and provides feedback to the processing unit 1104 through the ADC 1110. The processing unit 1104 controls the ultrasonic transducer drive signals based on the acoustic feedback signal and/or the power monitoring signal to achieve a desired ultrasonic acoustic wave inside the body of the patient 1122. In one aspect, at least one ultrasonic transducer 1114 is configured to output selectively convergent and divergent acoustic waves. The transducer 1114 may be configured in an annular array or a grid array. The transducer 1114 may be configured with multiple electrodes. The transducer 1114 may be configured to receive reflected acoustical signals.

The processing unit 1104 is coupled to the temperature sensors 1118 and receives patient temperature feedback through the ADC 1010. The processing unit 1104 controls the cooling system 1120 based at least in part on the patient temperature feedback signal.

In one aspect, the processing unit 1102 is configured to produce a pulsed acoustical signal with temporal-average intensity output of 30 $W/cm^2$, 25 $W/cm^2$, 20 $W/cm^2$, 15 $W/cm^2$, 10 $W/cm^2$ and below, below 8 $W/cm^2$ (e.g., 7.0 $W/cm^2$, 6.5 $W/cm^2$, 6.0 $W/cm^2$, 5.5 $W/cm^2$, 0.05 $W/cm^2$, 4.5 $W/cm^2$, 4.0 $W/cm^2$, 3.5 $W/cm^2$, 3.0 $W/cm^2$, 2.5 $W/cm^2$, 2.0 $W/cm^2$, 1.5 $W/cm^2$, 1.0 $W/cm^2$, 0.5 $W/cm^2$, 0.4 $W/cm^2$, 0.3 $W/cm^2$, 0.2 $W/cm^2$, 0.1 $W/cm^2$, 0.05 $W/cm^2$), and any values and ranges therein, such as 1-30, 1-20, 1-10, 2-30, 2-20, 2-25, 2-20, 2-15, 2-10, 2-5, 5-30, 5-25, 5-20, 5-15, 5-10, 10-30, 10-25, 10-20, 10-15 $W/cm^2$ and values therein. In various embodiments, acoustic intensity is produced from each active element in an array. In one embodiment, an intensity is produced from one or more active elements in the array. The processing unit 1102 is adapted to apply amplitude-modulated acoustical signals including constructive interference over a plurality of wave cycles. The processing unit 1102 further may be configured to output packets of acoustic waves at various delayed sequences to provide diffused tissue coverage. The processing unit 1102 may be configured to execute frequency adaptive algorithms to optimize transmission of acoustical signals. The processing unit 1102 may be configured to control phased randomization of acoustical signals.

In various aspects, the present disclosure provides a sonodynamic therapy device comprising a transducer 904, a patient interface 906, and a controller 902 adapted to activate a sensitizer 908 within the body of the patient 1122. The transducer 904 may comprise one or more than one transducer 1114, 1116 where the controller 902 is configured to generate a broadband range of ultrasonic frequencies to drive the transducer 904 and produce divergent, convergent, or planar acoustic waves.

In one aspect, the patient interface 906 is configured to transmit acoustic waves produced by the transducer(s) 904 into the body of the patient 1122 thus acoustically coupling the transducer(s) 904 to the patient 1122. In one aspect, the patient interface 906 provides a cooling system 1120 to remove any excess heat that builds up in the patient 1122 as a result of the coupling acoustic energy to the body of the patient 1122. In one aspect, the patient interface 906 may comprise an integral cooling system 1120. The patient interface 906 may comprise a hydrogel cap filled with gel or a water-filled cap with cooling channels. In one aspect, the patient interface 906 comprises one or more than one sensor 1118 to provide feedback to the processing unit 1104 of the controller 902. The sensors 1118 may include, for example, temperature sensors, optical temperature sensors to measure temperature in a particular direction, acoustic sensors, which may include the same transducers 904 used for transmitting acoustic signals. The patient interface 906 may be configured to remove air from the patient interface 906 to improve acoustic coupling between the transducer 904 and the body of the patient 1122. In another aspect, the patient interface 906 may be configured to cool the patient 1122. In yet another aspect, the patient interface 906 may be configured to cool the transducers 904, for example, to keep the transducers at the same temperature to achieve frequency stability.

In one aspect, the patient interface 906 may be adapted and configured to fit various patient anatomies. For example, the patient interface 906 may be adapted and configured to fit patient anatomies for sonodynamic therapy specifically adapted to treat tumors located in the brain, lung, breast, stomach, liver, pancreas, intestines, rectum, colon, vagina, testes, among others, for example. A sonodynamic therapy device may be adapted to wrap around the torso or limb of the patient and/or employed to treat osteosarcoma into the bone. The controller 902 may be adapted to detect either the patient interface 906 or the sonodynamic therapy device such as the transducer 904 or patient interface 906 and select a treatment algorithm to produce acoustic waves optimized for treating the various tumors. The transducer 904 or patient interface 906 may be identified using identification (ID) circuits 1115, 1119 comprising a single-wire serial EEPROM, for example. The ID circuit 1115, 1119 EEPROM may contain both a preprogrammed unique serial number and memory sections. Any or all of the memory sections can be permanently locked by the end-equipment manufacturer to allow tracking of products and identifying attachments. Other identification techniques may include detecting the impedance of the transducer 904 or patient interface 906 and associating the impedance with a treatment algorithm.

In one aspect, the controller 902 is configured to generate electrical drive signals to actuate one or more than one ultrasonic transducer 904 to produce an acoustic wave to activate a sensitizer 908 located within the body of the patient 1122. In one aspect, the electrical drive signals generated by the controller 902 may actuate the one or more than one ultrasonic transducer 904 to produce acoustic waves of varying intensities, amplitudes, or frequencies. In another aspect, the acoustic waves may be amplitude modulated, frequency modulated, phase modulated, continuous, discontinuous, pulsed, randomized, or combinations thereof. In other aspects, the acoustic waves may be produced in a packet of wave cycles, where the number of cycles per packet may be predetermined to achieve a desired outcome that is different from a focused ultrasound pulse, for example. In other aspects, the controller 902 is configured to generate a frequency modulation signal to produce a frequency-modulated acoustic wave. In one aspect, the controller may be configured to generate an intra or inter pulse variation signal that can be used to reduce standing acoustic waves.

In one aspect, the controller 902 is configured to apply an amplitude-modulated acoustic ultrasound signal which constructively interferes over a plurality of wave cycles. In one aspect, the intensity of each of the plurality of acoustic waves remain within a safe range wherein the ultrasound energy carried by each of the plurality of acoustic waves is safe to the tissue of the patient 1122, such as the brain or other body part. In one aspect, the controller 902 may be configured to drive the transducer 904 to generate an amplitude-modulated acoustic wave which produces a constructive wavefront. In one embodiment, ultrasound modifies the blood brain barrier (BBB). In one embodiment, ultrasound facilitates delivery of a drug and/or sonosensitizer across the blood brain barrier. In one embodiment, ultrasound energy causes vibrations to induce a temporary disruption to the blood brain barrier.

In one aspect where the sonodynamic therapy device comprises one transducer 904 and the controller 902 may be configured to generate a drive signal to actuate the transducer 904 to produce a long acoustic ultrasonic wave packet. In one aspect, the controller 902 may be configured to generate a drive signal to actuate the transducer 904 to produce an ultrasonic acoustic wave packet composed of a sinusoidal wave amplitude modulated by a Gaussian pulse (see FIG. 10 for example). In another aspect, the controller 902 may be configured to generate a drive signal to actuate the transducer 904 to produce an ultrasonic acoustic wave packet composed of a sinusoidal wave amplitude modulated by a rectangular pulse. In another aspect, the controller 902 may be configured to generate a drive signal to actuate the transducer 904 to produce an ultrasonic acoustic wave packet composed of a sinusoidal wave amplitude modulated by a triangular pulse. The ultrasonic acoustic wave packet may comprise intra or inter wave packet variation. In one aspect, the controller 902 may be configured to generate a drive signal to actuate the transducer 904 to produce an acoustic ultrasonic pulse. The acoustic wavefronts of the ultrasonic pulse may either converge to focus the ultrasonic energy to a specific region or diverge to spread the ultrasonic energy to a larger region.

In other aspects, where the sonodynamic therapy device comprises two or more transducers 904 and the controller 902 may be configured to generate a drive signal to actuate the two or more transducers 904 to produce acoustic ultrasonic pulses where the individual wavefronts, whether converging or diverging, will meet at the same location at the same time to focus the ultrasonic energy. In one aspect, the controller 902 may adapt the frequency drive for each transducer 904.

Figure 23:
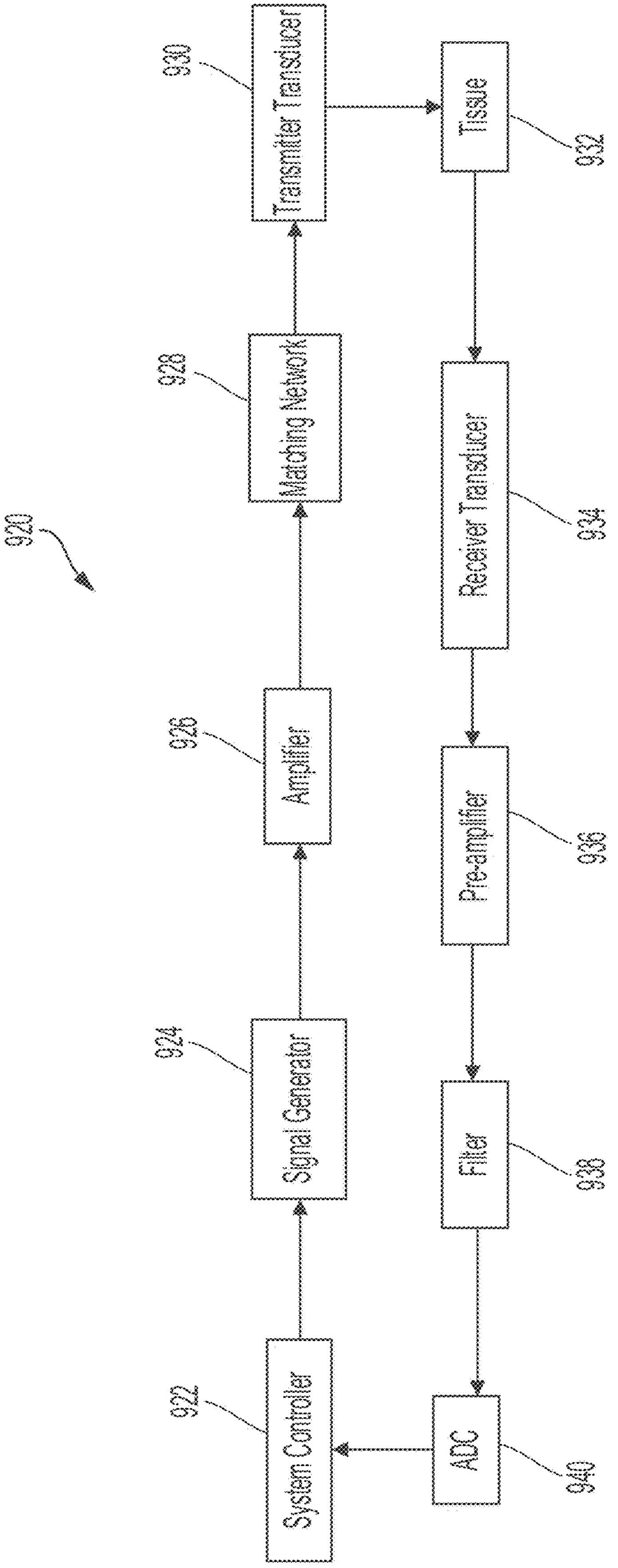
FIG. 23 is a schematic diagram of a sonodynamic therapy system with separate transmitting and receiving transducers, according to at least one aspect of the present disclosure.

FIG. 23 is a schematic diagram of a sonodynamic therapy system 920 with a separate transmitter transducer 930 and receiver transducer 934, according to at least one aspect of the present disclosure. The sonodynamic therapy system 920 comprises a system controller 922 to control a signal generator 924 to generate an electrical signal to drive the transmitter transducer 930. The electrical signal is amplified by an amplifier 926 and the drive signal is coupled to the transmitter transducer 930 by a matching network 928 to maximize power transferred to the transmitter transducer 930. The transmitter transducer 930 transmits an acoustic wave into tissue 932 (e.g., lesions) in the treatment region. A receiver transducer 934 detects acoustic waves emitted by the tissue 932. The output of the receiver transducer 934 is a weak electrical signal that is provided to an electronic pre-amplifier 936 that converts the weak electrical signal into an output signal strong enough to be noise-tolerant and strong enough for further processing such as filtering by a filter 938. The output of the filter 938 is provided to an analog-to-digital converter 940 (ADC) that provides a feedback signal to the system controller 922 in digital form. Based on the feedback signal received from the receiver transducer 934 the system controller 922 can adjust the drive signal applied to the transmitter transducer 930. The adjustment may include adjusting the modulation, strength, frequency, phase, or randomization, of the drive signal, or any combinations thereof. The feedback signal may represent tissue depth, tissue thickness, tissue volume, skull thickness, temperature, distance to the treatment region, or a combination thereof.

Figure 24:
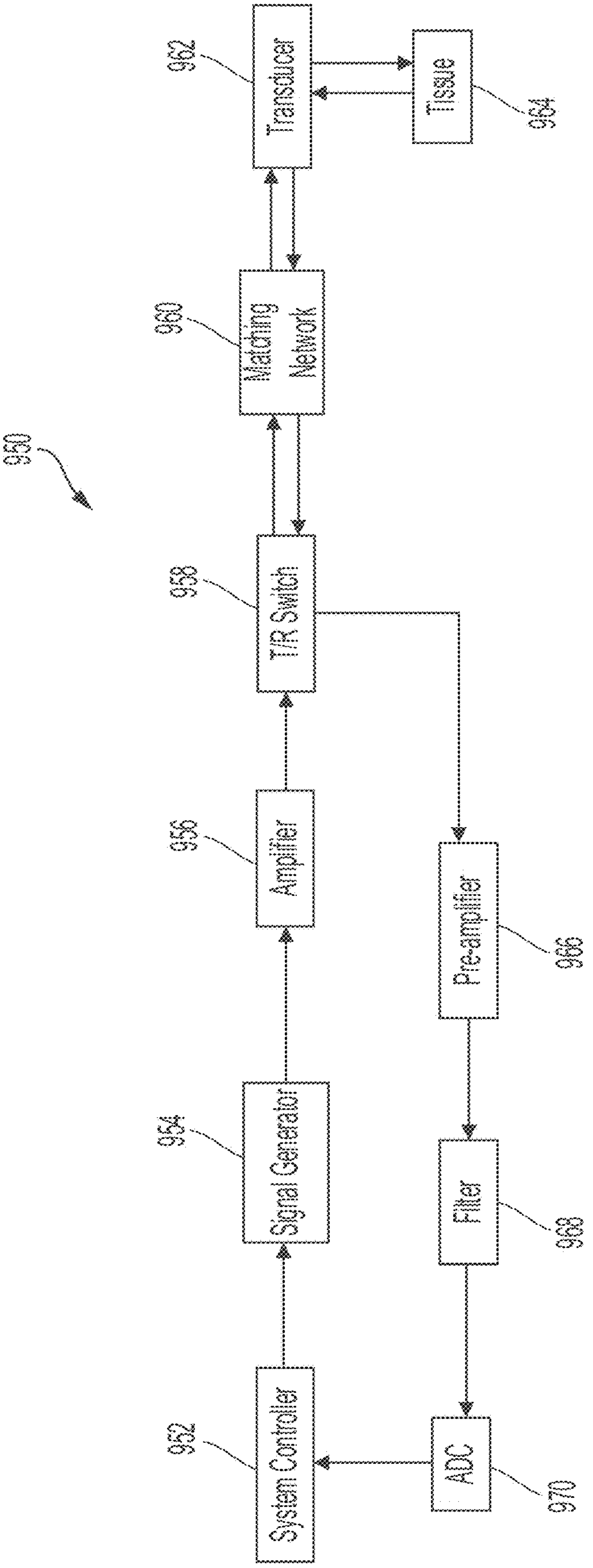
FIG. 24 is a schematic diagram of a sonodynamic therapy system with a single transmitting and receiving transducer, according to at least one aspect of the present disclosure.

FIG. 24 is a schematic diagram of a sonodynamic therapy system 950 with a single transmitting and receiving transducer 962, according to at least one aspect of the present disclosure. The sonodynamic therapy system 950 comprises a system controller 952 to control a signal generator 954 to generate an electrical signal to drive the transducer 962 in transmitter mode. The electrical signal is amplified by an amplifier 956 and is applied to a transmitter/receiver (T/R) switch 958. When the transducer 962 is in transmitter mode, the T/R switch 958 couples the drive signal to the transducer 962 via a matching network 960 to optimize power transferred to the transducer 962. In transmitter mode, the transducer 962 transmits an acoustic wave into tissue 964 (e.g., lesions) in the treatment region. In receiver mode, the transducer 962 detects acoustic waves emitted by the tissue 964. The output of the transducer 962 is a weak electrical signal that is coupled to the T/R switch 958 by the matching network 960. The T/R switch 958 provides the weak electrical signal to an electronic pre-amplifier 966 that converts the weak electrical signal into an output signal strong enough to be noise-tolerant and strong enough for further processing such as filtering by a filter 968. The output of the filter 968 is provided to an ADC 970 that provides a feedback signal to the system controller 952 in digital form. Based on the feedback signal received from the transducer 962 in receiver mode, the system controller 952 can adjust the drive signal applied to the transducer 962 in transmitter mode. The adjustment may include adjusting the modulation, strength, frequency, phase, or randomization, of the drive signal, or any combinations thereof. The feedback signal may represent tissue depth, tissue thickness, skull thickness, temperature, distance to the treatment region, or a combination thereof.

Having described various aspects of a sonodynamic therapy system 900, 920, 950, 1000, 1100 and components of the sonodynamic therapy system 900, 920, 950, 1000, 1100, the disclosure now turns to a description of the present disclosure that is directed to various aspects of ensonification drive patterns to create an incoherent field for distributing low intensity energy. In various embodiments, low intensity energy is 20 $W/cm^2$ to 0.01 $W/cm^2$, including 15 $W/cm^2$, 10 $W/cm^2$, 8 $W/cm^2$, 7.0 $W/cm^2$, 6.5 $W/cm^2$, 6.0 $W/cm^2$, 5.5 $W/cm^2$, 0.05 $W/cm^2$, 4.5 $W/cm^2$, 4.0 $W/cm^2$, 3.5 $W/cm^2$, 3.0 $W/cm^2$, 2.5 $W/cm^2$, 2.0 $W/cm^2$, 1.5 $W/cm^2$, 1.0 $W/cm^2$, 0.5 $W/cm^2$, 0.4 $W/cm^2$, 0.3 $W/cm^2$, 0.2 $W/cm^2$, 0.1 $W/cm^2$, 0.05 $W/cm^2$, and any values and ranges therein down to 0.01 $W/cm^2$. The ensonification drive patterns may be generated with multiple ultrasonic transducer elements arranged in a preferred array or subarray structure for generating an incoherent field. The number of ultrasonic transducer elements and arrangement of the array is a location dependent solution for each disease state. Various aspects of ultrasonic transducer arrays are described herein in connection with FIGS. 1-24 and more particularly in connection with FIGS. 29-42B.

Having described various aspects of a sonodynamic therapy system 900, 920, 950, 1000, 1100 and components of the sonodynamic therapy system 900, 920, 950, 1000, 1100, the disclosure now turns to a description of the present disclosure that is directed to various aspects of ultrasound transducer array geometries, element placement, element shapes, and lens design for activating a sonosensitizer in conjunction with providing sonodynamic therapy. The ultrasound transducer array aspects described contribute to an incoherent pressure field with a preferred energy profile for activating a sonosensitizer. It will be appreciated that the sonodynamic therapy system 900, 920, 950, 1000, 1100 and components thereof may be adapted and configured to drive the ultrasonic transducer arrays described hereinbelow in connection with aspects of FIGS. 25-35 and 37-38.

In another aspect, the present disclosure is directed to ensonification drive patterns that are applied as a pulsed therapy based on the rate limiting step that depletes local oxygen supply when the sonosensitizer is activated to produce reactive oxygen species.

In another aspect, the present disclosure is directed to ensonification drive patterns that include phase randomization amongst the ultrasonic transducer elements to create the incoherent distributed acoustic field.

In another aspect, the present disclosure is directed to ensonification drive patterns that include element weighting amongst the ultrasonic transducer elements, where select elements are driven at increased or decreased frequency and/or amplitude to create the incoherent distributed acoustic field.

In another aspect, the present disclosure is directed to ensonification drive patterns that also may include frequency, amplitude, and/or phase modulation within each elements pulse to create the incoherent distributed field.

In another aspect, the present disclosure is directed to ensonification drive patterns that also may include inverse apodization or standard apodization techniques across the array or sub-array element patterns to create the incoherent distributed field.

In another aspect, the present disclosure is directed to ensonification drive patterns that also may include alternating drive patterns that utilize only a subset of the elements as a sub-array for adding energy to specific locations in the distributed field. The intensity, amplitude, and frequency of the ensonification drive patterns as well as resultant peak negative pressures are delivered in a range that contributes to a cavitational environment that is safe for healthy tissue within the therapeutic operating field.

The present disclosure is directed to various aspects of ensonification drive patterns for activating a sonosensitizer in conjunction with providing sonodynamic therapy. The ensonification drive pattern creates an incoherent field for distributing low intensity energy. In one embodiment, the drive patterns involving multiple ultrasonic transducer elements to be arranged in a preferred array or subarray structure. The number of ultrasonic transducer elements and arrangement of the array structure is a location dependent solution for each disease state. Due to the spatial element location differences in the array, coherence will only occur at specific location(s) in the therapeutic operating field. As used herein, coherence may be used to describe the properties of the interrelation between the ensonification waves produced by the disease specific array.

Coherence is a measure of a wave's correlation with another wave or another part of the same wave. Temporal coherence is the degree to which a wave can be shifted in time and still correlate well with another wave. Two waves that are continuous, have constant phase differences, and are the same frequency remain correlated even when shifted in time relative to one another. Spatial coherence is the degree to which a wave can be shifted in space and still correlate well with another wave or another part of the same wave. Coherence between two waves may be measured as a spatial difference between the sources of the two waves, as a time difference between the two waves such that one wave is delayed relative to the other wave, or a combination thereof. Two waves may be considered to be coherent when they have a constant relative phase or when they have zero or constant phase difference and the same frequency. By way of example and not limitation, characteristics of coherent sources may include, for example, waves that have a constant phase difference (e.g. are in phase with each other) and have the same frequency. At the same frequency, the phases of the two waves be randomized while maintaining the same phase difference and preventing the phases from combining by constructive or destructive interference. Although the amplitude of the waves does not necessarily contribute to the coherence of the waves, manipulating the amplitude can be used to achieve a more diffuse acoustic field.

FIGS. 20-24 illustrate various sonodynamic therapy systems 900, 1000, 1100, 920, 950 for generating ensonification drive patterns for sonodynamic therapy. The sonodynamic therapy systems 900, 1000, 1100, 920, 950 can be adapted and configured to drive an array of ultrasonic transducer elements to generate incoherent ensonification drive patterns for activating a sonosensitizer in conjunction with providing sonodynamic therapy.

In various embodiments, cancerous tissue in the lung, breast, colorectal region, prostate and pancreas may be treated using several embodiments described herein using for example, one or more sonosensitizers along with the ultrasound parameters described herein. Tumors that are difficult to access including those surrounded by bony structures are treated in various embodiments, including but not limited to brain or spinal tumors. Treatment of undesired tissue in joints and other orthopedic applications are also provided herein. In some embodiments, sonodynamic therapy is used to improve efficiency of chemotherapeutic molecules, sonoporation, and/or gene delivery. In various embodiments, sonodynamic therapy with an ultrasound array delivering a temporal-average intensity output below 8, 10, 15, 20 $W/cm^2$ (e.g., 0.1-8 $W/cm^2$, 0.1-4 $W/cm^2$, 0.5-5 $W/cm^2$ etc.) to cancer tissue can be used to induce and activate sonosensitizer at relative deep depths within a patient's body with or without cavitation to produce reactive a thermal effect, an oxygen species, and/or free radicals in a cascade of events that activate the sonosensitizer and in turn damage the cancer cells. In various embodiments, sonodynamic therapy can be used with or without photodynamic therapy.

Several embodiments described herein are used synergistically with other cancer therapies, including for example, radiation, chemotherapy, immunotherapy, and cell therapies. In one embodiment, the combination of ultrasound and a sonosensitizer as described herein reduces or eliminates the need for one or more additional complementary treatments. For example, lower doses or fewer additional treatments of chemotherapy, radiation, cell therapy etc. may be needed when cancerous tissue is treated by the combination of ultrasound and a sonosensitizer as described herein, thus enhancing patient care and reducing side effects.

Figure 25:
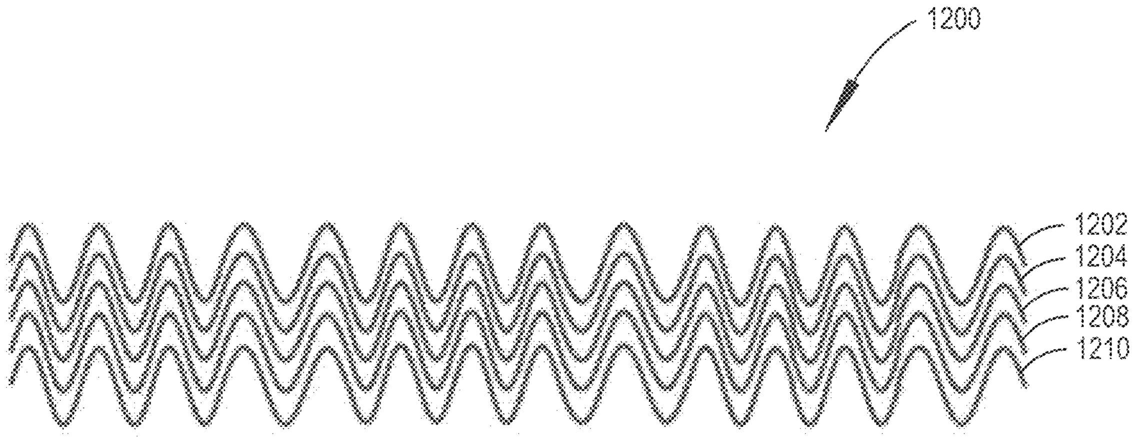
FIG. 25 is a diagram of a coherent drive field in accordance with at least one aspect of the present disclosure.

FIG. 25 shows a diagram of a coherent acoustic field 1200 produced by an array of coherent ultrasonic transducer elements in accordance with at least one aspect of the present disclosure. The coherent acoustic field 1200 comprises, or consists essentially of, a plurality of waveforms 1202, 1204, 1206, 1208, 1210 at the same frequency, phase, and amplitude, for example. Examples of ultrasonic transducer elements are described in connection with FIGS. 29-42B.

Incoherent sources are the exact opposite of coherent sources. Incoherent sources emit ensonification drive patterns that randomize phase difference across an ultrasonic transducer array. In addition, the frequency and/or amplitude within an ensonification drive pattern also may be modulated to achieve an incoherent source.

Figure 26:
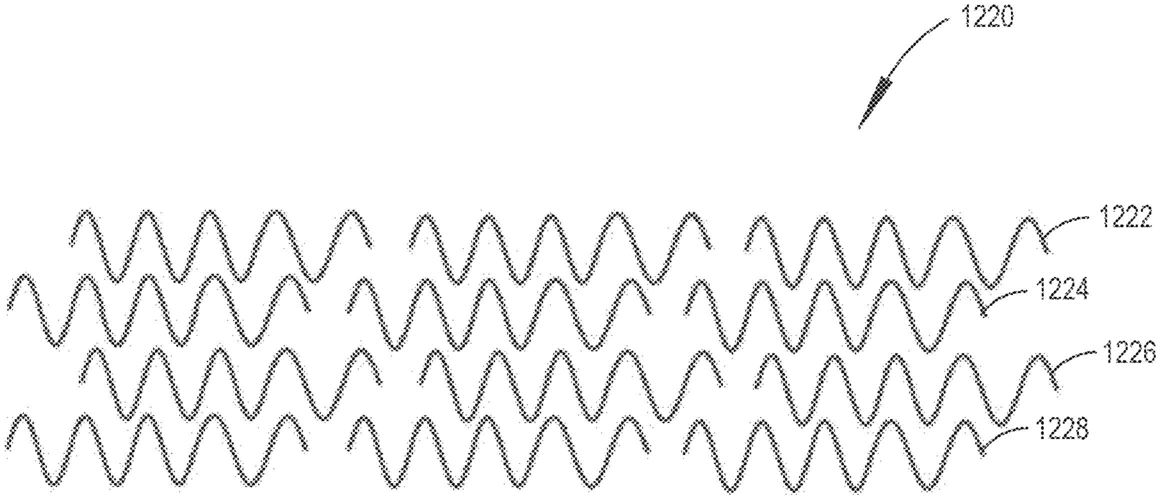
FIG. 26 is a diagram of an incoherent field in accordance with at least one aspect of the present disclosure.

FIG. 26 shows a diagram of an incoherent acoustic field 1220 produced by an array of incoherent ultrasonic transducer elements in accordance with at least one aspect of the present disclosure. The incoherent acoustic field 1220 comprises, or consists essentially of, a plurality of waveforms 1222, 1224, 1226, 1228 at different phases relative to each other, for example. As shown in the example of FIG. 26, waveforms 1222-1228 are generated in bursts that are out of phase with other. Examples of ultrasonic transducer elements are described in connection with FIGS. 29-42B. In some embodiments, the burst frequency is 0.3-3 MHZ (e.g., 0.5-1.5, 0.6-1.8, 0.7-1.1, 0.5-2.0 MHZ, etc.).

In one embodiment, uniquely emitting incoherent field driving patterns contributes to a preferred cavitational environment for activating the sonosensitizer and promoting sonodynamic therapy. The intensity, amplitude, and frequency of the ensonification drive patterns as well as resultant variable peak negative pressures are additional key contributors to the cavitational environment for activating a sonosensitizer. In one embodiment, uniquely emitting incoherent field driving patterns contributes to a preferred environment for activating the sonosensitizer and promoting sonodynamic therapy without cavitation. The intensity, amplitude, and frequency of the ensonification drive patterns as well as resultant variable peak negative pressures are additional contributors to the environment for activating a sonosensitizer. Also and additionally, incoherent field driving patterns continually shift energy collection points within the therapeutic operating field such that after many cycles of the drive pattern a large treatment volume can gradually be saturated with ultrasonic pressures to broadly activate the sonosensitizer. This ensures extraneous cancer cells in and all around the target treatment site receive therapy. In some instances, anatomic structures may disrupt and/or attenuate the ultrasonic pressures within the preferred treatment region. Where known disruptions may occur in the desired treatment region, the ensonification drive pattern may employ a combination of coherent and incoherent driving patterns to selectively add energy to any weak spots in the therapeutic operating field.

The ensonification drive patterns are applied as a pulsed therapy according to one embodiment. The ensonification drive patterns are applied as a continuous therapy according to one embodiment. There are inherent patient safety benefits in applying pulsed drive patterns instead of continuous wave. This avoids the buildup of energy as heat, especially at locations where significant reflections may be occurring. The pulsed drive pattern also dramatically reduces the ability for standing waves to form, thereby mitigating risks associated with continuous wave patterns. The pulsed drive pattern is also important to allowing broad activation of the sonosensitizers in some embodiments. With one embodiment of sonodynamic therapy there is a rate limiting step when the sonosensitizer is activated to produce reactive oxygen species, this process momentarily depletes local oxygen supply. A pulsed drive pattern enables the local oxygen supply to re-saturate, thereby enabling subsequent sonosensitizer activations to occur during subsequent pulses. In one embodiment, continuous wave drive patterns not only introduce a significant increase in potential patient safety hazards, but also could be detrimental to effective administration of sonodynamic therapy as continuous wave drive patterns may not broadly allow for restoration of local oxygen supplies.

Figure 27A:
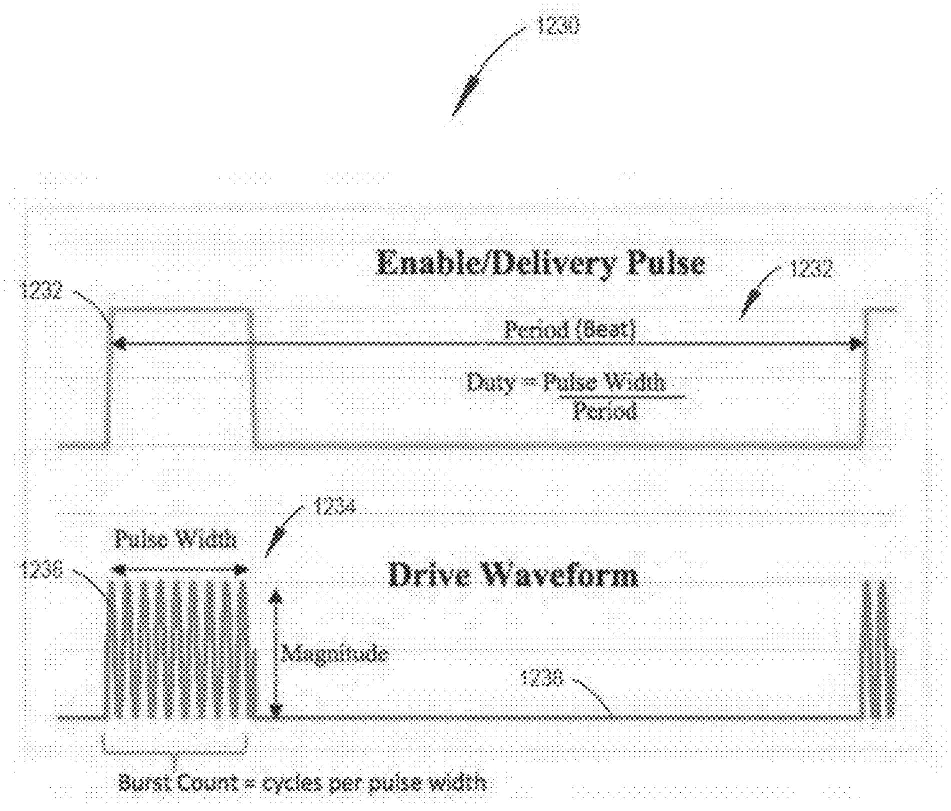
FIG. 27A is a diagram of a pulsed therapy in accordance with at least one aspect of the present disclosure.

FIG. 27A shows a diagram of a pulsed therapy 1230 in accordance with at least one aspect of the present disclosure. An enable/delivery pulse 1232 activates a drive waveform 1234 over a period (beat) at a predetermined duty cycle defined as the ratio of the pulse width to the period. The drive waveform 1234 has the same pulse width as the enable/delivery pulse 1232 and repeats over the same period. The drive waveform 1234 also is defined by the magnitude (amplitude) and burst count—the number of cycles of a periodic wave per pulse width 1232.

The pulsed nature of the drive pattern for enabling activation of a sonosensitizers can be defined by the pulse width of the pulsed drive waveform 1234 pattern. Each pulse width includes a burst 1236 of drive pattern cycles. In one embodiment, this burst 1236 of drive patterns creates a preferred cavitation environment to activate the sonosensitizers. In one embodiment, this burst 1236 of drive patterns creates a non-cavitational environment to activate the sonosensitizers. Applying a pulsed burst 1236 of drive patterns enables application of relatively higher peak intensity, while still maintain low temporal intensity. Each pulse width preferentially includes a burst 1236 of ten to one-thousand drive pattern cycles to create the preferred activation profile of the sonosensitizer. The time 1238 between bursts 1236 accounts for the restoration of local oxygen supplies, and additionally can be manipulated to manage temperature and safety concerns in highly reflective environments.

Figure 27B:
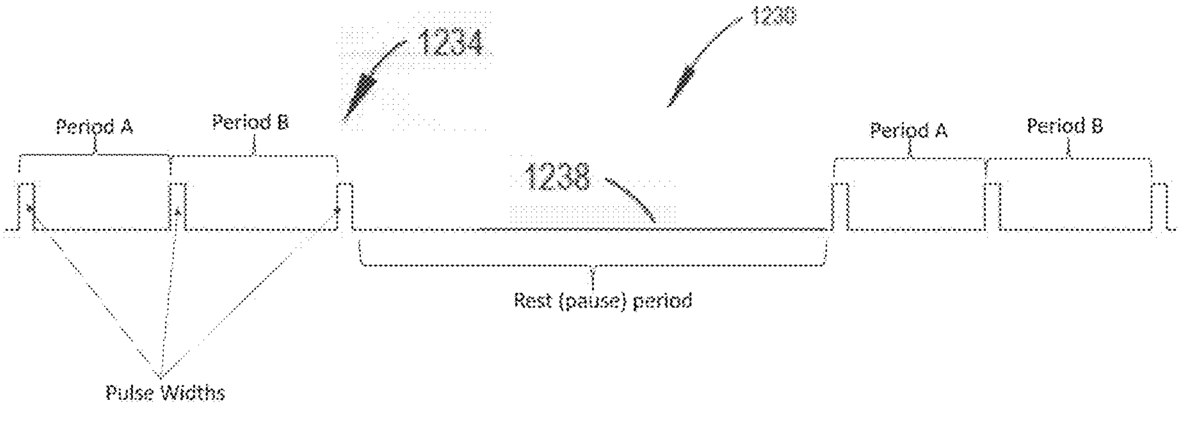
FIG. 27B is a diagram of a pulsed therapy in accordance with at least one aspect of the present disclosure.

FIG. 27B shows a diagram of a pulsed therapy 1230 in accordance with at least one aspect of the present disclosure that includes a pulsed drive waveform 1234 pattern with variable length periods followed by a periodic rest or pause cycle 1238. In various embodiments, a time delay is in a range of 0.1 μs to 100 s, including 0.1 μs, 0.2 μs, 0.3 μs, 0.4 μs, 0.5 μs, 1 μs, 5 μs, 10 μs, 15 μs, 20 μs, 25 μs, 30 μs, 35 μs, 40 μs, 50 μs, 60 μs, 70 μs, 80 μs, 90 μs, 0.1 ms, 0.2 ms, 0.3 ms, 0.4 ms, 0.5 ms, 1 ms, 5 ms, 10 ms, 50 ms, 100 ms, 500 ms, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s and any values and ranges therein. In various embodiments, a period rest or pause cycle is in a range of 0.1 μs to 100 s, including 0.1 μs, 0.2 μs, 0.3 μs, 0.4 μs, 0.5 μs, 1 μs, 5 μs, 10 μs, 15 μs, 20 μs, 25 μs, 30 μs, 35 μs, 40 μs, 50 μs, 60 μs, 70 μs, 80 μs, 90 μs, 0.1 ms, 0.2 ms, 0.3 ms, 0.4 ms, 0.5 ms, 1 ms, 5 ms, 10 ms, 50 ms, 100 ms, 500 ms, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s and any values and ranges therein.

In one embodiment, each pulse has the potential to create cavitation bubbles, and in some instances the cavitation bubbles can accumulate in a cloud that may obstruct or attenuate subsequent pulses. Various combinations of different period lengths as well as rest/pause cycles can be utilized to improve dissipation of the cavitation cloud prior to subsequent pulses. These pulsing parameters also provide additional means to manage and prevent temperature increases in the patient tissues exposed to the ultrasound field.

FIG. 27B illustrates a pulsed therapy in accordance with at least one aspect of the present disclosure that includes an initial period A followed by a slightly longer period B, followed by a rest or pause period before repeating the pulsing sequence. Additional subsequent periods of continually differing lengths may follow periods A and B. In various embodiments, period lengths and the rest/pause interval may provide additional benefit for activating a sonosensitizer by providing additional time for restoration of local oxygen supplies beneficial for sonodynamic therapy. In one embodiment, the period defines the pulse repetition frequency. In one embodiment, ultrasound transducers create high pitched audible noises when pulsing at a uniform pulse repetition frequency. Such audible noises may not be acceptable in clinical setting while treating patients, especially in a brain cancer application where the transducer is coupled to the head which can amplify the audible noise from the patient's perspective. In one embodiment the period length is randomized from pulse to pulse to reduce audible noise output from the transducer. In various embodiments, the Period A, Period B, and Rest (pause) Period 1238 are in a range of 0.1 μs to 100 s, including 0.1 μs, 0.2 μs, 0.3 μs, 0.4 μs, 0.5 μs, 1 μs, 5 μs, 10 μs, 15 μs, 20 μs, 25 μs, 30 μs, 35 μs, 40 μs, 50 μs, 60 μs, 70 μs, 80 μs, 90 μs, 0.1 ms, 0.2 ms, 0.3 ms, 0.4 ms, 0.5 ms, 1 ms, 5 ms, 10 ms, 50 ms, 100 ms, 500 ms, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s and any values and ranges therein. In various embodiments, a period rest or pause cycle 1238 is in a range of 0.1 μs to 100 s, including 0.1 μs, 0.2 μs, 0.3 μs, 0.4 μs, 0.5 μs, 1 μs, 5 μs, 10 μs, 15 μs, 20 μs, 25 μs, 30 μs, 35 μs, 40 μs, 50 μs, 60 μs, 70 μs, 80 μs, 90 μs, 0.1 ms, 0.2 ms, 0.3 ms, 0.4 ms, 0.5 ms, 1 ms, 5 ms, 10 ms, 50 ms, 100 ms, 500 ms, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s and any values and ranges therein. In one embodiment, a pulsed therapy is 0.1 μs and a period rest or pause cycle 1238 is 0.1 μs. In one embodiment, a pulsed therapy is 0.1 μs and a period rest or pause cycle is 0.2 μs. In one embodiment, a pulsed therapy is 0.1 μs and a period rest or pause cycle is 0.5 μs. In one embodiment, a pulsed therapy is 1 μs and a period rest or pause cycle is 1 μs. In one embodiment, a pulsed therapy is 1 μs and a period rest or pause cycle is 2 μs. In one embodiment, a pulsed therapy is 1 μs and a period rest or pause cycle is 5 μs. In one embodiment, a pulsed therapy is 1 ms and a period rest or pause cycle is 1 ms. In one embodiment, a pulsed therapy is 1 ms and a period rest or pause cycle is 2 ms. In one embodiment, a pulsed therapy is 1 ms and a period rest or pause cycle is 5 ms. In one embodiment, a pulsed therapy is 1 s and a period rest or pause cycle is 1 s. In one embodiment, a pulsed therapy is 1 s and a period rest or pause cycle is 2 s. In one embodiment, a pulsed therapy is 1 s and a period rest or pause cycle is 5 s.

In one embodiment, a pulsed drive waveform 1234 pattern includes bursts at discrete frequencies, such as in a range of about 20.00 kHz to about 12.00 MHZ, including, for example, 20 kHz, 50 kHz, 100 kHz, 250 kHz, 400 kHz, 500 kHz, 550 kHz, 600 kHz, 650 kHz, 700 kHz, 750 kHz, 800 kHz, 850 kHz, 900 kHz, 950 KHz, 1 MHZ, 1.1 MHZ, 1.2 MHZ, 1.3 MHZ, 1.4 MHZ, 1.5 MHZ, 2 MHZ, 3 MHz, 4 MHZ, 5 MHz, 10 MHZ, 12 MHZ, and any values and ranges therein, such 0.5 to 1.5 MHZ, 0.6 to 1.4 MHZ, 0.7 to 1.1 MHZ, 0.8 to 1.2 MHZ, 1 to 5 MHz, etc. More particularly, the transducers 150, 400, 450 may be driven at ultrasonic frequencies in a range of about 650.00 kHz to about 2.00 MHz. In one preferred range, the transducers 150, 400, 450 may be driven at ultrasonic frequencies in a range of about 500 kHz to about 1.3 MHZ, about 700 kHz to about 1.1 MHz, 900.00 kHz to about 1.20 MHZ, 975 kHz-1.1 MHZ, and as examples, in one embodiment, at about 1 MHZ, 1.03 MHZ, 1.06 MHZ, 1.10 MHZ, 1.20 MHZ, etc.) In one embodiment, a pulsed drive waveform 1234 pattern includes a burst at 0.1 MHz, 0.2 MHz, 0.4 MHz, 0.5 MHz, 0.6 MHZ, 0.7 MHz, 0.8 MHZ, 0.9 MHZ, 1.0 MHZ, 1.1 MHZ, 1.2 MHZ, 1.3 MHz, 1.4 MHZ, 1.5 MHz, 1.6 MHz, 1.7 MHz, 1.8 MHZ, 1.9 MHZ, 2.0 MHz, 2.5 MHZ, 3.0 MHz, 3.5 MHz, 4.0 MHZ, 4.5 MHZ, 5.0 MHz, 6 MHZ, 7 MHZ, 8 MHZ, 9 MHZ, 10 MHz and any values or ranges therein. In one embodiment, a pulsed drive waveform 1234 pattern includes one, two, three or more discrete bursts at 0.1 MHZ, 0.2 MHz, 0.4 MHz, 0.5 MHz, 0.6 MHz, 0.7 MHz, 0.8 MHz, 0.9 MHZ, 1.0 MHz, 1.1 MHz, 1.2 MHZ, 1.3 MHz, 1.4 MHz, 1.5 MHz, 1.6 MHz, 1.7 MHz, 1.8 MHz, 1.9 MHZ, 2.0 MHz, 2.5 MHz, 3.0 MHz, 3.5 MHz, 4.0 MHz, 4.5 MHz, 5.0 MHz, 6 MHz, 7 MHz, 8 MHZ, 9 MHZ, 10 MHz and any values or ranges therein, and including random bursts, sequential advancing bursts, sequential declining bursts, skipping bursts, and other burst patterns. In various embodiments, a repeating signal may be pulse-width modulated, duty-cycle modulated, phase modulated, frequency modulated, randomized phase modulated, or may be modulated using any suitable modulation technique to produce a desired acoustic pulse packet. In one embodiment, all elements in an array fire simultaneously. In one embodiment, all elements in an array fire sequentially. In one embodiment, all elements in an array fire randomly. In one embodiment, all elements in an array fire incrementally, such as at 0.5, 0.6, 0.7, 0.8, 0.9, 1.0, 1.1, 1.2, 1.3, 1.4, 1.5, 1.6, 1.7, 1.8, 1.9, 2.0 MHz and any values therein. In one embodiment, a reverse incremental sequence is used. In one embodiment, a lower frequency results in less cavitation. In one embodiment, a lower frequency provides for a greater potential to collapse bubbles. In one embodiment, a higher frequency provides for a greater potential for more cavitation.

The ensonification drive patterns include phase randomization amongst ultrasonic transducer elements according to one embodiment. The phase differences amongst the waves generated are randomized. This drive pattern provides an important aspect in creating the incoherent distributed therapeutic operating field. The randomization technique may utilize a normal distribution, or in other aspects it may be advantageous to pull from various random distributions to setup random phases. In one aspect, the method comprises selecting the phase of each element across the array in a randomized manner between 0-220 degrees (e.g., 0-45, 0-90, 1-135, 0-180, 0-200, 45-90, 45-135, 45-180, 45-220, 90-135, 90-180, 90-220, 120-220, 120-180, 120-150, 180-220, and/or 200-220 degrees of the phase, followed by dispersion adjustments to select groups of elements for the remaining 140-360 degrees of the phase (e.g., 140-300, 140-270, 140-225, 140-180, 140-150 degrees.

The ensonification drive patterns may include frequency modulation within each elements pulse to enhance the incoherent distributed field according to one embodiment. Varying the frequency within the burst of wave packets blurs the wave fronts, thereby providing a more homogenous therapeutic operating field. Broadly and evenly spreading the energy is necessary for robust activation of the sonosensitizers.

The ensonification drive patterns may include inverse and standard apodization profiles across the array elements, as well as a flat apodization profile according to one embodiment. Temporal apodization profiles within a drive pattern cycle are also a means that may be utilized to enhance the incoherent distributed field. Apodization is usually an ultrasound imaging technique that involves varying the amplitude across the aperture of the ultrasonic transducer, such that the transducer elements at the center of the probe head are electrically excited with a voltage of greater amplitude to those at the edges. Ultrasound imaging apodization seeks to reduce the amplitude of side lobes for better overall image resolution. An inverse of this drive pattern can be uniquely applied for directing energy into a therapeutic operating field for activating a sonosensitizer according to one embodiment. The unique inverse apodization for sonodynamic therapy provides greater energy to the ultrasonic transducer elements at the outer edges of the array compared to those near the center of the array axis. For this reason, inverse apodization both broadens the beam width, as well as results in deeper ensonification regions. The excitation scheme may involve smooth and/or discrete steps that help collect and distribute the energy across the therapeutic operating field. In the context of this therapeutic device, array or subarray based apodization may be utilized to focus energy in a smaller therapeutic operating field. This can be helpful when optimizing the therapeutic operating field in response to varying skull thicknesses, for example.

The ensonification drive patterns are likely to include alternating drive patterns according to one embodiment. Furthermore, some of the alternating drive patterns utilize only a subset of the elements as a sub-array for adding energy to specific locations in the distributed field. This is achieved through a selective process of coherently selecting the elements with directivity to the location of interest then providing phase randomization across those sub-array elements in order to have a field as incoherent as possible in the location of interest. The pulsed nature of the preferred drive patterns for sonodynamic therapy was previously disclosed. Each pulse could include the same burst of drive patterns, or additionally some alternating frequency of pulses could provide alternative drive patterns. The alternative drive patterns provide means to further saturate the therapeutic operating field with preferred waveform characteristics for activating a sonosensitizer. The alternating drive patterns may use all the ultrasonic transducer elements in the array, while other alternating drive patterns may use only a subset of the transducer elements in the array as a sub-array. Alternating drive patterns within a sub-array enables energy to be added to specific weak spots in the therapeutic operating field, without employing any type of coherent focused drive pattern.

FIG. 28 is a logic flow diagram 1240 for generating ensonification drive patterns for sonodynamic therapy in accordance with at least one aspect of the present disclosure. The logic flow diagram 1240 depicts a method of generating an acoustic ensonification drive pattern for activating a sonosensitizer in conjunction with providing sonodynamic therapy. The acoustic ensonification drive pattern creates an incoherent acoustic field for distributing low intensity energy. In accordance with the method, generate 1242 a first signal to drive a first ultrasonic transducer element to generate a first acoustic ensonification drive pattern having a first phase, a first frequency, and a first amplitude. Generate 1244 a second signal to drive a second ultrasonic transducer element to generate a second acoustic ensonification drive pattern having a second phase, a second frequency, and a second amplitude. At least one of the relative phase difference, frequency, and amplitude of the first and second signals is selected to generate a third incoherent acoustic ensonification pattern to activate a sonosensitizer located in a patient tissue.

FIGS. 29-42B illustrate various aspects of ultrasonic transducer arrays and techniques for packing elements of the ultrasonic transducer arrays according to various embodiments. The ultrasonic transducer arrays may be driven by the sonodynamic therapy systems 900, 1000, 1100, 920, 950 shown in FIGS. 20-24. The sonodynamic therapy systems 900, 1000, 1100, 920, 950 may be adapted and configured to drive the ultrasonic transducer arrays described hereinbelow to generate ensonification drive patterns for sonodynamic therapy.

An ultrasonic transducer is a device that is capable of generating and receiving ultrasonic vibrations according to one embodiment. An ultrasonic transducer comprises an active element. The active element is a piezoelectric or single crystal material which converts electrical energy to ultrasonic energy.

Various aspects of ultrasound array geometries for sonodynamic therapy may include large apertures, that contour with and/or are close fitting to the body according to one embodiment. Large apertures are defined as those that are the same size or larger than the lesion being treated. The aspect ratio of the aperture to lesion size enables initiation of a broad incoherent field to ensure the lesion and surrounding tissue receive therapy. In one embodiment, the array is close fitting with the body. For example, in a brain cancer aspect the array could be a close-fitting helmet, or even individual elements placed in an array pattern directly on the head. In one embodiment, ultrasound modifies the blood brain barrier (BBB). In one embodiment, ultrasound facilitates delivery of a drug and/or sonosensitizer across the blood brain barrier.

Ultrasonic transducer element arrays geometries include, without limitation, one, several or all of the following: close-fitting helmet, dome helmet, individual elements placed on head or body, flat arrays, hemispherical arrays, and/or curved linear arrays according to various embodiments.

In various aspects, the ultrasonic transducer elements that make up an array may be configured in a linear array, rectangular array, circular array, concentric circular array, spiral array, Archimedean spiral array, or sunflower spiral array, or any combination thereof, or sparse variations thereof, as described herein according to various embodiments. The ultrasonic transducer elements configured in such an arrangement may be packed according to a predetermined element packing density or distribution. In addition to linear rectangular arrays as shown in FIGS. 6 and 8 and concentric circular arrays shown in FIG. 7, various aspects of ultrasound element array geometries for sonodynamic therapy also may include ultrasonic transducer elements arranged in an Archimedean spiral, otherwise known as a linear, array. The Archimedean spiral has the property that any ray from the origin intersects successive turnings of the spiral in points with a constant separation distance (equal to $2\pi b$ if $\theta$ is measured in radians), hence the name "arithmetic spiral." The active transducer elements are disposed along the Archimedean spiral at various predetermined element packing density including sparse Archimedean spiral arrays.

Figure 29:
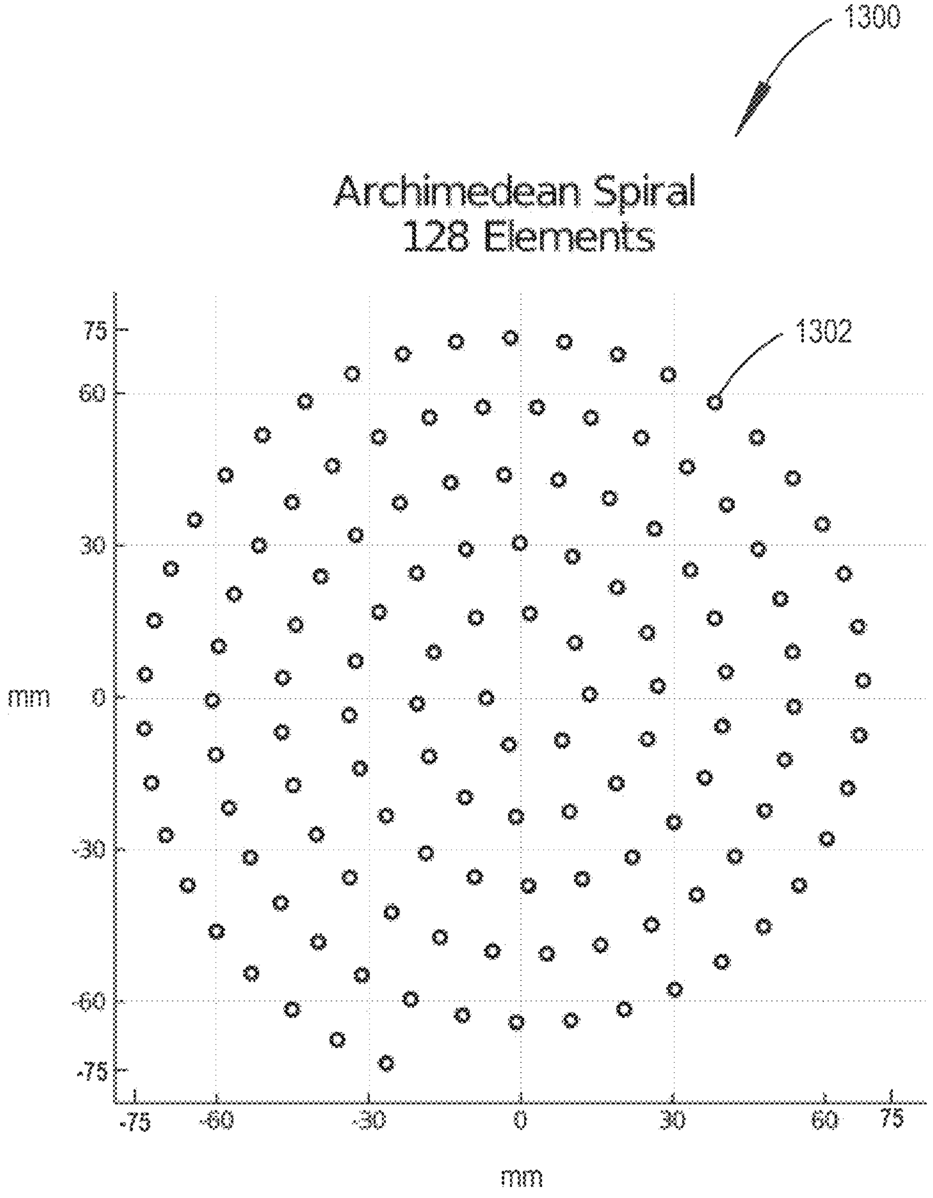
FIG. 29 is an array of ultrasonic transducer elements arranged in an Archimedean spiral (e.g., linear spiral) in accordance with at least one aspect of the present disclosure.

FIG. 29 is an array 1300 of ultrasonic transducer elements 1302 arranged in an Archimedean spiral (linear spiral) in accordance with at least one aspect of the present disclosure. In the illustrated example, the overall diameter of the Archimedean spiral array 1300 is about 150 mm, without limitation, and the diameter of the ultrasonic transducer elements 1302 can be selected in the range of 0.5 mm to 20 mm, without limitation. In various embodiments, the ultrasonic transducer elements 1302 have a dimension (e.g., length, radius, diameter) in the range of 0.5 mm to 20 mm, 1 mm to 10 mm, 3 mm to 7 mm, 4 mm to 6 mm, including 0.5 mm, 1 mm, 3 mm, 4 mm, 5 mm, 6 mm, 7 mm, 10 mm, 12 mm, 15 mm, 18 mm, and 20 mm including any values and ranges therein.

More particularly according to one embodiment, the diameter of the ultrasonic transducer elements 1302 can be selected based on the wavelength of a 1.5 MHz ultrasonic wave propagating in water at the speed of sound (~1,480 meters per second). The wavelength A is the ratio of the speed of sound to frequency. At these values, the nominal diameter of the ultrasonic transducer element 1032 is ~1 mm. The diameter of the ultrasonic transducer elements 1302 may be selected in the range of $0.5\lambda$ to $20\lambda$ (e.g., 0.5 mm to 20 mm). In one aspect, each of the ultrasonic transducer elements 1302 may have the same diameter and in other aspects, the ultrasonic transducer elements 1302 may have different diameters selected within the range described in this disclosure.

Figure 30:
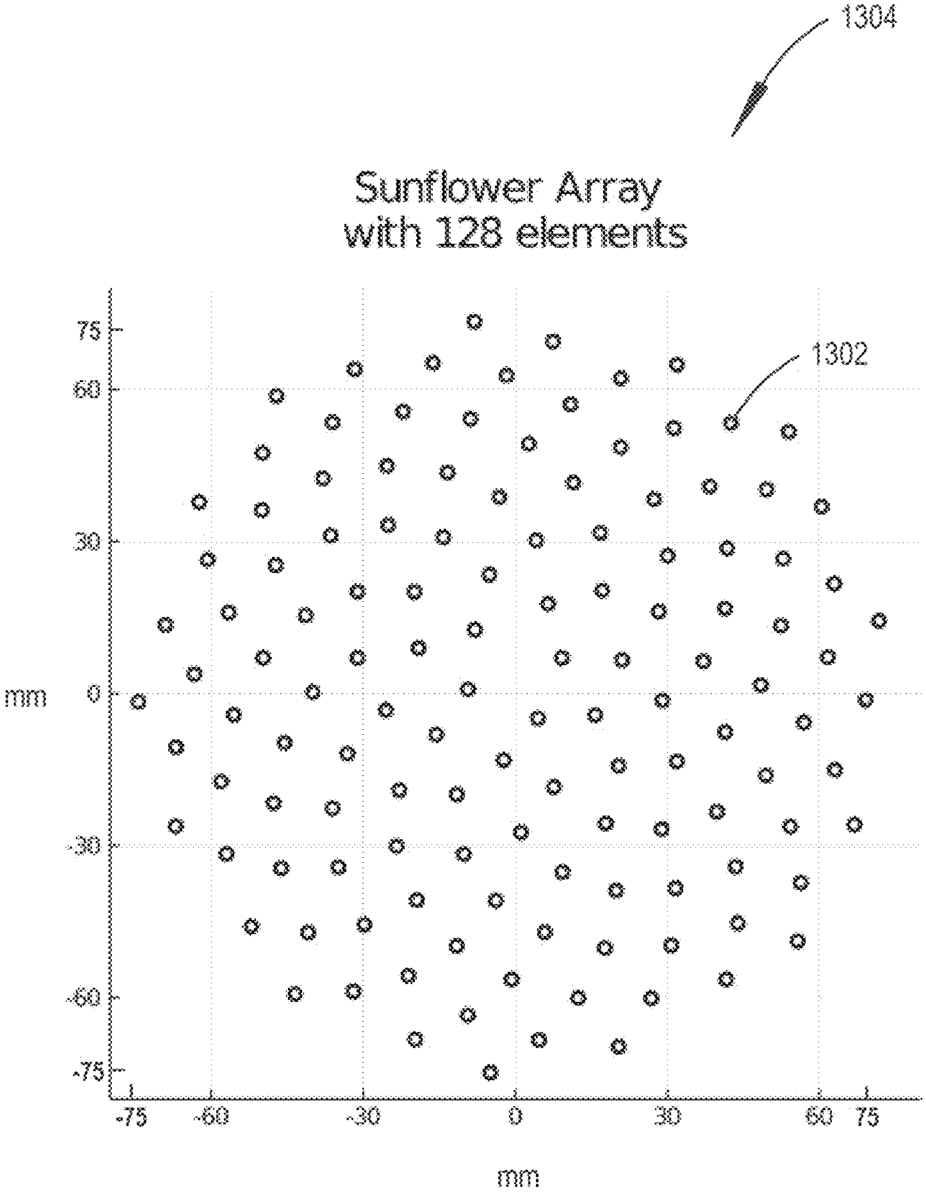
FIG. 30 is a sunflower spiral array of ultrasonic transducer elements in accordance with at least one aspect of the present disclosure.

Other aspects of ultrasound element array geometries for sonodynamic therapy also may include ultrasonic transducer elements arranged in a sunflower spiral pattern or grid according to various predetermined element packing density techniques including sparse sunflower spiral arrays. FIG. 30 is a sunflower spiral array 1304 of ultrasonic transducer elements 1302 arranged on a grid in accordance with at least one aspect of the present disclosure. As previously discussed, the diameter of the sunflower spiral array 1304 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or different within the dimension range set forth in this disclosure. It will be appreciated that some of the ultrasonic transducer elements 1302 may be deactivated. The sunflower spiral is a special case of a Fermat spiral defined by a divergence angle that determines the angular distance between two consecutive elements. The radial position of each element is determined by the square root of its angular position.

Other variations of the sunflower spiral array 1304 shown in FIG. 30 include variations comprising sparse sunflower spiral arrays and sunflower spiral arrays that include additional transducer elements disposed on certain rings of the sunflower spiral array according to a predetermined element packing density as shown in FIGS. 31-37.

The sunflower spiral array provides advantages over other sparse array configurations in terms of beamforming performance and array uniformity. Sunflower arrays are known for their good element packing property and having beam patterns with low side lobe energy. In addition, it is advantageous to choose the active ultrasonic transducer elements out of the sunflower spiral array since the sunflower pattern is considered the densest among the spiral patterns.

The present disclosure describes several configurations of sparse spiral arrays of active ultrasonic transducer elements arranged on a sunflower spiral grid in accordance with various packing densities according to various embodiments. Also disclosed is an algorithm for generating a variety of sparse spiral arrays arranged on a sunflower spiral grid at various packing densities with an equal number of active ultrasonic transducer elements to simplify the electronic circuitry for driving the ultrasonic transducer elements to achieve a desired sonodynamic therapy.

Sunflower spiral array patterns of ultrasonic transducer elements may be generated according to the following algorithm, function, or pseudocode.

The following is an example code for generating sunflower spirals according to various embodiments:

```
α = 137.51°                     # Magic or Golden angle
N_e = 128                       # Number of active elements
multiplier = 3                  # Number of elements to skip
N = N_e*multiplier              # Total elements including skipped elements
D = 150                       # Actual array diameter
I_0 = D/(sqrt((N 1)*α))         # From eq. 16 in Yoon et. al
n = 1:N                       # Element index
φ = n .* α                      # Polar angle of each element
r = I_0 .* sqrt.(φ)             # Polar radius of each element
# Create an array of Cartesian locations
C = polar2cart.(φ, r);
C = hcat(C...)';
# Create vectors of locations
inds = 1:multiplier:N
x,y = C[inds,1], C[inds,2]      # actual elements
xx,yy = C[:,1], C[:,2]          # all elements including skipped
# Plotting
scatter(xx,yy, ma=0.5, markercolor=:white,
markerstrokealpha=0.2, markerstrokecolor=:grey)
scatter!(x,y, markercolor=:blue)
plot!(aspect_ratio=:equal, size=(500,500), title="$(N) skipping every
$(multiplier) elements = 128")
savefig("sunflower_$(N)_skip$(multiplier).png")
```

The following is an example equations that can be used for generating sunflower grid points according to various embodiments:

$$\alpha \approx 137.51^\circ$$

$$i = 1 \ldots N$$

$$l = \frac{D}{2\sqrt{(N-1)\alpha}}$$

$$\theta_i = i\alpha$$

$$r_i = l\sqrt{\theta_i}$$

$$X_i = r_i \cos(\theta_i)$$

$$y_i = r_i \sin(\theta_i)$$

The equations above define the grid points of a sunflower array in polar coordinates ($\theta_i$, $r_i$) and cartesian coordinates ($x_i$, $y_i$) confined within a diameter, D. The sunflower grid points are incrementally positioned around the polar axis by steps of an angle, a, defined to be a Golden angle, approximately 137.51°. The sunflower grid points are incrementally positioned radially in steps of a length, l, defined to confine the points to a diameter, D. The sunflower grid point index, i, is an integer from 1 to N, where Nis the number of grid points.

Sparse rectangular and spiral arrays are presented in Yoon, Hansol and Tai-kyong Song. "Sparse Rectangular and Spiral Array Designs for 3D Medical Ultrasound Imaging." Sensors (Basel, Switzerland) 20 (2020): n. page, which is hereby incorporated by reference.

Figure 31:
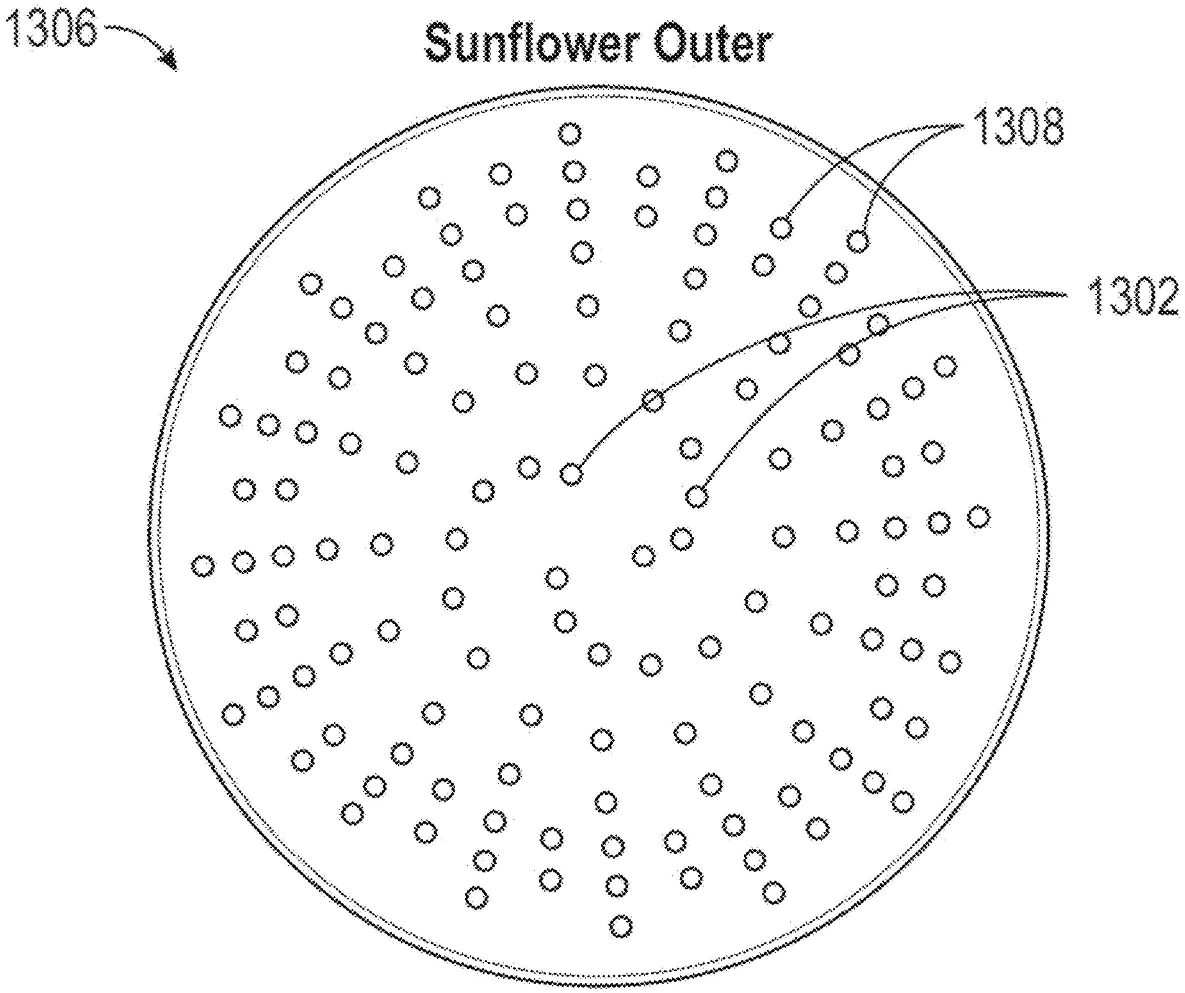
FIG. 31 is a sunflower spiral array of ultrasonic transducer elements with additional ultrasonic transducer elements added to outer regions of the sunflower spiral in accordance with at least one aspect of the present disclosure.

Turning to FIG. 31, there is shown an array 1306 of ultrasonic transducer elements 1302 that define an internal sunflower spiral with additional ultrasonic transducer elements 1308 located on the outer regions of the sunflower spiral array in accordance with at least one aspect of the present disclosure. As previously discussed, the diameter of the sunflower spiral array 1304 is about 150 mm, without limitation, and the diameter of the ultrasonic transducer elements 1302, 1308 can be selected in the range of 0.5 mm to 20 mm, without limitation, depending on the frequency of the excitation signal and the speed of sound in water. As previously discussed, the diameter of the ultrasonic transducer elements 1302, 1308 may be same or may be different with the diameters of the transducer elements 1302, 1308 selected within the range set forth in this disclosure. It will be appreciated that some of the ultrasonic transducer elements 1302, 1308 may be deactivated.

Figure 32:
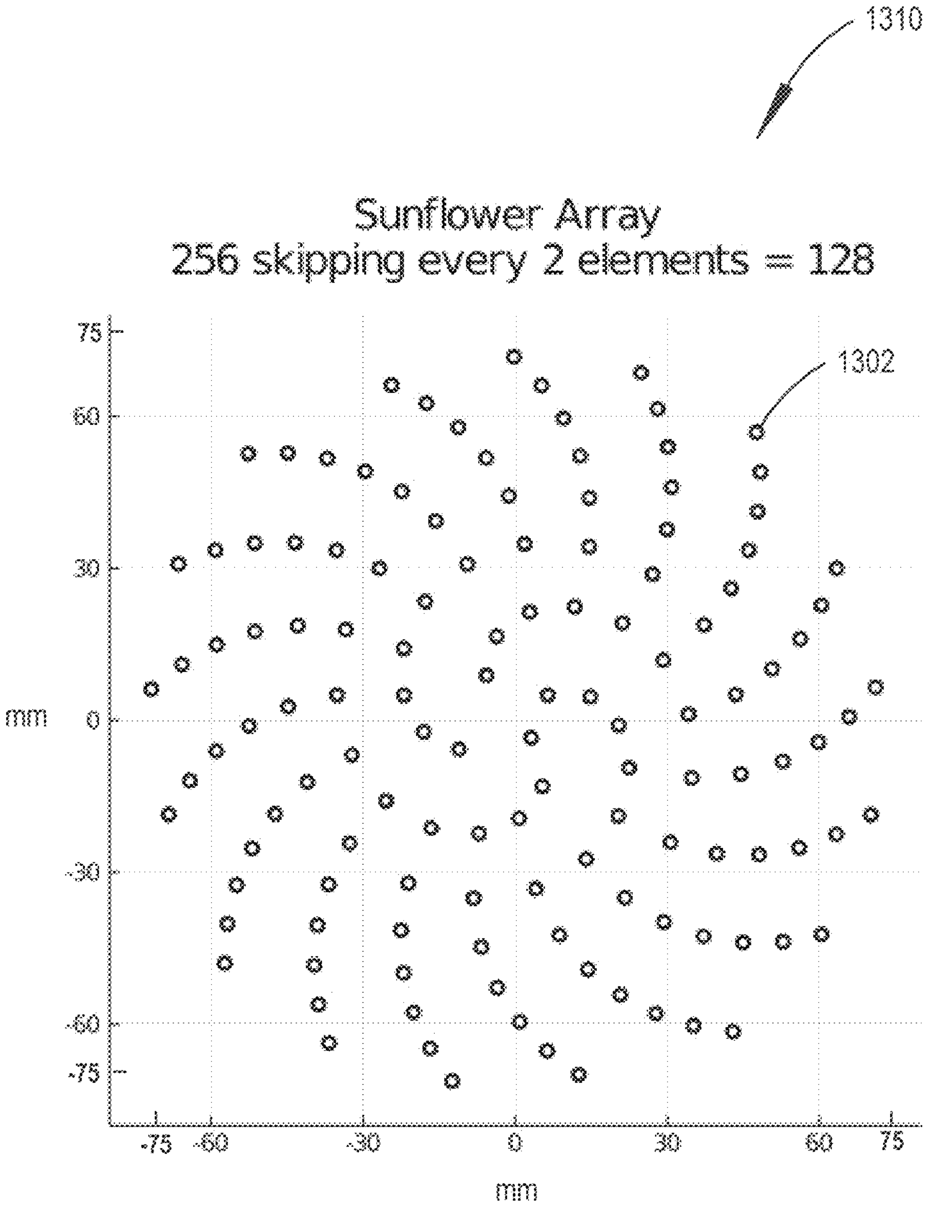
FIG. 32 is a sparse sunflower spiral array comprising 128 active ultrasonic transducer elements arranged on a 256 element grid skipping every 2 elements in accordance with at least one aspect of the present disclosure.

FIG. 32 is a sparse sunflower spiral array 1310 comprising 128 active ultrasonic transducer elements 1302 arranged on a 256 element grid skipping every 2 elements in accordance with at least one aspect of the present disclosure. As previously discussed, the diameter of the sunflower spiral array 1310 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 33:
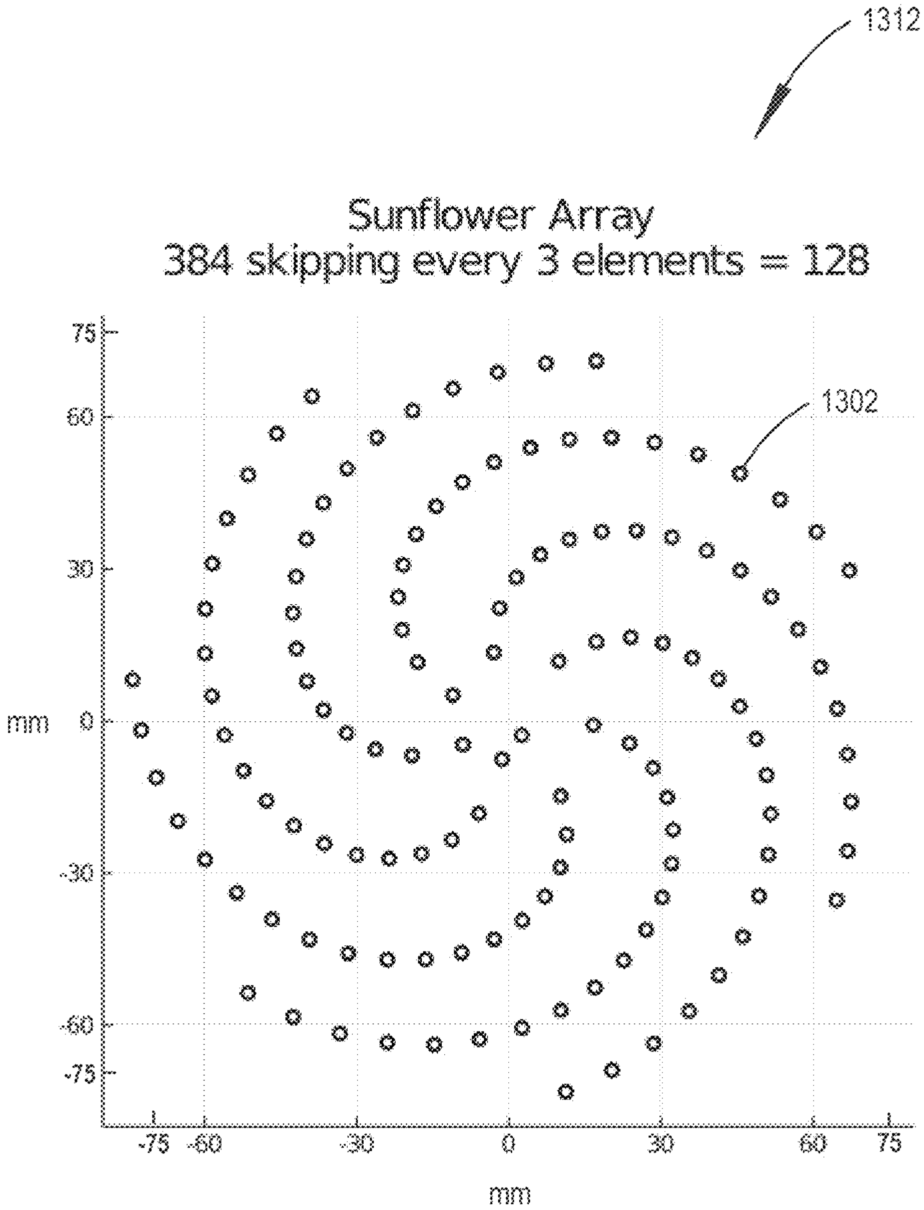
FIG. 33 is a sparse sunflower spiral array comprising 128 active ultrasonic transducer elements arranged on a 384 element grid skipping every 3 elements in accordance with at least one aspect of the present disclosure.

FIG. 33 is a sparse sunflower spiral array 1312 comprising 128 active ultrasonic transducer elements 1302 arranged on a 384 element grid skipping every 3 elements in accordance with at least one aspect of the present disclosure. As previously discussed, the diameter of the sunflower spiral array 1312 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 34:
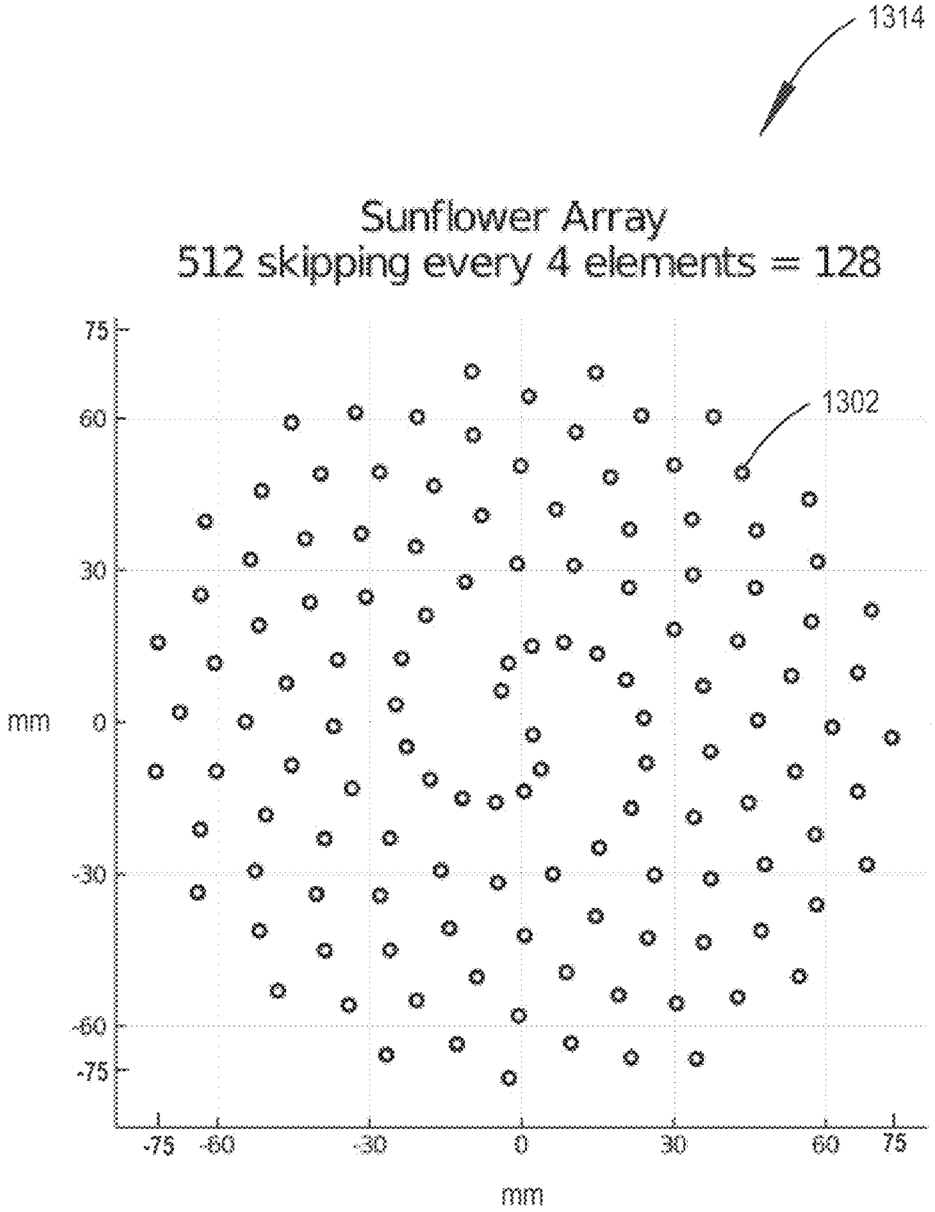
FIG. 34 is a sparse sunflower spiral array comprising 128 active ultrasonic transducer elements arranged on a 512 element grid skipping every 4 elements in accordance with at least one aspect of the present disclosure.

FIG. 34 is a sparse sunflower spiral array 1314 comprising 128 active ultrasonic transducer elements 1302 arranged on a 512 element grid skipping every 4 elements in accordance with at least one aspect of the present disclosure. As previously discussed, the diameter of the sunflower spiral array 1314 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 35:
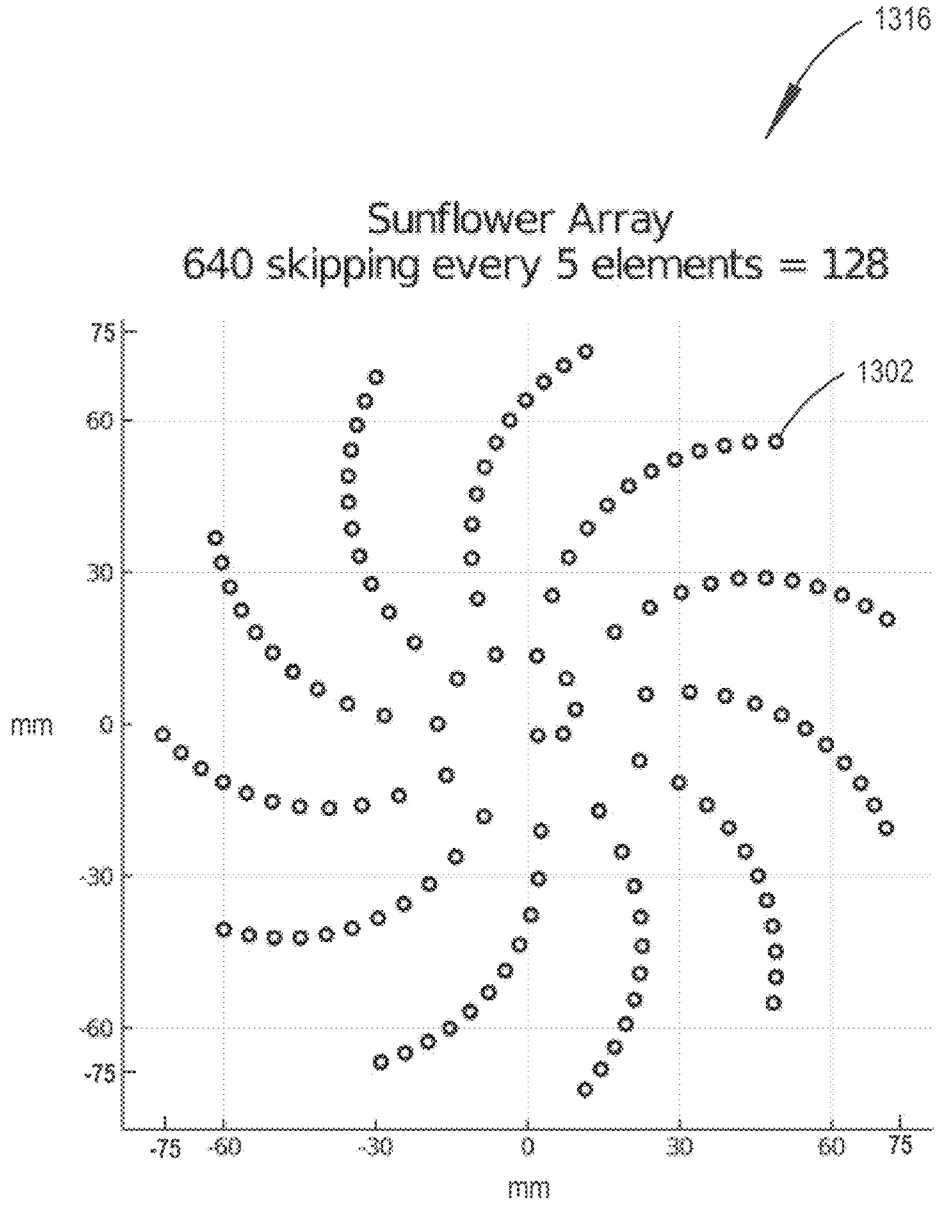
FIG. 35 is a sparse sunflower spiral array comprising 128 active ultrasonic transducer elements arranged on a 640 element grid skipping every 5 elements in accordance with at least one aspect of the present disclosure.

FIG. 35 is a sparse sunflower spiral array 1316 comprising 128 active ultrasonic transducer elements 1302 arranged on a 640 element grid skipping every 5 elements in accordance with at least one aspect of the present disclosure. As previously discussed, the diameter of the sunflower spiral array 1316 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 36:
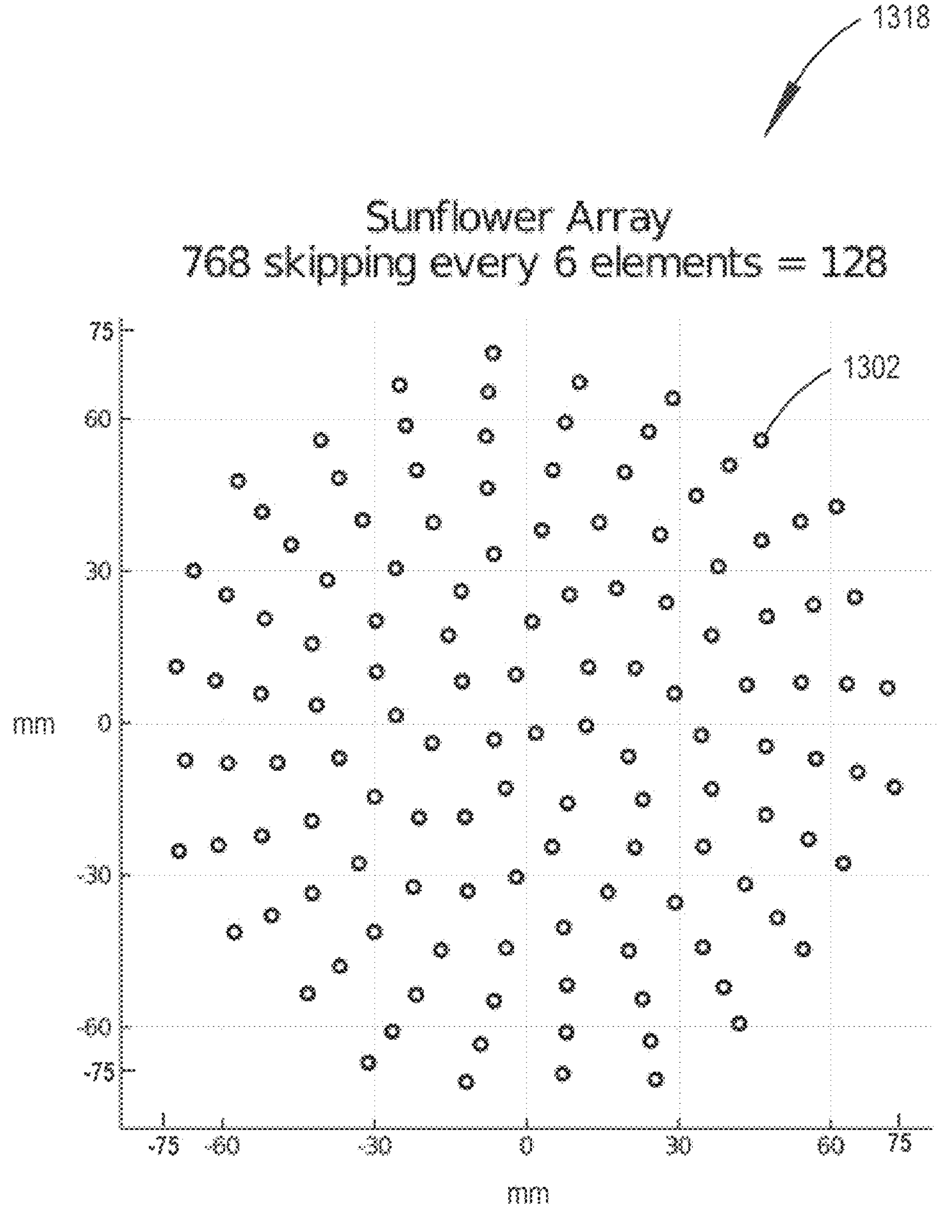
FIG. 36 is a sparse sunflower spiral array comprising 128 active ultrasonic transducer elements arranged on a 768 element grid skipping every 6 elements in accordance with at least one aspect of the present disclosure.

FIG. 36 is a sparse sunflower spiral array 1318 comprising 128 active ultrasonic transducer elements 1302 arranged on a 768 element grid skipping every 6 elements in accordance with at least one aspect of the present disclosure. As previously discussed, the diameter of the sunflower spiral array 1318 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 37:
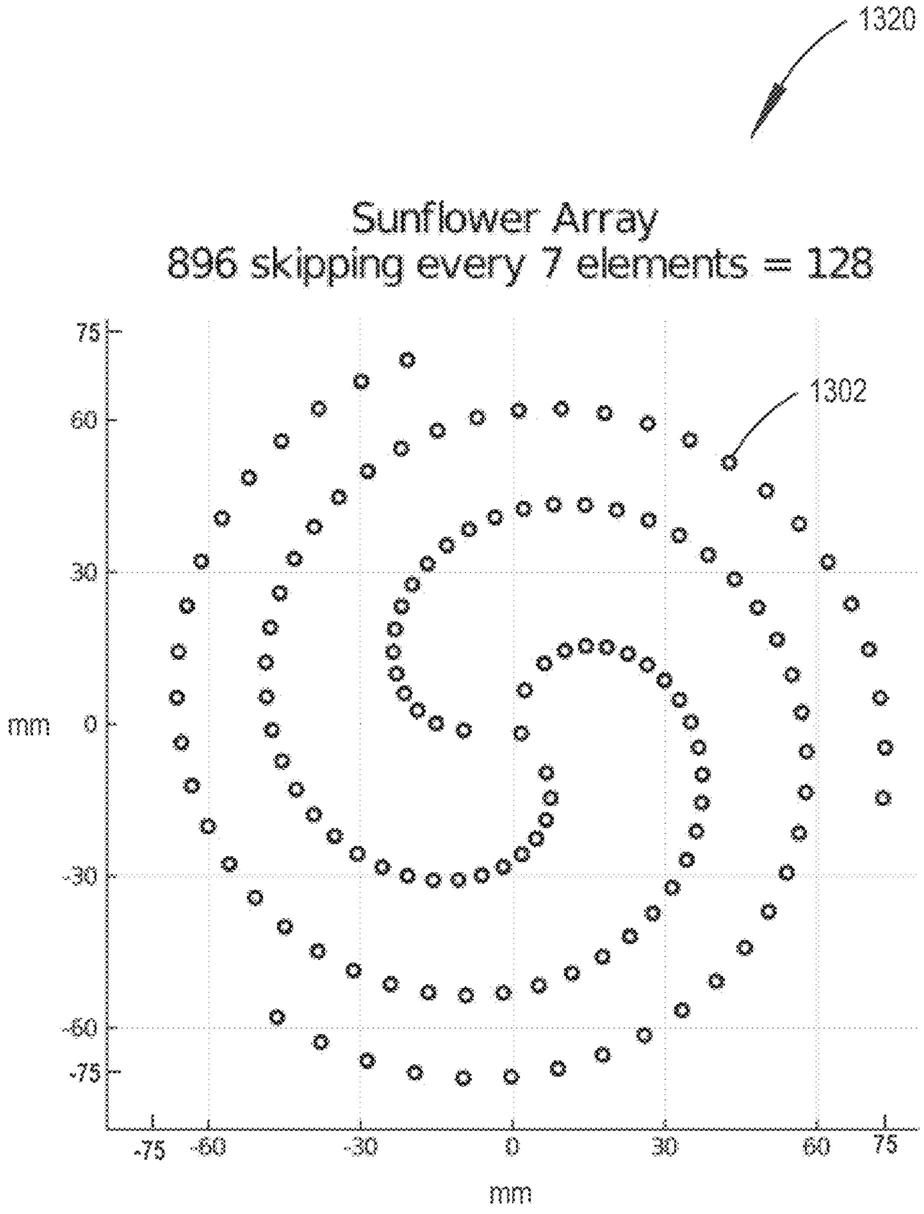
FIG. 37 is a sparse sunflower spiral array comprising 128 active ultrasonic transducer elements arranged on a 896 element grid skipping every 7 elements in accordance with at least one aspect of the present disclosure.

FIG. 37 is a sparse sunflower spiral array 1320 comprising 128 active ultrasonic transducer elements 1302 arranged on a 896 element grid skipping every 7 elements in accordance with at least one aspect of the present disclosure. As previously discussed, the diameter of the sunflower spiral array 1320 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 38:
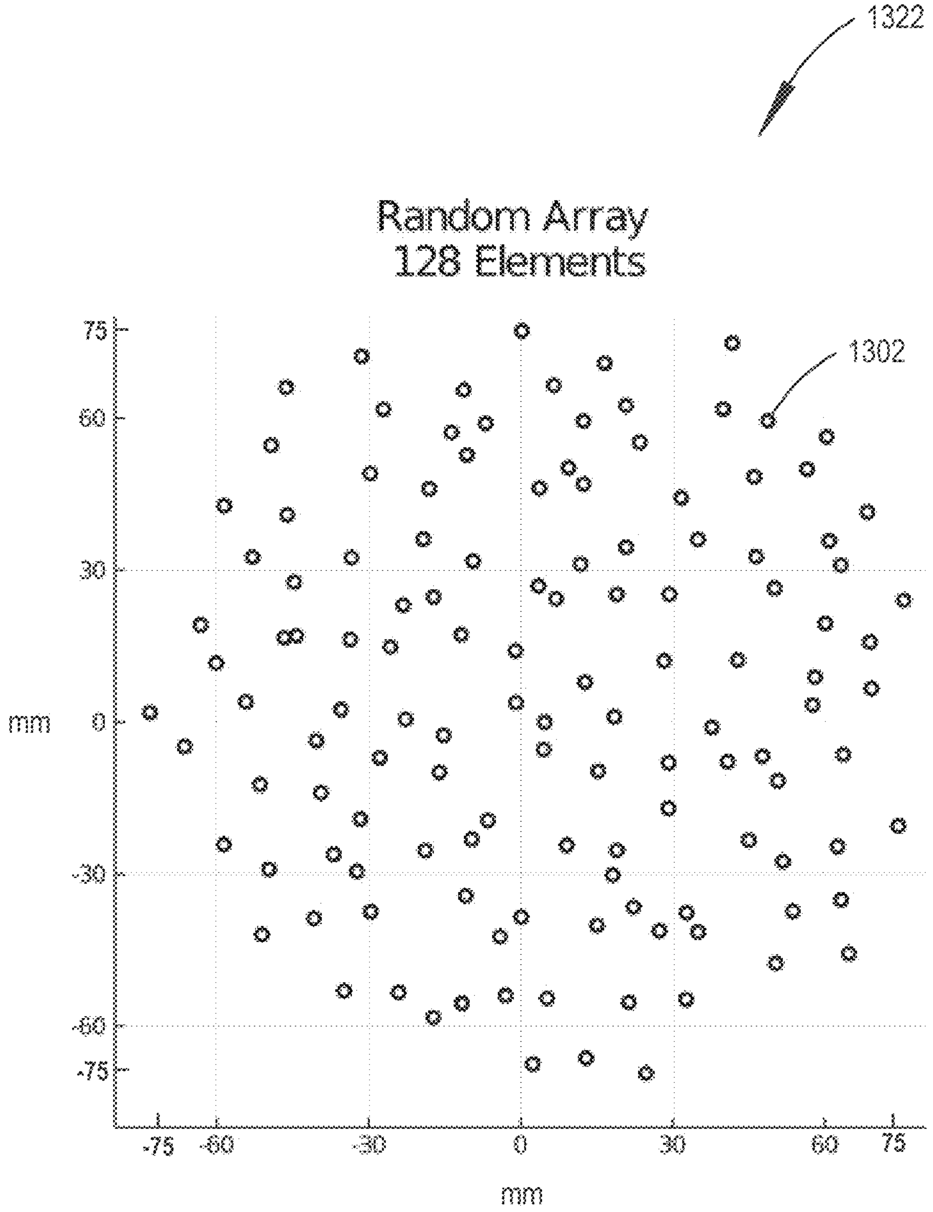
FIG. 38 is an array comprising 128 active ultrasonic transducer elements randomly arranged and irregularly placed in a non-uniform distribution in accordance with at least one aspect of the present disclosure.

FIG. 38 is an array 1322 comprising 128 active ultrasonic transducer elements randomly arranged and irregularly placed in a non-uniform distribution in accordance with at least one aspect of the present disclosure. As previously discussed, the diameter of the random array 1322 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302 may be same or may be different with the diameter of the transduce elements 1302 selected within the range set forth in this disclosure. It will be appreciated that some of the ultrasonic transducer elements 1302 may be deactivated.

Figure 39A:
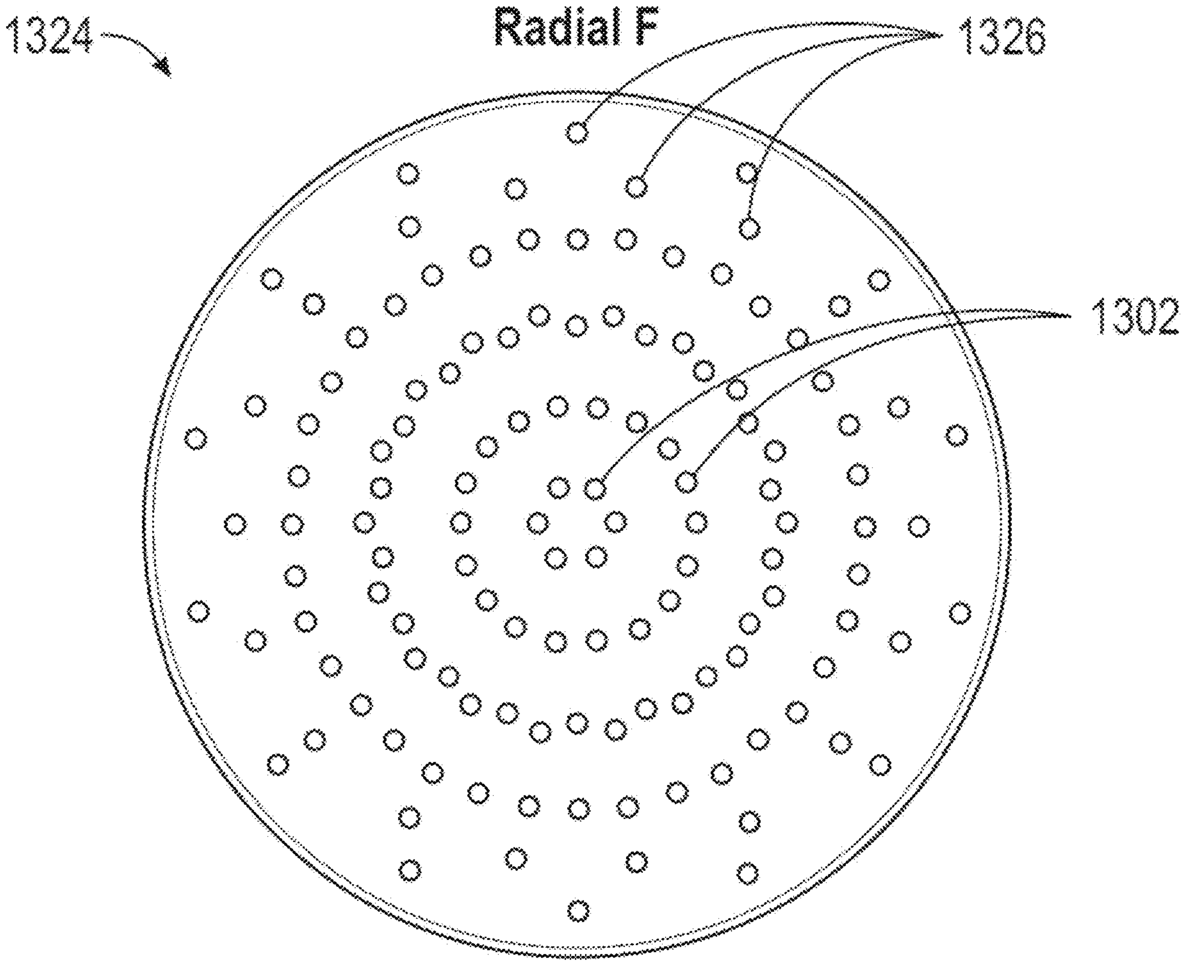
FIG. 39A is an array of active ultrasonic transducer elements arranged in concentric circles with additional active ultrasonic transducer elements disposed on outer portion of the outer ring according in accordance with at least one aspect of the present disclosure.

In various aspects, ultrasonic transducer element shapes include circular or disc shapes and concentric rings and FIGS. 1-3 and 7, for example. FIG. 39A is an array 1324 of active ultrasonic transducer elements 1302 arranged in concentric circles with additional active ultrasonic transducer elements 1326 disposed on outer portion of the outer ring according in accordance with at least one aspect of the present disclosure. As previously discussed, the diameter of the array 1324 is about 150 mm, without limitation, and the diameter of the ultrasonic transducer elements 1302 can be selected in the range of 0.5 mm to 20 mm, without limitation, depending on the frequency of the excitation signal and the speed of sound in water. As previously discussed, the diameter of the ultrasonic transducer elements 1302, 1326 may be same or may be different with the diameter of the transduce elements 1302, 1326 selected within the range set forth in this disclosure. It will be appreciated that some of the ultrasonic transducer elements 1302, 1326 may be deactivated.

Figure 39B:
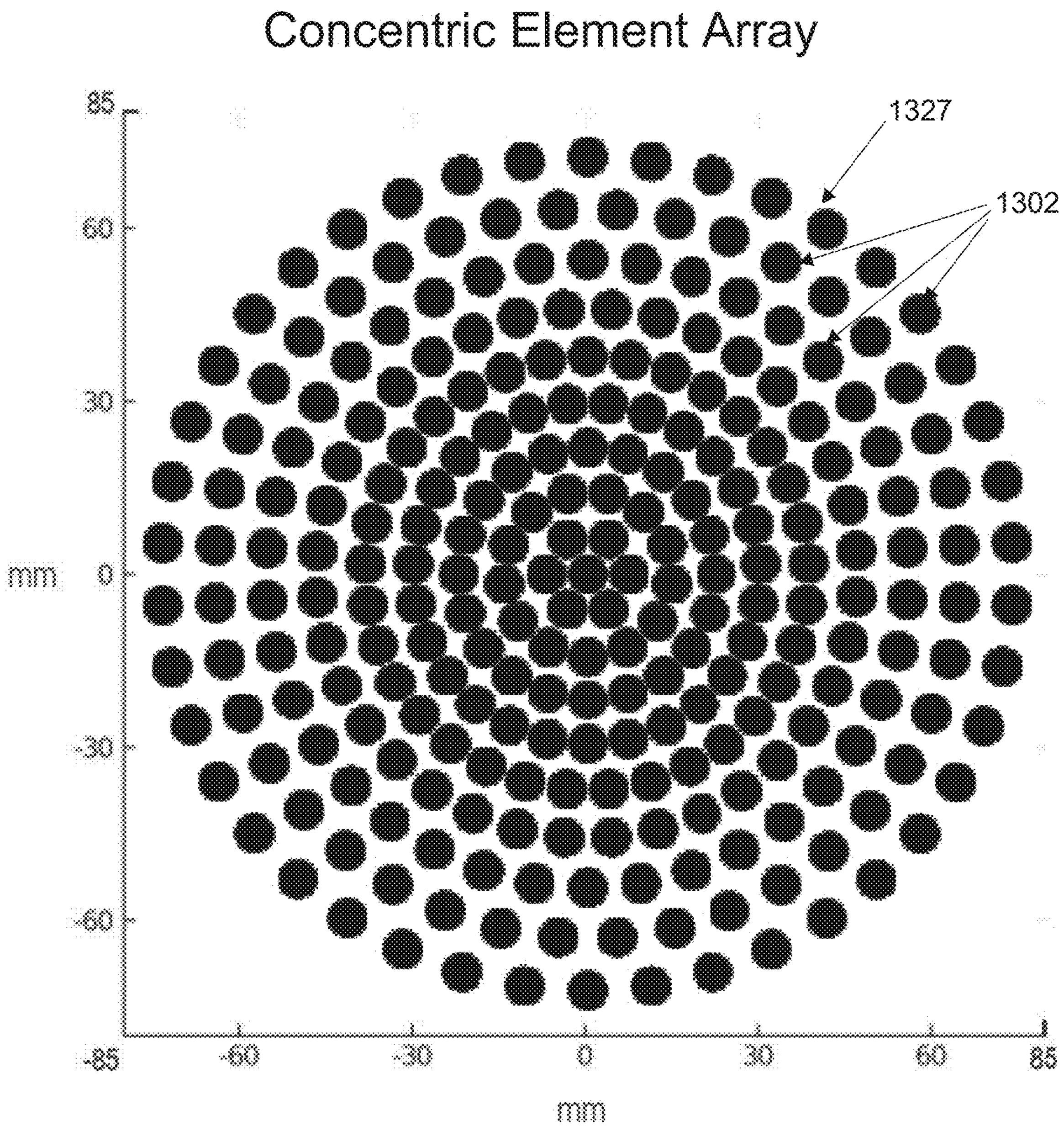
FIG. 39B is an array of ultrasonic transducer elements arranged in concentric circles in accordance with at least one aspect of the present disclosure.

FIG. 39B is an array 1327 of ultrasonic transducer elements 1302 arranged in concentric circles in accordance with at least one aspect of the present disclosure. In various embodiments, the diameter of the overall array 1324 is in a range of about 100 mm-200 mm, including but not limited to 100 mm, 125 mm, 150 mm, 165 mm, 175 mm, 200 mm and any values therein without limitation, and the diameter of the ultrasonic transducer elements 1302 can be selected in the range of 0.5 mm to 20 mm, including 0.5 mm, 1 mm, 3 mm, 5 mm, 7 mm, 10 mm, 12 mm, 15 mm, 18 mm, and 20 mm without limitation, depending on the frequency of the excitation signal and the speed of sound in water. In various embodiments, the diameter of the ultrasonic transducer elements 1302 may be same or may be different with the diameter of the transducer elements 1302 selected within the range set forth in this disclosure. It will be appreciated that some of the ultrasonic transducer elements 1302 may be activated or deactivated collectively, in groups, or individually. In various embodiments, the array 1327 comprises 1 to 1024 ultrasonic transducer elements 1302, including 1, 2, 4, 8, 16, 32, 64, 128, 256, 384, 512, 640, 678, 896, 1024 elements. In various embodiments the array 1327 comprises 100, 200, 300, 400, 500, 600, 700, 800, 900, or 1000 ultrasonic transducer elements 1302. In one embodiment, the array 1327 has 256 transducer elements 1302 that each have a 5 mm diameter. In one embodiment, the spacing between adjacent elements is constant. In one embodiment, spacing between adjacent elements incrementally increases from the center of the array outward toward an outer diameter of the array, wherein the spacing between adjacent valences and/or concentric rings of elements incrementally increases from the center of the array toward an outer diameter or circumference of the array. In one embodiment, spacing between adjacent elements incrementally decreases from the center of the array outward toward an outer diameter of the array, wherein the spacing between adjacent valences and/or concentric rings of elements incrementally decreases from the center of the array toward an outer diameter or circumference of the array.

Figure 40:
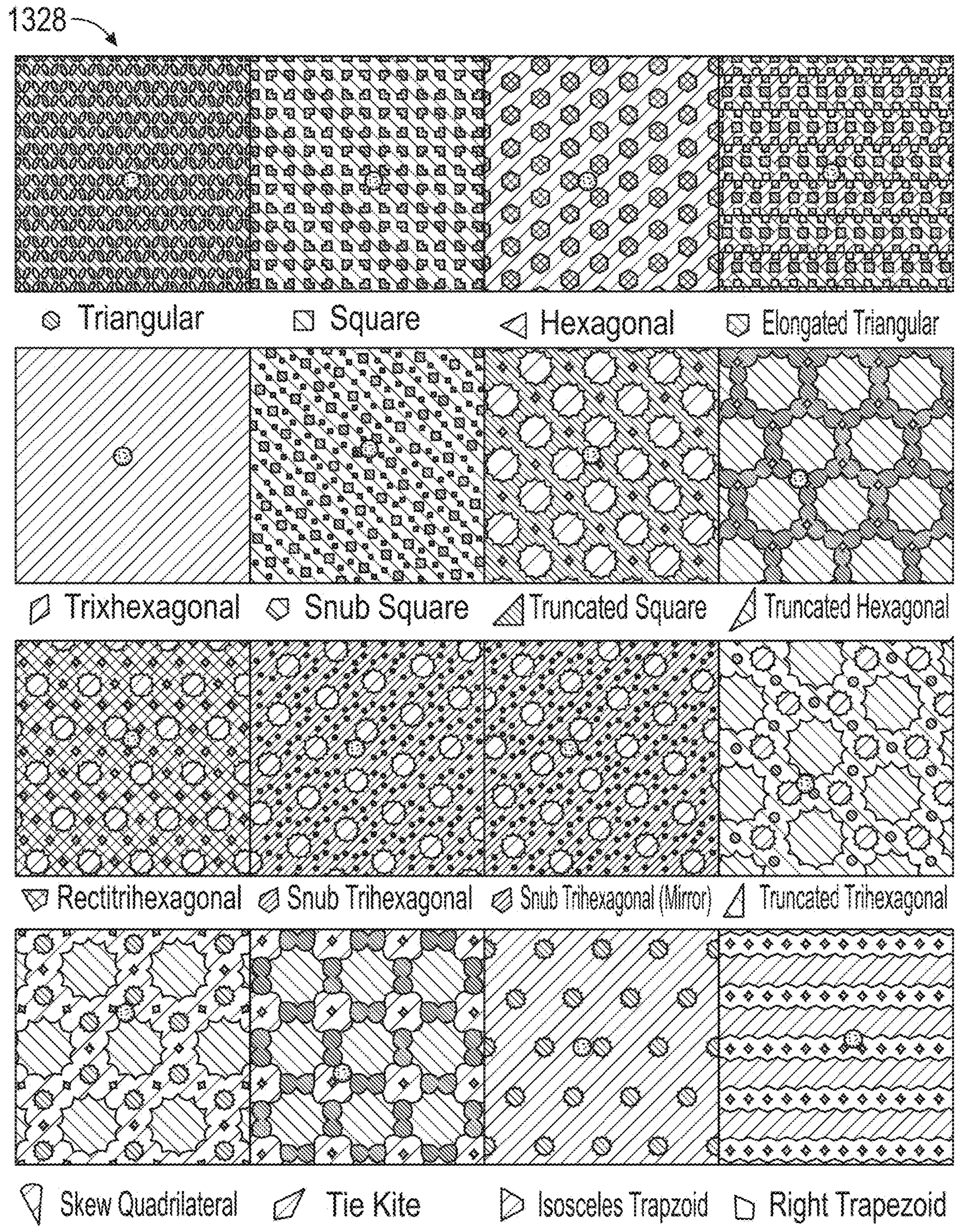
FIG. 40 illustrates several uniform element packing techniques for arranging ultrasonic transducer elements in accordance with at least one aspect of the present disclosure.

FIG. 40 illustrates several uniform element packing techniques 1328 for arranging ultrasonic transducer elements in accordance with at least one aspect of the present disclosure. In various aspects, the ultrasonic transducer elements that make up an array such as linear, rectangular, circular, concentric circular, spiral, Archimedean spiral, or sunflower spiral, or any combination thereof, or sparse variations thereof, as described herein may be packed according to a predetermined element packing density or distribution. Regular element packing densities or distributions is the arrangement of circular active transducer elements (of equal or varying sizes) on a given surface such that no overlapping occurs between the transducer elements and such that no circular transducer element can be enlarged without creating an overlap. The associated packing density, n, of an arrangement is the proportion of the surface covered by the circles. Regular element packing is further described at https://en.wikipedia.org/wiki/Circle_packing#Uniform_packings, which is herein incorporated by reference.

FIGS. 4 and 5 show different aspects of a transducer lens defining concave and convex surfaces, respectively, according to various embodiments. Creating a broad, diffuse field through the skull presents several challenges. The skull attenuates a lot of ultrasonic energy. Geometrically focusing the ultrasonic transducer elements to the same point help overcome the attenuation from the skull. This geometric focus of array receives energy from every element in the array. Points closer to the array (e.g., within the skull) can be too far off-axis from many elements to receive much energy due to the individual element directivity. While the skull still attenuates a significant fraction of energy from any one element, the total amount of energy between points close to the array and the focal point is high. Thus, the geometric focus helps to offset the transmission loss of the skull.

This geometric focusing comes at a cost, as it naturally restricts the size of the field relative to a flat array. In other words, while geometric focusing helps with transmitting enough energy, it prevents the field from being as broad and diffuse as it could be. Additionally, for many arrays, the geometric focus is fixed because the position and orientation of the elements are fixed within the array.

To help alleviate this trade-off, lenses, such as the type shown in FIGS. 4 and 5, can be added to the emitting surface of an array according to various embodiments. Lenses can manipulate the direction and vergence of a field. In some aspects, lenses are added to change the geometric focus of the array. For example, a lens may be added to the transducer to move the focus closer to the array. In another aspect, a lens may be added to the transducer to disperse the beam of energy from each element within the array. This beam dispersion may not change the geometric focus of the array, but points closer to the array can receive energy from a greater number of elements.

In one aspect, a large piece of acoustic lens material could be shaped to form an array of lenses. In some cases, the lens array can be repositioned to move the array relative to the emitting elements. In some aspects, the lens could be rotated along a single axis. For example, a lens array could be rotated 180° from an "off" position into an "on" position relative an Archimedean spiral array. In the off position, the outer surface of the lens array just over the elements is parallel to the emitting surfaces of the elements. This parallel surface does not significantly modify the direction or vergence of the ultrasound waves. In this off position, the regions of the lens array which do modify the ultrasound field are placed around an Archimedean spiral which is interleaved with the spiral along which the elements are placed. In the on position, the lens array is rotated so that the spiral that crosses the effective lensing regions and the spiral that crosses the element locations overlap.

In some aspects, there may be several positions that provide different degrees of focusing. The lens array can be repositioned to a finite number of locations which each has a different effect on the resulting field. In some cases, the lens array may be rotated to any intermediate position (an infinite number of positions). For example, the lens array may be shaped with a continuous spiral valley which can be rotated to many relative positions with respect to the element spiral. When the bottom of the groove is aligned with the element spiral, there will be one effect on the array focus and element dispersion. When the crest between two grooves is aligned with the element spiral, there will be another effect on the array focus and element dispersion. Similarly, the lens array can be rotated so the leading slope between a crest and valley is aligned with the element spiral. The trailing slope between a valley and a crest can be aligned with the element spiral. All intermediate position provides a different effect on the resulting field.

In some aspects, the lens can rotate with three rotational degrees of freedom (a spherical kinematic pair).

Dispersion Lensing can also be applied to the elements in order to broaden the acoustic beam produced by each element. This dispersion lensing could be incorporated within the acoustic stack design proper, or it could be achieved through a plastic (Pebax 300 series, for example)

overlay that fits over the face of the transducer array, coupled in an appropriate manner. This type of overlay could be interchangeable, such that different dispersion lenses could be created in order to optimize the therapeutic operating field for various skull sizes and thicknesses.

In another aspect, this dispersion lensing could have more or less beam broadening impact on an element to element basis, in order to randomize the acoustic beam summation from various elements. This dispersion randomization could be applied on a localized element subarray basis—to enhance the overlap of acoustic beams from adjacent elements, or alternately, a patterned randomization across the entire array could be applied. For example, more beam broadening could be applied to elements closer to the array center, and less beam broadening applied to outer array elements to compensate for the geometric acoustic beam spreading for elements farther from the targeted brain tissue therapy area-outer elements.

Whereas elements situated along a concave surface allows for energy summation close to the geometric focus of the concave surface, it may be advantageous in this application to add an overall array dispersion lens to lessen the effect of the geometric focusing and reduce geometric side lobe focusing, as well. This functionality, in the interest of enhancing the ability to broaden the therapeutic operating field. In one aspect, this could involve a small randomized acoustic delay applied as parts of the transducer acoustic stack design, or as a separate overlay lens, as noted herein. Note that while this technique is similar to electronic transmit pulse phase randomization, the acoustic properties of the element beam profile may be altered by the introduction of this physical acoustic offset. This acoustic offset can be modeled and optimized in order to provide the best overall acoustic beam performance.

This overlay lensing could also be utilized to focus the energy of the standard array to focus closer or farther, to better optimize the therapeutic operating field for different skull sizes and/or thicknesses.

In another aspect, this overlay lensing could be utilized to focus different areas of the array at different depth locations-similar to an annular array. For example, outer array elements could be focused deeper and inner array element focused closer, with middle array elements focused at a depth between those two extremes in order to elongate and broaden the therapeutic operating field.

In another aspect, the focusing might be enhanced-outer elements focused closer, inner elements focused deeper, in order to ensure overlap of the energy profile across the therapeutic area of the brain targeted. These examples illustrate that this type of array focusing overlay lens could be generalized to any sub-array or overall array focusing mechanism (for example, a Fresnel type lens).

Figure 41:
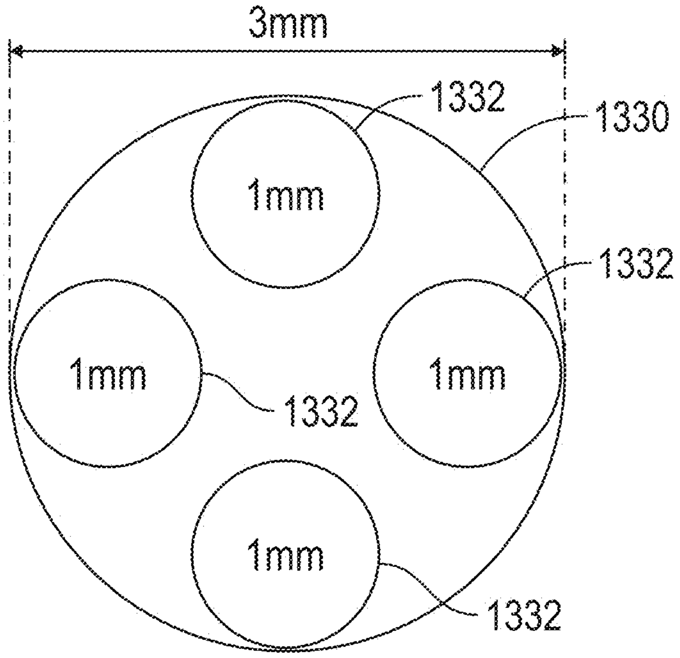
FIG. 41 is a 3 mm diameter transducer aperture replaced by four 1 mm diameter aperture elements in accordance with at least one aspect of the present disclosure.

FIG. 41 illustrates a 3 mm diameter transducer aperture element 1330 replaced by four 1 mm diameter aperture elements 1332 in accordance with at least one aspect of the present disclosure. In terms of array element grouping, a number of different techniques could result in improvements to the overall therapeutic operating field. In a first element grouping technique, smaller ultrasonic transducer elements 1332 replace larger ultrasonic transducer elements 1330. In this instance, the larger ultrasonic transducer element 1330 is replaced with an array of smaller elements 1332 in order to broaden the overall acoustic beam produced by the elements. (Smaller elements generally have broader beam patterns and better angular response compared with larger elements.) For example, a 3 mm circular element 1330 may be replaced with four 1 mm elements 1332, as illustrated in FIG. 38 in accordance with at least one aspect of the present disclosure. In one aspect, these four 1 mm elements 1332 may be combined into a subarray and connected together to form an equivalent 3 mm aperture element 1330. Whereas, as a practical solution to limit system requirements this might be desirable, it would not be a requirement.

Figure 42A:
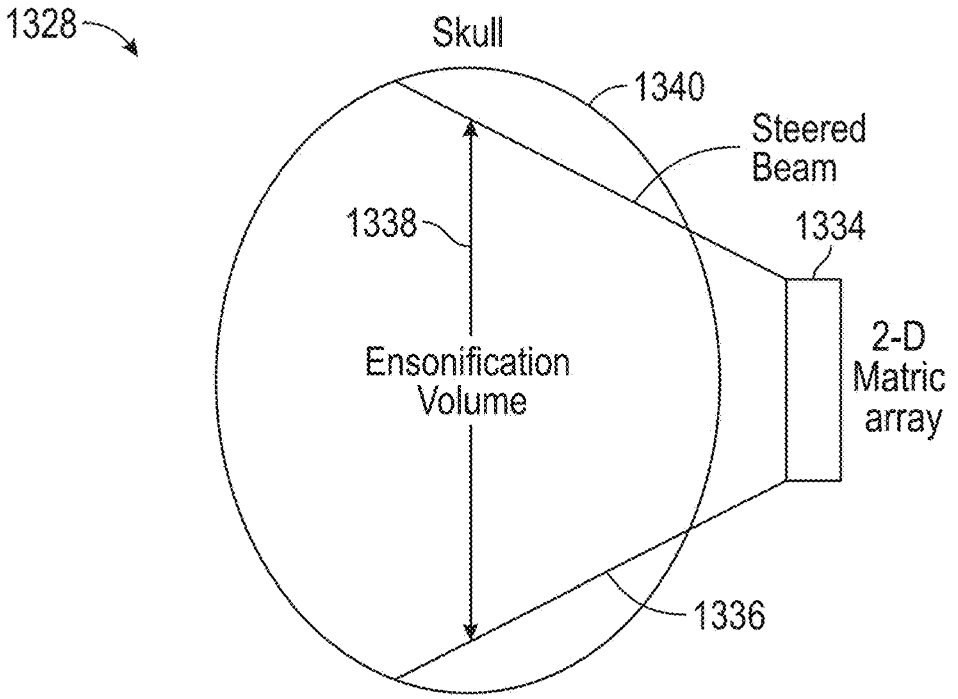
FIG. 42A is a side view of a 2D matrix array of ultrasonic transducer elements configured to generate a steered beam in accordance with at least one aspect of the present disclosure.
Figure 42B:
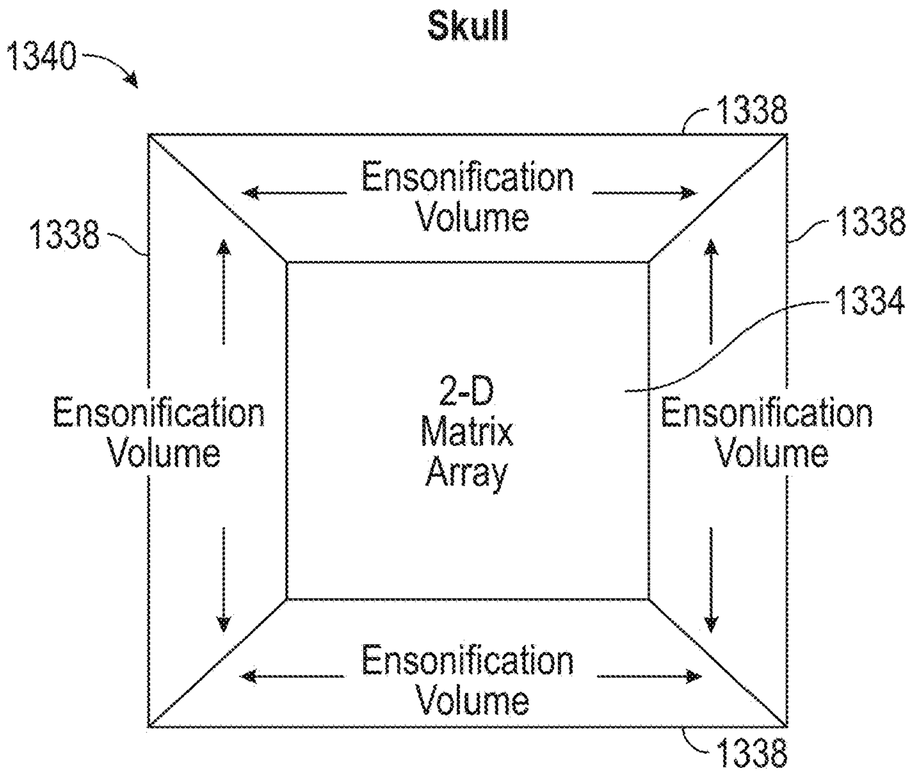
FIG. 42B is an end view of the 2D matrix array shown in FIG. 42A in accordance with at least one aspect of the present disclosure.

FIG. 42A is a side view of a 2D matrix array 1334 of ultrasonic transducer elements configured to generate a steered beam 1336 in accordance with at least one aspect of the present disclosure and FIG. 42B is an end view of the 2D matrix array 1334 shown in FIG. 42A in accordance with at least one aspect of the present disclosure. The technique shown in FIGS. 42A-B utilizes a 2D matrix array 1334 of ultrasonic transducer elements. Rather than rely on the geometric focus of a larger concave ultrasonic transducer, a 2D matrix array 1334 provides ensonification of a volume 1338 of the skull 1340 due to the ability to steer in three dimensions. This 2D matrix array 1334 may be implemented as a subarray configuration (groups of individual elements tied together in a subarray formation, driven by a single source), sparse array configuration (to limit the number of elements and/or driving array electronics), or a combination of both subarray and sparse array configurations. Additional enhancement of the therapeutic operating field provided by the 2D matrix array 1334 of ultrasonic transducer elements could be provided by dispersion lensing techniques previously described. Note that the 2D matrix array 1334 could be in a circular or elliptical configuration—as these configurations may be superior to the square or rectangular 2D array 1334 shown in FIGS. 42A-B for illustrative purposes only. The diameter of the individual ultrasonic transducer elements of the 2D matrix array 1334 may be selected as previously described. For example, the diameter of the 2D matrix array 1334 may be about 150 mm, without limitation, and the diameter of the ultrasonic transducer elements of the 2D matrix array 1334 can be selected in the range of 0.5 mm to 20 mm, without limitation, depending on the frequency of the excitation signal and the speed of sound in water. As previously discussed, the diameter of the ultrasonic transducer elements may be same or may be different with the diameter of the transduce elements selected within the range set forth in this disclosure. It will be appreciated that some of the ultrasonic transducer elements may be deactivated.

The 2D matric array 1334 or the individual ultrasonic transducer elements of the array 1334 can include automated movement (lateral, axial, rotational) of the to further distribute the incoherent field for preferred activation of sensitizer according to various embodiments.

Having described various aspects of a sonodynamic therapy system 900, 920, 950, 1000, 1100 and components of the sonodynamic therapy system 900, 920, 950, 1000, 1100, the disclosure now turns to a description of the present disclosure that is directed to various aspects of apparatuses, systems, and methods for selectively locating and holding an ultrasonic transducer array in preferred locations for treatment, coupling that array to a patient's head or other body part for efficient and safe transfer of energy, as well as transcranial optimization routines that take into account, and compensate as necessary for, variations in transmission through the skull to enable a therapeutic operating field with appropriate energy profile for activating a sonosensitizer.

In various aspects, a wearable receptacle referred to as a patient interface is placed over/on and fitted to the patient's head or other body part. The patient interface provides location registration between a patient specific anatomy and an ultrasonic transducer array detachably coupled to or integrated with the patient interface, which in turn guides placement and location of the therapeutic operating field for providing sonodynamic therapy.

In various aspects, the patient interface includes one or more alignment and/or orientation features establish a true location registration. The alignment and/or orientation features are shaped and/or sized to interface with and receive bony landmarks on the head such as the zygomatic arch, mastoid process, mastoid tip of temporal bone, lateral eye, and middle arch of eyebrows to establish a true location registration for providing sonodynamic therapy. In one aspect, the patient interface includes alignment and/or orientation features that are shaped and sized to receive at least two anatomical features on a patient's head. In one embodiment a targeting template is placed on the patient to facilitate alignment of the transducer to the various treatment sites. In various embodiments, the targeting template is a wearable elastic template with markers to facilitate treatment, such as by demarking a grid, positions based on anatomy, or marking of the skin with indicators. In one embodiment, the targeting template is a cap. In one embodiment, the targeting template is a band configured to wrap around a head, neck, chest, torso, back, waist, leg, buttock, genital area or other body part. In one embodiment, the targeting template is drawn on the body. In one embodiment, the targeting template includes measurement gradients that allow the user to customize treatment locations to patient specific anatomical size. In some embodiments, the targeting template remains in place during ultrasound treatment. In some embodiments, the targeting template is made to be removable prior to ultrasound treatment.

Once the patient interface is properly aligned and placed on the patient, it can be effectively fixed in place by straps, adhesive, tape, or any other suitable fixtures that tightly secure the patient interface to the patient. In certain aspects, the patient interface is coupled to a robotic arm that can perform minor and/or major adjustments to the position of the patient interface with respect to the patient's head. In at least one example, the robotic arm is decoupled from the patient interface once it is secured to the patient's head in a preferred treatment position.

In various aspects, the patient interface provides a receptacle to receive a preferred ultrasound probe configured for sonodynamic therapy. Therefore, the ultrasound probe treatment location is established by the patient interface device. This location ultimately determines the placement of the therapeutic operating field for providing sonodynamic therapy. The patient interface may alternatively include multiple receptacles for receiving multiple ultrasound probes and/or for discreetly moving a single probe through multiple defined treatment locations. Preferred treatment locations may be a fixed predetermined pattern, or alternatively maybe customized based on specific disease location for each patient.

In certain aspects, the patient interface includes structures and/or features that guide placement of an ultrasonic transducer array into a preferred position for activating a sonosensitizer. In certain aspects, the patient interface includes multiple structures or features that guide placement of multiple transducer arrays into preferred positions for activating a sonosensitizer.

In other aspects, the patient interface provides a progression of discrete steps utilizing a single array serially across the preferred treatment positions. In certain aspects, the patient interface includes an array holder, which can be adjusted, automatically or manually, to move the array into preferred treatment locations. Preferred treatment locations for the array may include areas on the skull that are more conducive to acoustical coupling based on geometry, anatomy, and/or preferred anatomical attenuation. Preferred treatment locations may also be indexed to or correlated with a CT or other imaging data that provides known anatomical inputs to guide placement and/or therapy parameters for the array. Furthermore, the preferred treatment location takes into account the diseased location as an input, thereby placing the array in a position that ensures ultrasonic energy is directed to the diseased region and surrounding tissue.

In various aspects, a controller such as, for example, the controller 902 may receive imaging data such as, for example, a CT or other imaging data that provides known anatomical inputs to guide placement and/or therapy parameters for the array. Based on the imaging data, the controller 902 may select a preferred treatment location for the ultrasonic transducer array. In certain aspects, the array holder is operably coupled to a motor. In such aspects, the controller 902 may cause the motor to move the array holder relative to the patient interface to a selected treatment location. In various aspects, the controller 902 may cause the user interface 1004 to communicate a selected treatment location to a user.

In another aspects, the ultrasonic transducer array is integrated with the patient interface, such that placing and locating the patient interface, is also placing and locating the array.

Once the array is placed in the proper position(s) for treatment, it is properly coupled to the patient for transmission according to one embodiment. For brain cancer patients, all hair will be removed so as not to interfere with acoustic coupling. An acoustically conductive gel is common in the industry. In various aspects, an acoustic coupling membrane is attached over the exit plane of the ultrasonic transducer array. The acoustic coupling membrane can be selectively inflated and deflated to further guide placement and location of the ultrasonic transducer array, further guiding placement of the therapeutic operating field. In various aspects, the acoustic coupling membrane comprises an elastic material with acoustically neutral properties so as to provide minimal ultrasound attenuation.

In various aspects, the acoustic coupling membrane defines a cavity with the patient interface. The ultrasonic transducer array may project from the patient interface toward the cavity. An acoustical coupling agent such as, for example, degassed water can be utilized to fill the cavity to a predetermined volume. The volume of the acoustical coupling agent contained within the membrane can be selectively adjusted to reposition the location of the ultrasound array. Selectively controlling position of the array with the coupling membrane enables selective guidance of the therapeutic operating field. The compliance in the membrane allows it to conform to patient's anatomy at the treatment location for acoustical coupling.

Any suitable valve can be utilized to insert and/or remove the acoustical coupling agent into the cavity to inflate and/or deflate the acoustic coupling membrane according to one embodiment. One or more sensors such as, for example, pressure sensors can be employed by the controller 902 to assess the volume of the acoustical coupling agent in the cavity.

In certain aspects, the volume of the acoustic coupling agent can be selectively adjusted to reposition the location of the ultrasonic transducer array. Selectively controlling position of the array with the coupling membrane enables selective guidance of the therapeutic operating field according to one embodiment. In certain aspects, the inflation and/or deflation of the acoustic coupling membrane can be used in concert with the array holder to control the location of the array and distance away from the skull. This distance can be discretely adjusted or dynamically adjusted to vary the therapeutic operating field position and penetration depth during treatment according to one embodiment.

In certain aspects, the acoustic coupling agent is circulated to remove residual heat from the therapeutic operating field during treatment. In certain aspects, the acoustic coupling agent is also chilled to remove residual heat from the therapeutic operating field during treatment. In certain aspects, the temperature of the acoustic coupling agent is monitored as a safety provision. For example, the patient interface can include one or more temperature sensors according to one embodiment. In one example, as described elsewhere herein, a processing unit 1104 is coupled to temperature sensors 1118 and receives patient temperature feedback through the ADC 1010. The processing unit 1104 controls a cooling system 1120 based at least in part on the patient temperature feedback signal.

Transcranial ultrasound delivery has many challenges. The skull acts as a strong reflector, as well as scatterer and absorber of ultrasound energy. There is also a known large patient to patient variation in skull attenuating characteristics. Patient specific information is desirable that takes into account variations in transmission through the patient's skull to optimize a therapeutic operating field for activating a sonosensitizer. The patient specific information could be an input from a CT or MRI or other image file that includes skull thickness data by location. The output of the individual ultrasound elements, and/or the entire array collectively, and/or subsections of the array could be adjusted based on inputs from the CT, MRI, or other image file. Additionally, or alternatively, a sonodynamic therapy system itself (e.g. system 900, described in greater detail in connection with FIGS. 21, 22) could be used to collect patient specific transcranial transmission data for calibrating the optimal ultrasound array output(s).

In various examples, a sonodynamic therapy system (e.g. system 900, described in greater detail in connection with FIGS. 21, 22) includes one or more transcranial optimization routines for calibrating the ultrasonic transducer array 904 to patient specific attributes to establish appropriate ultrasound ensonification parameters according to one embodiment. The controller 902 may be configured to execute one or more control algorithms to calibrate the ultrasonic transducer array 904 to patient specific attributes such as, for example, a skull thickness according to one embodiment. Furthermore, the controller may be configured to cause the ultrasound transducer array 904 to activate a sonosensitizer in a treatment region in the anatomical structure per ultrasound ensonification parameters established by calibrating the ultrasound transducer array to the patient specific attributes. In one embodiment, a patient specific attribute is anatomical. In one embodiment, a patient specific attribute is non-anatomical.

In certain examples, the controller 902 may determine whether skull thickness measurements are within the acceptable nominal range according to one embodiment. In one aspect, a digital imaging and communications (DICOM) image from a computerized tomography (CT) or other imaging source could be an input to the device controller 902. The imaging data can be analyzed by the controller 902 to determine whether skull thickness measurements are within the acceptable nominal range. Accordingly, the controller 902 may employ imaging data such as, for example, a CT scan as a screening tool, whereby only patients whose skull thickness measurements fall within a nominal or prescribed range are indicated for treatment. Imaging data indicative of a skull thickness could also be utilized to optimize frequency, and array location for most beneficial therapeutic operating field.

Additionally, or alternatively, the controller 902 may cause the ultrasonic transducer array 904 to generate pulses to interrogate the skull at several different frequencies in a calibration algorithm according to one embodiment. The controller 904 then assesses the percent of reflected energy at the various frequencies. In some cases, the frequency with lowest relative reflected energy correlates with the frequency that has highest transmitted energy through the skull. In at least one example, the calibration process involves measuring distances to the skull using time of flight (with short pulses). It may also be possible to measure the inclination of the skull relative various element. If the skull is too inclined relative to nearby elements, in one embodiment, the controller 902 is configured to limit the energy going to those elements.

As described above in greater detail, it can be possible to take measurements or get a rough image of the skull 510 as shown in FIG. 11 according to one embodiment. This can be facilitated if the transducers 150 are fixed to a rigid shell and their relative positions and orientations are known. Rough measurements can be used to adjust the treatment algorithm by measured parameters such as skull thickness, "t," or skull density, "p." Each transducer 150 may send out an acoustic pulse and listen for an echo. The echoes can be used for a quick estimate of the skull thickness, "t," or skull density, "p," under each transducer 150. For treatment of tumors in other body parts of the patient, the sonodynamic therapy system 900 may be adapted and configured to couple to the body of the patient.

Further to the above, the calibration process may include a check that the probe is adequately coupled to the patient by air/bubble ultrasound detection techniques according to one embodiment.

Figure 46:
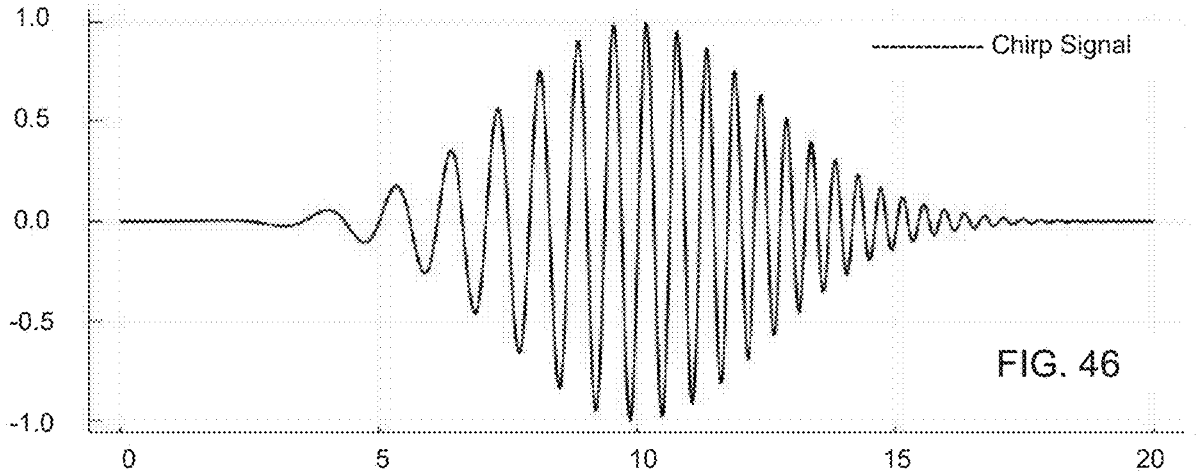
FIG. 46 is a graph that illustrates a chirp signal, in accordance with at least one aspect of the present disclosure.
Figure 47:
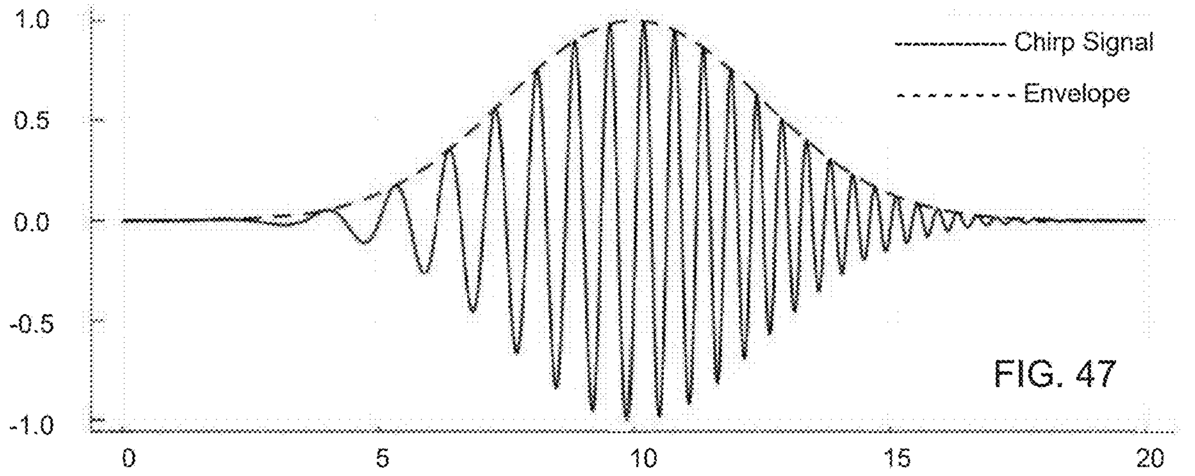
FIG. 47 is a graph that illustrates an enveloped chirp signal, in accordance with at least one aspect of the present disclosure.

In various aspects, one or more calibration algorithms, which can be executed by the controller 902, include a chirp signal input, which can be similar to a sinusoid with a continuously varying frequency. An example of a chirp signal is illustrated in FIG. 46. Multiple overlapping echoes of a chirp signal can be separated in time. Because a sinusoid is identical with respect to shifts in 1 cycle, it cannot be easily separated out in time. In other words, the autocorrelation of a sinusoid has periodic peaks in time spaced 1 cycle apart. The varying frequency of the chirp signal causes the peaks and valleys of a chirp signal to only line up with itself in one way—the autocorrelation has a single peak. In various aspects, the chirp signal can be a longer signal in time than a short "ping," so more energy can be used as an input to perform the calibration. In certain examples, the chirp signals are shaped with an envelope function to have a gently increasing and decreasing peaks according to one embodiment. An example enveloped chirp signal is illustrated in FIG. 47. A chirp signal with a rectangular envelope has abrupt changes. The abrupt changes in the echo that is returned from a rectangular envelope chirp could be from the input signal or from the thing being imaged. The received chirp signal can be integrated in the frequency domain to investigate the transmission across multiple frequencies with one integration. Furthermore, the received chirp signal can be convolved with the time reversed of the transmitted chirp signal to accurately calculate the skull boundary.

Figure 50:
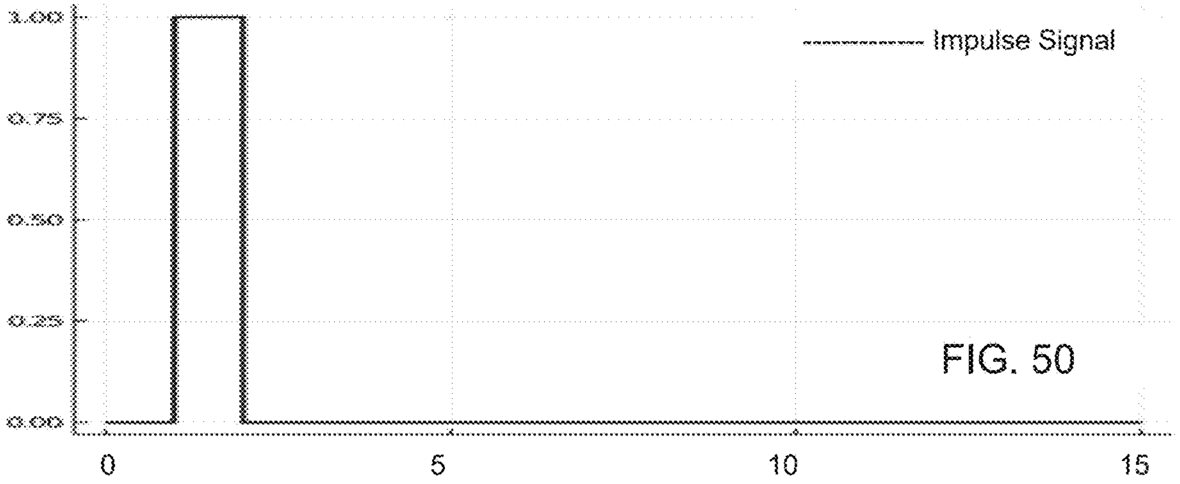
FIG. 50 is a graph that illustrates an impulse signal, in accordance with at least one aspect of the present disclosure.
Figure 51:
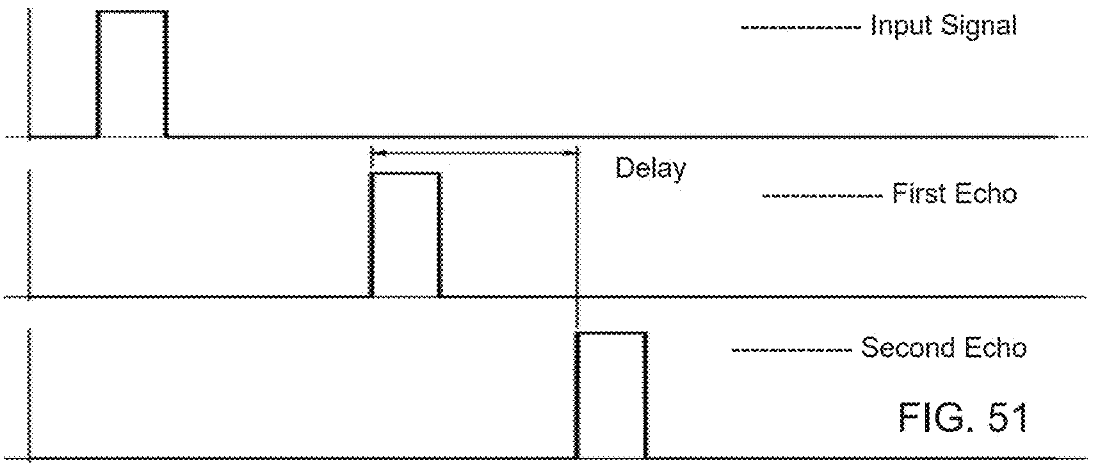
FIG. 51 is a graph that illustrates an impulse input signal and first and second echoes with a time delay, in accordance with at least one aspect of the present disclosure.

Additionally, or alternatively, an impulse input signal can be utilized in the calibration process according to one embodiment. The impulse input signal may include a sharply increasing and decreasing pulse. An example impulse input signal is illustrated in FIG. 50. This short signal facilitates echoes resolution in time. Typically, an impulse does not contain significant energy—it's limited by the duration and peak pressure. Therefore, a series of impulses separated by x nsec can be utilized for an application intended for an integrated temporal energy. FIG. 51 illustrates an impulse input signals and the resulting echoes. Other input signals might be used. The delay between the two echoes is indicative of a skull thickness. The delay from the impulse input signal to the first echo signal is indicative of the distance to the skull surface.

Figure 48:
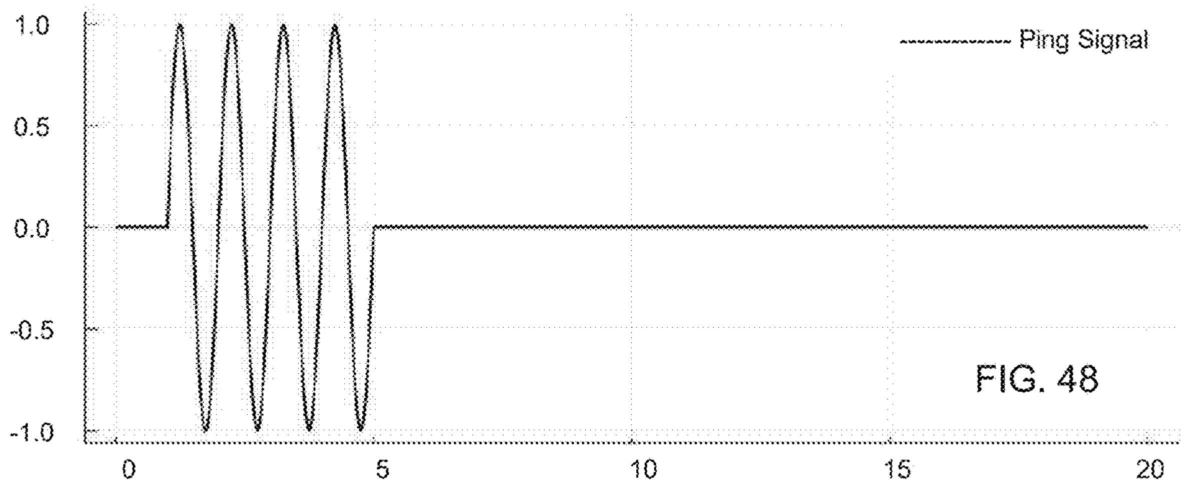
FIG. 48 is a graph that illustrates a square ping signal, in accordance with at least one aspect of the present disclosure.
Figure 49:
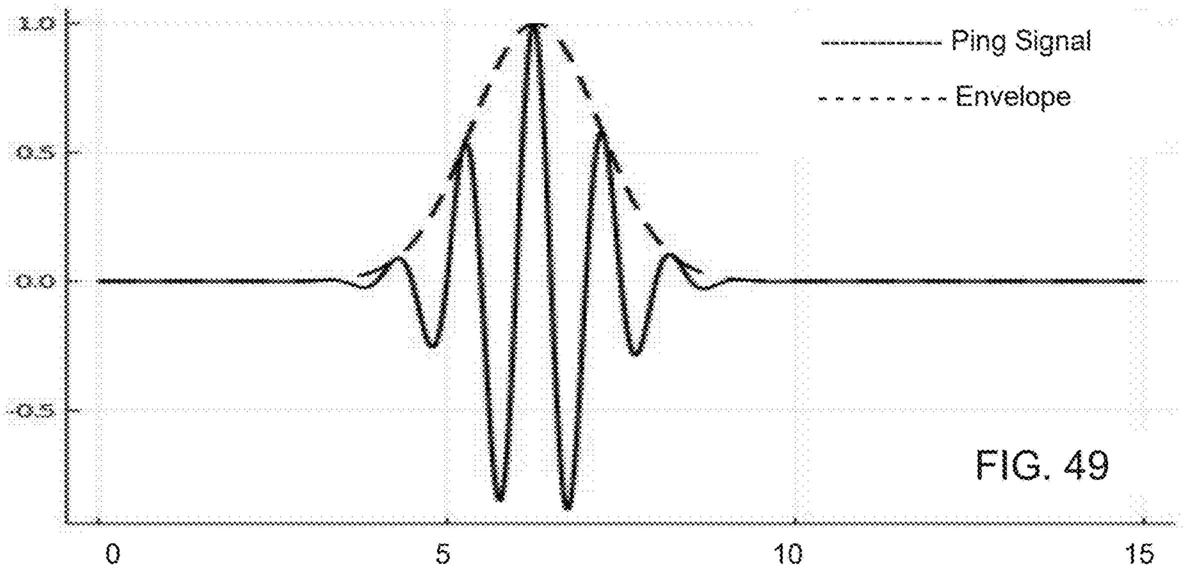
FIG. 49 is a graph that illustrates a smooth ping signal, in accordance with at least one aspect of the present disclosure.

Additionally, or alternatively, a ping input signal can be utilized in the calibration process according to one embodiment. A ping is defined by a short burst of pulses at a particular frequency. An example of a square ping signal and a smooth ping signal are illustrated in FIG. 48 and FIG. 49, respectively. A ping input signal typically include a lesser frequency content than a chirp input signal. Because the input pulse correlates with itself at several locations, the returning echoes are more difficult to distinguish. Additionally, or alternatively, an element by element frequency altered pulse bursts can be utilized in the calibration process. This may include outer elements utilizing lower frequency than inner elements. In the case where outer array elements are farther from the desired therapeutic operating field this can improve the energy available from the outer elements. Additionally, the element frequency is optimized for skull penetration either directly related to skull thickness or alternately, frequency-dependent transmission efficiency. Additionally, randomized local frequency content similar to the chirp, but temporally overlapping frequencies transmitted into the brain could be utilized in the calibration process. In one embodiment, randomization could be spread over a localized sub-array (nearest neighbor elements), in another embodiment frequency randomization over the entire array could be deployed in order to optimize the therapeutic operating field.

Further to the above, in various examples, the calibration process will include combinations of one or more of the chirp, ping, and/or impulse input signals at various suitable frequencies and/or amplitudes according to one embodiment. In at least one example, short pings are utilized to interrogate the skull at several different frequencies and/or amplitudes. This overcomes one of the downsides of a short ping, the low frequency content. Additionally, or alternatively, Amplitude modulated pulse bursts can be utilized. Along the length of the pulse burst, the amplitude could change. This would have the effect of focusing deeper or shallower or moving energy to a different part of the therapeutic operating field when applied on a sub-array basis to target specific areas of the brain based on a prior knowledge of skull topology and thickness, for example.

In various examples, the calibration process assesses the position of a target tissue such as, for example, a tumor within an anatomical structure in contact with the patient interface of the sonodynamic therapy system according to one embodiment. For example, the controller 904 may utilize external imaging data and/or ultrasonic imaging data collected by the sonodynamic therapy system itself. The controller 904 may adjust the output of various elements of the ultrasonic transducer array based on the relative position of the individual elements with respect to the target tissue. In at least one example, the outer elements, which are further away from the target tissue, are adjusted to a lower frequency than inner elements that are closed to the target tissue. Additionally, or alternatively, the calibration process optimizes the output of the elements for skull penetration either directly related to localized skull thickness or alternately, frequency-dependent transmission efficiency.

Furthermore, in certain examples, the calibration process employs randomized local frequency content similar to the Chirp, but temporally overlapping frequencies transmitted into the brain according to one embodiment. In various aspects, randomization could be spread over a localized sub-array that can include the nearest or neighboring elements. In another example, the frequency randomization over the entire array could be deployed in order to optimize the therapeutic operating field.

The controller 902, employing one or more of the previously-described optimization techniques of the calibration process, may determine the distance to a skull surface of a patient (e.g. skull 510 as shown in FIG. 11) wearing the sonodynamic therapy system 900 according to one embodiment. In one example, the time of flight is employed to estimate the distance from transducers 150 to the skull 510. Furthermore, the controller 902 can also estimate the thickness of the skull based on echoes received from the outer and inner skull surfaces. The differences between the time of flight of these two echoes can inform the approximate skull thickness.

Within the transducer frequency bandwidth, it is likely that some frequencies would have lower reflected energy characteristics and correspondingly better skull transmission characteristics which could be beneficial for optimizing the therapeutic operating field according to one embodiment. In particular, one frequency may result in lower reflected energy. In some cases, this frequency with lowest relative reflected energy correlates with the frequency that has highest transmitted energy through the skull. Accordingly, the controller 902, employing one or more of the previously-described optimization techniques of the calibration process, may interrogate the skull 510 at different frequencies, and compare the energy reflected by the skull for each of the frequencies to determine frequencies with the highest skull transmission to maximize the amount of energy transmitted though the skull. Furthermore, in certain examples, the controller 902, employing one or more of the previously-described optimization techniques of the calibration process, may maximize the size of the therapeutic operating field through changes in pulses or system components for treating brain cancer.

In various embodiments, ultrasound array sonodynamic treat of cancerous tissue throughout the body may be treated using several embodiments described herein using for example, one or more sonosensitizers along with the ultrasound parameters described herein. In some embodiments, sonodynamic therapy is used to improve efficiency of sonoporation, gene therapy, and/or chemotherapeutic treatments. In various embodiments, sonodynamic therapy is used to activate a sonosensitizer within a patient's body, or on the surface of the patient's body. In various embodiments, sonodynamic therapy can be used with or without photodynamic therapy. Several embodiments described herein are used synergistically with other cancer therapies, including for example, radiation, chemotherapy, immunotherapy, and cell therapies.

Figure 43:
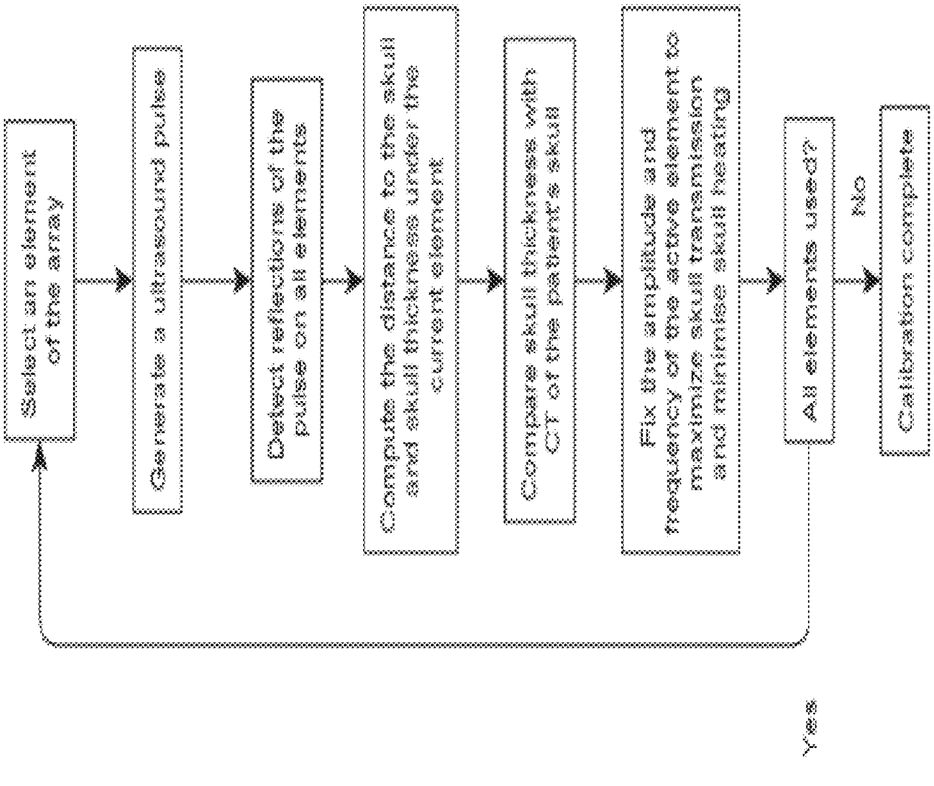
FIG. 43 is a logic flow diagram for calibrating an ultrasonic transducer array of a sonodynamic treatment system, in accordance with at least one aspect of the present disclosure.

FIG. 43 is a logic flow diagram of a process depicting a control program or a logic configuration for calibrating an ultrasonic transducer array of a sonodynamic treatment system (e.g. system 900), in accordance with at least one aspect of the present disclosure. The calibration process of FIG. 43 includes selecting an element of the ultrasonic transducer array 904, generating an ultrasound pulse with this element, and detecting reflections of the pulse on all elements of the ultrasonic transducer array 904. The calibration process of FIG. 43 further includes computing a minimum distance from the one of the plurality of elements to the skull, wherein the minimum distance is a distance from the one of the plurality of elements to a skull portion adjacent, or under, the one of the plurality of elements, and wherein the controller is configured to compute a skull thickness at the skull portion. The calibration process of FIG. 43 further includes comparing the computed skull sickness with imaging data of the patient's skull such as, for example, CT scans. The calibration process of FIG. 43 further includes setting, or fixing, amplitude and frequency of the active element to maximize an ultrasound transmission rate, or efficiency, through the skull. Additionally, or alternatively, the calibration process of FIG. 43 further includes fixing the amplitude and frequency of the active element to minimize skull heating during a sonodynamic treatment performed by the system 900. In certain aspects, the calibration process of FIG. 43 is repeated until all, or at least a predetermined subset, of the elements of ultrasonic transducer array 904 are calibrated to maximize skull transmission and/or minimize skull heating.

Maximization of skull transmission and/or minimization of skull heating are assessed based predetermined thresholds according to one embodiment. For example, acceptable values for a maximized skull transmission are values equal to or greater than a predetermined threshold indicative of skull transmission. Likewise, acceptable values for a minimized skull heating are values equal to or less than a predetermined threshold indicative of skull heating.

Figure 44:
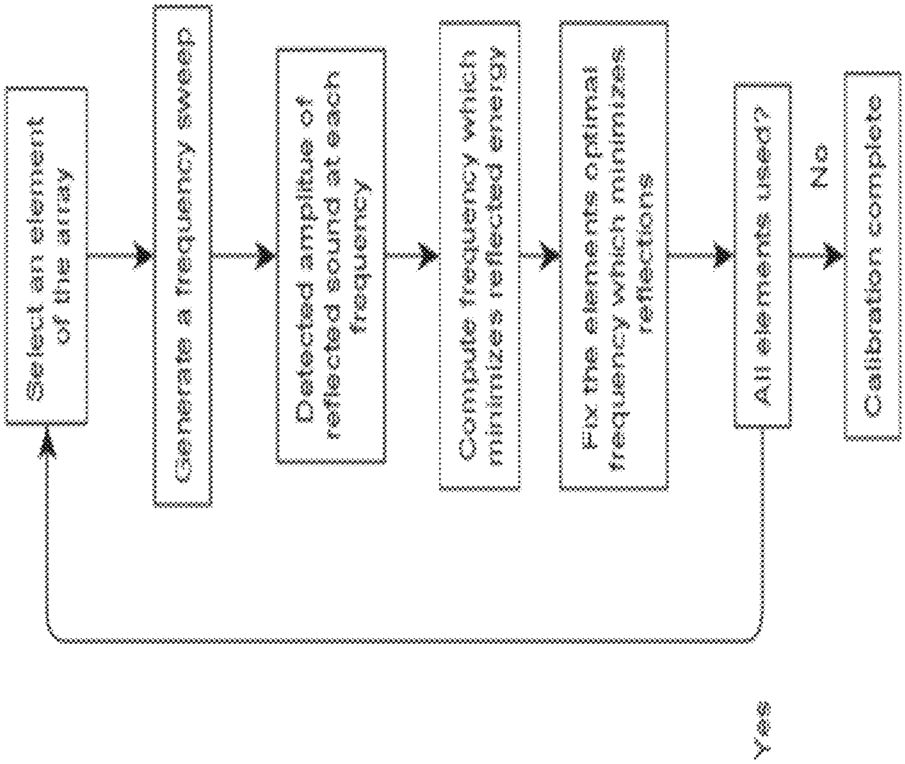
FIG. 44 is a logic flow diagram for calibrating an ultrasonic transducer array of a sonodynamic treatment system, in accordance with at least one aspect of the present disclosure.

FIG. 44 is a logic flow diagram of a process depicting a control program or a logic configuration for calibrating an ultrasonic transducer array of a sonodynamic treatment system, in accordance with at least one aspect of the present disclosure. The calibration process of FIG. 44 includes selecting an element of the ultrasonic transducer array 904, generating a frequency sweep with this element, and detecting Amplitude of energy reflected at each frequency of the frequency sweep. The calibration process of FIG. 44 further includes computing an optimal frequency for the element, wherein the optimal frequency is one that minimizes the energy reflected beyond a predetermined threshold. The calibration process of FIG. 44 further includes setting the element to the optimal frequency. In certain aspects, the calibration process of FIG. 44 is repeated until all, or at least a predetermined subset, of the elements of ultrasonic transducer array 904 are calibrated to optimal frequencies.

Figure 45:
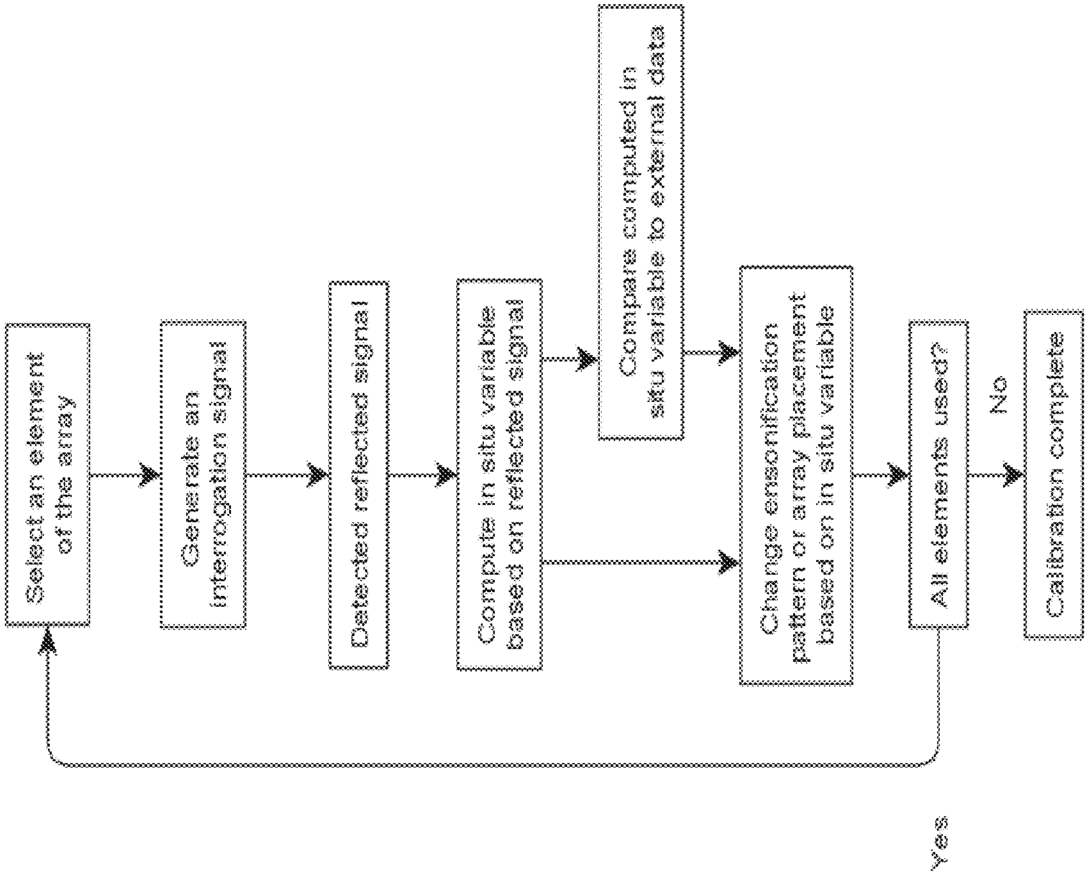
FIG. 45 is a logic flow diagram for calibrating an ultrasonic transducer array of a sonodynamic treatment system, in accordance with at least one aspect of the present disclosure.

FIG. 45 is a logic flow diagram of a process depicting a control program or a logic configuration for calibrating an ultrasonic transducer array of a sonodynamic treatment system, in accordance with at least one aspect of the present disclosure. The calibration process of FIG. 45 includes selecting an element of the ultrasonic transducer array 904, generating an interrogation signal with this element, and detecting a reflected signal in response to the interrogation signal, wherein the reflected signal is reflected by a skull of the patient. The calibration process of FIG. 45 further includes computing an in-situ variable based on the reflected signal. In certain instances, the calibration process of FIG. 45 further includes comparing the in-situ variable computed by controller to an external data. The calibration process of FIG. 45 further includes adjusting an ensonification pattern or an array placement of the ultrasonic transducer array 904, or both, based on the in-situ variable. In instances where the in-situ variable is compared to the external data, the calibration process includes adjusting an ensonification pattern or an array placement of the ultrasonic transducer array 904, or both, based on the result of the comparison. In certain aspects, the calibration process of FIG. 45 is repeated until all, or at least a predetermined subset, of the elements of ultrasonic transducer array 904 are calibrated to optimal frequencies.

One or more of the calibration processes depicted in FIGS. 43-44 can be executed by a control circuit. In another aspect, one or more of the calibration processes depicted in FIGS. 43-44 are executed by a combinational logic circuit. In yet another aspect, one or more of the calibration processes depicted in FIGS. 43-44 are executed by a sequential logic circuit. These examples are, however, not limiting. The calibration processes depicted in FIGS. 43-44 can be executed by circuitry that can include a variety of hardware and/or software components and may be located in or associated with various suitable systems described by the present disclosure.

Upon administration of the sonosensitizer, the controller 902 may utilize a combination of different ultrasound treatments at different time points according to one embodiment. For example, shortly after administering the sonosensitizer, it may be beneficial to apply an initial ultrasound treatment that helps enhance further uptake of the sonosensitizer. Once uptake of the sonosensitizer is considered within an optimal window based on time duration since the initial ultrasound treatment or other means, additional ultrasound treatment(s) can then subsequently be initiated. Applying different ultrasound treatments at different time points post administration of the sonosensitizer both encourages further uptake of the sonosensitizer, as well as enhances overall therapeutic effects. In another embodiment, instead of initiating ultrasound treatment based on time duration since the sonosensitizer and/or ultrasound treatment was administered, an apparatus could be used to directly monitor patient specific uptake of the sonosensitizer, and subsequently apply ultrasound treatment(s) when uptake is considered to be in an optimal range.

Research indicates that sonodynamic therapy depends on the creating of reactive oxygen species. These reactive oxygen species react with other molecules and damage organelles in the cancer cell. To enhance the oxidative damage within the cancer cells, the patient could be monitored for the amount of dissolved oxygen within cancer the cells, and/or alternatively monitored for peripheral capillary oxygen saturation levels according to one embodiment. The oxygen monitoring is then used as an additional patient specific input to guide application of ultrasound treatment(s) when parameters are considered to be in an optimal range.

Having described various aspects of a sonodynamic therapy system 900, 920, 950, 1000, 1100 and components of the sonodynamic therapy system 900, 920, 950, 1000, 1100, the disclosure now turns to a description of the present disclosure that is directed to various aspects of enhancing a sonodynamic therapeutic treatment that can be attenuated and enhanced to further produce complementary adjuvant effects which enhance the destruction of targeted cells and/or tissues according to various embodiments.

According to some non-limiting aspects of the present disclosure, the aforementioned apparatuses, systems, and methods for enhancing a sonodynamic therapeutic treatment can be attenuated and enhanced to further produce complementary adjuvant effects which enhance the destruction of targeted cells and/or tissues. For example, the treatments disclosed herein can reduce the level of ultrasonic energy required to destroy a targeted cell and/or tissue and therefore, can limit the ensuing damage to healthy cells of surrounding organs. Thus, the apparatuses, systems, and methods disclosed herein provide numerous technical improvements, including the efficient use of resources (e.g. ultrasonic energy) and an advantageous ability to preserve the patient's overall health (e.g. eliminating destructive cells and preserving healthy cells). According to some non-limiting aspects of the present disclosure, the therapies disclosed herein can produce such improvements, because they utilize complementary therapies (e.g. supplementary oxygenation, immunotherapy, anti-inflammatory therapy, microbubble enhanced cavitation, electromagnetic energy, magnetic energy, one or more bi-pole electrodes, an array of electrodes, hyperthermia, hypothermia, alternative sonosensitizers and/or sonosensitizers with nano-particle additives) to enhance the efficacy of the sonodynamic therapy, itself. In one embodiment, electromagnetic energy (e.g., light) complements the sonodynamic therapeutic treatment. In one embodiment, magnetic energy (e.g., use of oscillating magnetic fields at frequencies and durations proximate the treatment site) complements the sonodynamic therapeutic treatment. However, it shall be appreciated that the apparatuses, systems, and methods disclosed herein can further enhance the efficacy of the complementary therapy modalities, as will be discussed.

Figure 52:
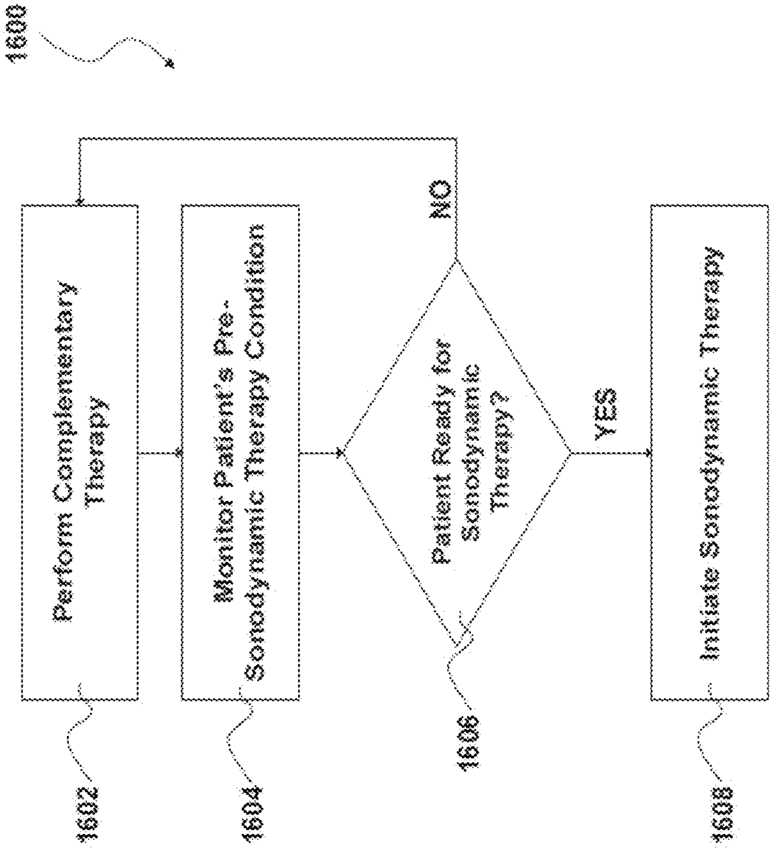
FIG. 52 is a flow diagram of a method of using a complementary and/or adjuvant therapy to enhance the efficacy of a sonodynamic therapy, according to at least one aspect of the present disclosure.

Referring now to FIG. 52, a flow diagram of a method 1600 of using a complementary adjuvant therapy to enhance the efficacy of a sonodynamic therapy is depicted in accordance with at least one non-limiting aspect of the present disclosure. According to the non-limiting aspect of FIG. 52, a clinician can perform a complementary therapy 1602 prior to initiating the sonodynamic therapy 1608. For example, after performing the complementary therapy on a patient 1602, the clinician can monitor the patient's pre-sonodynamic therapeutic condition 1604. In time, the clinician can assess the patient's pre-sonodynamic therapeutic condition 1606 to determine if the patient is properly prepared for the commencement of the sonodynamic therapy 1608. For example, the assessment 1606 can include a comparison of a biologic metric against a predetermined threshold, to assess if the complementary therapy has had the desired effect on the patient.

In further reference to FIG. 52, the threshold can be predetermined to correspond to the complementary therapy's ability to enhance the efficacy of the sonodynamic therapy according to one embodiment. Accordingly, the clinician can assess whether or not the patient requires additional therapy before the effects of the sonodynamic therapy can be optimized. If the patient is not exhibiting sufficient effects of the complementary therapy, the clinician can determine can decide to continue to perform the complementary therapy on the patient 1602. For example, after monitoring the patient's progress 1604, the clinician may determine that a particular biologic metric does not sufficiently meet or exceed the predetermined threshold and the complementary therapy will continue 1602. However, if the patient is exhibiting sufficient effects of the complementary therapy, the clinician can determine it is time to initiate the sonodynamic therapy on the patient 1608. For example, after monitoring the patient's progress 1604, the clinician may determine that a particular biologic metric sufficiently meets or exceeds the predetermined threshold, thereby concluding that the complementary therapy has had its effect and that ensuing sonodynamic therapy will result in enhanced efficacy.

As previously discussed, research indicates that sonodynamic therapies utilizes the creation and subsequent effects of ROS on organic molecules to target and destroy the organelles of an undesirable cell and/or tissue according to one embodiment. Accordingly, the method 1600 of FIG. 52 can include the use of a complementary therapy 1602 configured to enhance the oxidative damage within a targeted cell and/or tissue. The complementary therapy 1602 can include any number of means to increase the oxidative damage caused by ROS within the targeted cell and/or tissue. For example, the complementary treatment 1602 can be specifically configured to promote apoptosis, which accelerates the death of a targeted cell and/or tissue and inhibits reparative mechanisms within the targeted cell and/or tissue by enhancing oxidative damage.

Still referring to FIG. 52, the complementary therapy 1602 can be specifically configured to increase oxidative stress by inhibition and/or removal of anti-oxidants from the targeted cells and/or tissues according to one embodiment. For example, the oxidative stress can be enhanced by a complementary therapy's 1602 ability to reduce the amount of damage necessary to induce a cascade within a targeted cell and/or tissue, wherein the ensuing cascade accelerates cellular death. According to one non-limiting aspect of the present disclosure, the oxidative stress can be enhanced by inhibiting cellular repair mechanisms that restore the cell after an oxidative stress is incurred. In some aspects, a therapy that inhibits the ability of deoxyribonucleic acid (DNA) within the targeted cell and/or tissue to repair itself when the subsequent sonodynamic testing commences. The present disclosure contemplates an optimal use of complementary treatments that will maximize the degree of oxygenating sensitization incurred in targeted cells and/or tissues, while minimizing the targeted cell and/or tissue's sensitization to the sonodynamic therapy, itself.

According to another non-limiting aspect of the present disclosure, the complementary therapy 1602 of FIG. 52 can be specifically tailored to enhance the amount of cavitation in one or more tissues. As previously discussed, one embodiment of sonodynamic therapies depend on the creation of reactive oxygen species, which can be produced by ultrasonically-induced cavitation. For example, the complementary therapy 1602 can include injecting the patient with microbubbles (e.g. micro-bubble ultrasound contrast agents). The injected microbubbles can be modified to accumulate on the targeted cells and/or tissues (e.g. tumors) upon injection, and further configured to cavitate upon exposure to ultrasound.

According to yet another non-limiting aspect of the present disclosure, the complementary therapy 1602 of FIG. 52 can further include injecting a patient with a drug that accumulates in a targeted cell and/or tissue such that the drug creates a nucleation site for enhanced cavitation. Nucleation sites can lower the pressure threshold required for cavitation. Accordingly, if the complementary therapy 1602 can be configured to create such nucleation sites, the conditions required for cavitation—and subsequently, oxidative stress—can be preferentially developed within target tissues to occur at lower pressures in the targeted cells and/or tissue. This can enable the sonodynamic destruction of targeted cells and/or tissue 1608 to occur at a lower level of ultrasonic radiation, thereby preserving the unaffected surrounding cells, tissues, and/or organs.

According to other non-limiting aspects of the present disclosure, the complementary therapy 1602 of FIG. 52 can further include ultrasonic imaging used to detect cavitation occurring within various tissues. For example, an ultrasonic imaging transducer can apply pulses of increasing pressure to the anatomical subject to monitor for signals produced by and indicative of cavitation. As such, the ultrasonic transducer can focus ultrasonic pulses to various locations of the anatomical subject to assess the degree and effect of cavitation at multiple locations within a region of the anatomical subject. A clinician can utilize these pulses to assess the ultrasonic threshold for cavitation at the targeted cells and/or tissues, as well as throughout the rest of the anatomical subject. Accordingly, the sonodynamic therapy 1608 can be timed or modified based on the results of such cavitation monitoring, thereby enhancing its efficacy.

Figure 53:
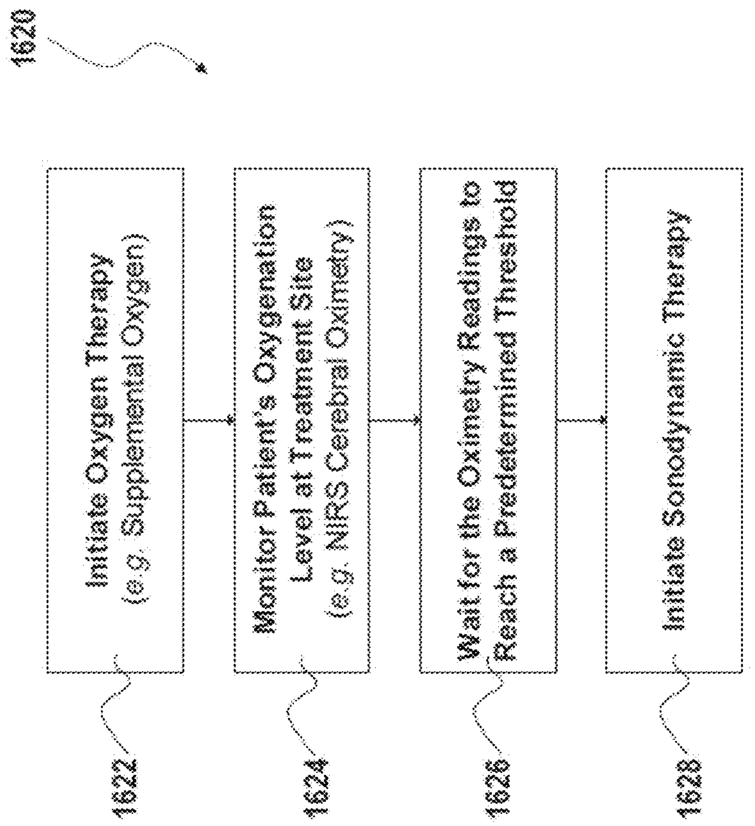
FIG. 53 is a flow diagram of a method of using a supplemental oxygenating therapy to enhance the efficacy of a sonodynamic therapy, according to at least one aspect of the present disclosure.
Figure 56A:
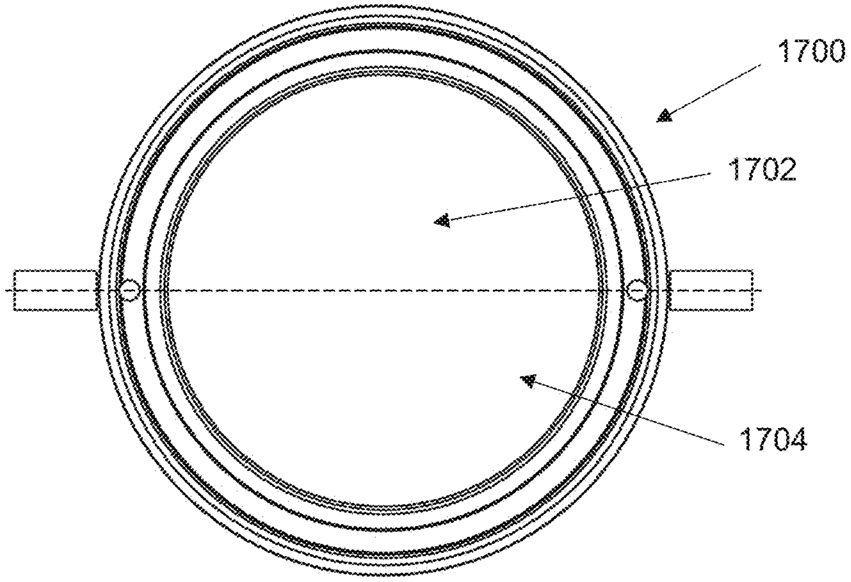
FIG. 56A is a schematic bottom view of an ultrasound transducer system according to at least one aspect of the present disclosure.
Figure 56B:
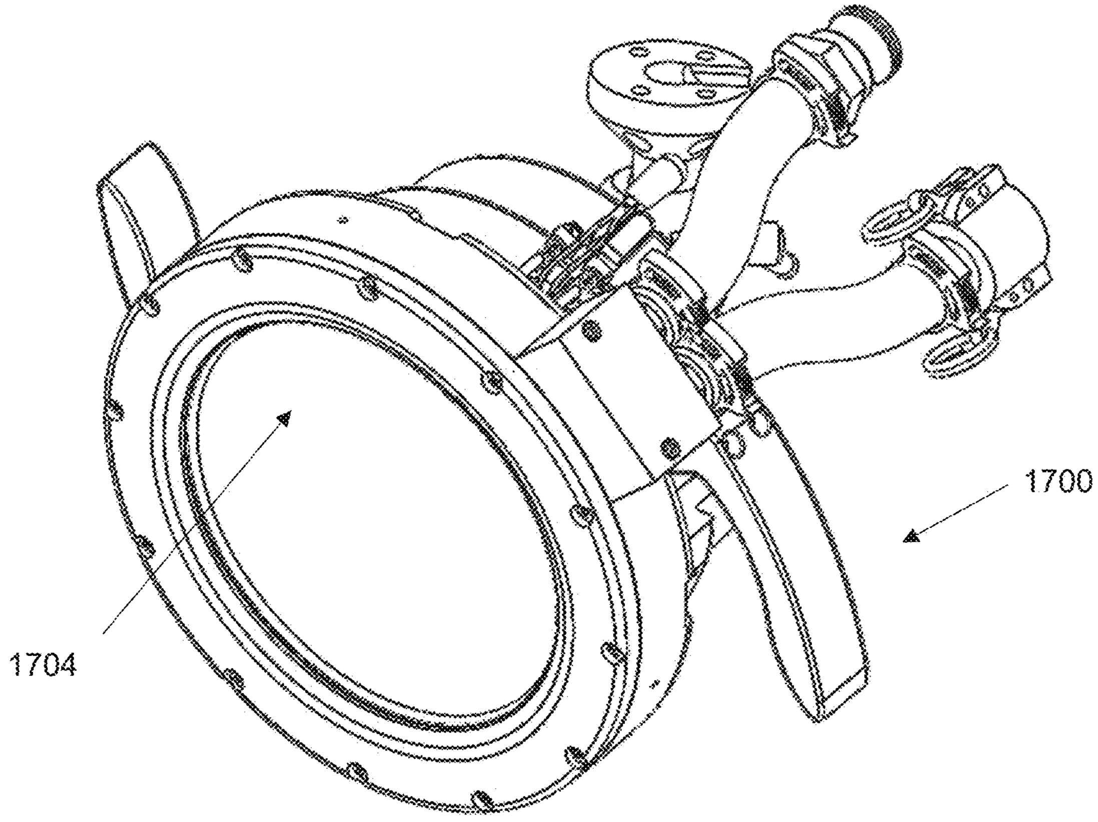
FIG. 56B is a schematic isometric view of an ultrasound transducer system according to at least one aspect of the present disclosure.
Figure 57:
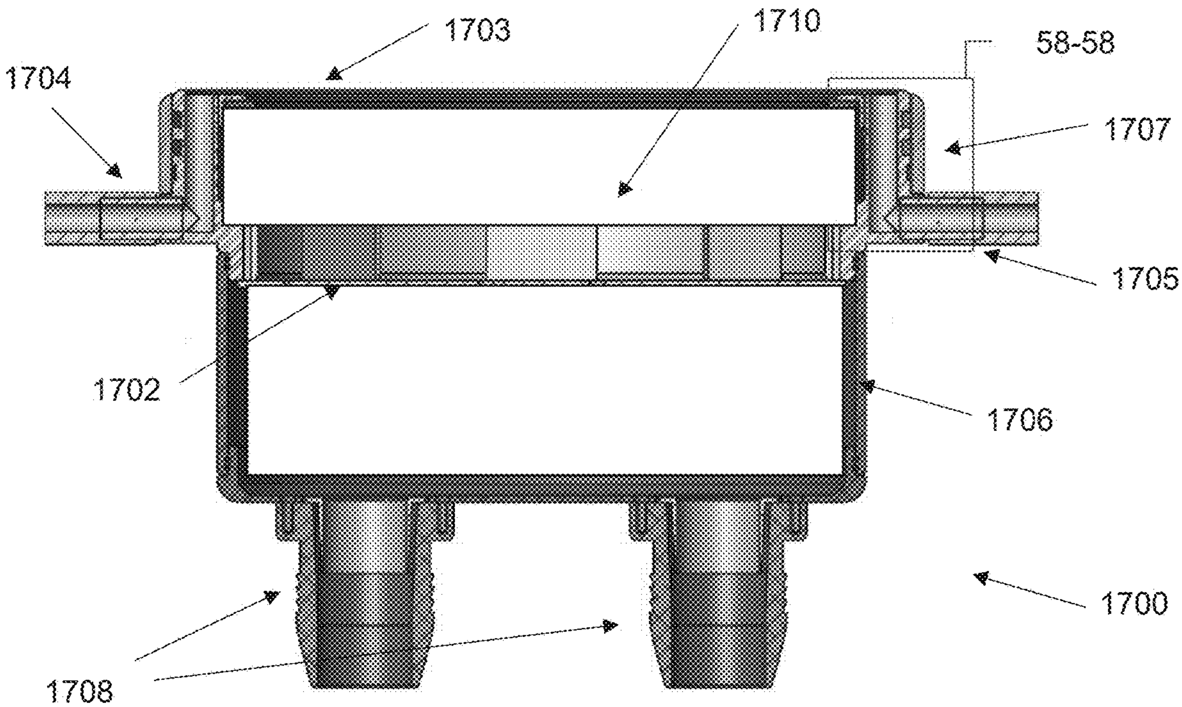
FIG. 57 is a schematic side cross-section view the ultrasound transducer system of FIG. 56.
Figure 58:
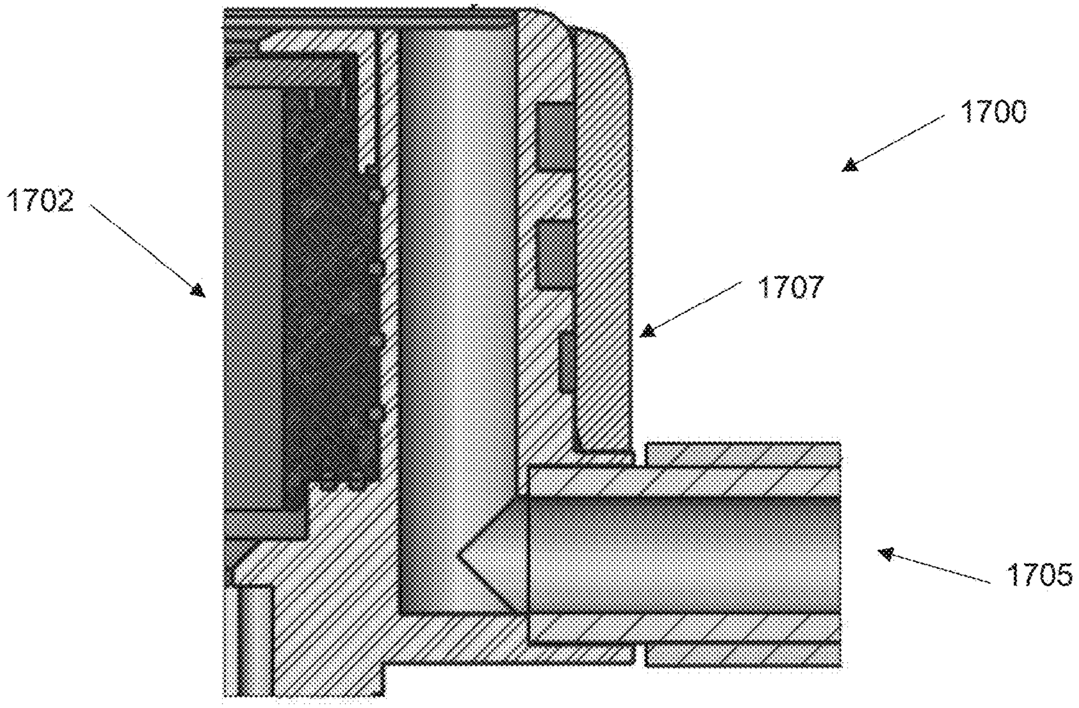
FIG. 58 is an enlarged view of the section 58-58 denoted in FIG. 57.

Referring now to FIG. 53, a flow diagram of a method 1620 of using a supplemental oxygenating therapy to enhance the efficacy of a sonodynamic therapy is depicted in accordance with at least one non-limiting aspect of the present disclosure. As previously discussed, the sonosensitizers-specifically, the ROS—can be particularly configured to produce an intended reaction with predetermined molecules. For example, the reaction can include intentional damage (e.g. oxidative damage) to a targeted cell and organelles within the targeted cell. Accordingly, the method 1620 of performing a supplemental oxygenating therapy 1622 prior to initiating a sonodynamic therapy 1628 can increase the amount of dissolved oxygen within a targeted cell, thereby increasing the oxidative damage within the cancer cells and enhancing the efficacy of the sonodynamic therapy.

In further reference to the method 1620 of FIG. 53, a clinician can perform a supplemental oxygenating therapy 1602 prior to initiating the sonodynamic therapy 1608 according to one embodiment. The present disclosure contemplates various means of providing the patient with the supplemental oxygen 1622. For example, initiating the supplemental oxygenating therapy 1622 can include delivering a supplemental supply of oxygen into the respiratory system of a patient. According to other non-limiting aspects of the present disclosure, initiating the supplemental oxygenating therapy 1622 can include introducing supplemental oxygen intravenously into the patient's bloodstream.

Still referring to FIG. 53, initiating the supplemental oxygenating therapy 1622 can include injecting the patient with gas-filled microparticles according to one embodiment. According to this non-limiting aspect, the gas-filled microparticles include the supplemental oxygen, which are injected into the patient's bloodstream. The microparticles can be modified and specifically configured such that the supplemental oxygen, upon entering the patient's bloodstream, collect in at, or in the general area of, a targeted cell, tissue, and/or organ. Accordingly, the microparticles can be specifically configured to target the location of targeted tissue, thereby enabling a clinician to use lower radiation to destroy the targeted cell and/or tissue and thereby, minimizing the collateral damage of the sonodynamic procedure.

In further reference to FIG. 53, initiating the supplemental oxygenating therapy 1622 can include removing a portion of the patient's blood, oxygenating the removed portion of blood with the supplemental oxygen, and reinjecting the oxygenated sample of blood back into the patient (e.g. extracorporeal membrane oxygenation (EMCO)) according to one embodiment. According to other non-limiting aspects of the present disclosure, initiating the supplemental oxygenating therapy 1622 includes administering (e.g., injecting) the supplemental oxygen directly into a targeted tissue, thereby enhancing the efficacy of the sonodynamic therapy in a manner similar to the use of the microparticles. According to still other non-limiting aspects of the present disclosure, initiating the supplemental oxygenating therapy 1622 includes the delivery of oxygen at pressures above atmospheric pressure (hyperbaric oxygen therapy), thereby increasing increase in blood oxygen level in a targeted tissue function to promote healing and fight infection.

Still referring to FIG. 53, initiating the supplemental oxygenating therapy 1622 can include removing the use of a drug to enhance the oxygen concentration in a targeted cell and/or tissue according to one embodiment. For example, the present disclosure contemplates the use of an antihypoxic drug, such as trans sodium crocetinate, vinpocetine, 1-eburnamonine, vinconate, and/or vincamine, amongst others, which can be modified and/or packaged to specifically increase the levels of oxygen in a particular cell and/or tissue. According to still other non-limiting aspects of the present disclosure, initiating the supplemental oxygenating therapy 1622 can include reducing the rate at which oxygen is used by the cell. For example, the clinician can reduce the patient's metabolism, thereby indirectly increasing the oxygenation of a targeted cell and/or tissue.

It shall be appreciated that the aforementioned aspects describe specific means of initiating a supplemental oxygenating therapy 1622 for illustrative purposes only according to various embodiments. As such, it shall be further appreciated that the present disclosure contemplates the use of any supplemental oxygenating therapy 1622 that can assist in the oxygenation of a targeted cell and/or tissue. Accordingly, a clinician can use any such supplemental oxygenating therapy in the method 1620 of FIG. 53 to improve ROS destruction of targeted cells and/or tissue and therefore, enhance the efficacy of the subsequent sonodynamic therapy 1628.

In further reference to the method 1620 of FIG. 53, the clinician can monitor the patient's level of oxygenation 1624 according to one embodiment. According to the non-limiting aspect of FIG. 53, blood oxygen levels can be monitored with an oximeter. For example, in the non-limiting aspect where the targeted tissue and/or cells are located in the patient's brain, oxygenation of the brain could be monitored with cerebral oximetry. Accordingly, near-infrared spectroscopy (NIRS) cerebral oximetry can be used to monitor the brain oxygenation. According to other non-limiting aspects of the present disclosure, various other light sources and/or detectors can be utilized in varying configurations to detect oxygen levels at different depths of the anatomical subject. According to still other non-limiting aspects of the present disclosure, magnetic resonance imaging (MRI) can be employed to assess and oxygen concentration within a targeted cell, tissue and/or organ, such as the brain. For example, blood oxygen level dependent (BOLD) contrast imaging can be used to visualize an anatomical structure (e.g. the brain) via functional magnetic resonance imaging (fMRI) to observe targeted cells, tissues, and/or organs and detect oxygen levels therein.

However, it shall be further appreciated that the aforementioned aspects describe specific means of monitoring a patient's oxygenation level at a treatment site 1624 for illustrative purposes only. As such, it shall be further appreciated that the present disclosure contemplates the use of any means of monitoring a patient's oxygenation level at a treatment site 1624 to assess whether the patient is ready for a subsequent sonodynamic therapy 1628, thereby ensuring the sonodynamic therapy 1628 is enhanced according to one embodiment.

Still referring to FIG. 53, a clinician can continually monitor the oximetry readings and wait for them to meet or exceed a predetermined threshold 1626 prior to initiating sonodynamic therapy 1628 according to one embodiment. Similar to the aspect depicted in FIG. 52, the clinician can assess the patient's pre-sonodynamic therapeutic condition 1606 to determine if the patient is properly prepared for the commencement of the sonodynamic therapy 1608. However, in the non-limiting aspect of FIG. 53, the patient's pre-sonodynamic therapeutic condition corresponds to the oxygenation level at a treatment site. As such, the assessment 1626 can include a comparison of the oxygenation level at the treatment site against a predetermined oxygenation threshold, to assess if the complementary therapy has properly oxygenated the patient. Accordingly, the assessment of the patient's oxygen levels 1626 can provide the clinician with confidence in the efficacy of the subsequent sonodynamic therapy 1629.

In further reference to FIG. 53, a clinician can decide to alter and/or time the initiation of sonodynamic therapy 1628 based, at least in part, on the assessment of the patient's level of oxygenation 1626 according to one embodiment. For example, if the clinician determines that the patient—or a target cell, tissue, and/or organ of the patient—is oxygenated below the predetermined threshold 1626, the clinician might decide to extend the oxygen therapy 1622 and delay the subsequent sonodynamic therapy 1628. According to some non-limiting aspects, the determination 1626 can be specific to the targeted cell, tissue, and/or organ of the patient. For example, if the target tissue is a tumor located within the brain, an NIRS cerebral oximeter is placed on the head (perhaps a shaven head) as close to the tumor as possible, and the clinician makes the determination 1626 based on the specific oxygenation levels produced by the NIRS cerebral oximeter. Alternatively and/or additionally, the NIRS cerebral oximeter can be configured to continuously monitor the oxygenation of the targeted region and/or tissue until the predetermined threshold is met and/or exceeded. Accordingly, a system can be configured to autonomously notify the clinician and/or initiate the sonodynamic therapy 1628 when it is determined that the threshold has been met or is exceeded 1626.

Referring now to FIG. 54, a flow diagram of a method 1630 of using immunotherapy to enhance the efficacy of a sonodynamic therapy is depicted in accordance with at least one non-limiting aspect of the present disclosure. The method includes initiating a sonodynamic treatment 1632 to imbue an immunotherapeutic effect on targeted cells, tissues, and/or organs 1638. For example, the sonodynamic therapy can be used to damage the cancerous cells while mitigating damage to and enhancing the effectiveness of the cellular immunity.

For example, the method 1630 of FIG. 54 can employ a sonodynamic treatment 1632 that utilizes a specific sonosensitizer 1634 configured to inhibit the recurrence of a targeted cell and/or tissue that was destroyed via the sonodynamic therapy 1636 according to one embodiment. According to some non-limiting aspects, the sonosensitizer utilized to destroy the targeted cells and/or tissue can indirectly produce an immunotherapeutic effect upon activation 1636, thereby resulting in a desired immunity (e.g. resistivity to the recurrence of the destroyed cell) in response to the sonodynamic therapy 1638. For example, damage-associated molecular patterns (DAMP) can result from the killing of targeted cells and/or tissues via sonodynamic therapy, leading to the creation of molecular patterns that elicit an immunotherapeutic response. Accordingly, the method 1630 of employing an enhanced sonodynamic therapy depicted in FIG. 54 can fortify surrounding cells, tissues, and/or organs by altering and training them to resist a recurrence of the targeted cells and/or tissues.

Referring now to FIG. 55, a block diagram 1640 depicting various therapeutic sonosensitizers 1642, 1644, 1646 configured to enhance the efficacy of a sonodynamic therapy is depicted in accordance with at least one non-limiting aspect of the present disclosure. As previously discussed, sonodynamic therapeutic drugs—or sonosensitizers—can be specifically configured to improve accumulation on targeted cells and/or tissues and to produce an enhanced cytotoxic effect. For example, sonosensitizers can be specifically configured to improve the sonosensitizer's acoustic cavitation as well as the associated thermal, chemical or luminescent phenomena, all of which can improve enhance accumulation and acoustic reactivity during sonodynamic therapies.

According to the non-limiting aspect of FIG. 55, an overall sonosensitizers configuration 1642 can include a type-specific sonosensitizer 1644, a location-specific sonosensitizer 1646, a wavelength-specific sonosensitizer 1648, and/or any combination thereof according to one embodiment. The sonosensitizers 1642, 1644, 1666 can be either experimental or approved by the FDA or other regulatory agency. Although the non-limiting aspect of FIG. 55 depicts an overall sonosensitizer 1642 including a combination of sonosensitizers 1644, 1646, 1648, the present disclosure further contemplates aspects in which the overall sonosensitizer 1642 includes a single specifically tailored sonosensitizer 1644, 1646, 1648 to achieve the desired effect. For example, the overall sonosensitizer 1642 can be specifically configured to target a specific type of cell, in a specific location of an anatomical subject, and react to ultrasonic stimulation from the transducers including a specific wavelength to improve the accumulation of overall sonosensitizers 1642 on a targeted cell and/or tissue and improve the acoustic reactivity of the overall sonosensitizer 1642.

For example, the overall sensitizer 1642 can be specifically configured to target a wound, ulcer, abscess, tumor, or any combination thereof according to one embodiment. The overall sonosensitizer 1642 can be further configured to target any of the aforementioned types of cells regardless of their relative position in the patient's body, and to react to a particular wavelength based on the location, therefore improving the destruction of targeted cells and/or tissues while leaving surrounding cells and/or tissues unharmed. Accordingly, an operating clinician can use the overall sonosensitizer 1642 to tailor the sonodynamic therapy based on the specific implementation and/or intended use. As such, the design of an overall sonosensitizer 1642, itself can enhance the efficacy of the sonodynamic therapy.

In further reference to FIG. 55, the overall sonosensitizer 1642 or any of the specifically tailored sonosensitizers 1644, 1646, 1648 can include a nanoparticle sonosensitizer according to one embodiment. Nanoparticle sonosensitizers can be used for their beneficial photocatalytic or sonocatalytic properties, which catalyze a reaction that produces reactive oxygen species. For example, titanium dioxide (TiO2), can be used to attenuate and/or regulate a desired cytotoxic effect. As such, the overall sonosensitizer 1642 can be specifically tailored to reduce toxicity, increase biodegradability, and improve cell and/or tissue targeting.

According to one non-limiting aspect of the present disclosure, the sonodynamic therapy can be further enhanced to increase the concentration of protoporphyrin IX (PpIX) by limiting how much of it gets converted into Heme. For example, at least one of the overall sonosensitizer

1642, or any of the specifically tailored sonosensitizers 1644, 1646, 1648 of FIG. 55 can include 5-aminolevulinic acid (5-ALA). Amongst other things, 5-ALA can be utilized as a prodrug to induce the accumulation of PpIX in targeted cells and/or tissues. PpIX can induce cellular damage when exposed to ultrasonic wavelengths. 5-ALA is used in the endogenic production of a Heme group. For example, the final process of the Heme biosynthesis pathway includes inserting an iron ion into PpIX to form Heme, which is accomplished with ferrochelatase. Glioblastoma multiforme (GBM) has lower expression of the gene that produces ferrochelatase, which is why PpIX accumulates in GBM. ALA sonodynamic therapy (SDT) might be enhanced by further inhibiting the action of ferrochelatase. In some aspects, iron ions are removed from some target cells to reduce the production of Heme and thus increase the concentration of PpIX. In other aspects, the enzyme ferrochelatase removed from the cell. In other aspects, a drug is delivered to reduce or eliminate the activity of ferrochelatase. In some embodiments, a sonosensitizer and/or product thereof accumulates in a tumor cell. In some embodiments, a sonosensitizer and/or product thereof accumulates in a mitochondria of a tumor cell. Gliomas, glial cells and/or astrocytomas are targeted and treated (e.g., selectively or preferentially) in several embodiments.

In various aspects, the sonodynamic therapy techniques described in this disclosure may be adapted to other parts of the body. These other parts of the body may be accessed through a natural orifice (mouth, nasal cavity, ear, anus, vagina) or minimally invasive processes such as intravascular access. Implantable ultrasound devices that are at least partially implantable may also be used. The sonodynamic therapy device may be specifically adapted to have a flexible, navigable catheter shaft to reach tumors in specific organs such as liver, stomach, breast, or lungs, for example. The sonodynamic therapy device may be adapted to wrap around the torso or limb and may be employed to treat osteosarcoma into the bone.

In various aspects, the sonodynamic therapy techniques described in this disclosure may be adapted for use with adjuvant therapies. The disclosed sonodynamic therapy techniques may be employed in other cancer therapies including chemotherapy, immunotherapy, radiotherapy, HIFU/hyperthermia. Further, the disclosed sonodynamic therapy techniques employ additional drugs which increase oxygen in the brain or increase oxygen in a brain tumor to a preferential oxygen concentration to provide an effective sonodynamic therapy. The disclosed sonodynamic therapy techniques may employ a sensitizer which is modified or encapsulated to effectively target a tumor. The disclosed sonodynamic therapy techniques may deliver $O_2$ systematically with nose tubes. The disclosed sonodynamic therapy techniques may employ multiple sensitizers in conjunction and may include the introduction of gas bubbles into the tumor to oxygenate the tumor, create more cavitation, and provide a possible contrast mechanism for imaging.

In various aspects, the sonodynamic therapy techniques described in this disclosure may be adapted for use with ultrasound imaging according to one embodiment. The process may include the addition of a contrast agent for ultrasound which goes to the tumor. In various embodiments, CT, X-Ray, MRI, or other imaging may be used.

As used herein a processor or processing unit is an electronic circuit which performs operations on some external data source, usually memory or some other data stream. The term is used herein to refer to the central processor (central processing unit) in a system or computer systems (e.g., systems on a chip (SoCs) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions-all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be a LM4F230H5QR ARM Cortex-M4F Processor Core, available from Texas Instruments, for example, comprising on-chip memory of 256 KB single-cycle flash memory, or other non-volatile memory, up to 40 MHZ, a prefetch buffer to improve performance above 40 MHZ, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4× known under the trade name Hercules ARM Cortex R4, also by Texas Instruments according to one embodiment. The safety controller may be configured specifically for IEC 61508 and ISO 26262 safety critical applications, among others, to provide advanced integrated safety features while delivering scalable performance, connectivity, and memory options.

As used herein, the terms "component," "system," "module" and the like can refer to a computer-related entity, either hardware, a combination of hardware and software, software, or software in execution, in addition to electro-mechanical devices. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. The word "exemplary" is used herein to mean serving as an example, instance, or illustration. Any aspect or design described herein as "exemplar" is not necessarily to be construed as preferred or advantageous over other aspects or designs.

As used herein, the term control circuit may be any stand alone or combination electronic circuit such as, for example, a processing unit, processor, microcontroller, microcontroller unit, controller, digital signal processor (DSP), programmable gate array (PGA), field PGA (FPGA), programmable logic device (PLD), system on chip (SoC), application specific integrated circuit (ASIC), graphics processing unit (GPU), and the like. According to various aspects, process flow diagrams described herein may be implemented by a digital device such as a control circuit.

Although the various aspects of the present disclosure describe instruction handling and distribution in the context of execution units and logic circuits, other aspects of the present disclosure can be accomplished by way of data and/or instructions stored on a machine-readable, tangible medium, which when performed by a machine cause the machine to perform functions consistent with at least one aspect. In one aspect, associated functions of the present disclosure are embodied in machine-executable instructions. The instructions can be used to cause a general-purpose or special-purpose processor that is programmed with the instructions to perform the steps of the functions described in the present disclosure. Aspects of the present disclosure may be provided as a computer program product or software which may include a machine or non-transitory computer-readable medium having stored thereon instructions which may be used to program a computer (or other electronic devices) to perform one or more operations according to aspects of the present disclosure. Alternatively, functions according to the present disclosure might be performed by specific hardware components that contain fixed-function logic for performing the functions, or by any combination of programmed computer components and fixed-function hardware components.

Instructions used to program logic to perform various disclosed aspects can be stored within a memory in the system, such as DRAM, cache, flash memory, or other storage according to one embodiment. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

In various embodiments, an ultrasound transducer system 1700 comprises an array 1702 of transducer elements configured to emit an acoustic wave through an elastic, flexible membrane 1703 configured to conform to a shape of a portion of a body (e.g., head, skull, hips, abdomen, arm, leg, torso, back, waist, neck, etc.) for treatment. Referring now to FIGS. 56A, 56B, 57-58 illustrate schematic views of an ultrasound transducer system 1700 according to at least one aspect of the present disclosure. In one embodiment, the ultrasound transducer system is a transcranial sonodynamic therapy device 1700 configured for placement over the head of a patient.

In one embodiment, an acoustic wave 200, 312, 314, 1202, 1204, 1206, 1208, 1210, 1222, 1224, 1226, 1228 can be planar or defocused to minimize the spatial variation of the acoustic wave intensity in the brain. In various embodiments, the array 1702 comprises multiple transducer elements 150*a*-150*h*, 410, 420, 452, 454, 1302 that can be individually energized to produce a variety of acoustic waves, according to at least one aspect of the present disclosure. In one aspect, the array may be implemented as a single transducer comprising multiple piezoelectric elements with acoustically/electrically-independent sections arranged in the array 1702. The transducer elements 150*a*-150*h*, 1302 can be arranged in an array 1702 to produce converging, diverging, or planar, acoustic waves. In one embodiment, one or more of the individual elements 150*a*-150*h*, 1302 includes a flat, planar emitting surface that produces a planar acoustic wave. In one embodiment, the transducer element is flat, which may help reduce manufacturing costs.

In one embodiment, the element is made of a material with higher acoustic impedance than the target medium (water/tissue). Accordingly, an acoustic wave originates in the high-impedance material and transitions to the low-acoustic impedance target medium causing the acoustic wave to "defocus" or diverge to the target tissue.

In various embodiments, the transducer elements 150*a*-150*h*, 410, 420, 452, 454, 1302 can be activated in a predetermined sequence to selectively generate convergent/divergent/planar acoustic waves, such as, for example, a divergent acoustic wave. The transducer elements 150*a*-150*h*, 410, 420, 452, 454, 1302 may be energized in an order to produce a diverging acoustic wave using equal or different time delays. The transducer elements 150*a*-150*h* can be interchangeably configured to transmit or receive acoustic waves.

In one embodiment, the transducer elements 150*a*-150*h*, 410, 420, 452, 454, 1302 are arranged in a 2-dimensional (2D) grid array. In one embodiment, one or more elements in the 2-dimensional (2D) grid array includes at least one flat, planar emitting surface that produces a planar acoustic wave. Each transducer element of the 2D grid transducer array can be driven with a same signal or a different signal. In one embodiment of producing a defocused diverging acoustic wave from the dimensional (2D) grid array, the acoustic wave produced by the outer elements may be progressively more delayed relative to the inner element.

In one aspect, the transducer element may be made of piezoelectric or single crystal material which converts electrical energy to ultrasonic energy. The transducer element also can receive back ultrasonic energy and convert it to electrical energy. Each transducer element may be selectively energized and actuated to produce convergent, divergent, or planar acoustic waves. In one embodiment, the transducer element has a zero vergence to produce a planar acoustic wavefront that does not converge or diverge. In one embodiment, a single converging/diverging acoustic wavefront may be produced by multiple elements of a transducer.

In various aspects, ultrasonic transducer element shapes include circular or disc shapes and concentric arrangements of elements. In various embodiments, the arrangement of transducer elements may be any of the embodiments disclosed herein, including any of the embodiments and equivalents described in FIGS. 29-41.

In various embodiments, ultrasound transducer system 1700 includes a cooling system 1710. In one embodiment, the cooling system 1710 includes a fluid input tube 1704 and a fluid output tube 1705. In one embodiment, the fluid is water. In one embodiment, a membrane 1703 extends along an entry plane of the fluid input tube 1704 and along an exit plane of the fluid output tube 1705, forming a fluid port relief gap to cool the membrane 1703 with circulating fluid. The membrane 1703 is configured as any of the membrane embodiments herein. In one embodiment, the ultrasound transducer system includes a transducer housing 1706 attached to the array 1702 of transducer elements. In one embodiment, the transducer housing comprises one or more electrical connection ports 1708. In one embodiment, the cooling system 1710 comprises a bezel 1707 attached to the membrane 1703, fluid input tube 1704, and fluid output tube 1705. In one embodiment, the cooling system 1710 bezel 1707 is removably attachable to and detachable from the transducer housing 1706. In one embodiment, the membrane 1708 is detachable and replaceable. In one embodiment, the bezel 1707 is detachable and replaceable. In one embodiment, the cooling system 1710 is detachable and replaceable. In one embodiment, the cooling system 1710 bezel 1707 is permanently attached to the transducer housing 1706.

In one embodiment, the ultrasound transducer system 1700 comprises one or more handles for manually gripping and positioning the transducer system.

FIGS. 59A-F are schematic images of placements of an ultrasound transducer system at multiple locations around a head for treatment of tissue in the head according to at least one aspect of the present disclosure. At any one placement, one or multiple treatments may be performed. In one embodiment, the placements overlap. In one embodiment, the placements do not overlap. Moving the ultrasonic transducer array relative to the patient interface between a plurality of treatment positions or placements are configured to cause the ultrasonic transducer array to activate a sonosensitizer in a treatment region in the anatomical structure.

Figure 59A:
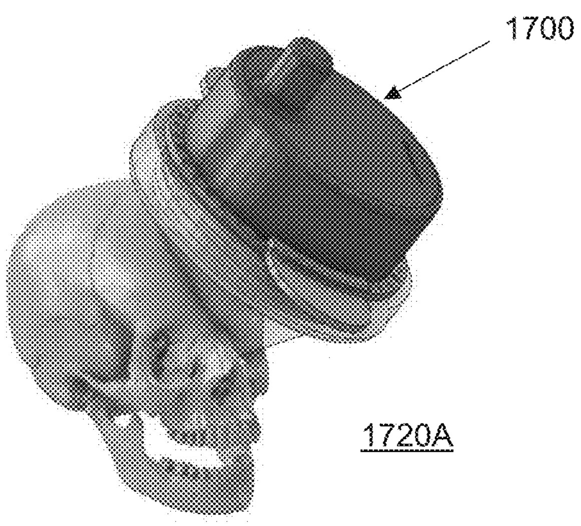
FIGS. 59A-59F are schematic images of placements of an ultrasound transducer system at multiple locations around a head for overlapping treatment of tissue in a head according to at least one aspect of the present disclosure.

Placement A 1720A illustrated at FIG. 59A comprises placement at the frontal bone of the skull for treatment embodiments including the frontal lobe.

Figure 59B:
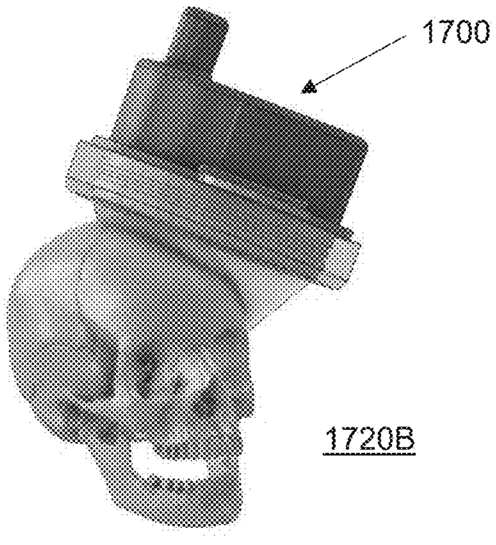

Placement B 1720B illustrated at FIG. 59B comprises placement at a lateral aspect of the frontal bone of the skull for treatment embodiments including the frontal and temporal lobes and thalamus.

Figure 59C:
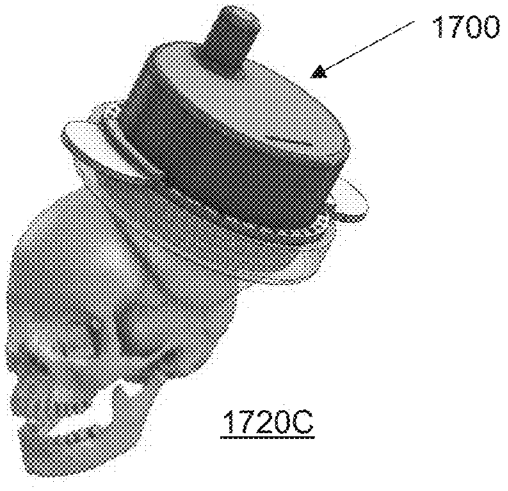

Placement C 1720C illustrated at FIG. 59C comprises placement at the parietal bone of the skull for treatment embodiments including the parietal lobe.

Figure 59D:
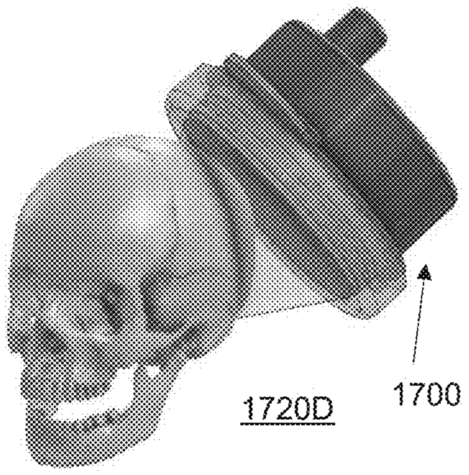

Placement D 1720D illustrated at FIG. 59D comprises placement at an anterior aspect of the parietal bone of the skull for treatment embodiments including the parietal and occipital lobes.

Figure 59E:
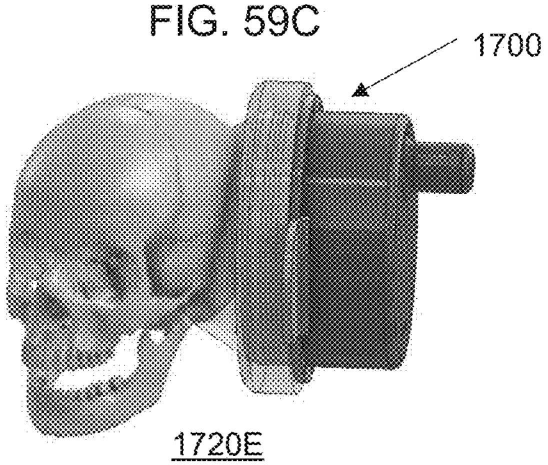

Placement E 1720E illustrated at FIG. 59E comprises placement at a lateral aspect of the parietal bone of the skull for treatment embodiments including the occipital lobe, midbrain, and cerebellum.

Figure 59F:
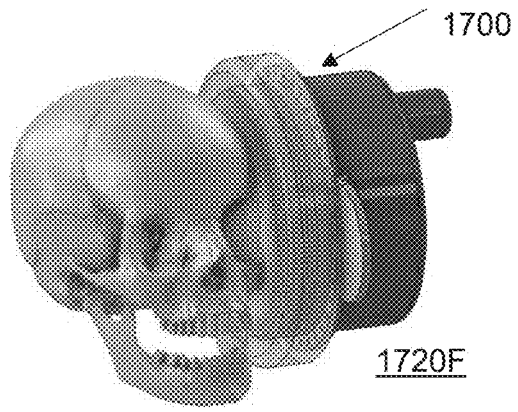

Placement F 1720F illustrated at FIG. 59F comprises placement at the temporal bone of the skull for treatment embodiments including the temporal, parietal, and frontal lobes.

FIGS. 60A-I are schematic images of placements of an ultrasound transducer system at multiple locations around a head for treatment of tissue in the head according to at least one aspect of the present disclosure. At any one placement, one or multiple treatments may be performed. In one embodiment, the placements overlap. In one embodiment, the placements do not overlap. Moving the ultrasonic transducer array relative to the patient interface between a plurality of treatment positions or placements are configured to cause the ultrasonic transducer array to activate a sonosensitizer in a treatment region in the anatomical structure.

Figure 60A:
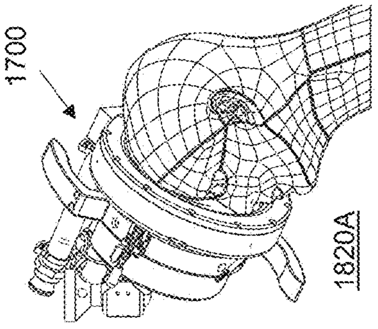
FIGS. 60A-60J are schematic images of placements of an ultrasound transducer system at multiple locations around a head for overlapping treatment of tissue in a head according to at least one aspect of the present disclosure.

Placement A 1820A illustrated at FIG. 60A comprises placement at the frontal bone of the skull for treatment embodiments including the frontal lobe.

Figure 60B:
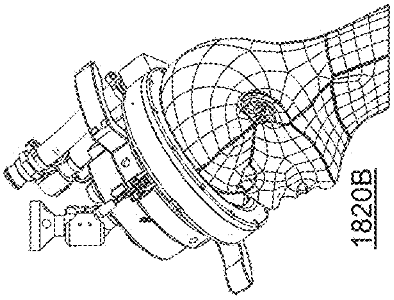

Placement B 1820B illustrated at FIG. 60B comprises placement at a lateral aspect of the frontal bone of the skull for treatment embodiments including the frontal and temporal lobes and thalamus.

Figure 60C:
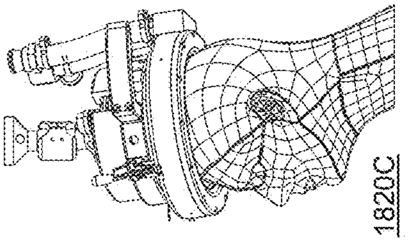

Placement C 1820C illustrated at FIG. 60C comprises placement at the parietal bone of the skull for treatment embodiments including the parietal lobe.

Figure 60D:
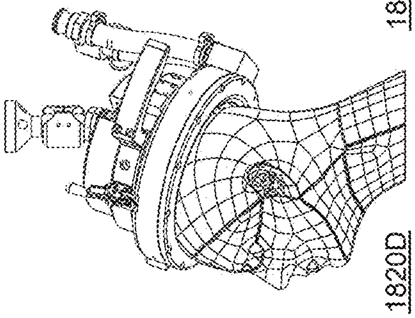

Placement D 1820D illustrated at FIG. 60D comprises placement at an anterior aspect of the parietal bone of the skull for treatment embodiments including the parietal and occipital lobes.

Figure 60E:
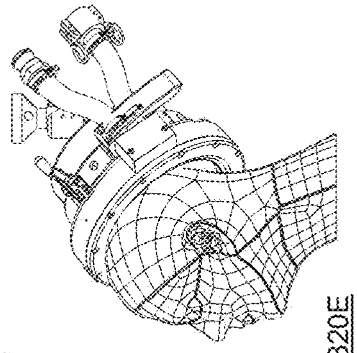
Figure 60F:
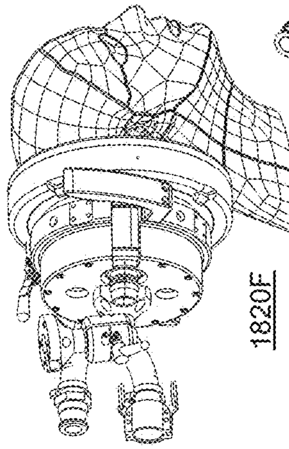

Placement E 1820E illustrated at FIG. 60E comprises placement at an anterior aspect of the parietal bone of the skull for treatment embodiments including the parietal and occipital lobes Placement F 1820F illustrated at FIG. 60F comprises placement at the temporal bone of the skull for treatment embodiments including the temporal, parietal, and frontal lobes.

Figure 60G:
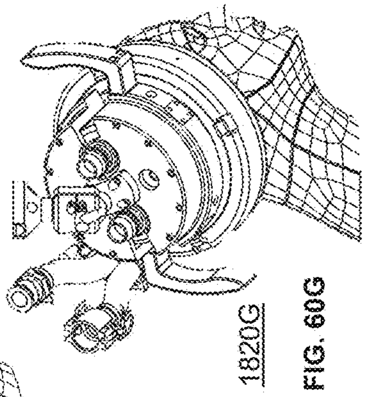

Placement G 1820G illustrated at FIG. 60G comprises placement at a lateral aspect of the parietal bone of the skull for treatment embodiments including the occipital lobe, midbrain, and cerebellum.

Figure 60H:
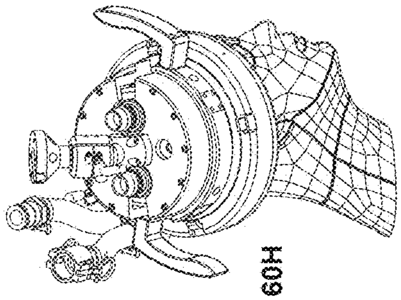

Placement H 1820B illustrated at FIG. 60H comprises placement at a lateral aspect of the frontal bone of the skull for treatment embodiments including the frontal and temporal lobes and thalamus.

Figure 60I:
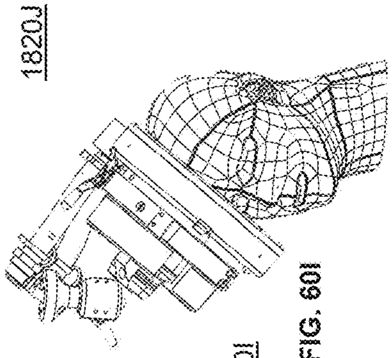

Placement I 1820I illustrated at FIG. 60I comprises placement at the frontal bone of the skull for treatment embodiments including the frontal lobe.

Figure 60J:
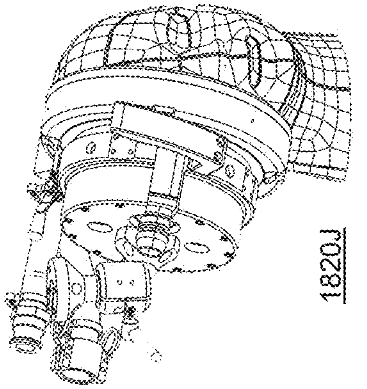
Figure 61B:
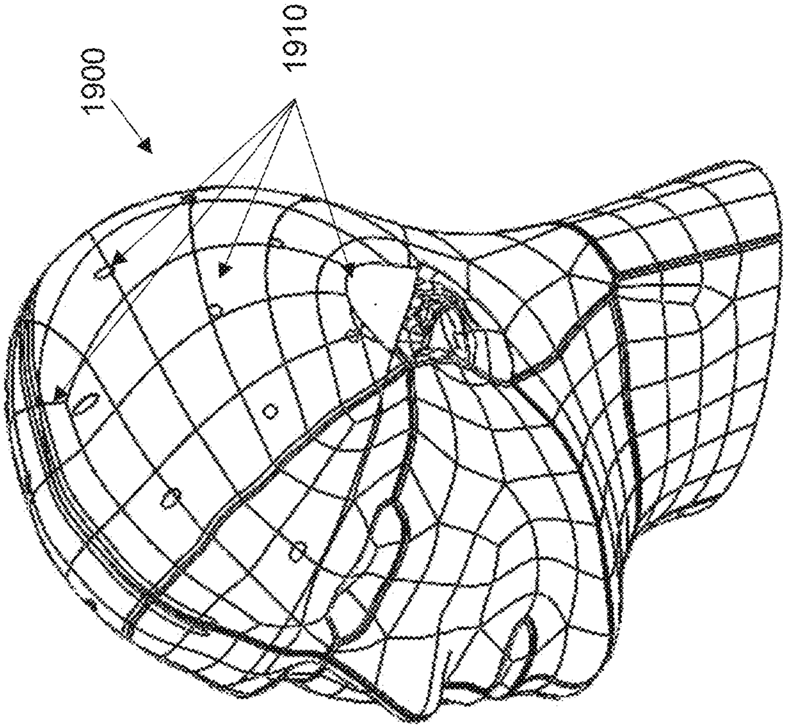
FIGS. 61A and 61B are schematic images of a targeting template with markers placed on a patient to facilitate alignment of the transducer to the various treatment sites according to various embodiments.
Figure 61A:
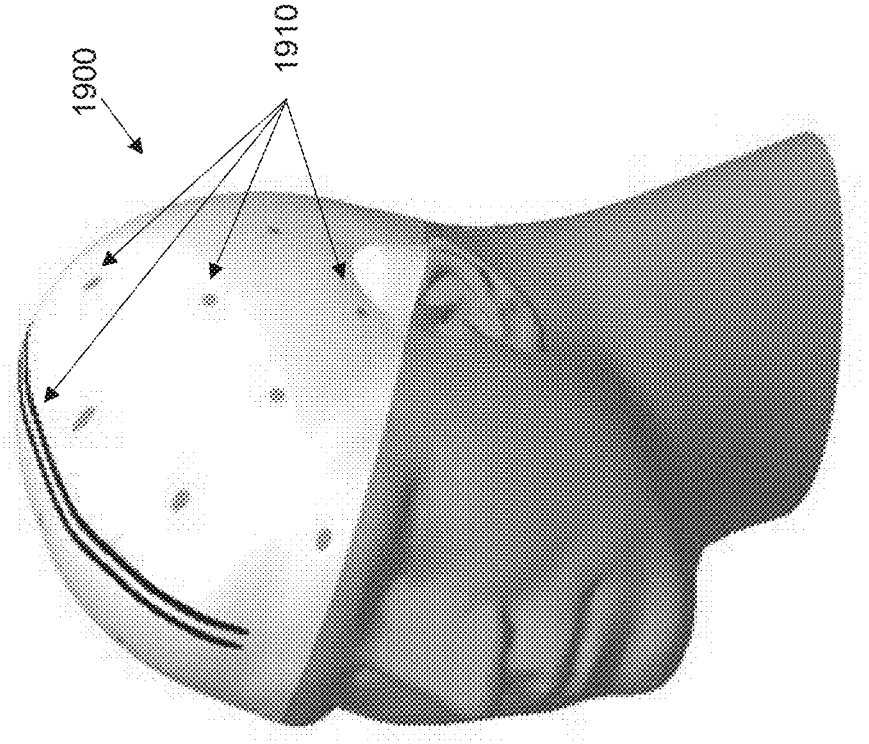

Placement J 1820J illustrated at FIG. 60J comprises placement at the temporal bone of the skull for treatment embodiments including the temporal, parietal, and frontal lobes.

Figure 62A:
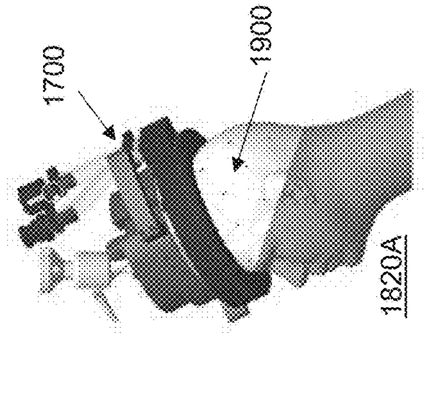
FIGS. 62A-62J are schematic images of placements of an ultrasound transducer system at multiple locations around a head with a targeting template according to at least one aspect of the present disclosure.
Figure 62B:
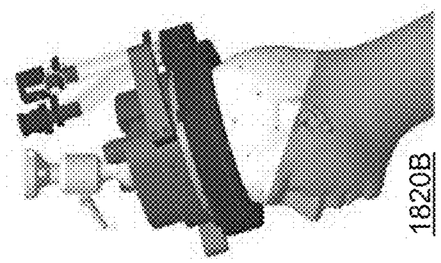

In one embodiment a targeting template 1900 is placed on the patient to facilitate alignment of the transducer to the various treatment sites. In various embodiments, the targeting template 1900 is a wearable elastic template with one, two, three, four, five, six, ten, twelve, fifteen or more markers 1910 to facilitate treatment, such as by demarking a grid, positions based on one or more anatomical features, and/or marking of the skin with indicators. In one embodiment, the targeting template includes measurement gradients that allow the user to customize treatment locations to patient specific anatomical size. In some embodiments, the targeting template remains in place during ultrasound treatment. In some embodiments, the targeting template is made to be removable prior to ultrasound treatment. In various embodiments, a targeting template is an elastic cap 1900 configured to fit over the head of a patient, as shown in FIGS. 62A and 62B. In one embodiment, the targeting template 1900 is a band configured to wrap around a head, neck, chest, torso, back, waist, leg, buttock, genital area or other body part. In one embodiment, the targeting template is drawn on the body.

FIGS. 62A-I are schematic images of placements of an ultrasound transducer system at multiple locations around a targeting template 1900 with a plurality of markers 1910 for treatment of tissue in the head according to at least one aspect of the present disclosure. At any one placement, one or multiple treatments may be performed. In one embodiment, the placements overlap. In one embodiment, the placements do not overlap. Moving the ultrasonic transducer array relative to the patient interface between a plurality of treatment positions or placements are configured to cause the ultrasonic transducer array to activate a sonosensitizer in a treatment region in the anatomical structure.

Placement A 1820A illustrated at FIG. 62A comprises placement at the frontal bone of the skull for treatment embodiments including the frontal lobe.

Placement B 1820B illustrated at FIG. 62B comprises placement at a lateral aspect of the frontal bone of the skull for treatment embodiments including the frontal and temporal lobes and thalamus.

Figure 62C:
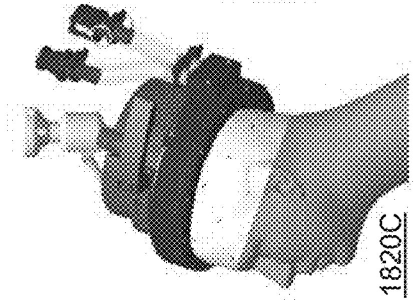

Placement C 1820C illustrated at FIG. 62C comprises placement at the parietal bone of the skull for treatment embodiments including the parietal lobe.

Figure 62D:
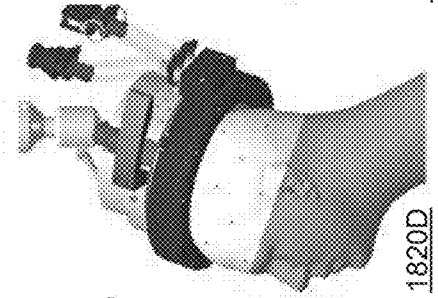

Placement D 1820D illustrated at FIG. 62D comprises placement at an anterior aspect of the parietal bone of the skull for treatment embodiments including the parietal and occipital lobes.

Figure 62E:
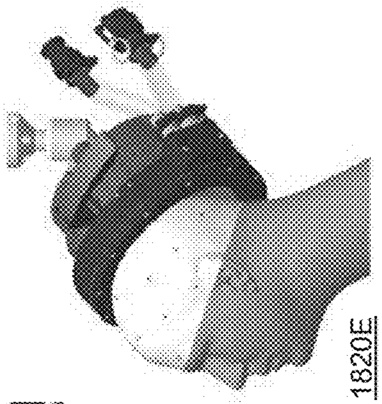
Figure 62F:
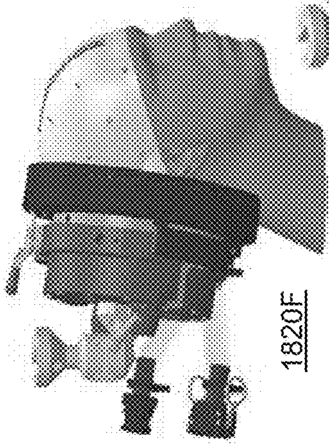

Placement E 1820E illustrated at FIG. 62E comprises placement at an anterior aspect of the parietal bone of the skull for treatment embodiments including the parietal and occipital lobes Placement F 1820F illustrated at FIG. 62F comprises placement at the temporal bone of the skull for treatment embodiments including the temporal, parietal, and frontal lobes.

Figure 62G:
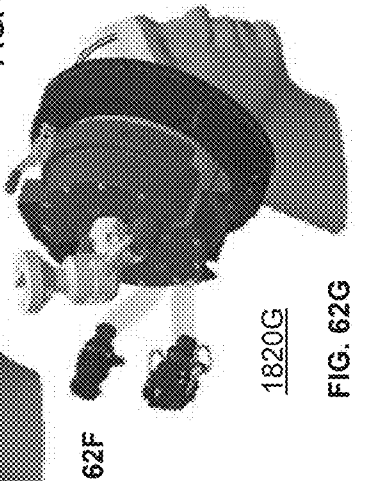

Placement G 1820G illustrated at FIG. 62G comprises placement at a lateral aspect of the parietal bone of the skull for treatment embodiments including the occipital lobe, midbrain, and cerebellum.

Figure 62H:
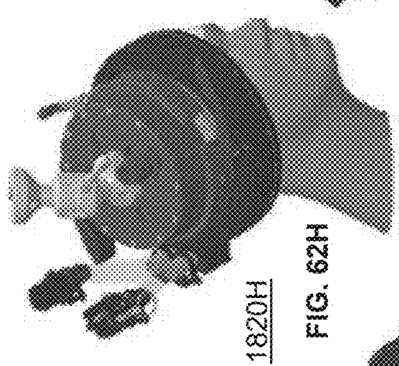

Placement H 1820B illustrated at FIG. 62H comprises placement at a lateral aspect of the frontal bone of the skull for treatment embodiments including the frontal and temporal lobes and thalamus.

Figure 62I:
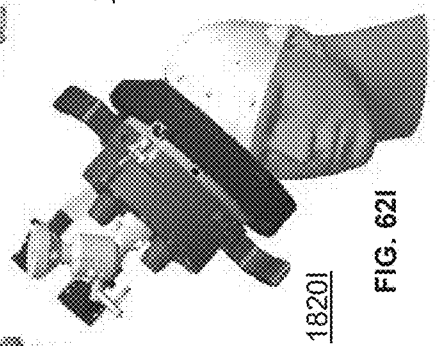

Placement I 1820I illustrated at FIG. 62I comprises placement at the frontal bone of the skull for treatment embodiments including the frontal lobe.

Figure 62J:
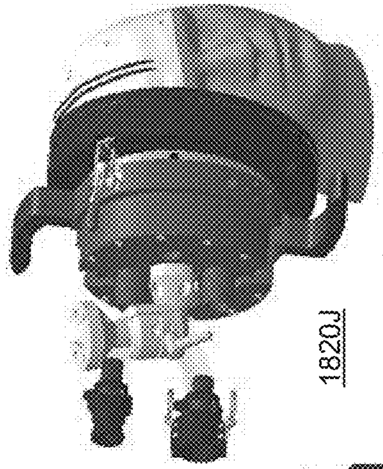

Placement J 1820J illustrated at FIG. 62J comprises placement at the temporal bone of the skull for treatment embodiments including the temporal, parietal, and frontal lobes.

Figure 63C:
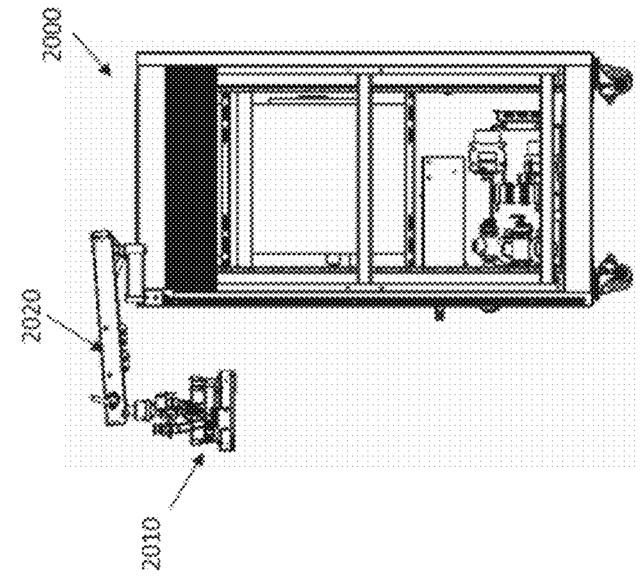
FIGS. 63A-63C are schematic images of an embodiment of a sonodynamic treatment system with a transducer array, support arm, cart, console/controller, ultrasound generator, user interface, and/or a cooling fluid circulation unit.
Figure 63B:
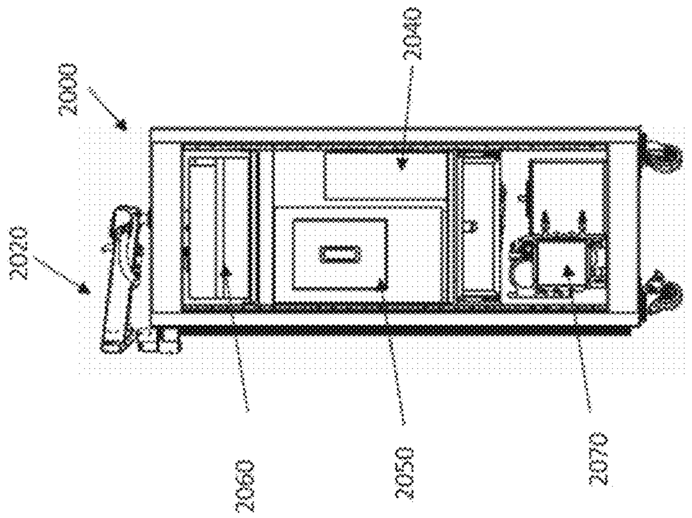
Figure 63A:
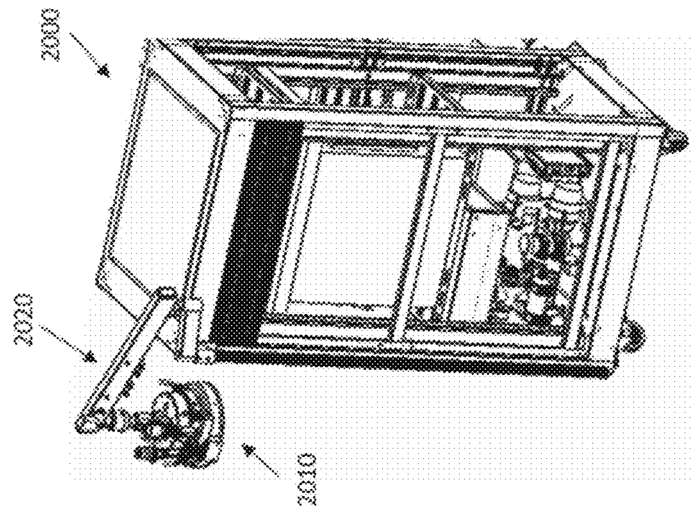

In various embodiments, a sonodynamic treatment system 2000 includes a transducer array 2010, support arm 2020, cart 2030, console/controller 2040, ultrasound generator 2050, user interface 2060, and/or a cooling fluid circulation unit 2070 according to any of the embodiments herein. In one embodiment, the support arm 2020 is counterbalanced to facilitate placement of the transducer array 2010 in one or more positions (e.g., 1, 2, 3, 4, 5, 6, 8, 10, 12, 15, 20 or more positions) during a sonodynamic treatment. FIGS. 63A-63C illustrate views of one embodiment of a mobile sonodynamic treatment system 2000 according any of the embodiments of any of the components described herein.

Various examples have been described with reference to certain disclosed aspects. The various aspects are presented for purposes of illustration and not limitation. One skilled in the art will appreciate that various changes, adaptations, and modifications can be made without departing from the scope of the disclosure or the scope of the appended claims.

The detailed description is exemplary in nature and provides some practical illustrations and examples. Those skilled in the art will recognize that many of the noted examples, aspects, and/or embodiments have a variety of suitable alternatives. A number of various exemplary transcranial sonodynamic therapy devices are disclosed herein using the description provided in addition to the accompanying drawings. Each of the aspects disclosed herein can be employed independently or in combination with one or more (e.g., single, two, three, four, five, and any number including all) of the other aspects disclosed herein. In various embodiments, an embodiment may comprise, consist essentially of, or consist of recited elements.

Unless otherwise defined, all technical and scientific terms used herein have the same meaning as commonly understood by one of ordinary skill in the art to which this disclosure pertains. For example, as used herein, the term "about" includes values within 10%, 5%, or 1% of the recited values. For example, as used herein, the term "substantial" or "substantially" includes values within 10%, 5%, or 1% of the recited values. Although apparatuses, methods, and materials similar or equivalent to those described herein can be used to practice the various aspects of the claimed subject appended hereto, suitable methods and materials are described herein. All publications, patent applications, patents, and other references mentioned herein are incorporated by reference in their entirety. In case of conflict, the present specification, including definitions, will control. In addition, the embodiments, aspects, materials, methods, and examples are illustrative only and not intended to be limiting. In various aspects, the present disclosure provides ensonification drive patterns for activating a sonosensitizer in conjunction with providing sonodynamic therapy. In various aspects, the present disclosure provides methods and systems of treating cancer. The term "aspect" includes non-limiting embodiments. When numbers are provided, values and ranges therein should be included where stated or understood from a fair reading. For example, disclosure of "10-50% (e.g., 10, 20, 30, 40, 50% and values and ranges therein)" would include 10-20%, 20-40%, etc. as well as 10%, 15%, 35% etc.).

Unless otherwise defined, all technical and scientific terms used herein have the same meaning as commonly understood by one of ordinary skill in the art to which this disclosure pertains. Although apparatuses, methods, and materials similar or equivalent to those described herein can be used to practice various aspects of the claimed subject matter appended hereto, suitable apparatuses, methods, and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more aspects of various embodiments are set forth in the accompanying drawings and the description herein. Other features and advantages of the present disclosure will be apparent from the description and drawings, and from the claims appended hereto.

What is claimed is:

1. An ultrasound transducer system that generates a diffuse incoherent acoustic pressure field for activating a sonosensitizer in conjunction with providing sonodynamic therapy, the ultrasound transducer system comprising:

an ultrasound transducer array comprising a plurality of ultrasonic piezoelectric transducer elements, wherein the plurality of ultrasonic piezoelectric transducer elements is configured to generate the diffuse incoherent acoustic pressure field with an energy profile to saturate a treatment volume to ensure treatment of a lesion of cancer cells located within a tissue of a patient by activating the sonosensitizer located within the tissue of the patient, wherein the plurality of ultrasonic piezoelectric transducer elements is driven by a signal to generate the diffuse incoherent acoustic pressure field, wherein the signal comprises one or more of the group consisting of:

a modulated phase across the plurality of ultrasonic piezoelectric transducer elements, a modulated frequency across the plurality of ultrasonic piezoelectric transducer elements, and a modulated amplitude across the plurality of ultrasonic piezoelectric transducer elements;

wherein each ultrasonic piezoelectric transducer element in the plurality of ultrasonic piezoelectric transducer elements comprises an emitting surface configured to emit planar acoustic waves or defocused acoustic waves, wherein the signal is configured to minimize a spatial variation of an acoustic wave intensity to activate the sonosensitizer at the lesion of cancer cells with the planar acoustic waves or the defocused acoustic waves, and wherein the signal is configured with a duty cycle to drive each ultrasonic piezoelectric transducer element in the plurality of ultrasonic piezoelectric transducer elements to generate (i) a high temporal peak acoustic intensity sufficient to activate the sonosensitizer at the lesion of cancer cells with the planar acoustic waves or the defocused acoustic waves and (ii) a low temporal average acoustic intensity to preserve tissue.

2. The ultrasound transducer system of claim 1, wherein the signal comprises the modulated phase across the plurality of ultrasonic piezoelectric transducer elements, and wherein the modulated phase comprises a randomized phase difference.

3. The ultrasound transducer system of claim 1, wherein the plurality of ultrasonic piezoelectric transducer elements comprises over 128 ultrasonic piezoelectric transducer elements.

4. The ultrasound transducer system of claim 1, further comprising a cooling system configured to remove excess heat from the patient, wherein the cooling system comprises a flexible cavity configured for circulation of a degassed fluid.

5. The ultrasound transducer system of claim 1, wherein the energy profile is driven at ultrasonic frequencies in a range of 20 kHz to 2 MHz.

6. The ultrasound transducer system of claim 1, wherein the sonosensitizer is selected from the group consisting of: aminolevulinic acid (ALA), hematoporphyrin, Rose Bengal, curcumin, titanium nanoparticles, and chlorine e6.

7. The ultrasound transducer system of claim 1, wherein the ultrasound transducer system is configured for treating cancerous tissue in a brain, lung, breast, liver, stomach, prostate, vagina, testes, pancreas, or intestines.

8. The ultrasound transducer system of claim 1, wherein the plurality of ultrasonic piezoelectric transducer elements are disposed on a patient interface comprising a detachable flexible membrane configured to couple to a head of the patient.

9. The ultrasound transducer system of claim 1, wherein the plurality of ultrasonic piezoelectric transducer elements are disposed on a helmet configured to couple to a head of the patient via a replaceable flexible membrane.

10. The ultrasound transducer system of claim 1, wherein the plurality of ultrasonic piezoelectric transducer elements comprises between 128 to 1024 ultrasonic piezoelectric transducer elements.

11. An ultrasound transducer system that generates a diffuse incoherent acoustic pressure field for activating a sonosensitizer in conjunction with providing sonodynamic therapy, the ultrasound transducer system comprising:

an ultrasound transducer array comprising a plurality of ultrasonic piezoelectric transducer elements, wherein the plurality of ultrasonic piezoelectric transducer elements is configured to generate the diffuse incoherent acoustic pressure field with an energy profile to saturate a large treatment volume to ensure treatment of a lesion of cancer cells located within a tissue of a patient by activating the sonosensitizer located within the tissue of the patient, wherein each ultrasonic piezoelectric transducer element in the plurality of ultrasonic piezoelectric transducer elements comprises an emitting surface configured to emit planar acoustic waves or defocused acoustic waves, wherein the plurality of ultrasonic piezoelectric transducer elements is driven by a signal to generate the diffuse incoherent acoustic pressure field, wherein the signal comprises a modulated phase across the plurality of ultrasonic piezoelectric transducer elements, wherein the signal is configured to minimize a spatial variation of an acoustic wave intensity to activate the sonosensitizer at the lesion of cancer cells with the planar acoustic waves or the defocused acoustic waves, wherein the signal is configured with a duty cycle to drive each ultrasonic piezoelectric transducer element in the plurality of ultrasonic piezoelectric transducer elements to generate (i) a high temporal peak acoustic intensity sufficient to activate the sonosensitizer at the lesion of cancer cells with the planar acoustic waves or the defocused acoustic waves and (ii) a low temporal average acoustic intensity to preserve tissue.

12. The ultrasound transducer system of claim 11, wherein the plurality of ultrasonic piezoelectric transducer elements are arranged in a hemispherical arrangement disposed on a patient interface comprising a detachable flexible membrane configured to couple to a head of the patient.

13. The ultrasound transducer system of claim 11, further comprising a therapy selected from radiation, chemotherapy, immunotherapy, radiotherapy, and hyperthermia.

14. The ultrasound transducer system of claim 11, wherein the plurality of ultrasonic piezoelectric transducer elements is acoustically coupled to the patient via a degassed fluid.

15. The ultrasound transducer system of claim 11, wherein the ultrasound transducer system is configured for treating cancerous tissue in a brain, lung, breast, liver, stomach, prostate, vagina, testes, pancreas, or intestines.

16. The ultrasound transducer system of claim 11, wherein the sonosensitizer is selected from the group consisting of: aminolevulinic acid (ALA), hematoporphyrin, Rose Bengal, curcumin, titanium nanoparticles, and chlorine e6.

17. The ultrasound transducer system of claim 11, wherein the plurality of ultrasonic piezoelectric transducer elements comprises between 128 to 1024 ultrasonic piezoelectric transducer elements.

18. The ultrasound transducer system of claim 11, wherein the modulated phase comprises a randomized phase difference.

19. The ultrasound transducer system of claim 11, further comprising a cooling system configured to remove excess heat from the patient, wherein the cooling system comprises a flexible cavity configured for circulation of a degassed fluid.

20. The ultrasound transducer system of claim 11, wherein the energy profile is driven at ultrasonic frequencies in a range of 20 kHz to 12 MHz.

* * * * *